US011655484B2

(12) United States Patent
Shaw, IV et al.

(10) Patent No.: US 11,655,484 B2
(45) **Date of Patent: *May 23, 2023**

(54) **ELECTRON CONSUMING ETHANOL PRODUCTION PATHWAY TO DISPLACE GLYCEROL FORMATION IN *S. CEREVISIAE***

(71) Applicant: Lallemand Hungary Liquidity Management LLC, Budapest (HU)

(72) Inventors: Arthur J. Shaw, IV, Grantham, NH (US); Aaron Argyros, White River Junction, VT (US); Trisha Barrett, Bradford, VT (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 19 days.

This patent is subject to a terminal disclaimer.

(21) Appl. No.: 17/098,057

(22) Filed: Nov. 13, 2020

(65) Prior Publication Data

US 2021/0147882 A1 May 20, 2021

Related U.S. Application Data

(63) Continuation of application No. 16/581,664, filed on Sep. 24, 2019, now abandoned, which is a continuation of application No. 15/828,729, filed on Dec. 1, 2017, now Pat. No. 10,465,208, which is a continuation of application No. 14/442,408, filed as application No. PCT/US2013/070964 on Nov. 20, 2013, now Pat. No. 9,988,650.

(60) Provisional application No. 61/792,731, filed on Mar. 15, 2013, provisional application No. 61/728,450, filed on Nov. 20, 2012.

(51) Int. Cl.

| | |
|---|---|
| ***C12N 9/88*** | (2006.01) |
| ***C12P 7/06*** | (2006.01) |
| ***C12N 9/04*** | (2006.01) |
| ***C12N 9/02*** | (2006.01) |
| ***C12N 9/10*** | (2006.01) |
| ***C12N 9/12*** | (2006.01) |
| ***C12N 15/52*** | (2006.01) |
| ***C12N 1/16*** | (2006.01) |
| ***C12N 9/16*** | (2006.01) |
| ***C12N 9/90*** | (2006.01) |

(52) U.S. Cl.

CPC .................. *C12P 7/06* (2013.01); *C12N 1/16* (2013.01); *C12N 9/0004* (2013.01); *C12N 9/0006* (2013.01); *C12N 9/0008* (2013.01); *C12N 9/1022* (2013.01); *C12N 9/1029* (2013.01); *C12N 9/1217* (2013.01); *C12N 9/16* (2013.01); *C12N 9/88* (2013.01); *C12N 9/90* (2013.01); *C12N 15/52* (2013.01); *C12Y 101/01001* (2013.01); *C12Y 101/01008* (2013.01); *C12Y 102/0101* (2013.01); *C12Y 197/01004* (2013.01); *C12Y 202/01001* (2013.01); *C12Y 202/01002* (2013.01); *C12Y 203/01008* (2013.01); *C12Y 203/01054* (2013.01); *C12Y 207/02012* (2013.01); *C12Y 301/03021* (2013.01); *C12Y 401/01001* (2013.01); *C12Y 401/02009* (2013.01); *C12Y 401/02022* (2013.01); *C12Y 501/03001* (2013.01); *C12Y 503/01006* (2013.01); *Y02E 50/10* (2013.01)

(58) Field of Classification Search

CPC ......... C12N 9/1029; C12N 15/52; C12N 9/16
See application file for complete search history.

(56) References Cited

U.S. PATENT DOCUMENTS

| | | | | |
|---|---|---|---|---|
| 9,988,650 | B2 * | 6/2018 | Shaw, IV | C12N 9/0004 |
| 10,465,208 | B2 * | 11/2019 | Shaw, IV | C12N 9/88 |
| 2005/0153411 | A1 | 7/2005 | Wahlbom et al. | |
| 2011/0171709 | A1 | 7/2011 | Bardsley | |
| 2014/0273144 | A1 | 9/2014 | Hawkins et al. | |

FOREIGN PATENT DOCUMENTS

WO 2012/138942 A1 10/2012

OTHER PUBLICATIONS

**Bro, C. et al., "In Silico Aided Metabolic Engineering of *Saccharomyces* cerevisiae for Improved Bioethanol Production," Metabolic Engineering 8:102-111, Elsevier Inc., US (2006).

**Canadian Office Acton for Application No. 2,891,455, dated Sep. 23, 2019, 5 pages.

**Czako, M., et al., "The Herpes Simplex Virus Thymidine Kinase Gene as a Conditional Negative-Selection Marker Gene in *Arabidopsis thaliana*," Plant Physiol. 104:1067-71, American Society of Plant Physiologists, U.S. (1994).

(Continued)

*Primary Examiner* — Tekchand Saidha

(74) *Attorney, Agent, or Firm* — Sterne, Kessler, Goldstein & Fox P.L.L.C.

(57) ABSTRACT

The present invention provides for a mechanism to completely replace the electron accepting function of glycerol formation with an alternative pathway to ethanol formation, thereby reducing glycerol production and increasing ethanol production. In some embodiments, the invention provides for a recombinant microorganism comprising a down-regulation in one or more native enzymes in the glycerol-production pathway. In some embodiments, the invention provides for a recombinant microorganism comprising an up-regulation in one or more enzymes in the ethanol-production pathway.

52 Claims, 34 Drawing Sheets

Specification includes a Sequence Listing.

(56) References Cited

OTHER PUBLICATIONS

**DSM IP Assets, B.V., et al. v. Lallemand Specialties, Inc., et al., Deposition Exhibit Winge 11 from Dec. 13, 2017 Deposition of Professor Dennis R. Winge, Allowed Claims from U.S. Appl. No. 14/442,408, as amended on Jun. 6, 2017, 6 pages.
**DSM IP Assets, B.V., et al. v. Lallemand Specialities, Inc., et al., Expert Report of Professor Dennis R. Winge on the issue of invalidity, May 26, 2017, pp. 5-6;16-69.
**DSM IP Assets, B.V., et al. v Lallemand Specialities, Inc., et al., pages from the Dec. 13, 2017 Deposition of Professor Dennis R. Winge, pp. 131-134.
**Gardiner, D.M., et al., "Negative Selection Using Thymidine Kinase Increases the Efficiency of Recovery of Trans Formants With Targeted Genes in the Filamentous Fungus Leptosphaeria Maculans," Curr. Genet. 45:249-55, Springer-Vertag, Germany (2004).
**Goldstein, A.L., et al., "Heterologous URA3MX Cassettes for General Replacement in *Saccharomyces* cerevisiae," Yeast ,15(6):507-11 (Apr. 1999).
**Güldener, U., et al., "A New Efficient Gene Disruption Cassette for Repeated Use in Budding Yeast," Nucleic Acids Research 24(13):2519-24, Oxford University Press, England (1996).
**Guo, Z.P., et al., "Interruption of Glycerol Pathway in Industrial Alcoholic Yeasts to Improve the Ethanol Production," Applied Microbiology & Biotechnology, Springer, Berlin, DE, v. 82, No. 2, pp. 287-292 (Nov. 2008).
**Hahn-Hagerdal, B., et al., "Metabolic Engineering of *Saccharomyces* cerevisiae for Xylose Utilization" Adv. in Biochem. Eng. Biotechnol., 73:53-84, Springer Verlag, Germany (2001).
**Hartzog, P.E., et al., "Cylosine Deaminase MX Cassettes as Positive/Negative Markers in *Saccharomyces* Cerevisiae," Yeast 22:789-98; Wiley InterScience, England (2005).
**International Search Report and Written Opinion for Application No. PCT/US2013/070964, dated Feb. 27, 2014 (11 pages).
**Khang, C.H., et al., "A Dual Selection Based, Targeted Gene Replacement Tool for Magnoporthe Grisea and Fusarium Oxysporum," Fungal Genetics and Biology 42:483-92, Elsevier Inc., United States (2005).
**Medina, V. et al., Elimination of Glycerol Production in Anaerobic Cultures of a *Saccaromyces* cerevisiae Strain Engineered to Use Acetic Acid as an Electron Acceptor, Appled & Environmental Microbiology, pp. 190-195 (Jan. 2010).
**Nissen, T.L., et al. "Optimization of Ethanol Production in *Saccharomyces* cerevisiae by Metabolic Engineering of the Ammonium Assimilation," Metab Eng. Jan. 2000.; 2(1):69-77.
**Sharp, P.M., et al., "The Codon Adaptation Index: A Measure of Directional Synonymous Codon Usage Bias, and Its Potential Applications" Nucleic Acids Res. 1987;15(3):1281-1295, IRL Press Limited, Oxford, England.
**Sonderegger, M. et al., Metabolic Engineering of a Phosphoketolase Pathway for Pentose Catabolism in *Saccharomyces* cerevisiae, Applied & Environomental Microbology, v. 70, No. 5 (May 2004) pp. 2892-2897.
**Szybalski, W., "Use of the HPRT Gene and the HAT Selection Technique in DNA-Mediated Transformation of Mammalian Cells: First Steps Toward Developing Hybridoma Techniques and Gene Therapy." BioEssays 14(7):495-500, The Company of Biologists Limited, England (1992).
**Wach, A., et al., "New Heterologous Modules for Classical or PCR-based Gene Disruptions in *Saccharomyces* cerevisiae," Yeast 10:1793-1808, John Wiley & Sons Ltd., England (1994).
**Welch, M., et al., "Designing Genes for Successful Protein Expression," Methods Enzymol. 2011;498:43-66. doi:10.1016/B978-0-12-385120-8. 00003-6.

* cited by examiner

M4408

A

MA415 + B adolescentis PHK and PTA

M4409

B

MA415 + L. plantarum PHK1 and B adoelscentis PTA

M4410

C

ADH3t
PDC1 term
A niger PHK
badoles PTA
FCY1 5'flankpTEF2
pADH1
FCY1 3'flank

MA415 + A. niger PHK and B adolescentis PTA

L. plantarum PHK1 expression cassette

L. plantarum PHK2 expression cassette

A. niger PHK

L. casei PHK expression cassette

N. crassa PHK expression cassette

ELECTRON CONSUMING ETHANOL PRODUCTION PATHWAY TO DISPLACE GLYCEROL FORMATION IN *S. CEREVISIAE*

CROSS REFERENCE

This is a continuation of U.S. Ser. No. 16/581,664 filed Sep. 24, 2019, which is a continuation of U.S. Ser. No. 15,828,729 filed Dec. 1, 2017, now U.S. Pat. No. 10,465,208, which is a continuation of U.S. Ser. No. 14/442,408 filed May 13, 2015, now U.S. Pat. No. 9,988,650, which is a § 371 of PCT/US13/70964 filed Nov. 20, 2013, which claims priority to U.S. provisional applications Nos. 61/728,450 filed Nov. 20, 2012 and 61,792,731 filed Mar. 15, 2013, each application of which is hereby incorporated by reference in its entirety.

REFERENCE TO SEQUENCE LISTING

The contents of the sequence listing attached herewith (entitled "115235-275_sequence.txt"; of size 348 kb, created on Sep. 24, 2019) are incorporated herein by reference in their entirety.

BACKGROUND OF THE INVENTION

Energy conversion, utilization and access underlie many of the great challenges of our time, including those associated with sustainability, environmental quality, security, and quality of life. New applications of emerging technologies are required to respond to these challenges. Biotechnology, one of the most powerful of the emerging technologies, can give rise to important new energy conversion processes. Plant biomass and derivatives thereof are a resource for the biological conversion of energy to forms useful to humanity.

Among forms of plant biomass, both grain-based biomass and lignocellulosic biomass (collectively "biomass") are well-suited for energy applications. Each feedstock has advantages and disadvantages. For example, because of its large-scale availability, low cost, and environmentally benign production lignocellulosic biomass has gained attention as a viable feed source for biofuel production. In particular, many energy production and utilization cycles based on cellulosic biomass have near-zero greenhouse gas emissions on a life-cycle basis.

However, grain-based feed stocks are more readily converted to fuels by existing microorganisms, although grain-based feed stock is more expensive than lignocellulosic feed stock and conversion to fuel competes with alternative uses for the grain.

Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations can occur in a single step in a process configuration called consolidated bioprocessing ("CBP"), which is distinguished from other less highly integrated configurations in that it does not involve a dedicated process step for cellulase and/or hemicellulase production.

CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants. Successful competition of desirable microbes increases the stability of industrial processes based on microbial cellulose utilization. Progress in developing CBP-enabling microorganisms is being made through two strategies: engineering naturally occurring cellulolytic microorganisms to improve product-related properties, such as yield and titer; and engineering non-cellulolytic organisms that exhibit high product yields and titers to express a heterologous cellulase and hemicellulase system enabling cellulose and hemicellulose utilization.

One way to meet the demand for ethanol production is to convert sugars found in biomass, i.e., materials such as agricultural wastes, corn hulls, corncobs, cellulosic materials, and the like to produce ethanol. Efficient biomass conversion in large-scale industrial applications requires a microorganism that is able to tolerate high concentrations of sugar and ethanol, and which is able to ferment more than one sugar simultaneously.

Bakers' yeast (*Saccharomyces cerevisiae*) is the preferred microorganism for the production of ethanol (Hahn-Hägerdal, B., et al., *Adv. Biochem. Eng. Biotechnol.* 73: 53-84 (2001)). Pathways for ethanol production in *S. cerevisiae* can be seen in FIGS. 1-3. Attributes in favor of this microbe are (i) high productivity at close to theoretical yields (0.51 g ethanol produced/g glucose used), (ii) high osmo- and ethanol tolerance, (iii) natural robustness in industrial processes, and also (iv) being generally regarded as safe (GRAS) due to its long association with wine and bread making, and beer brewing. Furthermore, *S. cerevisiae* exhibits tolerance to inhibitors commonly found in hydrolysates resulting from biomass pretreatment. Exemplary metabolic pathways for the production of ethanol are depicted in FIGS. 1-4.

However, glycerol is a required metabolic end-product of native yeast ethanolic fermentation (FIG. 5A). During anaerobic growth on carbohydrates, production of ethanol and carbon dioxide is redox neutral, while the reactions that create cell biomass and associated carbon dioxide are more oxidized relative to carbohydrates. The production of glycerol, which is more reduced relative to carbohydrates, functions as an electron sink to off-set cell biomass formation, so that overall redox neutrality is conserved. This is essential from a theoretical consideration of conservation of mass, and in practice strains unable to produce glycerol are unable (or only very poorly able) to grow under anaerobic conditions.

There is a strong commercial incentive to not produce glycerol, as it represents lost ethanol yield. In industrial corn ethanol fermentations, this yield loss can be up to 6% of theoretical, for a market of ~14 billion gallons/yr. At selling price of $2.50/gal, this is a total market value of $2 B/yr.

Strategies from the literature to address this problem include decreasing glycerol formation by engineering ammonia fixation to function with NADH instead of NADPH via up-regulation of GLN1, encoding glutamine synthetase, or GLT1, encoding glutamate synthase with deletion of GDH1, encoding the NADPH-dependent glutamate dehydrogenase. (Nissen, T. L., et al., *Metabolic Engineering* 2: 69-77 (2000)). Another strategy engineering cells to produce excess NADPH during glycolysis via expression of a NADPH linked glyceraldehyde-3-phosphate dehydrogenase. (Bro, C., et al., *Metabolic Engineering* 8: 102-111 (2006)).

However, most glycerol reduction strategies either only partially reduce the requirement for glycerol formation, or create a by-product other than ethanol. The present invention overcomes the shortcomings of these other strategies by redirecting electrons typically placed on glycerol into ethanol formation, thereby reducing glycerol production and increasing ethanol production (FIG. 5B, FIG. 6).

BRIEF SUMMARY OF THE INVENTION

Aspects of the invention are directed to a recombinant microorganism comprising a heterologous nucleic acid encoding a phosphoketolase; at least one heterologous nucleic acid encoding an enzyme in an acetyl-CoA production pathway; a heterologous nucleic acid encoding a bifunctional acetaldehyde-alcohol dehydrogenase; and, at least one genetic modification that leads to the down-regulation of an enzyme in a glycerol-production pathway. In some embodiments, the phosphoketolase is a single-specificity phosphoketolase with the Enzyme Commission Number 4.1.2.9. In some embodiments, the phosphoketolase is dual-specificity phosphoketolase with the Enzyme Commission Number 4.1.2.22. Aspects of the invention arc directed to a recombinant microorganism comprising at least one heterologous nucleic acid encoding an enzyme in an acetyl-CoA production pathway; a heterologous nucleic acid encoding a bifunctional acetaldehyde-alcohol dehydrogenase; and, optionally, at least one genetic modification that leads to the down-regulation of an enzyme in a glycerol-production pathway. In some embodiments, the enzyme in the acetyl-CoA production pathway is phosphotransacetylase with the Enzyme Commission Number 2.3.1.8. In some embodiments, the enzyme in the acetyl-CoA production pathway is acetate kinase with the Enzyme Commission Number 2.7.2.12. In some embodiments, the bifunctional acetaldehyde-alcohol dehydrogenase is selected from a group of enzymes having both of the following Enzyme Commission Numbers: EC 1.2.1.10 and 1.1.1.1. In some embodiments, the bifunctional acetaldehyde-alcohol dehydrogenase is an NADPH dependent bifunctional acetaldehyde-alcohol dehydrogenase selected from a group of enzymes having the following Enzyme Commission Numbers: EC 1.2.1.10 and 1.1.1.2. In some embodiments, the enzyme in the glycerol-production pathway is glycerol-3-phosphate dehydrogenase with the Enzyme Commission Number 1.1.1.8. In some embodiments, the enzyme in the glycerol-production pathway is glycerol-3-phosphate phosphatase with the Enzyme Commission Number 3.1.3.21.

In some embodiments, the microorganism further comprises at least one additional up-regulated enzyme. In some embodiments, transaldolase with the Enzyme Commission Number 2.2.1.2 is up-regulated. In some embodiments, transketolase with the Enzyme Commission Number 2.2.1.1 is up-regulated. In some embodiments, ribose-5-P isomerase with the Enzyme Commission Number 5.3.1.6 is up-regulated. In some embodiments, ribulose-5-P 3-epimerase with the Enzyme Commission Number 5.1.3.1 is up-regulated.

In some embodiments, at least one enzyme in a glycolysis pathway is up-regulated in the microorganism. In some embodiments, the enzyme in the glycolysis pathway is pyruvate decarboxylase with the Enzyme Commission Number 4.1.1.1. In some embodiments, the enzyme in the glycolysis pathway is alcohol dehydrogenase selected from a group of enzymes having the following Enzyme Commission Numbers: 1.1.1.1 and 1.1.1.2.

In some embodiments, the microorganism additionally comprises at least one genetic modification that leads to the down-regulation of aldehyde dehydrogenase selected from a group of enzymes having the following Enzyme Commission Numbers: 1.2.1.3, 1.2.1.4 and 1.2.1.10. In some embodiments, the microorganism additionally comprises at least one genetic modification that leads to the up-regulation of aldehyde dehydrogenase selected from a group of enzymes having the following Enzyme Commission Numbers: 1.2.1.3, 1.2.1.4 and 1.2.1.10. In some embodiments, the aldehyde dehydrogenase is acetaldehyde dehydrogenase.

In some embodiments, the microorganism additionally comprises at least one genetic modification that leads to the down-regulation of formate dehydrogenase selected from a group of enzymes having the following Enzyme Commission Numbers: 1.2.1.43 and 1.2.1.2.

In some embodiments, the microorganism additionally comprises at least one genetic modification that leads to the up-regulation of pyruvate formate lyase with the Enzyme Commission Number 2.3.1.54. In some embodiments, the microorganism additionally comprises at least one genetic modification that leads to the up-regulation of pyruvate formate lyase activating enzyme with the Enzyme Commission Number 1.97.1.4.

In some embodiments, the microorganism is yeast. In some embodiments, the microorganism is from the genus *Saccharomyces*. In some embodiments, the microorganism is *Saccharomyces cerevisiae.*

In some embodiments, the recombinant microorganisms described herein produce ethanol at a higher yield than an otherwise identical microorganism lacking said genetic modifications. In some embodiments, the microorganism produces an ethanol titer 1%-10% more than an otherwise identical microorganism lacking said genetic modifications.

In some embodiments, the recombinant microorganisms described herein produce glycerol at a lower yield than an otherwise identical microorganism lacking said genetic modifications. In some embodiments, the microorganism produces a glycerol titer of 10-100% less than an otherwise identical microorganism lacking said genetic modifications.

In some embodiments, the invention is directed to the host cells described herein and a carbon-containing feedstock. In some embodiments, the feedstock is selected from the group consisting of woody biomass, grasses, sugar-processing residues, municipal waste, agricultural wastes or any combination thereof. In some embodiments, the feedstock comprises recycled wood pulp fiber, sawdust, hardwood, softwood, rice straw, rice hulls, barley straw, corn cobs, cereal straw, wheat straw, canola straw, oat straw, oat hulls, corn fiber, stover, succulents, agave, cane bagasse, switchgrass, miscanthus, paper sludge, municipal waste or any combination thereof.

In some embodiments, the invention is directed to a method of producing a fermentation product using a composition described herein, wherein the host cell of the composition is capable of fermenting the carbon containing feedstock to yield the fermentation product.

In some embodiments, the invention is directed to a method of producing ethanol comprising providing any host cell described herein; culturing the host cell in the presence of a carbon containing feedstock for sufficient time to produce ethanol; and, optionally, extracting the ethanol.

In some embodiments, the invention is directed to a method of reducing glycerol production comprising providing any host cell described herein, wherein said glycerol production is 10-100% less than an otherwise identical microorganism lacking said genetic modifications. In some embodiments, the glycerol production of the host cell is reduced as compared to an otherwise identical microorganism lacking said genetic modifications, and wherein the ethanol titer increased by at least 1-10% when the host cell is cultured in the presence of a carbon containing feedstock for a sufficient time to produce ethanol.

In some embodiments, the invention is directed to a co-culture comprising at least two host cells wherein one of the host cells comprises a host cell described herein and another host cell that is genetically distinct from the host cell of the invention. In some embodiments, the genetically distinct host cell of the co-culture is a yeast or bacterium.

In some embodiments, the genetically distinct host cell is any organism from the genus *Saccharomyces, Issatchenkia, Pichia, Clavispora, Candida, Hansenula, Kluyveromyces, Trichoderma, Thermoascus, Escherichia, Clostridium, Caldicellulosiruptor, Zymomonas, Thermoanaerobacter* and *Thermoanaerobacterium.*

BRIEF DESCRIPTION OF THE DRAWINGS/FIGURES

Figure 8:
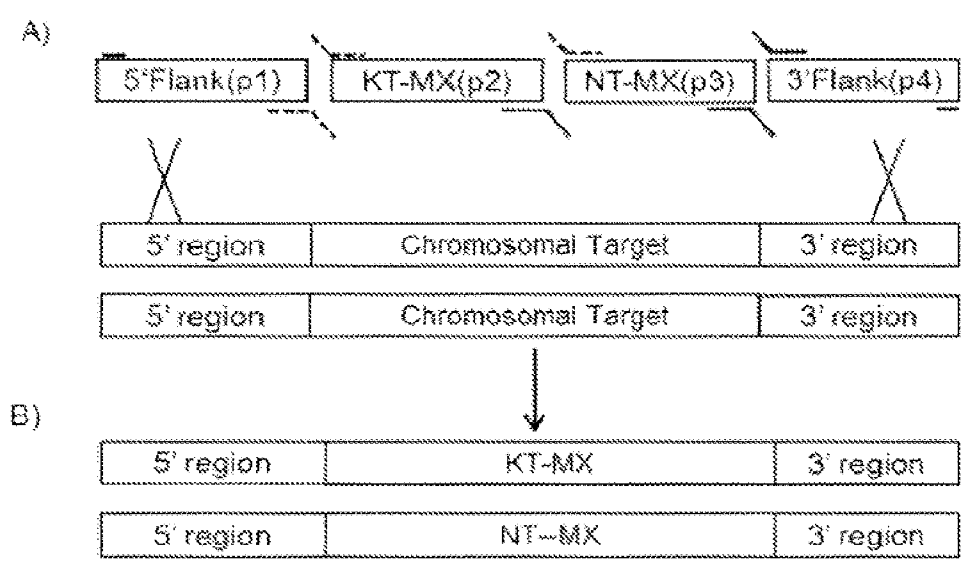

FIG. 8 depicts a schematic diagram for PCR construction and integration of KT-MX and NT-MX integration cassettes into both copies of each chromosome at a given target locus. (A) The transformed PCR assembly contains four PCR products, a 5' flank (p1) which is homologous to sequences upstream of the target site, KT-MX cassette (p2), NT-MX cassette (p3), and a 3' flank (p4) homologous to sequences downstream of the target site. Each component is amplified individually using primers which create homologous overlapping extensions of each PCR product. The bent dashed lines represent homology between the KT/NT-MX cassettes and the 5' flank and the bent solid lines represent homology with the 3' flank. (B) Schematic of the chromosome after replacement of the target site with KT-MX and NT-MX.

Figure 9:
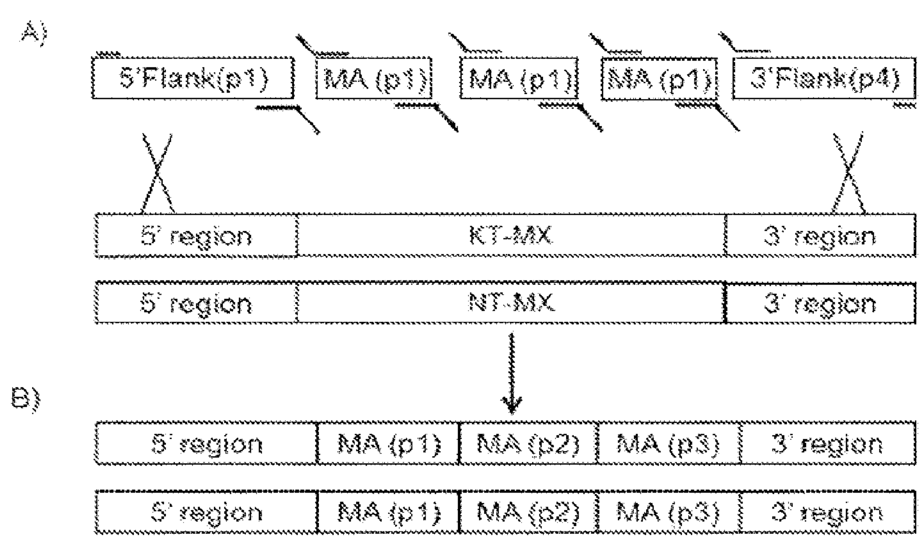

FIG. 9 depicts a schematic diagram of the strategy used to replace integrated KT-MX and NT-MX selection cassettes with a "Mascoma Assembly" on both chromosomes at a target locus. A Mascoma Assembly ("MA") is used to identify a series of overlapping PCR products that form the desired construction once they are recombined in the organism. In this document a MA number is given to represent a combination of molecular components to be assembled via recombination. (A) The transformed Mascoma Assembly contains a quantity of PCR products which is dependent on the desired engineering event (pX), a 5' flank (p1) which is homologous to sequences upstream of the target site, and a 3' flank (p4) homologous to sequences downstream of the target site. Each component is amplified individually using primers which create homologous overlapping extensions. The overlapping bent lines represent homology at the end of those PCR products. (B) Schematic diagram of chromosome following selection on FUDR and replacement of genetic markers with the Mascoma Assembly.

Figure 10:
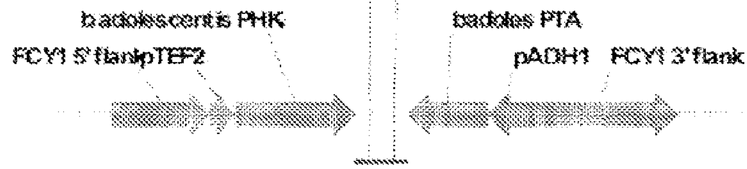
Figure 10:
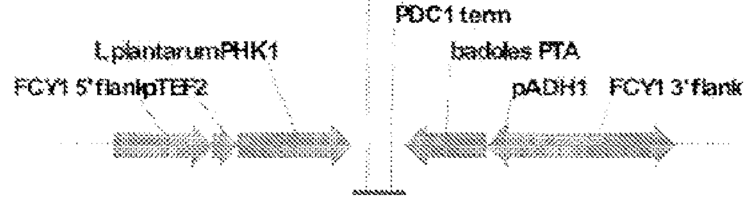

FIG. 10 depicts the integration schemes for *B. adolescentis* PTA and (A) *B. adolescentis* PHK, (B) *L. plantarum* PHK1, and (C) *A. niger* PHK at the *S. cerevisiae* FCY1 site.

Figure 11:
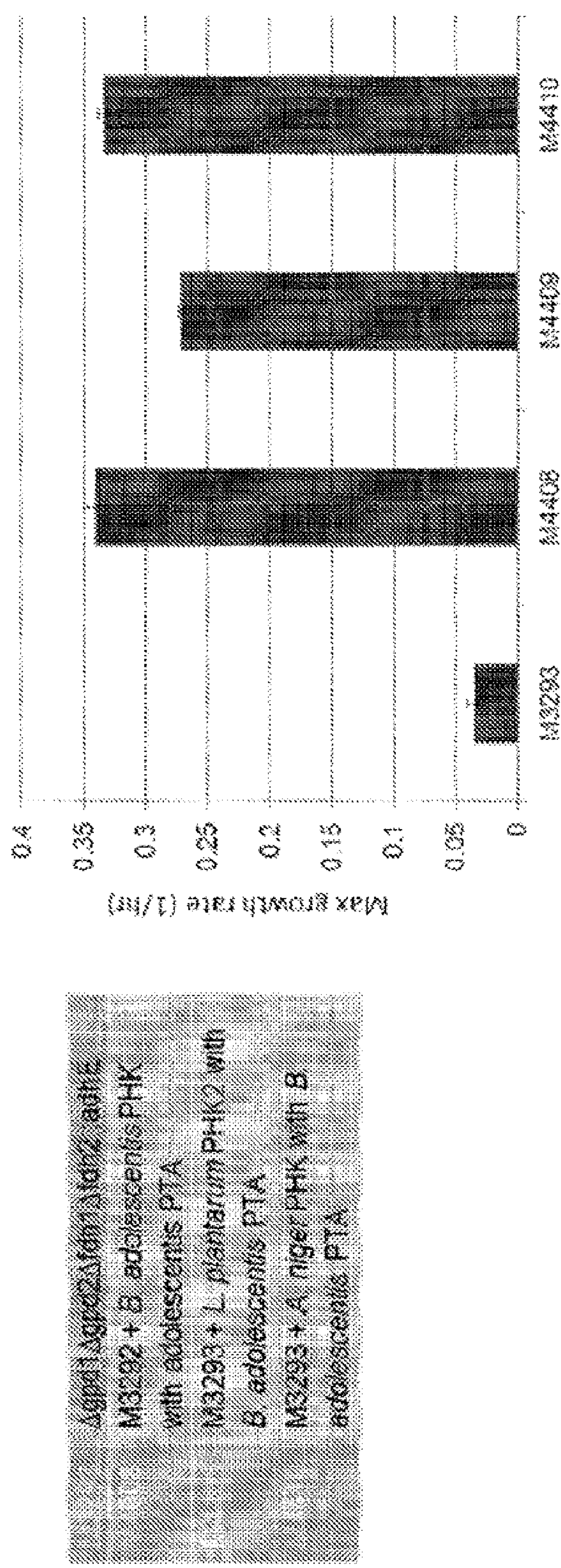

FIG. 11 depicts the improved anaerobic growth rate of *S. cerevisiae* strains containing integrated PTA and PHK, M4008, M4409, and M4410 compared to a strain that does not contain integrated PTA and PHK, M3293.

Figure 12:
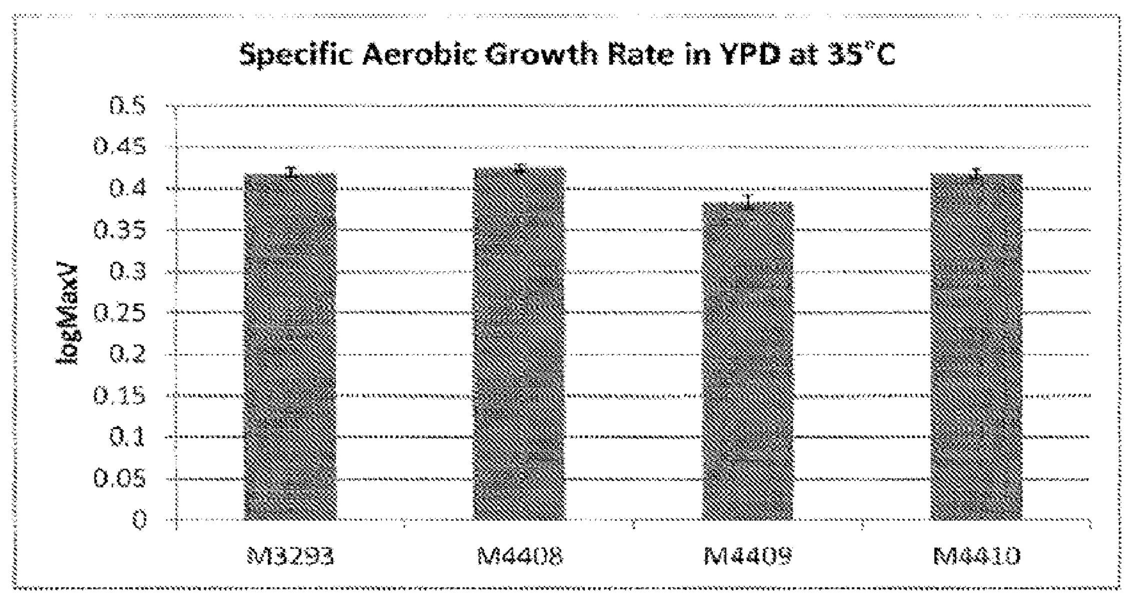

FIG. 12 depicts the aerobic growth rate of *S. cerevisiae* strains containing integrated PTA and PHK, M4008, M4409, and M4410 compared to a strain that does not contain integrated PTA and PHK, M3293.

Figure 13:
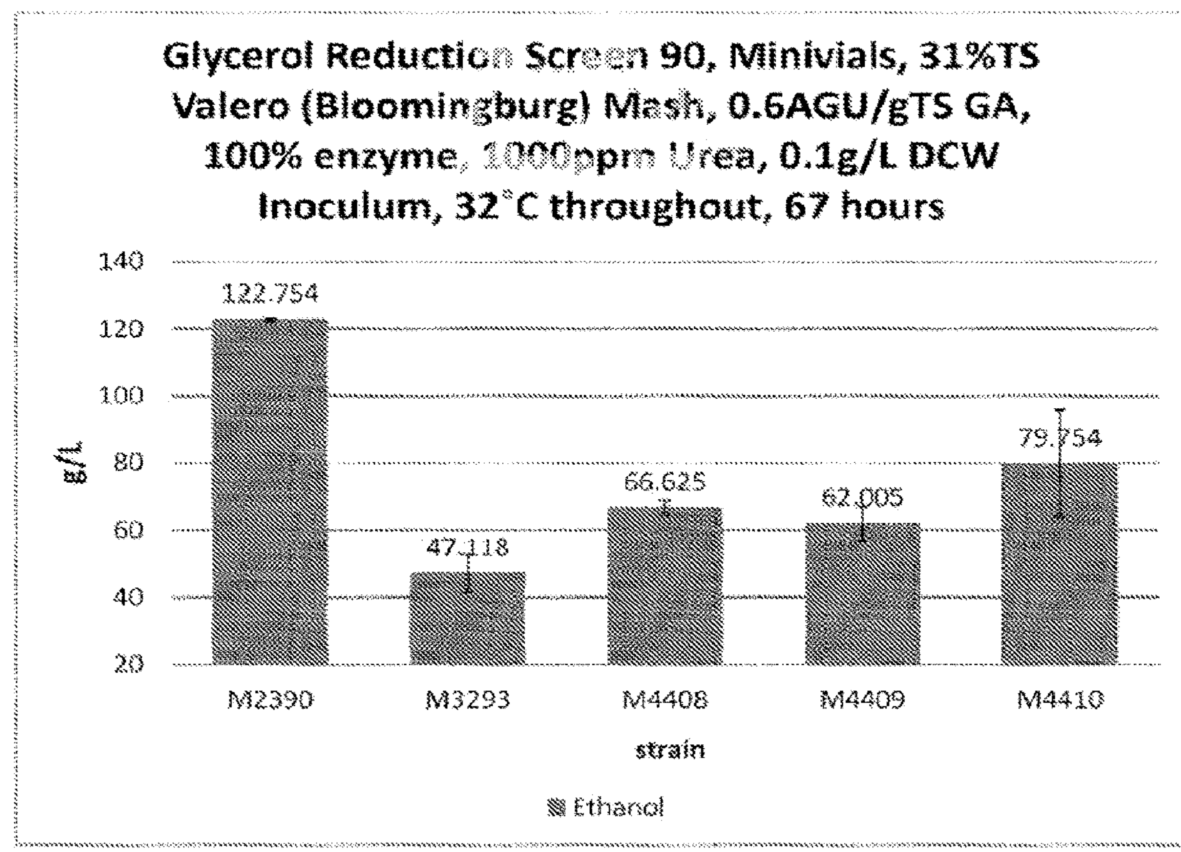

FIG. 13 depicts the ethanol production of *S. cerevisiae* strains containing integrated PTA and PHK, M4008, M4409, and M4410 compared to a strain that does not contain integrated PTA and PHK, M3293, for fermentation using 31% solids corn mash. M2390 is a wildtype control.

Figure 14:
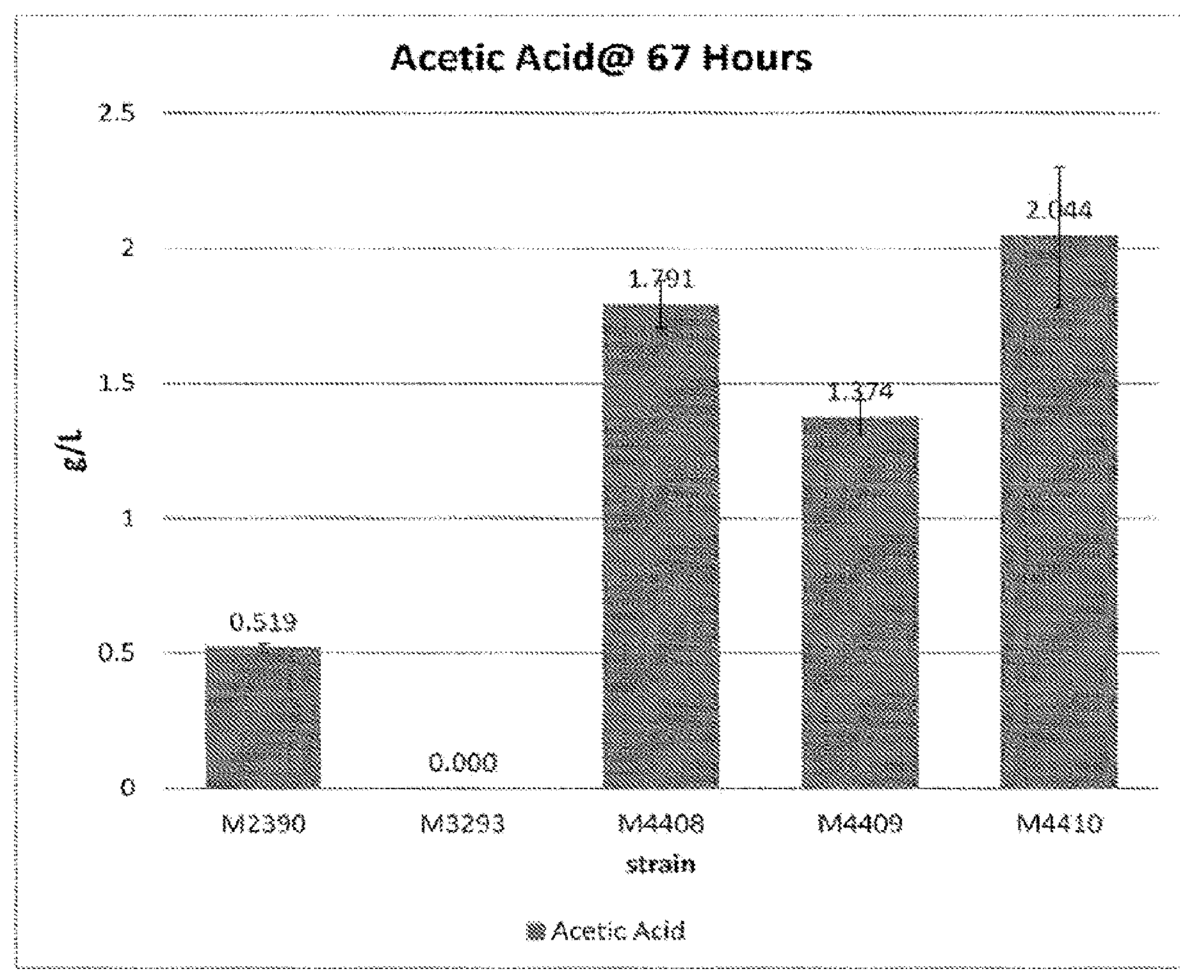

FIG. 14 depicts the production of acetic acid in *S. cerevisiae* strains containing integrated PTA and PHK, M4008, M4409, and M4410 compared to a strain that does not contain integrated PTA and PHK, M3293, during fermentation using 31% solids corn mash. M2390 is a wildtype control.

Figure 15:
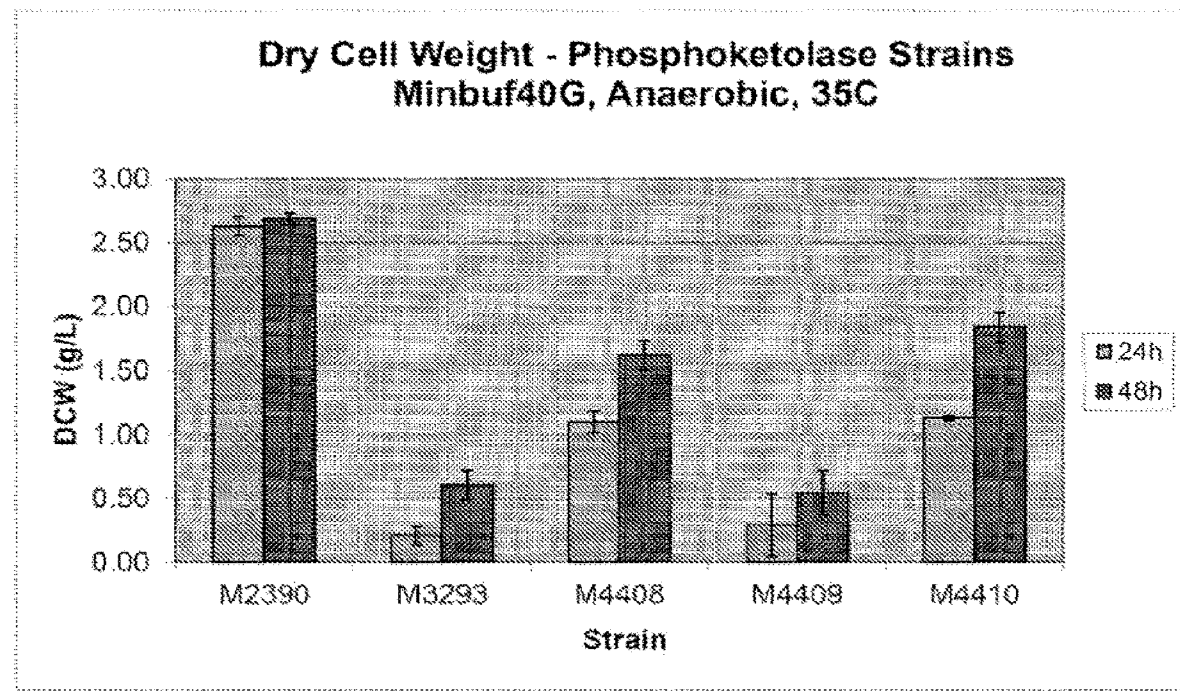

FIG. 15 depicts the improved growth of in *S. cerevisiae* strains containing integrated PTA and PHK, M4008, M4409, and M4410 compared to a strain that does not contain integrated PTA and PHK, M3293, during fermentation in defined media. M2390 is a wildtype control.

Figure 16:
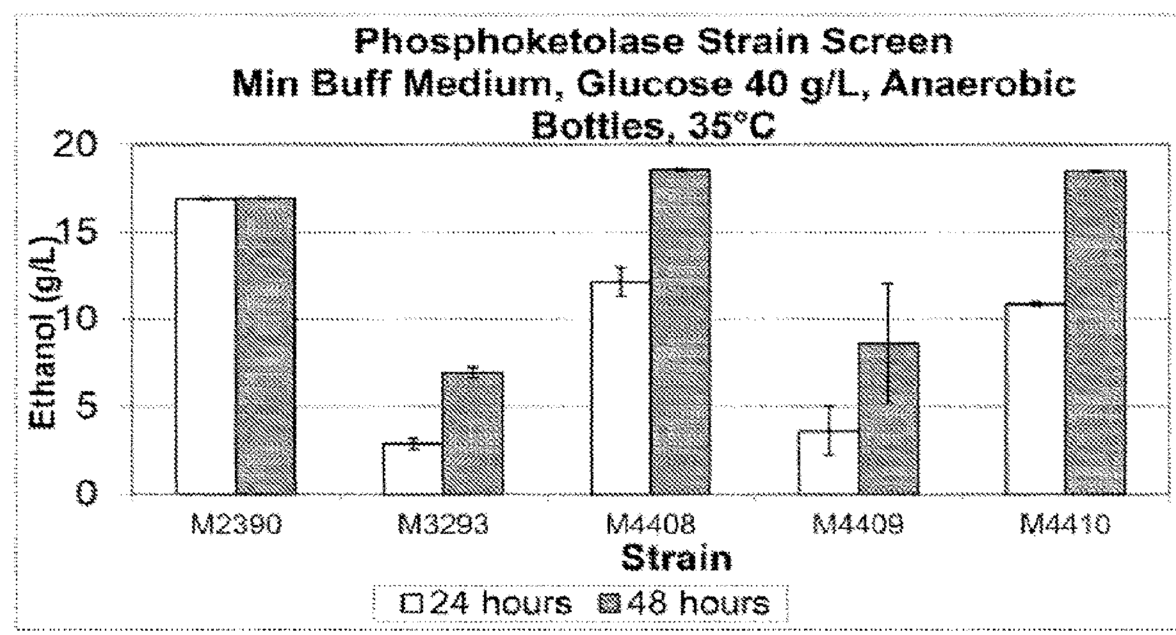

FIG. 16 depicts the ethanol production in defined media of *S. cerevisiae* strains containing integrated PTA and PHK, M4008, M4409, and M4410 compared to a strain that does not contain integrated PTA and PHK, M3293, during fermentation in defined media. M2390 is a wildtype control.

Figure 17:
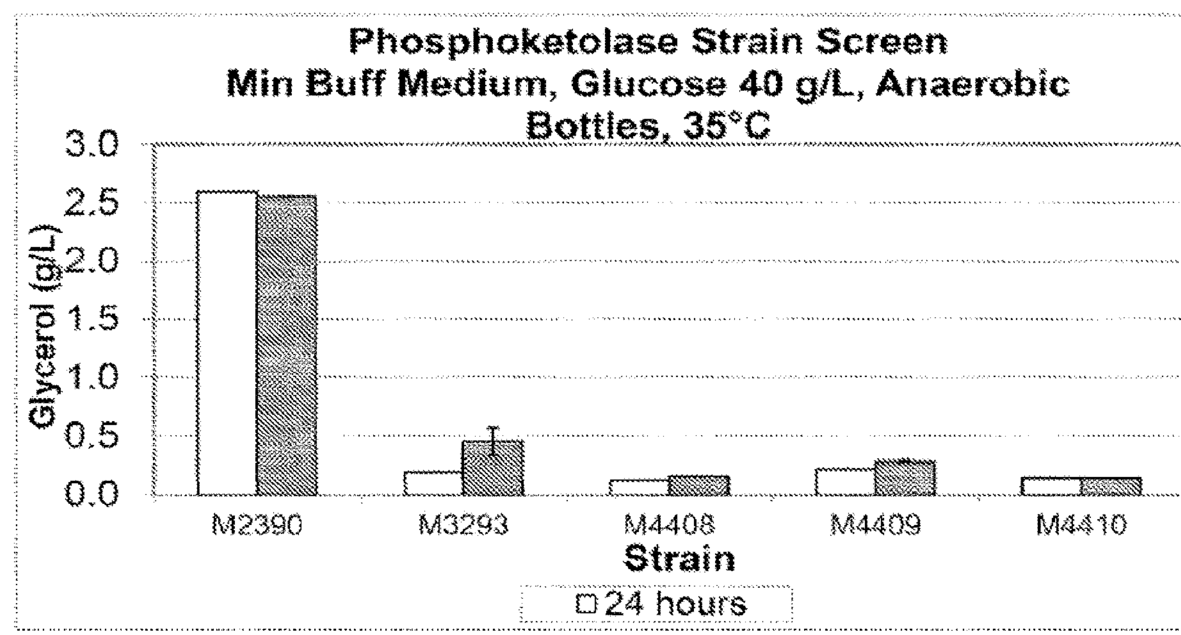

FIG. 17 depicts the glycerol production in defined media of *S. cerevisiae* strains containing integrated PTA and PHK, M4008, M4409, and M4410 compared to a strain that does not contain integrated PTA and PHK, M3293, during fermentation in defined media. M2390 is a wildtype control.

Figure 18:
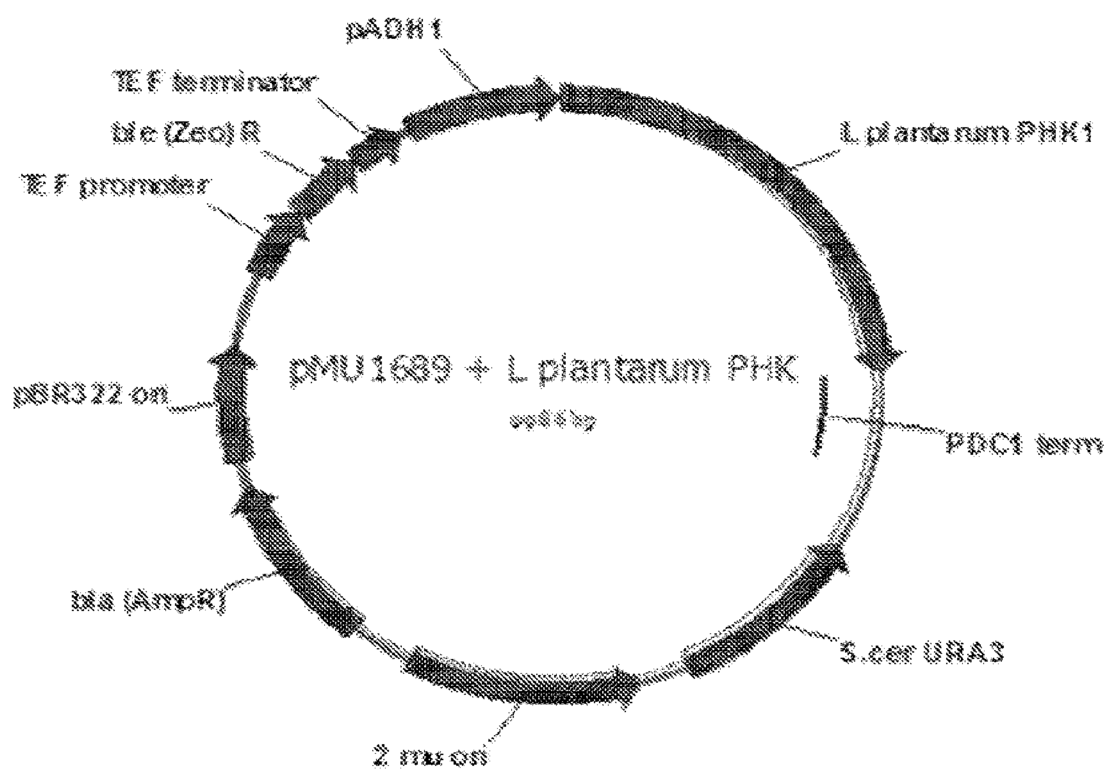

FIG. 18 depicts an *L. plantarum* PHK1 expression plasmid.

Figure 19:
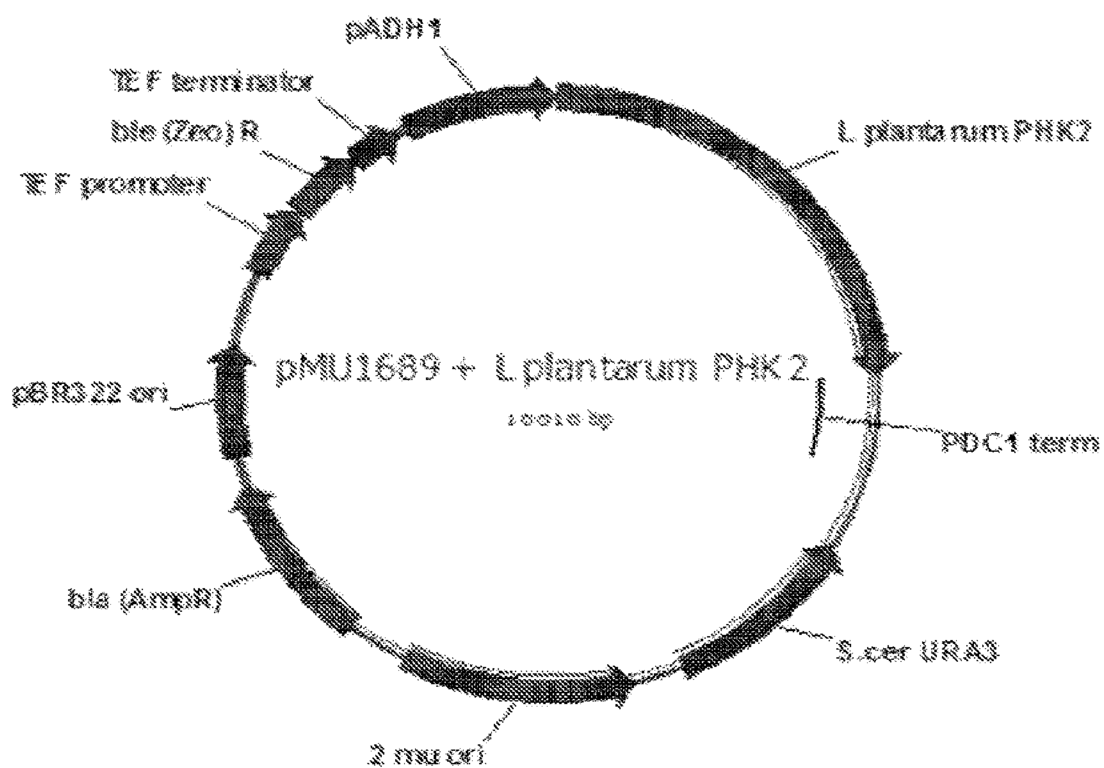

FIG. 19 depicts an *L. plantarum* PHK2 expression plasmid.

Figure 20:
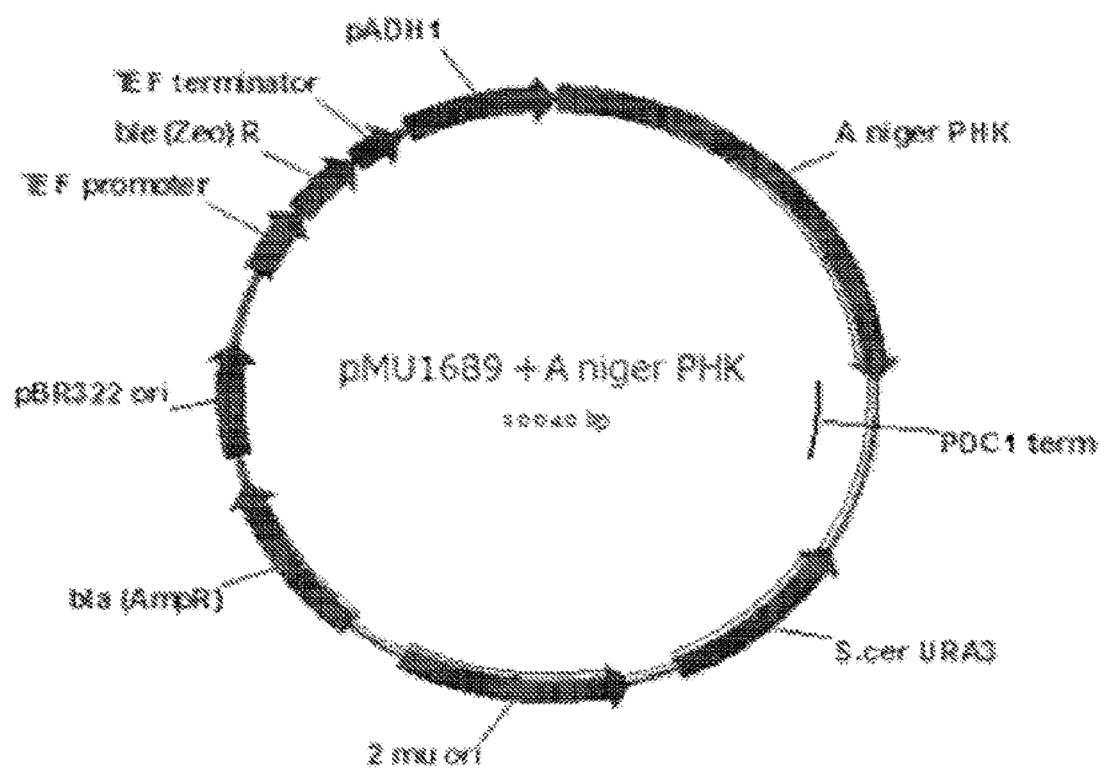

FIG. 20 depicts an *A. niger* PHK expression plasmid.

Figure 21:
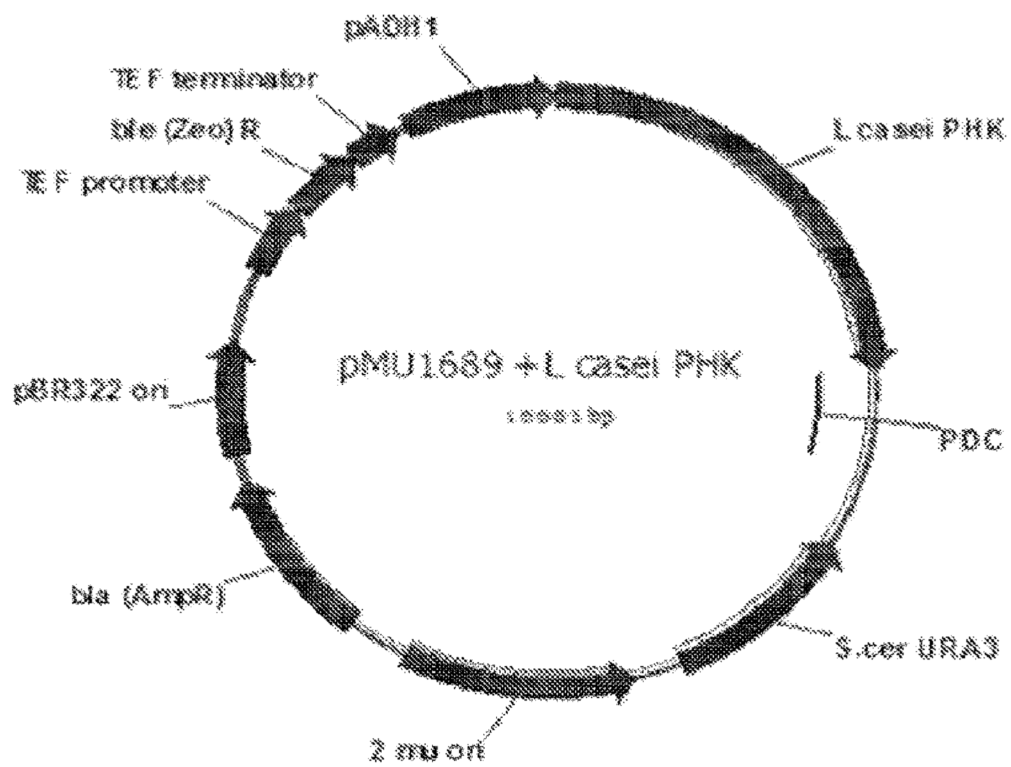

FIG. 21 depicts an *L. easel* PHK expression plasmid.

Figure 22:
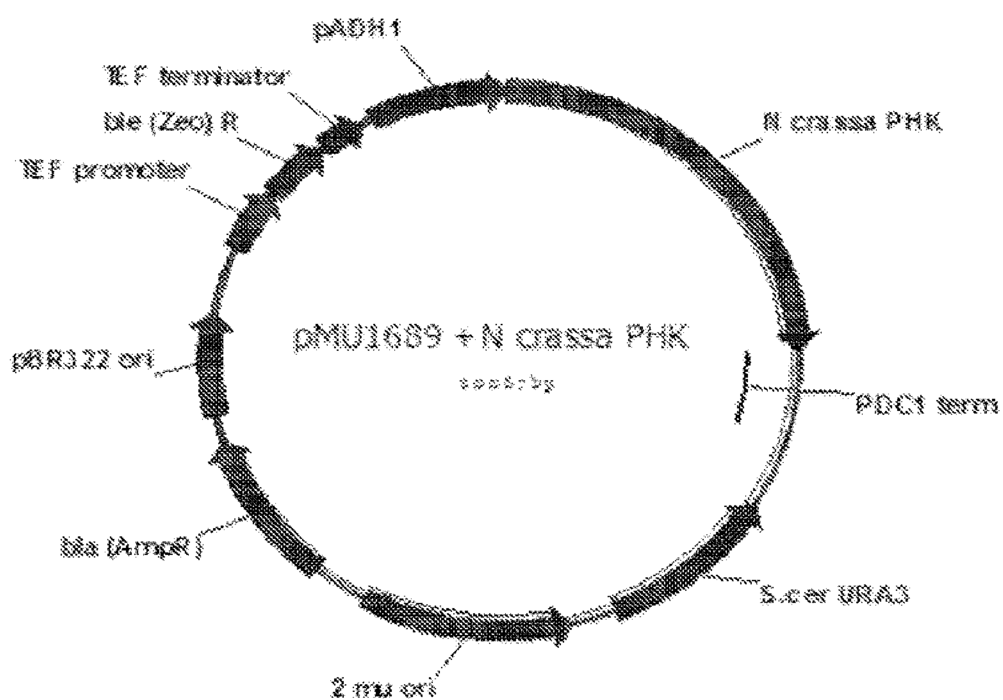

FIG. 22 depicts an *N. crassa* PHK expression plasmid.

Figure 23:
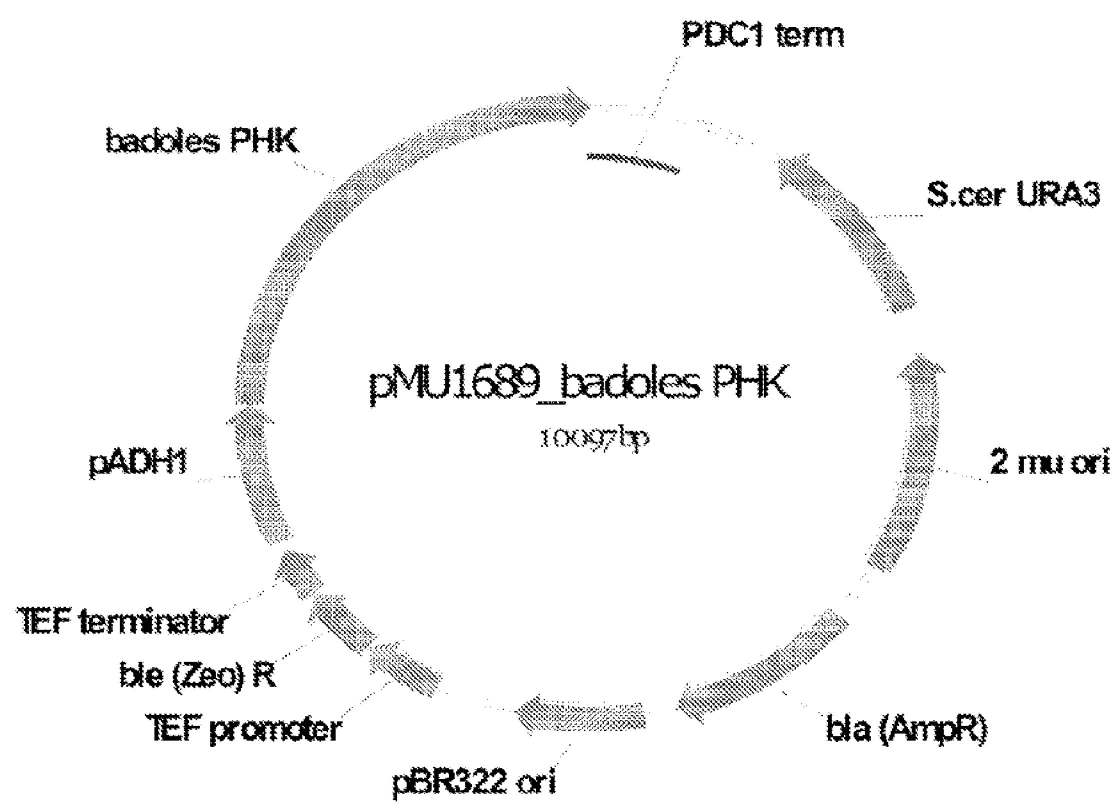

FIG. 23 depicts a *B. adolescentis* PHK expression plasmid.

Figure 24:
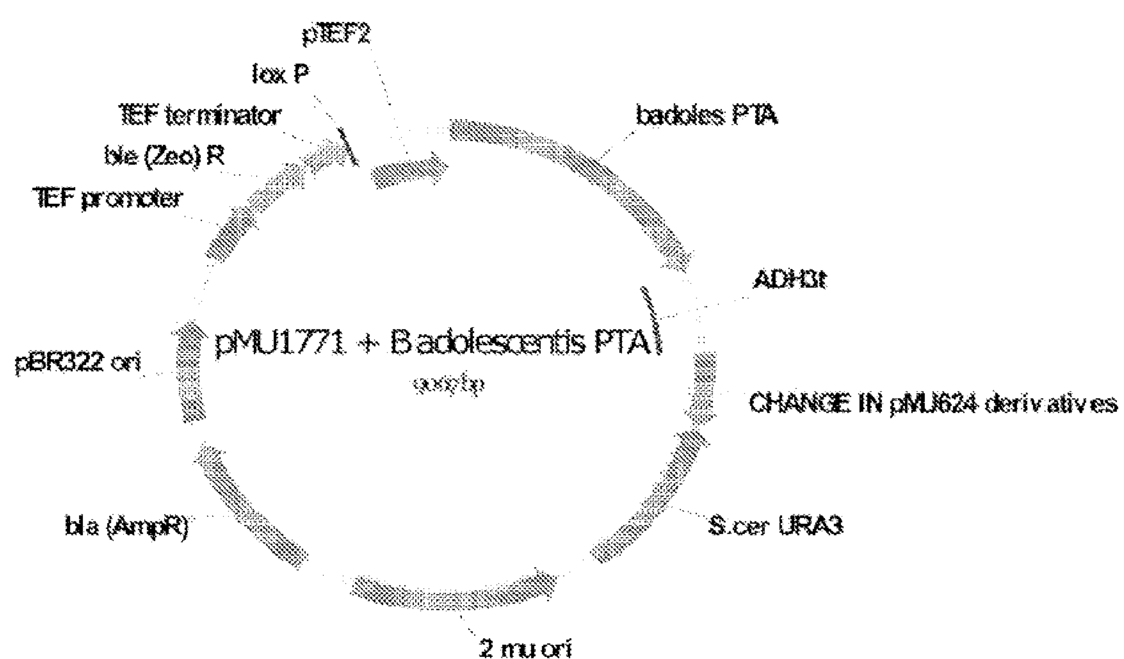

FIG. 24 depicts a *B. adolescentis* PTA expression plasmid.

Figure 25:
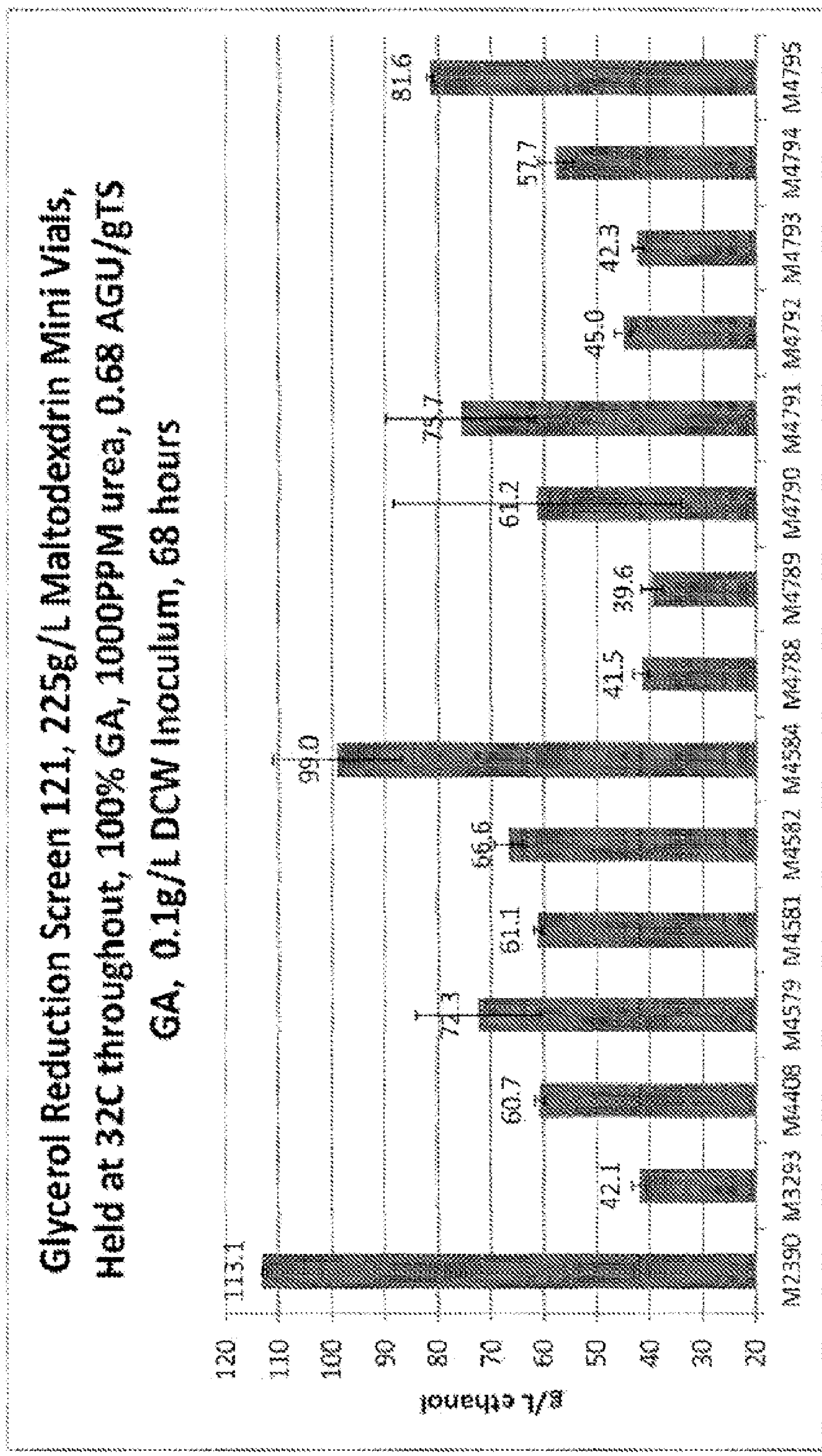

FIG. 25 depicts the ethanol production of *S. cerevisiae* strains M4408, M4579, M4581, M4582, M4584, M4788, M4789, M4790, M4791, M4792, M4793, M4794, and M4795 that contain pathway components in a M3293 background.

Figure 26:
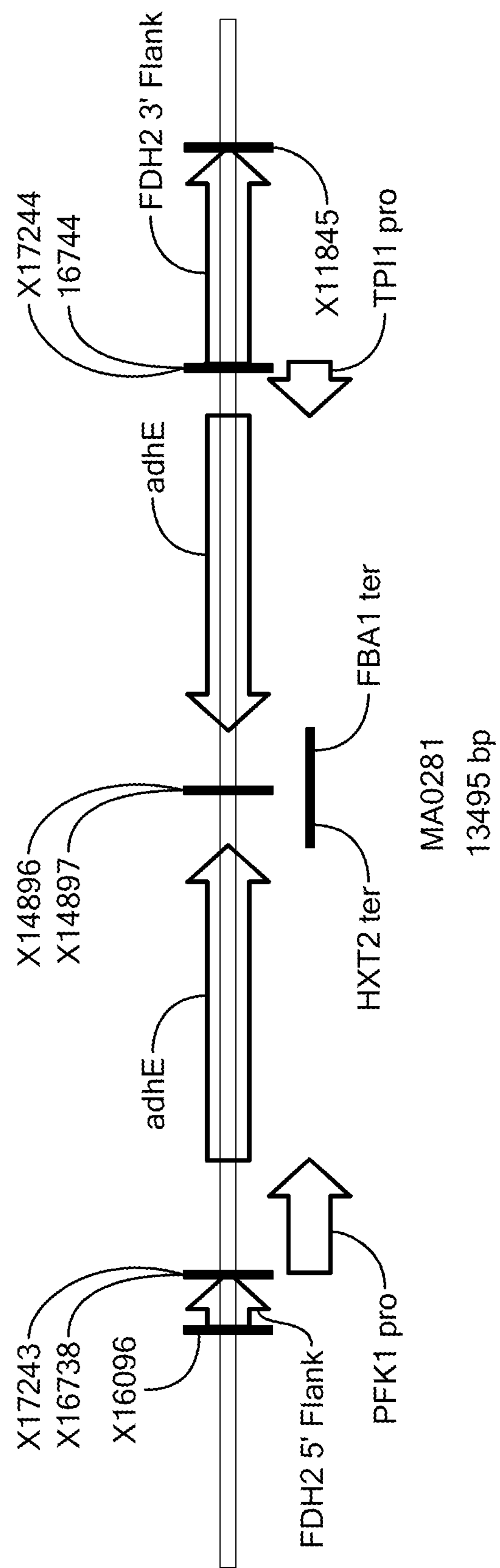

FIG. 26 depicts a schematic diagram of the MA0281 insertion cassette.

Figure 27:
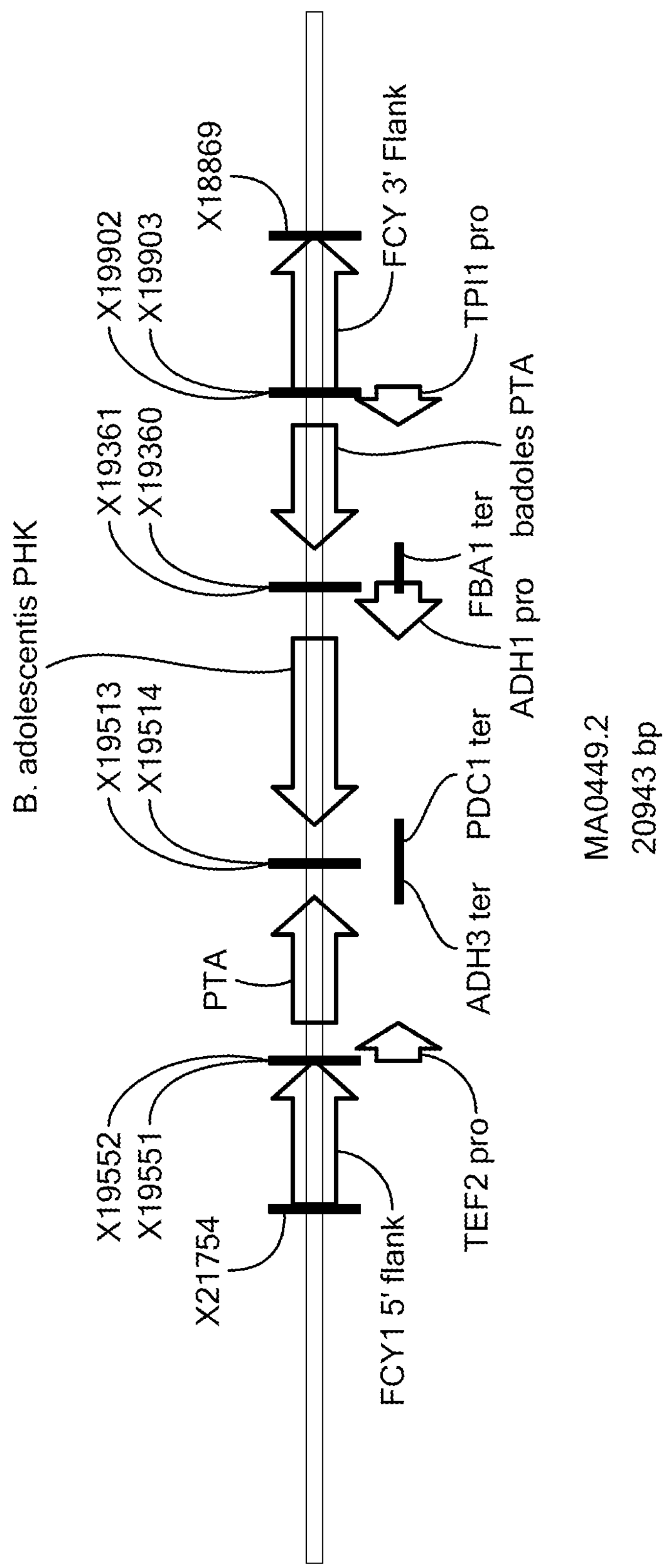

FIG. 27 depicts a schematic diagram of the MA0449.2 insertion cassette.

Figure 28:
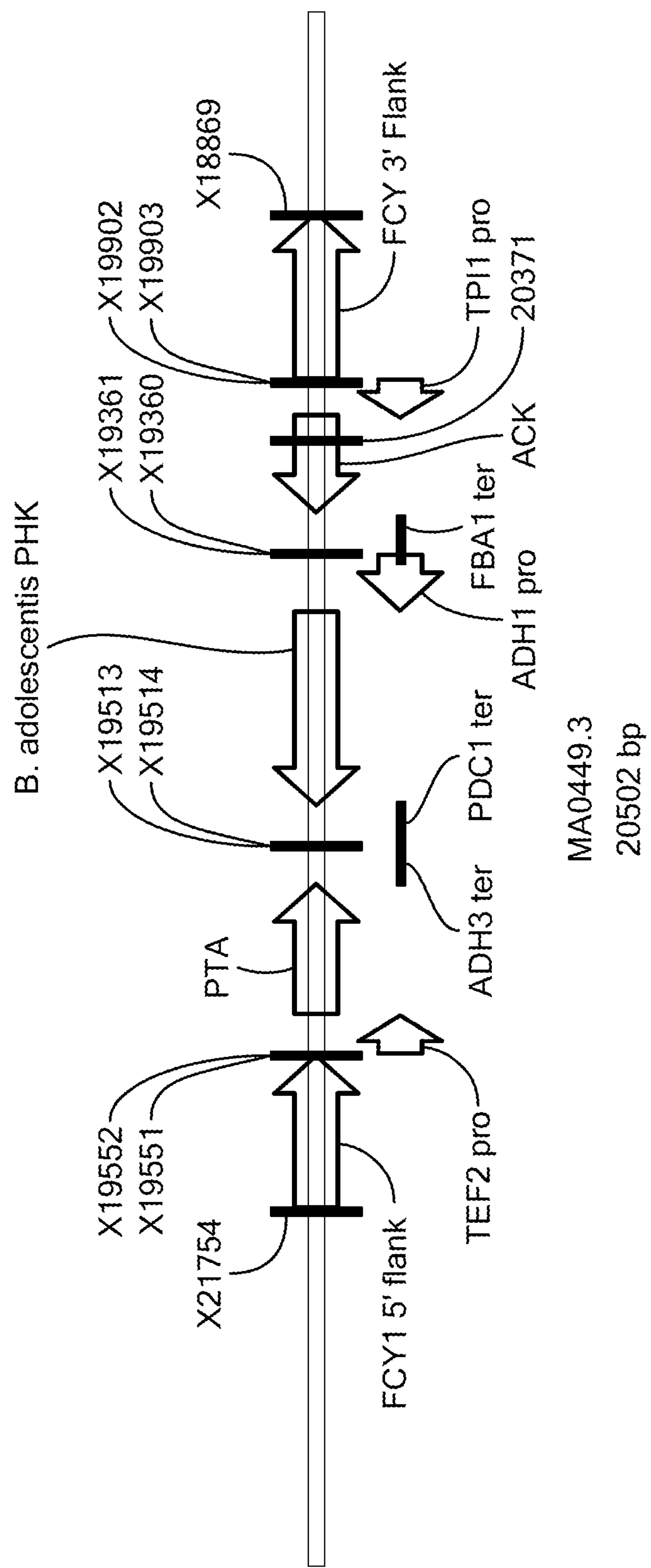

FIG. 28 depicts a schematic diagram of the MA0449.3 insertion cassette.

Figure 29:
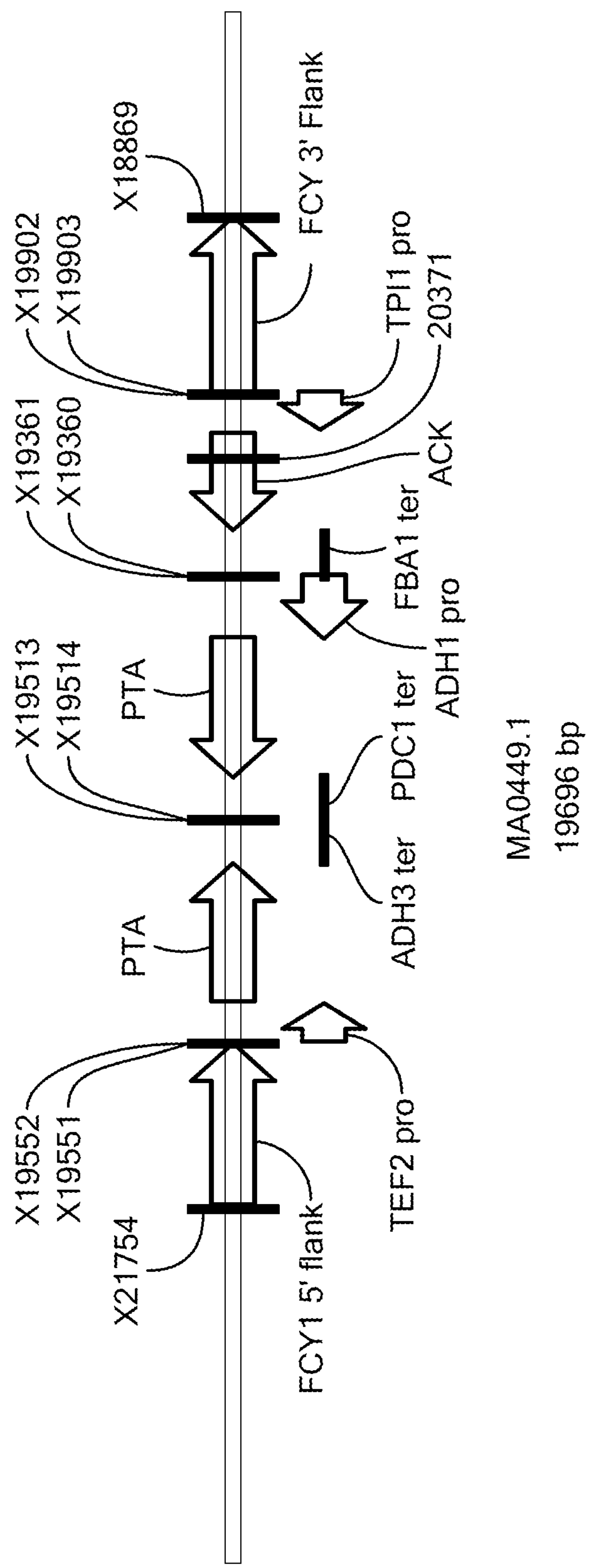

FIG. 29 depicts a schematic diagram of the MA0449.1 insertion cassette.

Figure 30:
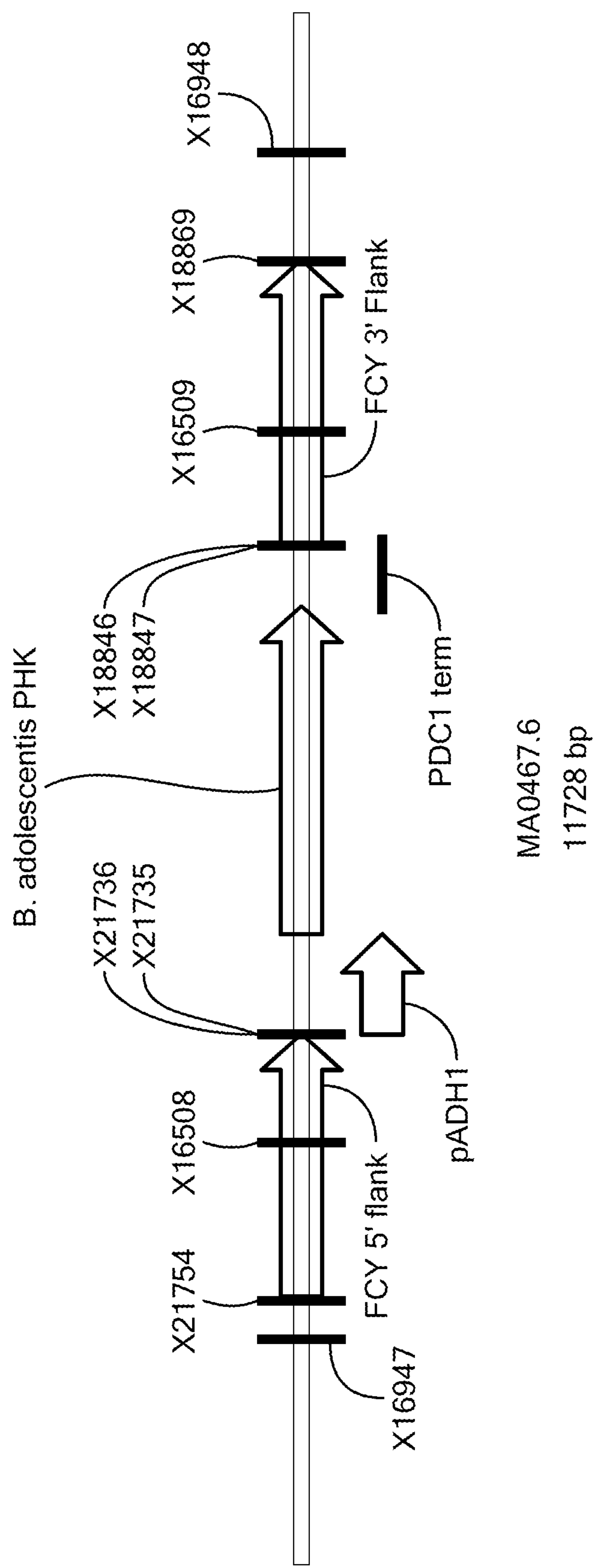

FIG. 30 depicts a schematic diagram of the MA0467.6 insertion cassette.

Figure 31:
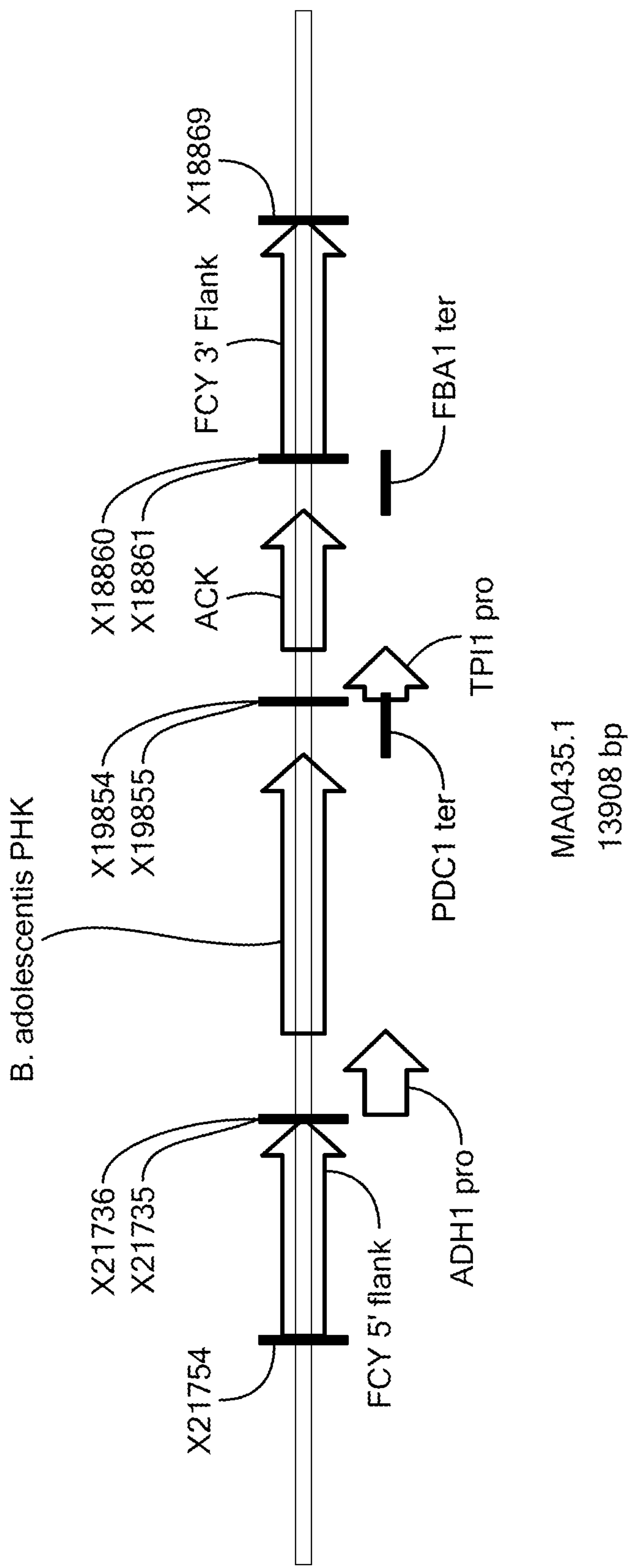

FIG. 31 depicts a schematic diagram of the MA0435.1 insertion cassette.

Figure 32:
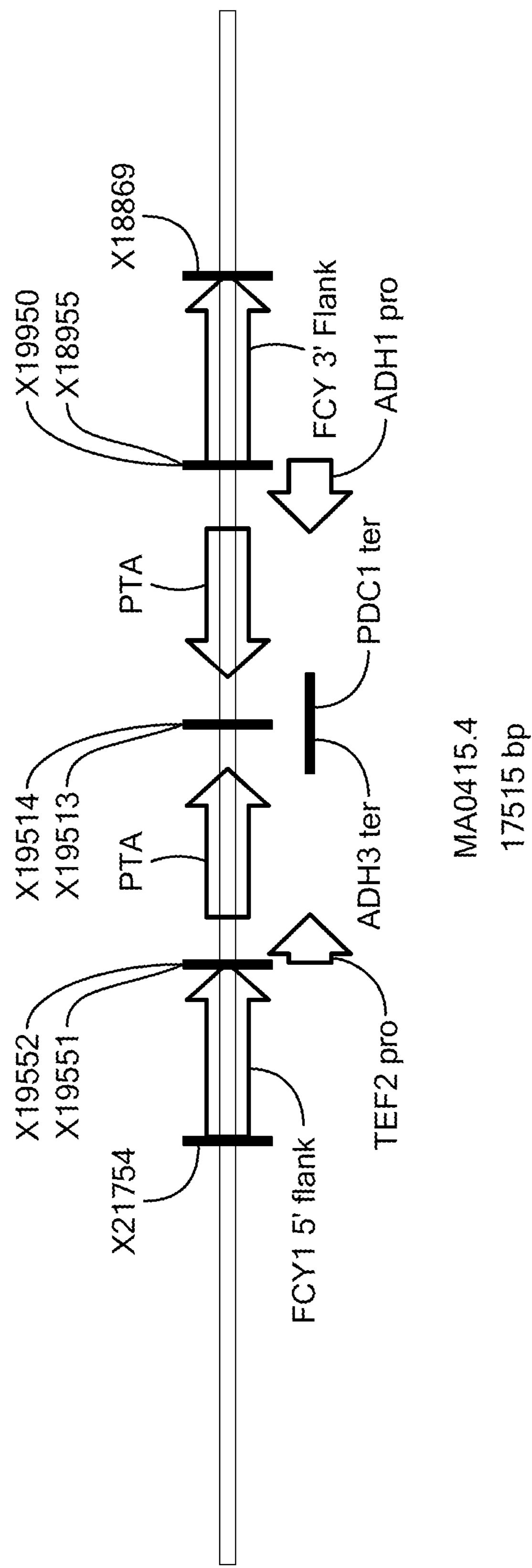

FIG. 32 depicts a schematic diagram of the MA0415.4 insertion cassette.

Figure 33:
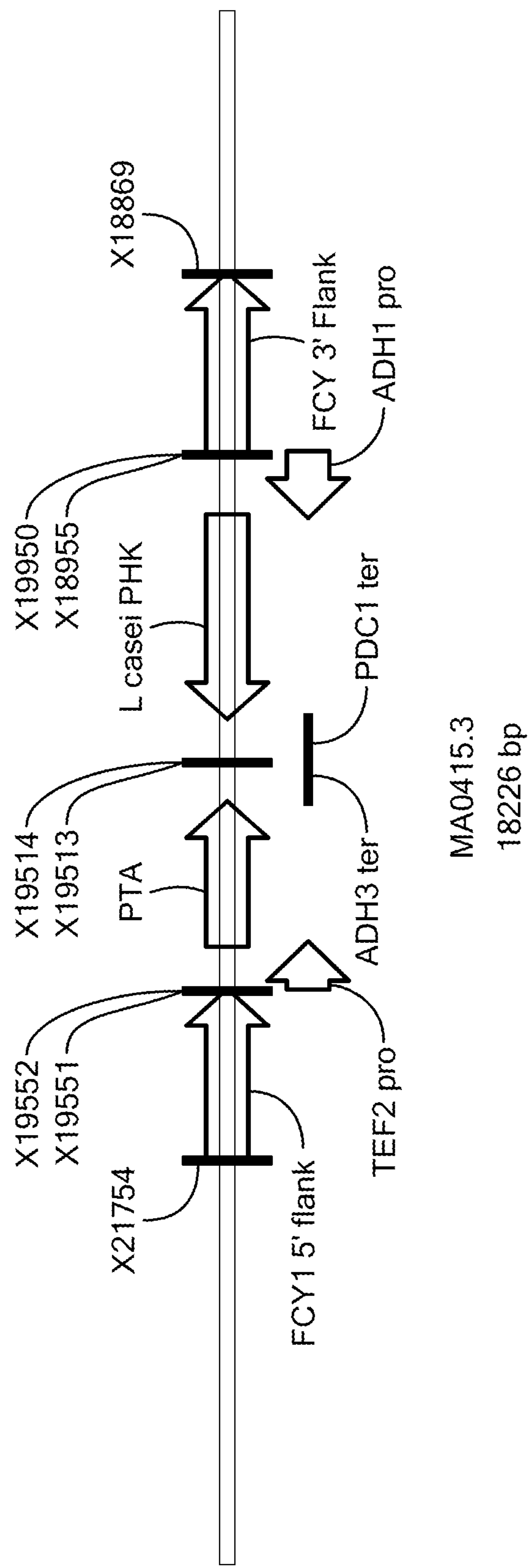

FIG. 33 depicts a schematic diagram of the MA0415.3 insertion cassette.

Figure 34:
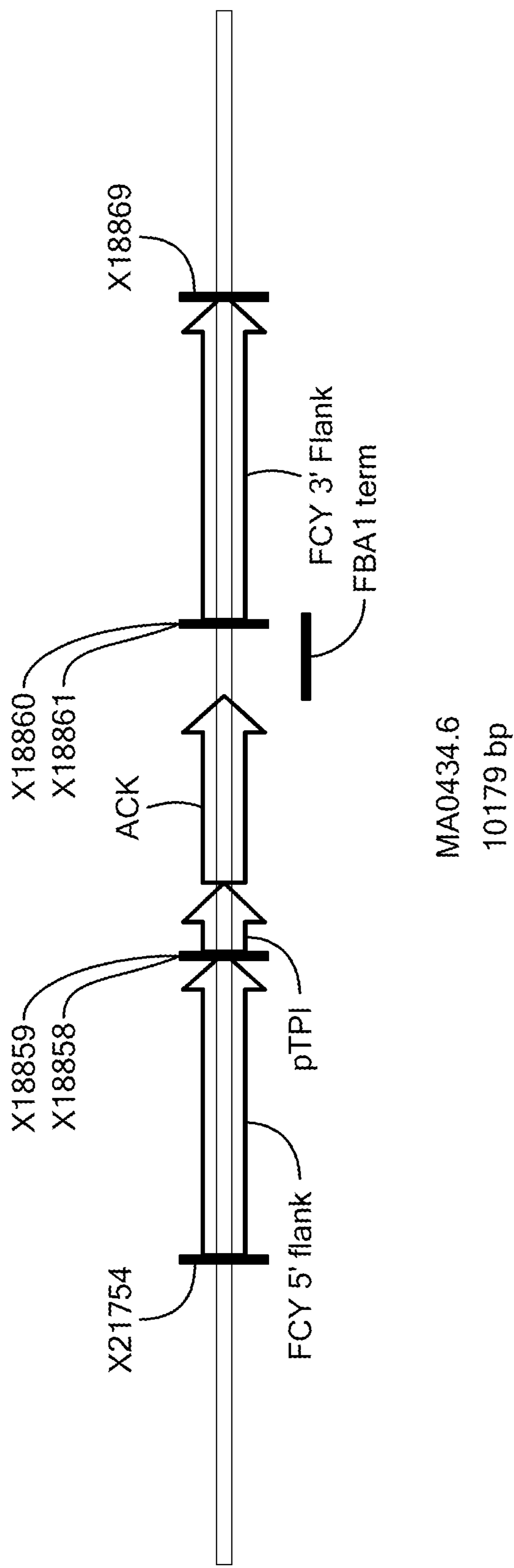

FIG. 34 depicts a schematic diagram of the MA0434.6 insertion cassette.

DETAILED DESCRIPTION OF THE INVENTION

Definitions

Unless defined otherwise, all technical and scientific terms used herein have the same meaning as commonly understood to one of ordinary skill in the art of microbial metabolic engineering. Although methods and materials similar or equivalent to those described herein can be used in the practice of the disclosed methods and compositions, exemplary methods, devices and materials are described herein.

The embodiments described, and references in the specification to "one embodiment", "an embodiment", "an example embodiment", etc., indicate that the embodiments described can include a particular feature, structure, or characteristic, but every embodiment does not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description of "a" or "an" item herein may refer to a single item or multiple items. It is understood that wherever embodiments are described herein with the language "comprising," otherwise analogous embodiments described in teams of "consisting of" and/or "consisting essentially of" are also provided. Thus, for example, reference to "a polynucleotide" includes a plurality of such polynucleotides and reference to "the microorganism" includes reference to one or more microorganisms, and so forth.

The term "heterologous" is used in reference to a polynucleotide or a gene not normally found in the host organism. "Heterologous" includes up-regulated or down-regulated endogenous genes. "Heterologous" also includes a native coding region, or portion thereof, that is reintroduced into the source organism in a form that is different from the corresponding native gene, e.g., not in its natural location in the organism's genome. "Heterologous" also includes any gene that has been modified and placed into an organism. A heterologous gene may include a native coding region that is a portion of a chimeric gene including a non-native regulatory region that is reintroduced into the native host or modifications to the native regulatory sequences that affect the expression level of the gene. Foreign genes can comprise native genes inserted into a non-native organism, or chimeric genes. A heterologous polynucleotide, gene, polypeptide, or an enzyme may be derived or isolated from any source, e.g., eukaryotes, prokaryotes, viruses, or synthetic polynucleotide fragments, and includes up-regulated endogenous genes.

The terms "gene(s)" or "polynucleotide" or "nucleic acid" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. Also, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA or RNA. The term "gene" is also intended to cover multiple copies of a particular gene, e.g., all of the DNA sequences in a cell encoding a particular gene product.

The term "expression" is intended to include the expression of a gene at least at the level of mRNA production, generally subsequently translated into a protein product.

As used herein, an "expression vector" is a vector capable of directing the expression of genes to which it is operably linked.

In some embodiments, the microorganisms contain enzymes involved in cellulose digestion, metabolism and/or hydrolysis. A "cellulolytic enzyme" can be any enzyme involved in cellulose digestion, metabolism, and/or hydrolysis. The term "cellulase" refers to a class of enzymes produced chiefly by fungi, bacteria, and protozoans that catalyze cellulolysis (i.e. the hydrolysis) of cellulose. However, there are also cellulases produced by other types of organisms such as plants and animals. Several different kinds of cellulases are known, which differ structurally and mechanistically. There are general types of cellulases based on the type of reaction catalyzed: endocellulase breaks internal bonds to disrupt the crystalline structure of cellulose and expose individual cellulose polysaccharide chains; exocellulase cleaves 2-4 units from the ends of the exposed chains produced by endocellulase, resulting in the tetrasaccharides or disaccharide such as cellobiose. There are two main types of exocellulases (or cellobiohydrolases, abbreviated CBH)—one type working processively from the reducing end, and one type working processively from the non-reducing end of cellulose; cellobiase or beta-glucosidase hydrolyses the exocellulase product into individual monosaccharides; oxidative cellulases that depolymerize cellulose by radical reactions, as for instance cellobiose dehydrogenase (acceptor); cellulose phosphorylases that depolymerize cellulose using phosphates instead of water. In the most familiar case of cellulase activity, the enzyme complex breaks down cellulose to beta-glucose. A "cellulase" can be any enzyme involved in cellulose digestion, metabolism and/or hydrolysis, including, for example, an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglueanase, endoxylanase, glucuronidase, acetylxylanesterase, arabinofuranohydrolase, swollenin, glucuronyl esterase, expansin, pectinase, and feruoyl esterase protein.

A "plasmid" or "vector" refers to an extrachromosomal element often carrying one or more genes, and is usually in the form of a circular double-stranded DNA molecule. Plasmids and vectors may also contain additional genetic elements such as autonomously replicating sequences, genome integrating sequences, phage or nucleotide sequences. They may also be linear, circular, or supercoiled, of a single- or double-stranded DNA or RNA, derived from any source. Plasmids and vectors may be constructed by known techniques in which a number of nucleotide sequences have been joined or recombined into a unique construction. Plasmids and vectors generally also include a promoter fragment and DNA sequence for a selected gene product along with appropriate 3' untranslated sequence. Generally, the plasmids of the present invention are stable and self-replicating.

As used herein, the term "anaerobic" refers to an organism, biochemical reaction or process that is active or occurs under conditions of an absence of gaseous $O_2$.

"Anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of fermentation until oxygen is unavailable to the microorganism as a terminal electron acceptor.

"Aerobic metabolism" refers to a biochemical process in which oxygen is used as a terminal electron acceptor to convert energy, typically in the form of ATP, from carbohydrates. Aerobic metabolism typically occurs, for example, via the electron transport chain in mitochondria in eukaryotes, wherein a single glucose molecule is metabolized completely into carbon dioxide in the presence of oxygen.

In contrast, "anaerobic metabolism" refers to a biochemical process in which oxygen is not the final acceptor of electrons generated. Anaerobic metabolism can be divided into anaerobic respiration, in which compounds other than oxygen serve as the terminal electron acceptor, and substrate level phosphorylation, in which no exogenous electron acceptor is used and products of an intermediate oxidation state are generated via a "fermentative pathway."

In "fermentative pathways", the amount of NAD(P)H generated by glycolysis is balanced by the consumption of the same amount of NAD(P)H in subsequent steps. For example, in one of the fermentative pathways of certain yeast strains, NAD(P)H generated through glycolysis donates its electrons to acetaldehyde, yielding ethanol. Fermentative pathways are usually active under anaerobic conditions but may also occur under aerobic conditions, under conditions where NADH is not fully oxidized via the respiratory chain.

As used herein, the term "end-product" refers to a chemical compound that is not or cannot be used by a cell, and so is excreted or allowed to diffuse into the extracellular environment. Common examples of end-products from anaerobic fermentation include, but are not limited to, ethanol, acetic acid, formic acid, lactic acid, hydrogen and carbon dioxide.

As used herein, "cofactors" are compounds involved in biochemical reactions that are recycled within the cells and remain at approximately steady state levels. Common examples of cofactors involved in anaerobic fermentation include, but are not limited to, $NAD^+$ and $NADP^+$. In metabolism, a cofactor can act in oxidation-reduction reactions to accept or donate electrons. When organic compounds are broken down by oxidation in metabolism, their energy can be transferred to $NAD^+$ by its reduction to NADH, to $NADP^+$ by its reduction to NADPH, or to another cofactor, $FAD^+$, by its reduction to $FADH_2$. The reduced cofactors can then be used as a substrate for a reductase.

As used herein, a "pathway" is a group of biochemical reactions that together can convert one compound into another compound in a step-wise process. A product of the first step in a pathway may be a substrate for the second step, and a product of the second step may be a substrate for the third, and so on. Pathways of the present invention include, but arc not limited to, the pyruvate metabolism pathway the lactate production pathway, the ethanol production pathway, and the glycerol-production pathway.

The term "recombination" or "recombinant" refers to the physical exchange of DNA between two identical (homologous), or nearly identical, DNA molecules. Recombination can be used for targeted gene deletion or to modify the sequence of a gene. The term "recombinant microorganism" and "recombinant host cell" are used interchangeably herein and refer to microorganisms that have been genetically modified to express or over-express endogenous polynucleotides, or to express heterologous polynucleotides, such as those included in a vector, or which have a modification in expression of an endogenous gene.

By "expression modification" it is meant that the expression of the gene, or level of a RNA molecule or equivalent RNA molecules encoding one or more polypeptides or polypeptide subunits, or activity of one or more polypeptides or polypeptide subunits is up regulated or down-regulated, such that expression, level, or activity, is greater than or less than that observed in the absence of the modification.

In one aspect of the invention, genes or particular polynucleotide sequences are partially, substantially, or completely deleted, silenced, inactivated, or down-regulated in order to inactivate the enzymatic activity they encode. Complete deletions provide maximum stability because there is no opportunity for a reverse mutation to restore function. Alternatively, genes can be partially, substantially, or completely deleted, silenced, inactivated, or down-regulated by insertion, deletion, removal or substitution of nucleic acid sequences that disrupt the function and/or expression of the gene.

As used herein, the term "down-regulate" includes the deletion or mutation of a genetic sequence, or insertion of a disrupting genetic element, coding or non-coding, such that the production of a gene product is lessened by the deletion, mutation, or insertion. It includes a decrease in the expression level (i.e., molecular quantity) of a mRNA or protein. "Delete" or "deletion" as used herein refers to a removal of a genetic element such that a corresponding gene is completely prevented from being expressed. In some embodiments, deletion refers to a complete gene deletion. Down-regulation can also occur by causing the repression of genetic elements by chemical or other environmental means, for example by engineering a chemically-responsive promoter element (or other type of conditional promoter) to control the expression of a desired gene product. Down-regulation can also occur through use of a weak promoter.

As used herein, the term "up-regulate" includes the insertion, reintroduction, mutation, or increased expression of a genetic sequence, such that the production of a gene product is increased by the insertion, reintroduction, or mutation. "Insert" or "insertion" as used herein refers to an introduction of a genetic element such that a corresponding gene is expressed. Up-regulation can also occur by causing the increased expression of genetic elements through an alteration of the associated regulatory sequence.

As used herein, the term "glycerol-production pathway" refers to the collection of biochemical pathways that produce glycerol from DHAP. Components of the pathway consist of all substrates, cofactors, byproducts, intermediates, end-products, and enzymes in the pathway.

As used herein, the term "ethanol production pathway" refers the collection of biochemical pathways that produce ethanol from pyruvate. Components of the pathway consist of all substrates, cofactors, byproducts, intermediates, end-products, and enzymes in the pathway.

As used herein, the term "acetyl-CoA production pathway" refers to the collection of biochemical pathways that produce acetyl-CoA from acetyl-phosphate. Components of the pathway consist of all substrates, cofactors, byproducts, intermediates, end-products, and enzymes in the pathway.

As used herein, the term "pyruvate metabolism pathway" refers to the collection of biochemical pathways that convert pyruvate into any product, including, but not limited to, ethanol, lactic acid, acetic acid and formate. It also includes the collection of pathways that result in the production of pyruvate, such as glycolysis. Components of the pathway consist of all substrates, cofactors, byproducts, intermediates, end-products, and enzymes in the pathway.

As used herein, the term "glycolysis" or "glycolytic pathway" refers to the canonical pathway of basic metabolism in which a sugar such as glucose is broken down into more oxidized products, converting energy and compounds required for cell growth. Components of the pathway consist of all substrates, cofactors, byproducts, intermediates end-products, and enzymes in the pathway.

Figure 1:
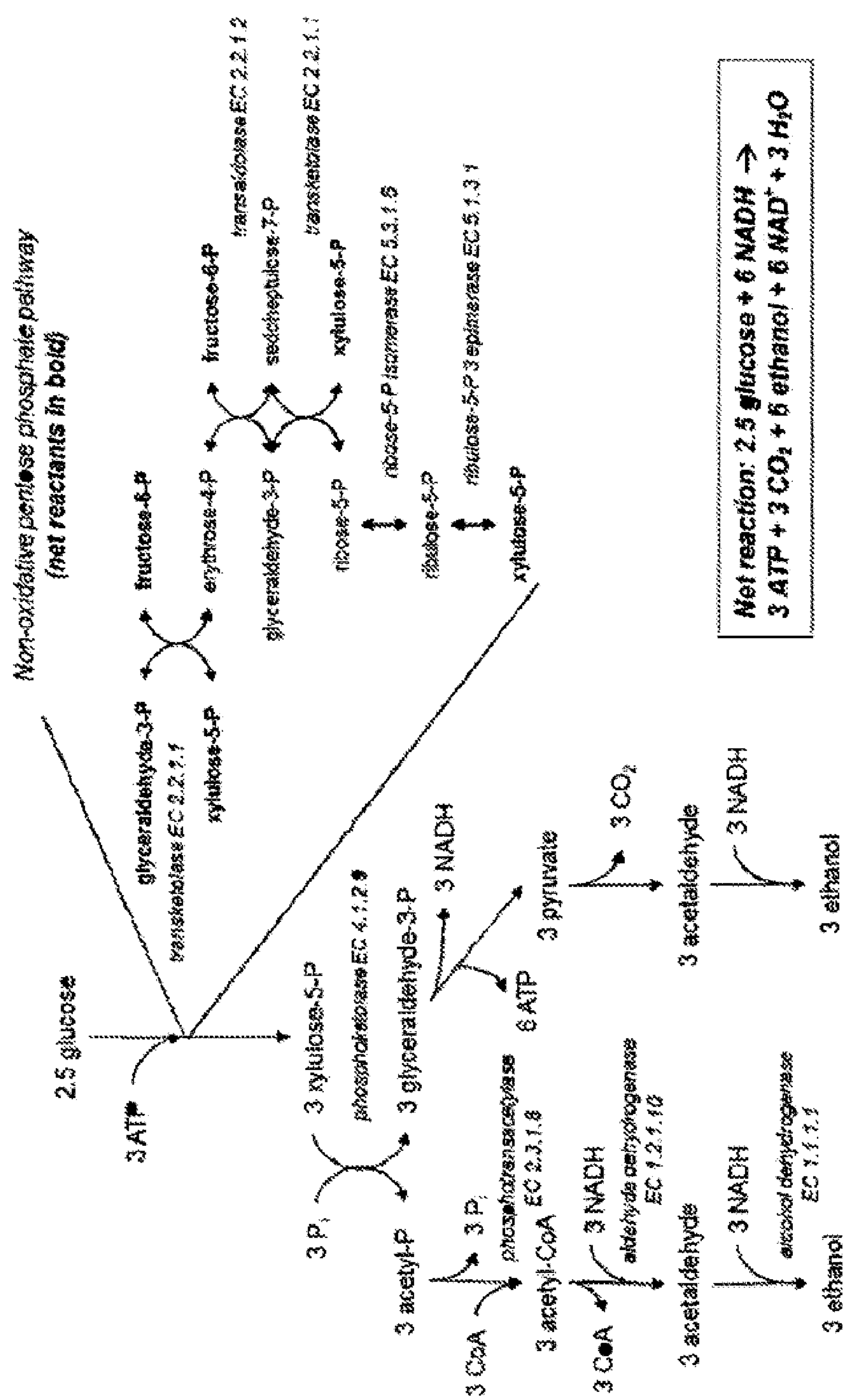
FIG. 1 depicts a simplified metabolic pathway from glucose to ethanol utilizing single-specificity phosphoketolase. The names of enzymes catalyzing steps applicable to the invention are shown in italics.
Figure 2:
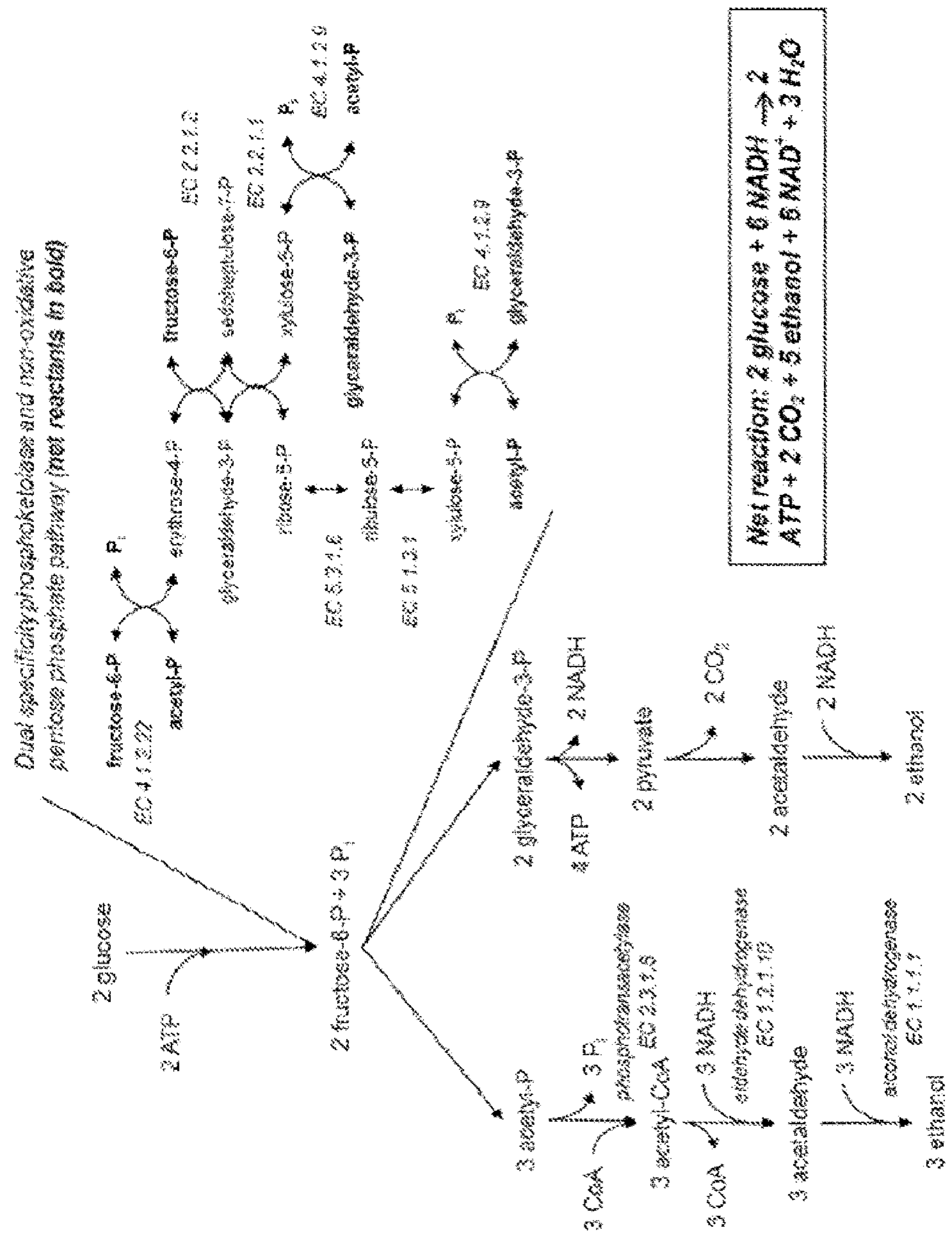
FIG. 2 depicts a simplified metabolic pathway from glucose to ethanol utilizing dual-specificity phosphoketolase. The names of enzymes catalyzing steps applicable to the invention are shown in italics.
Figure 3:
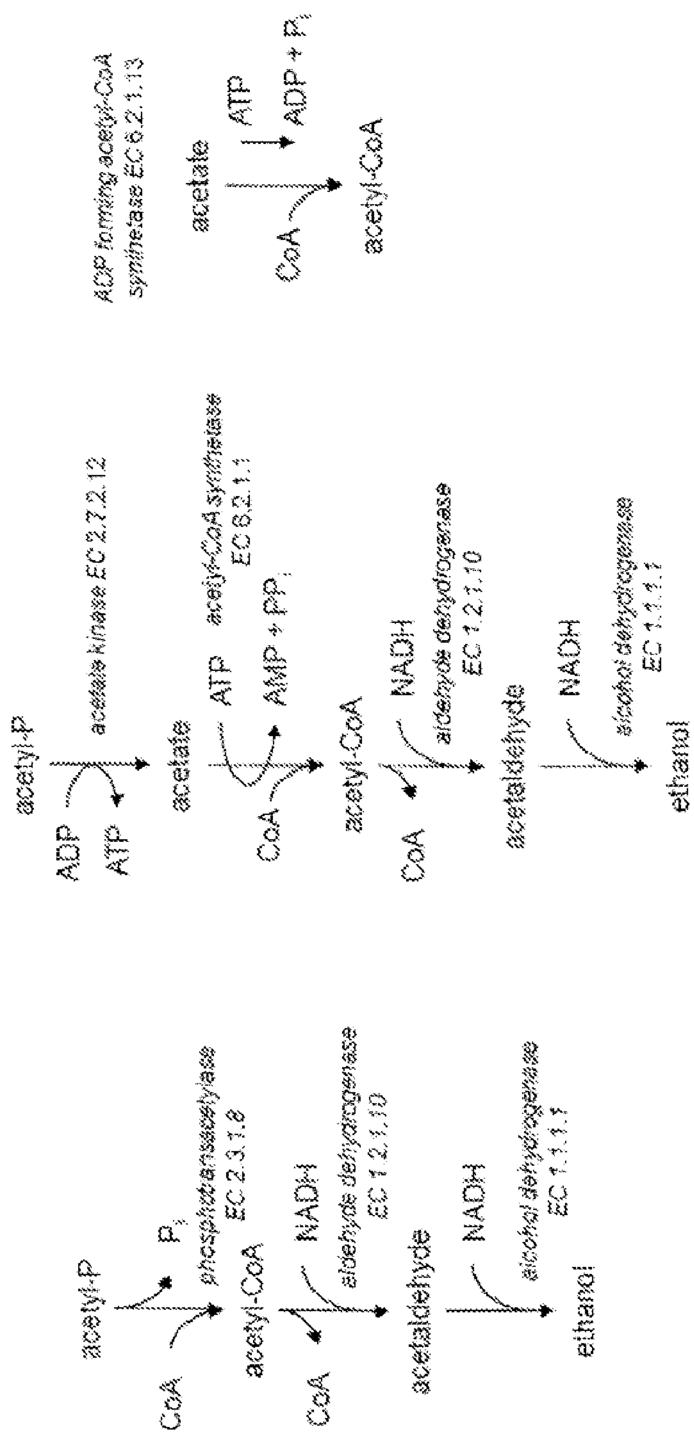
FIG. 3 depicts a simplified metabolic pathway from glucose to ethanol that does not utilize phosphoketolase. The names of enzymes catalyzing steps applicable to the invention are shown in italics.
Figure 4:
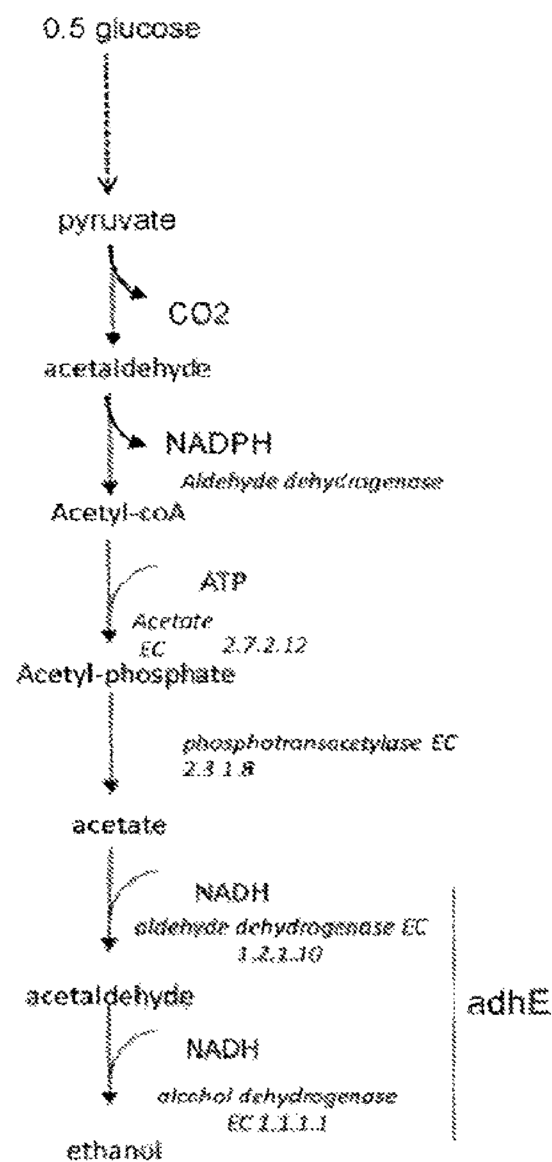
FIG. 4 depicts alternative conversions of acetyl-phosphate ("Acetyl-P") to ethanol.
Figure 5:
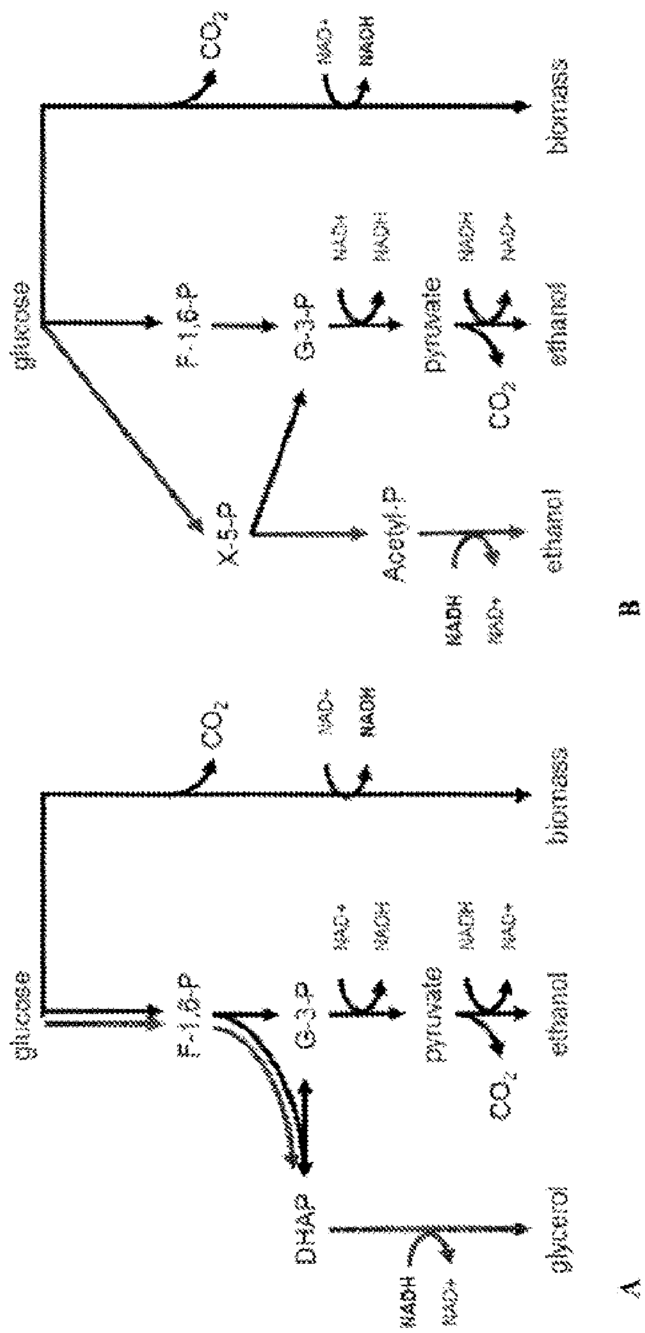
FIG. 5 depicts (A) simplified carbon and redox pathways utilized by wildtype *S. cerevisiae* during anaerobic growth. Ethanol formation is redox neutral while cell biomass formation generates net NADH, which is balanced by glycerol formation; and (B) *S. cerevisiae* engineered with the PHK-PTA-ADHE pathway balances NADH generated during cell biomass formation with production of ethanol.
Figure 6:
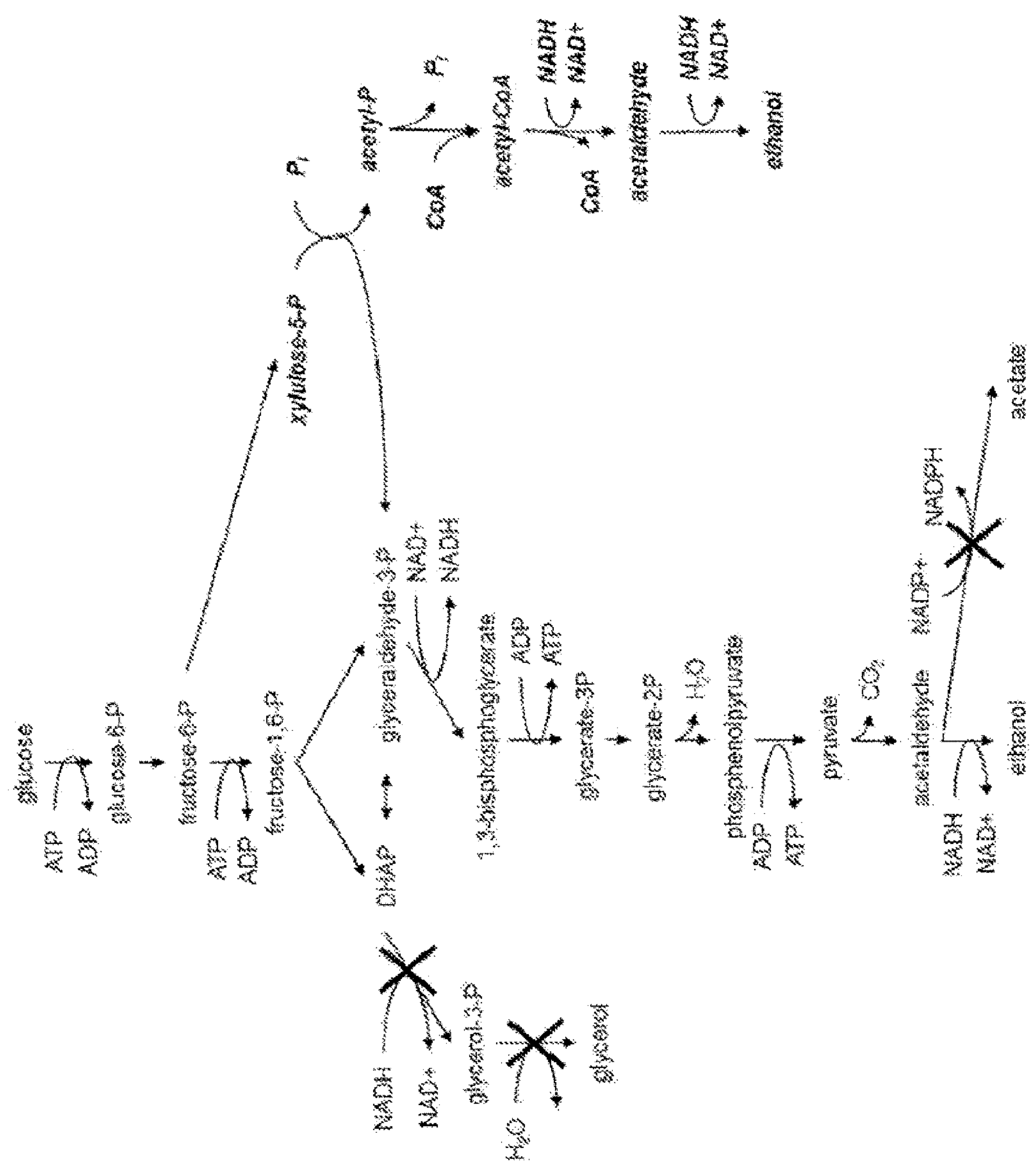
FIG. 6 depicts mechanisms by which glycerol formation could be deleted or down-regulated in the context of the overall metabolic pathway.
Figure 7:
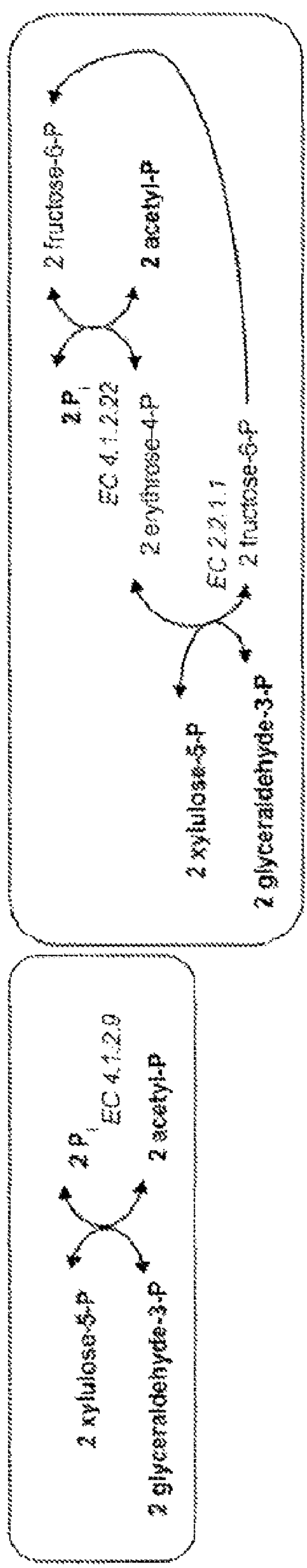
FIG. 7 depicts equivalent metabolic interconversions using single specificity and dual-specificity phosphoketolase.

As used herein, the term "phosphoketolase", "single-specificity phosphoketolase" or "dual-specificity phosphoketolase" is intended to include the enzymes that catalyze the conversion of D-xylulose 5-phosphate to D-glyceraldehyde 3-phosphate. Dual specificity phosphoketolase additionally includes the enzymes that catalyze the conversion of D-fructose 6-phosphate to D-erythrose 4-phosphate. Phosphoketolase, single-specificity phosphoketolase and dual-specificity phosphoketolase are referred to collectively as "PHKs" or "phosphoketolase" (FIG. 7). PHKs include those enzymes that correspond to Enzyme Commission Number (EC) 4.1.2.9 and 4.1.2.22. In some embodiments, PHK is from *A. niger* (SEQ ID NOs: 3 and 13), *N. crassa* (SEQ ID NOs: 4 and 14), *L. casei* PHK (SEQ ID NOs: 5 and 11), *L. plantarum* PHK1 (SEQ ID NOs: 7 and 9), *L. plantarum* PHK2 (SEQ ID NOs: 6 and 15), *B. adolescentis* (SEQ ID NOs: 8 and 12), *B. bifidum* (SEQ ID NOs: 61 and 62), *B. gallicum* (SEQ ID NOs: 63 and 64), *B. animalis* (SEQ ID NOs: 65 and 66), *L. pentosum* (SEQ ID NOs: 67 and 68), *L. acidophilus* (SEQ ID NOs: 69 and 70), *P. chrysogenum* (SEQ ID NOs: 71 and 72), *A. nidulans* (SEQ ID NOs: 73 and 74), *A. clavatus* (SEQ ID NOs: 77 and 78), *L. mesenteroides* (SEQ ID NOs: 93 and 94), or *O. oenii* (SEQ ID NOs: 101 and 102).

As used herein, the term "alcohol dehydrogenase" or "ADH" is intended to include the enzymes that catalyze the conversion of ethanol into acetylaldehyde. Very commonly, the same enzyme catalyzes the reverse reaction from acetaldehyde to ethanol, which is the direction more relevant to fermentation. Alcohol dehydrogenase includes those enzymes that correspond to EC 1.1.1.1 and 1.1.1.2 and exemplified by the enzymes disclosed in GenBank Accession No. U49975.

As used herein, the term "aldehyde dehydrogenase", "ALD" or "ALDH" is intended to include the enzymes that catalyze the oxidation of aldehydes. Aldehyde dehydrogenase enzymes include "acetaldehyde dehydrogenase", which catalyzes the conversion of acetaldehyde into acetyl-CoA. Very commonly, the same enzyme catalyzes the reverse reaction from acetyl-CoA to acetaldehyde, which is the direction more relevant to fermentation. Aldehyde dehydrogenase includes those enzymes that correspond to EC 1.2.1.3, 1.2.1.4 and 1.2.1.10. In some embodiments, acetaldehyde dehydrogenase is from *S. cerevisiae* (ALD2: SEQ ID NO: 17 and 18; ALD3: SEQ ID NO: 19 and 20; ALD4: SEQ ID NO: 21 and 22; ALD5: SEQ ID NO: 23 and 24; or ALD6 SEQ ID NO: 25 and 26).

As used herein, the term "phosphotransacetylase" or "PTA" is intended to include the enzymes capable of converting acetyl-CoA to acctylphosphate. PTA includes those enzymes that correspond to EC 2.3.1.8. In some embodiments, PTA is from *B. adolescentis* (SEQ ID NOs: 1 and 10), *C. cellulolyticum* (SEQ ID NOs: 79 and 80), *C. phytofermentans* (SEQ ID NOs: 81 and 82), *B. bifidum* (SEQ ID NOs: 83 and 84), *B. animalis* (SEQ ID NOs: 85 and 86), *L. mesenteroides* (SEQ ID NOs: 95 and 96), or *O. oenii* (SEQ ID NOs: 103 and 34).

As used herein, the term "acetate kinase" or "ACK" is intended to include the enzymes capable of converting acetylphosphate to acetate. ACK includes those enzymes that correspond to EC 2.7.2.12. In some embodiments, ACK is from *B. adolescentis* (SEQ ID NOs: 2 and 16), *C. cellulolyticum* (SEQ ID NOs: 87 and 88), *C. phytofermentans* (SEQ ID NOs: 75 and 76), *L. mesenteroides* (SEQ ID NOs: 91 and 92), or *O. oenii* (SEQ ID NOs: 99 and 100).

As used herein, the term "glycerol-3-phosphate dehydrogenase" or "GPD" is intended to include those enzymes capable of converting dihydroxyacetone phosphate to glycerol-3-phosphate. GPD includes those enzymes that correspond to EC 1.1.1.8. In some embodiments, the GPD is GPD1 and/or GPD2 from *S. cerevisiae* (GDP1: SEQ ID NO: 27 and 28, GDP2: SEQ ID NO: 29 and 30).

As used herein, the term "glycerol-3-phosphate phosphatase" is intended to include those enzymes capable of converting glycerol-1-phosphate to glycerol. Glycerol-3-phosphate is intended to include those enzymes that correspond to EC 3.1.3.21.

As used herein, the term "formate dehydrogenase" or "FDH" is intended to include those enzymes capable of converting formate to bicarbonate (carbon dioxide). Formate dehydrogenase includes those enzymes that correspond to EC 1.2.1.43 and EC 1.2.1.2. In some embodiments, the FDH is from *S. cerevisiae* (FDH1: SEQ ID NO: 31, and 32, FDH2: SEQ ID NO: 33).

As used herein, the term "transaldolase" is intended to include those enzymes capable of converting glyceraldehyde-3-phosphate to fructose-6-phosphate. Transaldolase is intended to include those enzymes that correspond to EC 2.2.1.2. In some embodiments, the transaldolase is from *S. cerevisiae* (TAL1: SEQ ID NO: 35 and 36).

As used herein, the term "transketolase" is intended to include those enzymes capable of converting sedoheptulose-7-P and glyceraldehyde-3-P to D-ribose-5-P and D-xylulose-5-P and those enzymes capable of converting fructose 6-phosphate and glyceraldehyde-3-P to D-xylulose-5-P and aldose erythrose-4-phosphate. Transketolase is intended to include those enzymes that correspond to EC 2.2.1.1. In some embodiments, the transketolase is from *S. cerevisiae* (TKL1: SEQ ID NO: 37 and 38).

As used herein, the term "ribose-5-P isomerase" or "ribose-5-phosphate isomerase" is intended to include those enzymes capable of converting ribose-5-phosphate to ribulose-5-phosphate. Ribose-5-P isomerase is intended to include those enzymes that correspond to EC 5.3.1.6. In some embodiments, the ribose-5-P isomerase is from *S. cerevisiae* (RKI1: SEQ ID NO: 39 and 40).

As used herein, the term "ribulose-5-P 3 epimerase", "ribulose-5-phosphate 3 epimerase" or "ribulose-phosphate 3-epimerase" is intended to include those enzymes capable of converting D-ribulose 5-phosphate to D-xylulose 5-phosphate. Ribulose-5-P 3 epimerase is intended to include those enzymes that correspond to EC 5.1.3.1. In some embodiments, the ribulose-5-P 3 epimerase is from *S. cerevisiae* (RPE1: SEQ ID NO: 41 and 42).

As used herein, the term "pyruvate decarboxylase" or "PDC" is intended to include those enzymes capable of converting pyruvic acid to acetaldehyde. PDC is intended to include those enzymes that correspond to EC 4.1.1.1.

As used herein, the term "bifunctional" is intended to include enzymes that catalyze more than one biochemical reaction step. A specific example of a bifunctional enzyme used herein is an enzyme (adhE) that catalyzes both the alcohol dehydrogenase and acetaldehyde dehydrogenase reactions, and includes those enzymes that correspond to EC 1.2.1.10 and 1.1.1.1. In some embodiments, the bifunctional acetaldehyde-alcohol dehydrogenase is from *B. adolescentis* (adhE: SEQ ID NO: 43 and 44). In some embodiments, the bifunctional enzyme is a NADPH specific bifunctional acetaldehyde-alcohol dehydrogenase, and includes those enzymes that correspond to EC 1.2.1.10 and 1.1.1.2. In some embodiments, the NADPH specific bifunctional acetaldehyde-alcohol dehydrogenase is from *L. mesenteroides* (SEQ ID NO: 89 and 90) or *Oenococcus oenii* (SEQ ID NO: 97 and 98).

As used herein, the term "pyruvate formate lyase" or "PFL" is intended to include the enzymes capable of converting pyruvate to formate and acetyl-CoA. PFL includes those enzymes that correspond to EC 2.3.1.54 and exemplified by SEQ ID NO: 47 and SEQ ID NO: 48.

As used herein, the term "PFL-activating enzymes" is intended to include those enzymes capable of aiding in the activation of PFL. PFL-activating enzymes include those enzymes that correspond to EC 1.97.1.4 and exemplified by SEQ ID NO: 45 and SEQ ID NO: 46.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a product in a fermentation process. A feedstock can contain nutrients other than a carbon source.

Biomass can include any type of biomass known in the art or described herein. The terms "lignocellulosic material," "lignocellulosic substrate" and "cellulosic biomass" mean any type of carbon containing feed stock including woody biomass, such as recycled wood pulp fiber, sawdust, hardwood, softwood, grasses, sugar-processing residues, agricultural wastes, such as, but not limited to, rice straw, rice hulls, barley straw, corn cobs, cereal straw, wheat straw, canola straw, oat straw, oat hulls, corn fiber, stover, succulents, agave, or any combination thereof.

The term "yield" is defined as the amount of product obtained per unit weight of raw material and may be expressed as gram product per gram substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to ethanol is 0.51 g EtOH per 1 g glucose. As such, a yield of 4.8 g ethanol from 10 g of glucose would be expressed as 94% of theoretical or 94% theoretical yield.

The term "titer" is defined as the strength of a solution or the concentration of a substance in solution. For example, the titer of a product in a fermentation broth is described as gram of product in solution per liter of fermentation broth (g/L) or as g/kg broth.

As used herein, the term "flux" is the rate of flow of molecules through a metabolic pathway, akin to the flow of material in a process.

"Bacteria", or "eubacteria", refers to a domain of prokaryotic organisms. Bacteria include gram-positive (gram+) bacteria and gram-negative (gram−) bacteria.

"Yeast" refers to a domain of eukaryotic organisms that are unicellular fungi.

The terms "derivative" and "analog" refer to a polypeptide differing from the enzymes of the invention, but retaining essential properties thereof. Generally, derivatives and analogs are overall closely similar, and, in many regions, identical to the enzymes of the invention. The terms "derived from", "derivative" and "analog" when referring to enzymes of the invention include any polypeptides which retain at least some of the activity of the corresponding native polypeptide or the activity of its catalytic domain.

Derivatives of enzymes disclosed herein are polypeptides which may have been altered so as to exhibit features not found on the native polypeptide. Derivatives can be covalently modified by substitution (e.g. amino acid substitution), chemical, enzymatic, or other appropriate means with a moiety other than a naturally occurring amino acid (e.g., a detectable moiety such as an enzyme or radioisotope). Examples of derivatives include fusion proteins, or proteins which are based on a naturally occurring protein sequence, but which have been altered. For example, proteins can be designed by knowledge of a particular amino acid sequence, and/or a particular secondary, tertiary, and quaternary structure. Derivatives include proteins that are modified based on the knowledge of a previous sequence, natural or synthetic, which is then optionally modified, often, but not necessarily to confer some improved function. These sequences, or proteins, are then said to be derived from a particular protein or amino acid sequence. In some embodiments of the invention, a derivative must retain at least about 50% identity, at least about 60% identity, at least about 70% identity, at least about 80% identity, at least about 90% identity, at least about 95% identity, at least about 97% identity, or at least about 99% identity to the sequence the derivative is "derived from." In some embodiments of the invention, an enzyme is said to be derived from an enzyme naturally found in a particular species if, using molecular genetic techniques, the DNA sequence for part or all of the enzyme is amplified and placed into a new host cell.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to 75% identical to the amino acid sequences disclosed herein, at least about 80%, at least about 85%, or at least about 90% identical to the amino acid sequences disclosed herein, or at least about 95%, at least about 96%, at least about 97%, at least about 98%, at least about 99%, or at least about 100% identical to the amino acid sequences disclosed herein. Suitable nucleic acid fragments are at least about 70%, at least about 75%, or at least about 80% identical to the nucleic acid sequences disclosed herein, at least about 80%, at least about 85%, or at least about 90% identical to the nucleic acid sequences disclosed herein, or at least about 95%, at least about 96%, at least about 97%, at least about 98%, at least about 99%, or at least about 100% identical to the nucleic acid sequences disclosed herein. Suitable nucleic acid fragments not only have the above identities/similarities but typically encode a polypeptide having at least about 50 amino acids, at least about 100 amino acids, at least about 150 amino acids, at least about 200 amino acids, or at least about 250 amino acids.

Codon Optimization

In some embodiments of the present invention, exogenous genes may be codon-optimized in order to express the polypeptide they encode most efficiently in the host cell. Methods of codon optimization are well known in the art. (See, e.g. Welch et al. "Designing genes for successful protein expression." *Methods Enzymol.* 2011. 498:43-66.)

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The Codon Adaptation Index is described in more detail in Sharp et al., "The Codon Adaptation Index: a Measure of Directional Synonymous Codon Usage Bias, and Its Potential Applications." *Nucleic Acids Research* 1987. 15: 1281-1295, which is incorporated by reference herein in its entirety.

A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can effect transcription negatively. Therefore, it can be useful to remove a run by, for example, replacing at least one nucleotide in the run with another nucleotide. Furthermore, specific restriction enzyme sites may be removed for molecular cloning purposes by replacing at least one nucleotide in the restriction site with another nucleotide. Examples of such restriction enzyme sites include PacI, AscI, BamHI, BglII, EcoRI and XhoI. Additionally, the DNA sequence can be checked for direct repeats, inverted repeats and mirror repeats with lengths of about 5, 6, 7, 8, 9 or 10 bases or longer. Runs of "As" or "Ts", restriction sites and/or repeats can be modified by replacing at least one codon within the sequence with the "second best" codons, i.e., the codon that occurs at the second highest frequency for a particular amino acid within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six triplets each, whereas tryptophan and methionine are coded for by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Host Cells

In some embodiments of the invention, the host cell is a eukaryotic microorganism. In some embodiments, the host cell is a yeast. In some embodiments, the host cell is able to digest and ferment cellulose. In some embodiments, the host cell is from the genus *Saccharomyces*. In some embodiments, the host cell is *Saccharomyces cerevisiae*.

In some embodiments, the host cells of the invention are cultured at a temperature above about 20° C., above about 25° C., above about 27° C., above about 30° C., above about 33° C., above about 35° C., above about 37° C., above about 40° C., above about 43° C., above about 45° C., or above about 47° C.

In some embodiments, the host cells of the invention contain genetic constructs that lead to the down-regulation of one or more genes encoding a polypeptide at least about 80%, at least about 85%, at least about 90%, at least about 95%, at least about 96%, at least about 97%, at least about 98%, at least about 99%, or about 100% identical to one or more of the polypeptides encompassed by EC 1.1.1.8, 3.1.3.21, 1.2.1.43, 1.2.1.10 and/or EC 1.2.1.2.

In some embodiments, the host cells of the invention contain genetic constructs that lead to the expression or up-regulation of one or more genes encoding a polypeptide at least about 80%, at least about 85%, at least about 90%, at least about 95%, at least about 96%, at least about 97%, at least about 98%, at least about 99%, or about 100% identical to one or more of the polypeptides encoded by SEQ ID NOs: 9, 10, 11, 12, 13, 14, 15, 16, 18, 20, 22, 24, 26, 34, 36, 38, 40, 42, 44, 46, 48, 62, 64, 66, 68, 70, 72, 74, 76, 78, 80, 82, 84, 86, 88, 90, 92, 94, 96, 98, 100, or 102. In some embodiments, the host cells of the invention contain genetic constructs that leads to the expression or up-regulation of a polypeptide encoding the activity associated with EC Nos.: 4.1.2.9, 4.1.2.22, 2.3.1.8, 1.2.1.10, 1.2.1.3, 1.2.1.4, 1.1.1.1, 1.1.1.2, 2.7.2.12, 2.2.1.2, 2.2.1.1, 5.3.1.6, 5.1.3.1, 2.3.1.54, 1.97.1.4, 1.2.1.3, 1.2.1.4, or 4.1.1.1.

In some embodiments, PHK is up-regulated. In some embodiments, single-specificity phosphoketolase is up-regulated. In some embodiments, dual-specificity phosphoketolase is up-regulated. In some embodiments, the up-regulated PHK is from an enzyme that corresponds to an EC number selected from the group consisting of: EC 4.1.2.9 and 4.1.2.22. In some embodiments, the PHK is from *A. niger*. In some embodiments, the PHK is from *N. crassa*. In some embodiments, the PHK is from *L. casei*. In some embodiments, the PHK is from *L. plantarum*. In some embodiments, the PHK is from *B. adolescentis*. In some embodiments, the PHK is derived from a genus selected from the group consisting of *Aspergillus, Neurospora, Lactobacillus, Bifidobacterium*, and *Penicillium*. In some embodiments, the phosphoketolase corresponds to a polypeptide selected from a group consisting of SEQ ID NOs: 9, 11, 12, 13, 14, 15, 62, 64, 66, 68, 70, 72, 74, 78, 94, or 102.

In some embodiments, phosphotransacetylase is up-regulated. In some embodiments, the up-regulated phosphotransacetylase is from an enzyme that corresponds to EC 2.3.1.8. In some embodiments, the phosphotransacetylase is from *B. adolescentis*. In some embodiments, the phosphotransacetylase is derived from a genus selected from the group consisting of *Bifidobacterium, Lactobacillus*, or *Clostridium*. In some embodiments, the phosphotransacetylase corresponds to a polypeptide selected from a group consisting of SEQ ID NOs: 10, 34, 80, 82, 84, 86, or 94.

In some embodiments of the invention, acetate kinase is up-regulated. In some embodiments, the up-regulated acetate kinase is from an enzyme that corresponds to EC 2.7.2.12. In some embodiments, the acetate kinase is from *B. adolescentis*. In some embodiments, the acetate kinase is derived from a genus selected from the group consisting of *Bifidobacterium, Lactobacillus*, or *Clostridium*. In some embodiments, the acetate kinase corresponds to a polypeptide selected from a group consisting of SEQ ID NOs: 16, 88, 76, 92, or 100.

In some embodiments, bifunctional acetaldehyde-alcohol dehydrogenase is up-regulated. In some embodiments, the up-regulated bifunctional acetaldehyde-alcohol dehydrogenase is from an enzyme that corresponds to an EC number selected from the group consisting of: EC 1.2.1.0 and 1.1.1.1. In some embodiments, the bifunctional acetaldehyde-alcohol dehydrogenase is a NADPH dependent bifunctional acetaldehyde-alcohol dehydrogenase selected from a group of enzymes having the following Enzyme Commission Numbers: EC 1.2.1.10 and 1.1.1.2. In some embodiments, the bifunctional acetaldehyde-alcohol dehydrogenase corresponds to a polypeptide selected from the group consisting of SEQ ID NOs: 44, 90, and 98

In some embodiments, transaldolase is up-regulated. In some embodiments, the up-regulated transaldolase is from an enzyme that corresponds to EC 2.2.1.2. In some embodiments, the transaldolase is from *S. cerevisiae* and corresponds to a polypeptide encoded by SEQ ID NO: 36. In some embodiments, transketolase is up-regulated. In some embodiments, the up-regulated transketolase is from an enzyme that corresponds to EC 2.2.1.1. In some embodiments, the transketolase is from *S. cerevisiae* and corresponds to a polypeptide encoded by SEQ ID NO: 38. In some embodiments, ribose-5-P isomerase is up-regulated. In some embodiments, the up-regulated ribose-5-P isomerase is from an enzyme that corresponds to EC 5.3.1.6. In some embodiments, the ribose-5-P isomerase is from *S. cerevisiae* and corresponds to a polypeptide encoded by SEQ ID NO: 40. In some embodiments, ribulose-5-P epimerase is up-regulated. In some embodiments, the up-regulated ribulose-5-P epimerase is from an enzyme that corresponds to EC 5.1.3.1. In some embodiments, the ribulose-5-P 3-epimerase is from *S. cerevisiae* and corresponds to a polypeptide encoded by SEQ ID NO: 42. In some embodiments, pyruvate decarboxylase is up-regulated. In some embodiments, the up-regulated pyruvate decarboxylase is from an enzyme that corresponds to EC 4.1.1.1. In some embodiments, alcohol dehydrogenase is up-regulated. In some embodiments, the up-regulated alcohol dehydrogenase is from an enzyme that corresponds to EC 1.1.1.1 and 1.1.1.2. In some embodiments, pyruvate formate lyase is up-regulated. In some embodiments, the up-regulated pyruvate formate lyase is from an enzyme that corresponds to EC 2.3.1.54. In some embodiments, the pyruvate formate lyase corresponds to a polypeptide encoded by SEQ ID NO: 48. In some embodiments, pyruvate formate lyase activating enzyme is up-regulated. In some embodiments, the up-regulated pyruvate formate lyase activating enzyme is from an enzyme that corresponds to EC 1.97.1.4. In some embodiments, the pyruvate formate lyase activating enzyme corresponds to a polypeptide encoded by SEQ ID NO: 46.

In some embodiments, the host cells of the invention contain genetic constructs that lead to the expression or down-regulation of one or more genes encoding a polypeptide at least about 80%, at least about 85%, at least about 90%, at least about 95%, at least about 96%, at least about 97%, at least about 98%, at least about 99%, or about 100% identical to one or more of the polypeptides encoded by SEQ ID NOs: 18, 20, 22, 24, 26, 28, 30, 32 or the polynucleotide encoded by SEQ ID NO: 33. In some embodiments, the host cells of the invention contain genetic constructs that leads to the expression or down-regulation of a polypeptide encoding the activity associated with EC Nos.: 1.2.1.3, 1.2.1.4, 1.2.1.10, 1.1.1.8 and 3.1.3.21.

In some embodiments, GPD is down-regulated. In some embodiments, the down-regulated GPD is from an enzyme that corresponds to EC 1.1.1.8. In some embodiments gpd1 and gpd2 from *S. cerevisiae* are down-regulated. In some embodiments, the glycerol-3-phosphate dehydrogenase is selected from the group consisting of glycerol-3-phosphate dehydrogenase 1, glycerol-3-phosphate dehydrogenase 2, and combinations thereof. In some embodiments, the glycerol-3-phosphate dehydrogenase 1 is from *S. cerevisiae* and corresponds to a polypeptide encoded by SEQ ID NO: 28. In some embodiments, the glycerol-3-phosphate dehydrogenase 2 is from *S. cerevisiae* and corresponds to a polypeptide encoded by SEQ ID NO: 30. In some embodiments, formate dehydrogenase is down-regulated. In some embodiments, the down-regulated formate dehydrogenase corresponds to an EC number selected from the group consisting of: EC 1.2.1.43 and EC 1.2.1.2. In some embodiments, formate dehydrogenase from *S. cerevisiae* is down-regulated. In some embodiments, the formate dehydrogenase from *S. cerevisiae* corresponds to a polypeptide corresponding to SEQ ID NO: 32 or a polynucleotide corresponding to SEQ ID NO: 33. In some embodiments, glycerol-3-phosphate phosphatase is down-regulated. In some embodiments, the down-regulated glycerol-3-phosphate phosphatase corresponds to EC 3.1.3.21.

In some embodiments, aldehyde dehydrogenase is down-regulated. In some embodiments, aldehyde dehydrogenase is up-regulated. In some embodiments, the aldehyde dehydrogenase is an enzyme that corresponds to EC 1.2.1.10, EC 1.2.1.3, or EC 1.2.1.4. In some embodiments, the aldehyde dehydrogenase is acetaldehyde dehydrogenase. In some embodiments, the acetaldehyde dehydrogenase enzyme is selected from Ald2, Ald3, Ald4, Ald5, and Ald6 in *S. cerevisiae*. In some embodiments, the acetaldehyde dehydrogenase from *S. cerevisiae* corresponds to a polypeptide sequence selected from the group consisting of: SEQ ID NO: 18, SEQ ID NO: 20, SEQ ID NO: 22, SEQ ID NO: 24, and SEQ ID NO: 26.

In some embodiments, phosphoketolase, phosphotransacetylase and bifunctional acetaldehyde-alcohol dehydrogenase are up-regulated, and at least one glycerol-3-phosphate dehydrogenase enzyme is down-regulated.

In some embodiments, phosphotransacetylase, bifunctional acetaldehyde-alcohol dehydrogenase, and at least one aldehyde dehydrogenase are up-regulated. In some embodiments, phosphotransacetylase, bifunctional acetaldehyde-alcohol dehydrogenase, at least one aldehyde dehydrogenase are up-regulated, and at least one glycerol-3-phosphate dehydrogenase enzyme is down-regulated. In some embodiments, phosphotransacetylase, acetate kinase, bifunctional acetaldehyde-alcohol dehydrogenase, and at least one aldehyde dehydrogenase are up-regulated. In some embodiments, phosphotransacetylase, acetate kinase and bifunctional acetaldehyde-alcohol dehydrogenase are up-regulated, and at least one glycerol-3-phosphate dehydrogenase enzyme is down-regulated. In some embodiments, at least one aldehyde dehydrogenase enzyme is also down-regulated. In some embodiments, the aldehyde dehydrogenase is acetaldehyde dehydrogenase.

In some embodiments, phosphoketolase, phosphotransacetylase, bifunctional acetaldehyde-alcohol dehydrogenase, pyruvate formate lyase, and pyruvate formate lyase activating enzyme are up-regulated, and at least one glycerol-3-phosphate dehydrogenase enzyme is down-regulated.

In some embodiments, phosphoketolase, acetate kinase and bifunctional acetaldehyde-alcohol dehydrogenase are up-regulated, and at least one glycerol-3-phosphate dehydrogenase enzyme is down-regulated.

In some embodiments, phosphoketolase, acetate kinase, bifunctional acetaldehyde-alcohol dehydrogenase, pyruvate formate lyase, and pyruvate formate lyase activating enzyme are up-regulated, and at least one glycerol-3-phosphate dehydrogenase enzyme is down-regulated.

In some embodiments, gpd1, gpd2, fdh1, and/or fdh2 arc down-regulated. In some embodiments, gpd1, gpd2, fdh1 and fdh2 are down-regulated, and PHK, bifunctional acetaldehyde-alcohol dehydrogenase (AdhE), and PTA are up-regulated. In some embodiments, gpd1, gpd2, fdh1 and fdh2 are down-regulated, and *B. adolescentis* PHK, AdhE, and *B. adolescentis* PTA are up-regulated in *S. cerevisiae* cells. In some embodiments, gpd1, gpd2, fdh1 and fdh2 are down-regulated, and *L. plantarum* PHK1, AdhE, and *B. adolescentis* PTA are up-regulated in *S. cerevisiae* cells. In some embodiments, gpd1, gpd2, fdh1 and fdh2 are down-regulated, and *L. plantarum* PHK2, AdhE, *B. adolescentis* PTA are up-regulated in *S. cerevisiae* cells. In some embodiments, gpd1, gpd2, fdh1 and fdh2 are down-regulated, and *A. niger* PHK, AdhE, and *B. adolescentis* PTA are up-regulated in *S. cerevisiae* cells. In some embodiments, gpd1, gpd2, fdh1 and fdh2 are down-regulated, and *L. casei* PHK1, AdhE, and *B. adolescentis* PTA are up-regulated in *S. cerevisiae* cells. In some embodiments, gpd1, gpd2, fdh1 and fdh2 are down-regulated, and *L. casei* PHK2, AdhE, and *B. adolescentis* PTA are up-regulated in *S. cerevisiae* cells. In some embodiments, gpd1, gpd2, fdh1 and/or fdh2 are down-regulated, PHK, *B. adolescentis* AdhE, and *B. adolescentis* PTA are up-regulated in *S. cerevisiae* cells. In some embodiments, the up-regulated enzymes are integrated. In some embodiments, the up-regulated enzymes are expressed using an expression vector. In some embodiments, gpd1, gpd2, fdh1 and/or fdh2 are down-regulated, and *B. adolescentis* PHK, *B adolescentis* bifunctional acetaldehyde-alcohol dehydrogenase, *B adolescentis* PTA, *B. adolescentis* pyruvate formate lyase, and *B adolescentis* pyruvate formate lyase activating enzyme are up-regulated. In some embodiments, fcy is down-regulated.

In some embodiments, gpd1, gpd2, fdh1 and/or fdh2 are down-regulated, and PHK, bifunctional acetaldehyde-alcohol dehydrogenase (AdhE), ACK and PTA are up-regulated. In some embodiments, gpd1, gpd2, fdh1 and/or fdh2 are down-regulated, and *B. adolescentis* PHK, AdhE, *B. adolescentis* ACK, and *B. adolescentis* PTA are up-regulated in *S. cerevisiae* cells. In some embodiments, gpd1, gpd2, fdh1 and/or fdh2 are down-regulated, and *L. plantarum* PHK1, AdhE, *B. adolescentis* ACK and *B. adolescentis* PTA are up-regulated in *S. cerevisiae* cells. In some embodiments, gpd1, gpd2, fdh1 and/or fdh2 are down-regulated, and *L. plantarum* PHK2, AdhE, *B. adolescentis* ACK, and *B. adolescentis* PTA are up-regulated in *S. cerevisiae* cells. In some embodiments, gpd1, gpd2, fdh1 and/or fdh2 are down-regulated, and *A. niger* PHK, AdhE, *B. adolescentis* ACK and *B. adolescentis* PTA are up-regulated in *S. cerevisiae* cells. In some embodiments, gpd1, gpd2, fdh1 and/or fdh2 are down-regulated, and *L. casei* PHK1, AdhE, *B. adolescentis* ACK and *B. adolescentis* PTA are up-regulated in *S. cerevisiae* cells. In some embodiments, gpd1, gpd2, fdh1 and/or fdh2 are down-regulated, and *L. casei* PHK2, AdhE, *B. adolescentis* ACK, and *B. adolescentis* PTA are up-regulated in *S. cerevisiae* cells. In some embodiments, gpd1, gpd2, fdh1 and/or fdh2 are down-regulated, PHK, *B. adolescentis* AdhE, *B. adolescentis* PTA and *B. adolescentis* ACK are up-regulated in *S. cerevisiae* cells. In some embodiments, the up-regulated enzymes are integrated. In some embodiments, the up-regulated enzymes are expressed using an expression vector. In some embodiments, gpd1, gpd2, fdh1 and/or fdh2 are down-regulated, and *B. adolescentis* PHK, *B adolescentis* bifunctional acetaldehyde-alcohol dehydrogenase, *B. adolescentis* PTA, *B. adolescentis* ACK *B. adolescentis* pyruvate formate lyase, and *B adolescentis* pyruvate formate lyase activating enzyme are up-regulated.

In some embodiments, gpd1, gpd2, fdh1 and/or fdh2 are down-regulated, and bifunctional acetaldehyde-alcohol dehydrogenase (AdhE), ACK and PTA are up-regulated. In some embodiments, gpd1, gpd2, fdh1 and/or fdh2 are down-regulated, and AdhE, *B. adolescentis* ACK, and *B. adolescentis* PTA are up-regulated in *S. cerevisiae* cells. In some embodiments, the up-regulated enzymes are integrated. In some embodiments, the up-regulated enzymes are expressed using an expression vector. In some embodiments, gpd1, gpd2, fdh1 and/or fdh2 are down-regulated, *B. adolescentis* AdhE, *B. adolescentis* PTA and *B. adolescentis* ACK are up-regulated in *S. cerevisiae* cells. In some embodiments, gpd1, gpd2, fdh1 and/or fdh2 are down-regulated, and *B adolescentis* bifunctional acetaldehyde-alcohol dehydrogenase, *B. adolescentis* PTA, *B. adolescentis* ACK *B. adolescentis* pyruvate formate lyase, and *B adolescentis* pyruvate formate lyase activating enzyme are up-regulated. In some embodiments, *S. cerevisiae* ALD2, ALD3, ALD4, or combinations thereof are down-regulated and *S. cerevisiae* ALD6, ALD5, or combinations thereof are up-regulated.

In some embodiments, gpd1, gpd2, fdh1 and/or fdh2 are down-regulated, *B. adolescentis* AdhE, *B. adolescentis* PTA and *B. adolescentis* ACK are up-regulated in *S. cerevisiae* cells.

Ethanol Production

For a microorganism to produce ethanol most economically, it is desired to produce a high yield. In one embodiment, the only product produced is ethanol. Extra products lead to a reduction in product yield and an increase in capital and operating costs, particularly if the extra products have little or no value. Extra products also require additional capital and operating costs to separate these products from ethanol.

Ethanol production can be measured using any method known in the art. For example, the quantity of ethanol in fermentation samples can be assessed using HPLC analysis. Additionally, many ethanol assay kits are commercially available, for example, alcohol oxidase enzyme based assays. Methods of determining ethanol production are within the scope of those skilled in the art from the teachings herein.

In some embodiments of the invention where redirected carbon flux generates increased ethanol production, the ethanol output can be improved by growth-coupled selection. For example, continuous culture or serial dilution cultures can be performed to select for cells that grow faster and/or produce ethanol (or any desired product) more efficiently on a desired feedstock.

One embodiment of the present invention relates to a method of producing ethanol using a microorganism described herein wherein said microorganism is cultured in the presence of a carbon containing feedstock for sufficient time to produce ethanol and, optionally, extracting the ethanol.

Ethanol may be extracted by methods known in the art. (See, e.g., U.S. Appl. Pub. No. 2011/0171709, which is incorporated herein by reference.)

Another embodiment of the present invention relates to a method of producing ethanol using a co-culture composed of at least two microorganisms in which at least one of the organisms is an organism described herein, and at least one of the organisms is a genetically distinct microorganism. In some embodiments, the genetically distinct microorganism is a yeast or bacterium. In some embodiments the genetically distinct microorganism is any organism from the genus *Issatchenkia, Pichia, Clavispora, Candida, Hansenula, Kluyveromyces, Saccharomyces, Trichoderma, Thermoascus, Escherichia, Clostridium, Caldicellulosiruptor, Thermoanaerobacter* and *Thermoanaerobacterium.*

In some embodiments, the recombinant microorganism produces about 2 to about 3% higher ethanol titer than a wildtype, non-recombinant organism; at least about 1 to at least about 2% higher ethanol titer than a wildtype, non-recombinant organism; at least about 1 to at least about 5% higher ethanol titer than a wildtype, non-recombinant organism; at least about 1 to at least about 7% higher ethanol titer than a wildtype, non-recombinant organism; at least about 1 to at least about 10% higher ethanol titer than a wildtype, non-recombinant organism; at least about 1 to at least about 15% higher ethanol titer than a wildtype, non-recombinant organism; at least about 1 to at least about 20% higher ethanol titer than a wildtype, non-recombinant organism; at least about 1 to at least about 30% higher ethanol titer than a wildtype, non-recombinant organism; at least about 1 to at least about 50% higher ethanol titer than a wildtype, non-recombinant organism; at least about 1 to at least about 75% higher ethanol titer than a wildtype, non-recombinant organism; at least about 1 to at least about 100% higher ethanol titer than a wildtype, non-recombinant organism.

In some embodiments, the recombinant microorganism produces at least about 0.5 g/L ethanol to at least about 2 g/L ethanol, at least about 0.5 g/L ethanol to at least about 3 g/L ethanol, at least about 0.5 g/L ethanol to at least about 5 g/L ethanol, at least about 0.5 g/L ethanol to at least about 7 g/L ethanol, at least about 0.5 g/L ethanol to at least about 10 g/L ethanol, at least about 0.5 g/L ethanol to at least about 15 g/L ethanol, at least about 0.5 g/L ethanol to at least about 20 g/L ethanol, at least about 0.5 g/L ethanol to at least about 30 g/L ethanol, at least about 0.5 g/L ethanol to at least about 40 g/L ethanol, at least about 0.5 g/L ethanol to at least about 50 g/L ethanol, at least about 0.5 g/L ethanol to at least about 75 g/L ethanol, or at least about 0.5 g/L ethanol to at least about 99 g/L ethanol per 24 hour incubation on a carbon-containing feed stock.

In some embodiments, the recombinant microorganism produces ethanol at least about 55% to at least about 75% of theoretical yield, at least about 50% to at least about 80% of theoretical yield, at least about 45% to at least about 85% of theoretical yield, at least about 40% to at least about 90% of theoretical yield, at least about 35% to at least about 95% of theoretical yield, at least about 30% to at least about 99% of theoretical yield, or at least about 25% to at least about 99% of theoretical yield.

In some embodiments, methods of producing ethanol can comprise contacting a biomass feedstock with a host cell or co-culture of the invention and additionally contacting the biomass feedstock with externally produced saccharolytic enzymes. In some embodiments, the host cells arc genetically engineered (e.g., transduced, transformed, or transfected) with the polynucleotides encoding saccharolytic enzymes.

A "saccharolytic enzyme" can be any enzyme involved in carbohydrate digestion, metabolism and/or hydrolysis, including amylases, cellulases, hemicellulases, cellulolytic, and amylolytic accessory enzymes, inulinases, levanases, and pentose sugar utilizing enzymes. Exemplary externally produced saccharolytic enzymes are commercially available and are known to those of skill in the art and include glucoamylases.

Glycerol Production

In some embodiments of the invention where redirected carbon flux generates increased ethanol production, the glycerol output can be decreased by growth-coupled selection. For example, continuous culture or serial dilution cultures can be performed to select for cells that produce less glycerol on a desired feedstock. Glycerol can be measured, for example, by HPLC analysis of metabolite concentrations.

In some embodiments, the recombinant microorganism produces at least about 20% to at least about 30% less glycerol than a wildtype, non-recombinant organism; at least about 15% to at least about 30% less glycerol than a wildtype, non-recombinant organism; at least about 10% to at least about 40% less glycerol than a wildtype, non-recombinant organism; at least about 10% to at least about 50% less glycerol than a wildtype, non-recombinant organism; at least about 10% to at least about 60% less glycerol than a wildtype, non-recombinant organism; at least about 10% to at least about 70% less glycerol than a wildtype, non-recombinant organism; at least about 10% to at least about 80% less glycerol than a wildtype, non-recombinant organism; at least about 10% to at least about 90% less glycerol than a wildtype, non-recombinant organism; at least about 10% to at least about 99% less glycerol than a wildtype, non-recombinant organism; at least about 10% to at least about 100% less glycerol than a wildtype, non-recombinant organism; at least about 5% to at least about 100% less glycerol than a wildtype, non-recombinant organism; at least about 1% to at least about 100% less glycerol than a wildtype, non-recombinant organism.

In some embodiments, the recombinant microorganism produces glycerol at least about 50% to at least about 99% of theoretical yield, at least about 45% to at least about 80% of theoretical yield, at least about 40% to at least about 85% of theoretical yield, at least about 30% to at least about 80% of theoretical yield, at least about 25% to at least about 50% of theoretical yield, at least about 20% to at least about 50% of theoretical yield, at least about 15% to at least about 50% of theoretical yield, at least about 10% to at least about 50% of theoretical yield, at least about 5% to at least about 50% of theoretical yield, at least about 4% to at least about 50% of theoretical yield, at least about 3% to at least about 50% of theoretical yield, at least about 2% to at least about 50% of theoretical yield, at least about 1% to at least about 50% of theoretical yield, at least about 1% to at least about 25% of theoretical yield, at least about 1% to at least about 20% of theoretical yield or at least about 1% to at least about 10% of theoretical yield. In some embodiments, the recombinant microorganism produces glycerol at less about 1% of theoretical yield. In some embodiments, the recombinant microorganism produces no glycerol.

In some embodiments, the recombinant microorganism has a growth rate at least about ½ to at least about equal to the growth rate of a wildtype, non-recombinant organism, at least about ¼ to at least about equal to the growth rate of a wildtype, non-recombinant organism, at least about ⅛ to at least about equal to the growth rate of a wildtype, non-recombinant organism, at least about 1/10 to at least about equal to the growth rate of a wildtype, non-recombinant organism, at least about 1/25 to at least about equal to the growth rate of a wildtype, non-recombinant organism, at least about 1/50 to at least about equal to the growth rate of a wildtype, non-recombinant organism or at least about 1/100th to at least about equal to the growth rate of a wildtype, non-recombinant organism.

In some embodiments, glycerol production is reduced as compared to a wildtype-non-recombinant organism and the organism produces ethanol at a rate of at least about 8-11 mM glycerol per gram dry cell weight (DCW) during anaerobic growth.

EXAMPLES

Example 1

Engineering *S. cerevisiae* to Express Integrated PKA and PTA

Phosphoketolase (PHK) enzymes from *Bifidobacterium adolescentis, Lactobacillus plantarum*, or *Aspergillus niger* were integrated at the *S. cerevisiae* FCY1 site in combination with the *Bifidobacterium adolescentis* phosphotransacetylase (PTA) gene. The genetic modification techniques utilized to develop *Saccharomyces cerevisiae* strain relied upon directed integration to insert genetic material at specific and known sites within the yeast chromosome. The directed integration approach creates transgenic strains with integration events that are stable and easy to characterize.

The MX cassettes are the most commonly used engineering tool when an insertion or deletion of a genetic element is desired at a given chromosomal loci (Wach A., et al., *Yeast.* 10(13):1793-1808 (1994)). A recyclable MX cassette contains one or more markers which enable both dominant and negative selection (Goldstein, A. L., et al., *Yeast.* 15: 507-511 (1999); Hartzog, P. E. et al., *Yeast.* 22: 789-798 (2005)). The dominant marker enables selection for the modification and the counter selectable marker enables subsequent removal of the marker system via Cre-Lox mediated recombination (Güldener, U., et al., *Nucleic Acids Research.* 24(13): 2519-2524 (1996)) or recombination between duplicated homologous regions flanking the cassette. Because the markers are removed, they can be reused during subsequent engineering steps and ensures no undesirable foreign genetic material remains in the strain.

To create stable homozygous integrations two new HSV-thymidine kinase (TDK) based MX cassettes were developed. Expression of thymidine kinase in *S. cerevisiae* results in sensitivity to the compound fluoro-deoxyuracil (FUDR). The cellular toxicity of FUDR is dependent on the presence of two enzymes involved in pyrimidine metabolism: thymidine kinase (Tdk) and thymidilate synthetase (ThyA). Tdk converts FUDR to fluoro-dUMP (F-dUMP) which is a covalent inhibitor of ThyA and the basis for counter selection in a variety of eukaryotic organisms (Czako, M., and Marton, L., *Plant Physiol.* 104:1067-1071 (1994); Gardiner, D. M., and Howlett, B. J., *Curr Genet.* 45:249-255 (2004);

Khang, C. H., et al., *Fungal Genet Biol.* 42:483-492 (2005); Szybalski, W., *Bioessays.* 14:495-500 (1992)).

The HSV-TDK expression cassette was independently fused to two commonly used dominant selectable markers which confer resistance to the drugs G418 (Kan) or nourseothricin (Nat) (Goldstein, A. L., et al., *Yeast.* 15: 507-511 (1999)). Transformation of both double expression cassettes, referred to as KT-MX and NT-MX, enabled positive selection for integration into both chromosomes as illustrated in FIG. 8A). For each round of engineering, PCR amplicons of upstream and downstream regions flanking the target site were designed to contain homologous tails for both the KT-MX and NT-MX cassettes. Both the flanks and the markers were transformed followed by selection on YPD medium containing both G418 and Nat (FIG. 8B).

After each engineering step taken in the construction, all markers were subsequently deleted and/or replaced with a desired expression cassette (Mascoma Assembly) resulting in a strain free of antibiotic markers (FIG. 9).

The integration scheme for each strain construction is shown in FIG. 10. Genotypes of the strains can be seen in Table 2.

TABLE 2

*S. cerevisiae* strains.

| Strain ID | Mascoma Assembly ID | Source | Strain description |
|---|---|---|---|
| M2390 | Wild type | Isolated from commercial source | Wild type control |
| M3293 | Glycerol reduction background | Constructed by Mascoma corporation | Δgpd1Δgpd2Δfdh1Δfdh2::adhE |
| M4408 | M3293 engineered with MA415 expressing *B. adolescentis* PHK and PTA | Constructed by Mascoma corporation | Δgpd1ΔgpdΔAfdh1Δfdh2::adhE Δfcy::*B. adolescentis* PHK 2/*B. adolescentis* PTA |
| M4409 | M3293 engineered with MA415 expressing *L. plantarum* PHK2 and *B. adolescentis* PTA | Constructed by Mascoma corporation | Δgpd1Δgpd2Δfdh1Δfdh2::adhE Δfcy::*L. plantarum* PHK2/*B. adolescentis* PTA |
| M4410 | M3293 engineered with MA415 expressing *A. Niger* PHK and *B. adolescentis* PTA | Constructed by Mascoma corporation | Δgpd1Δgpd2Δfdh1Δfdh2::adhE Δfcy::*A. niger* PHK2/*B. adolescentis* PTA |

Example 2

PKA and PTA Expression Rescues the Anaerobic Growth Defect in the M3293 Strain

The anaerobic growth of the strains expressing PHK and PTA from Example 1 was compared to the anaerobic growth of strains that did not express PHK and PTA. M2390, which has a complete anaerobic glycerol-production pathway, was used as a wildtype control strain. M3293, which contains deletions of both GPD1, GPD2, FDH1 and FDH2 and expression of the *B. adolescentis* adhE, did not have the ability to grow anaerobically unless acetate was supplied. A functional heterologous phosphoketolase/phosphotransacetylase pathway complemented the anaerobic growth defect of M3293.

Cells from all strains were grown overnight in YPD and inoculated to a final concentration of 0.1 g/l DCW in 96 well plates containing 100 μl YPD. The inoculated plates were allowed to equilibrate in the anaerobic chamber for 20 minutes prior to sealing the plates. As seen in FIG. 11, M3293 was not able to grow anaerobically, however, M4408, M4409, M4410, which contain a heterologous phosphoketolase pathway were able to grow. These results indicated that phosphoketolase enzymes from both *B. adolescentis, Lactobacillus plantarum*, and *Aspergillus niger* enabled anaerobic growth when expressed in combination with the phosphotransacetylase gene from *B. adolescentis*. The results shown in FIG. 12 indicated there were only minor differences in aerobic growth rate between M3293 and the phosphoketolase containing strains.

Example 3

Fermentation Analysis Using 31% Solids Corn Mash

In another embodiment, the ability of strains containing a deletion of both GPD1 and GPD2 expressing PHK and PTA from Example 1 to ferment corn mash was compared to the ability of strains containing deletions of both GPD1 and GPD2 but that did not express PHK and PTA to ferment corn mash (M3293). The fermentation was started by inoculating yeast to an initial concentration of 0.1 g/l DCW in 4 mls of 30% solids corn mash. The corn mash fermentation began with oxygen in both the medium and the headspace. Limited growth of M3293 was expected because the fermentation does not start anaerobically and there was acetate present. (During the corn mash fermentation, there was 0.3-0.5 g/l acetate present. The presence of the phosphoketolase/phosphotransacetylase pathway enabled growth after the supply of oxygen and acetate was depleted. All three phosphoketolase-containing strains reached a significantly higher titer than the M3293 control strain (FIG. 13). Acetate accumulation in M4408, M4409 and M4410 (FIG. 14) may have resulted in a lower pH and lower ethanol productivity.

Example 4

Fermentation Analysis in Defined Medium

All strains described in Table 2 were inoculated into defined medium without amino acids. Purged anaerobic bottles were prepared with medium as described below. The fermentations were started by inoculating these bottles with yeast strains to an initial concentration of 0.1 g/l DCW cells. After inoculation, bottles were placed in a shaking incubator at held at 35 C. Samples were withdrawn and metabolite concentrations were measured by HPLC analysis.

Defined Medium
1.7 g/l YNB-no AA without AS (Sigma)
40 g/l glucose
2.3 g/l Urea or 5.0 g/L ammonium sulfate
6.6 g/l $K_2SO_4$
0.5 g/l $MgSO_4$
3 g/l $KH_2PO_4$
1000×-Tween-80/Ergosterol (Final concentration: 20 mg/L ergosterol 420 mg/L Tween)
Verduyn vitamins & traces; 1 ml/L each The phosphoketolase containing strains M4408 and M4410 had improved growth relative to M3293 (FIG. 15); however, the strains had reduced biomass formation relative to the wild type control strain, M2390. The acetate formation observed in corn mash fermentation was not observed in defined medium. The ethanol titers of M4408 and M4410 were approximately 9% higher than M2390 (FIG. 16) while glycerol was reduced by approximately 2.4 g/l (FIG. 17).

Example 5

Engineering PHK and PTA Expression Vectors for *S. cerevisiae*

*S. cerevisiae* phosphoketolase expression vectors were created using the PMU1689 vector. *L. plantarum* PHK1, *L. plantarum* PHK2, *A. niger* PHK, *L. casei* PHK, *B. adolescentis* PHK or *N. crassa* PHK were cloned into PMU1689 To create, phosphoketolase expression vectors, PCR products were amplified from genomic DNA templates using primers and templates listed in Table 3 and recombined with linearized pMU1689 such that the ORF of each gene is immediately downstream of the ADH promoter and immediately upstream of the PDC1 terminator. Schematics of the PHK expression vectors can be seen in FIGS. 18-23.

*S. cerevisiae* phosphotransacetylase expression vectors were created using the pMU1771 expression vector (FIG. 24). The *B. adolescentis* phosphotransacetylase orf was amplified from *B. adolescentis* genomic DNA template using primers and templates listed in Table 3 and recombined with linearized pMU1771 such that the ORF of each gene is immediately downstream of the TEF2 promoter and immediately upstream of the ADH3 terminator.

TABLE 3

Phosphoketolase cloning templates and vectors

| Donor Organism | Template | Forward primer | Reverse primer | Vector | SEQ ID NO |
|---|---|---|---|---|---|
| *B. adolescentis* | *B. adolescentis* Genomic DNA | gctataccaagcatacaatc aactatctcatatacaatga cgagtcctgttattggcac | TTATAAAACTTTAACTAA TAATTAGAGATTAAATCG CTCACTCGTTATCGCCAG CGGTT | pMU1689 | 49, 50 |
| *L. plantarum* (1) | *L. plantarum* Genomic DNA | ctataccaagcatacaatca actatctcatatacaatgac aacagattactcatcacca | AAACTTTAACTAATAATT AGAGATTAAATCGCTTAT TTTAAACCCTTCCATTGC CAATC( | pMU1689 | 51, 52 |
| *L. plantarum* (2) | *L. plantarum* Genomic DNA | gctataccaagcatacaatc aactatctcatatacaatga gtgaagcaattaaatccaa | AAAACTTTAACTAATAAT TAGAGATTAAATCGCCTA CTTCAATGCAGTCCATTT CCAGT | pMU1689 | 53, 54 |
| *N. crassa* | *N. crassa* Genomic DNA | tataccaagcatacaatcaa ctatctcatatacaatgggc ggaacacagatcacaattc | AAAACTTTAACTAATAAT TAGAGATTAAATCGCCTA CTCGAACTTGGGCAGTTG GTAGA( | pMU1689 | 55, 56 |
| *A. niger* | *A. niger* Genomic DNA | ctataccaagcatacaatca actatctcatatacaatgcc tggagaggtcatcgacagg | AACTTTAACTAATAATTA GAGATTAAATCGCTTATT CAAAGGAGGGCATATCAT ACGTA | pMU1689 | 57, 58 |
| *L. casei* | *L. casei* Genomic DNA | tataccaagcatacaatcaa ctatctcatatacaatggat acaaaagtaaagactggt | AAACTTTAACTAATAATT AGAGATTAAATCGCTTAC TTGATTGGTTTCCAGGTC CATTC | pMU1689 | 59, 60 |

Example 6

Analysis of Components of the Phosphoketolase Pathway

To evaluate components of the phosphoketolase pathway, the strains listed in Table 4 were inoculated into vials containing 4 ml of YP medium (10 g/l yeast extract, 20 g/l peptone) supplemented with 225 g/L maltodexdrin. Maltodextrin hydrolysis was initiated upon addition of 0.6 AGU/gTS glucoamylase at the start of the fermentation. Vials were incubated at 32° C. for 68 hrs and sampled for HPLC analysis.

TABLE 4

| Strains used in the fermentation study. | |
|---|---|
| Strain | Genotype |
| M2390 | WT |
| M3293 | Δgpd1::MA0606Δgpd2::MA0607Δfdh1::MA0608Δfdh1::MA0281 |
| M4408 | Δgpd1::MA0606Δgpd2::MA0607Δfdh1::MA0608Δfdh1::MA0281Δfcy::MA0449.2 |
| M4579 | Δgpd1::MA0606Δgpd2::MA0607Δfdh1::MA0608Δfdh1::MA0281Δfcy::MA0415.3 |
| M4581 | Δgpd1::MA0606Δgpd2::MA0607Δfdh1::MA0608Δfdh1::MA0281Δfcy::MA0415.4 |
| M4582 | Δgpd1::MA0606Δgpd2::MA0607Δfdh1::MA0608Δfdh1::MA0281Δfcy::MA0449.2 |
| M4584 | Δgpd1::MA0606Δgpd2::MA0607Δfdh1::MA0608Δfdh1::MA0281Δfcy::MA0449.3 |
| M4788 | Δgpd1::MA0606Δgpd2::MA0607Δfdh1::MA0608Δfdh1::MA0281Δfcy::MA0449.1 |
| M4789 | Δgpd1::MA0606Δgpd2::MA0607Δfdh1::MA0608Δfdh1::MA0281Δfcy::MA0449.1 |
| M4790 | Δgpd1::MA0606Δgpd2::MA0607Δfdh1::MA0608Δfdh1::MA0281Δfcy::MA0467.6 |
| M4791 | Δgpd1::MA0606Δgpd2::MA0607Δfdh1::MA0608Δfdh1::MA0281Δfcy::MA0467.6 |
| M4792 | Δgpd1::MA0606Δgpd2::MA0607Δfdh1::MA0608Δfdh1::MA0281Δfcy::MA0434.6 |
| M4793 | Δgpd1::MA0606Δgpd2::MA0607Δfdh1::MA0608Δfdh1::MA0281Δfcy::MA0434.6 |
| M4794 | Δgpd1::MA0606Δgpd2::MA0607Δfdh1::MA0608Δfdh1::MA0281Δfcy::MA0435.1 |

M2390 is a conventional wild type yeast. M3293 contains deletion of both glycerol-3-phosphate dehydrogenase genes (GPD1 and GPD2), both formate dehydrogenase genes (FDH1 and FDH2), and expression of the *B. adolescentis* bifunctional alcohol/aldehyde dehydrogenase. This strain grows poorly under anaerobic conditions and is only able to produce a titer of 42 g/l ethanol whereas M2390 was able to reach 113 g/l ethanol (FIG. 25).

The addition of components of the phosphoketolase pathway to M3293 allowed for improved ethanol production. Expression of both *B. adolescentis* and *L. casei* PHK in combination with the *B. adolescentis* PTA gene resulted in production of 60.7 and 72.3 g/l respectively (FIG. 25) indicating the pathway partially complements the defect observed in M3293. Expression of *B. adolescentis* PHK, PTA and ACK genes resulted in production of 92 g/l ethanol. This combination produced titers that were significantly higher than when the *B. adolescentis* PHK and PTA were the only additions.

A description of the cassettes used to create the strains is seen below and in FIGS. 26-34. Strains were created as described, for example, in Example 1.

| Fragment | Primers | Template | Expected Size |
|---|---|---|---|
| MA0281 | | | |
| FDH2 5' Flank | X16096/X17243 | M2390 gDNA | 503 bp |
| PFK pro/HXT2 ter | X16738/X14897 | pMU2745 | 4233 bp |
| TPI pro/FBA1 ter | X14896/X16744 | pMU2746 | 3683 bp |
| FDH2 3' Flank | X17244011845 | M2390 gDNA | 1939 bp |
| MA467.6 PHK | | | |
| FCY 5' Flank | X21754021736 | M2390 gDNA | 2049 bp |
| ADH1pro/PDC1ter | X21735/X18847 | pMU3397(PHK) | 3728 bp |
| FCY 3' Flank | X18846/X18869 | M2390 gDNA | 2166 bp |
| MA449.2 4PTA/2PHK | | | |
| FCY 5' Flank | X21754/X19552 | M2390 gDNA | 2049 bp |
| TEF2pro/ADH3ter | X19551019513 | pMU3399(PTA) | 2671 bp |
| ADH1pro/PDC1ter | X19514019360 | pMU3397(PHK) | 3728 bp |
| TPIpro/FBA1ter | X19361/X19903 | pMU3402(PTA) | 2621 bp |
| FCY 3' Flank | X19902018869 | M2390 gDNA | 2166 bp |
| MA449.3 2PTA/2PHK/2ACK | | | |
| FCY 5' Flank | X21754/X19552 | M2390 gDNA | 2049 bp |
| TEF2pro/ADH3ter | X19551/X19513 | pMU3399(PTA) | 2671 bp |
| ADH1pro/PDC1ter | X19514/X19360 | pMU3397(PHK) | 3728 bp |
| TPIpro/FBA1ter | X19361/X19903 | pMU3407(ACK) | 2180 bp |
| FCY 3' Flank | X19902/X18869 | M2390 gDNA | 2166 bp |

-continued

| MA435.1 PHK/ACK | | | |
|---|---|---|---|
| FCY 5' Flank | X21754/X21736 | M2390 gDNA | 2049 bp |
| ADH1pro/PDC1ter | X21735/X19855 | pMU3397(PHK) | 3728 bp |
| TPIpro/FBA1ter | X19854/X18861 | pMU3407(ACK) | 2180 bp |
| FCY 3' Flank | X18860/X18869 | M2390 gDNA | 2166 bp |
| MA415.4 4PTA | | | |
| FCY 5' Flank | X21754/X19552 | M2390 gDNA | 2049 bp |
| TEF2pro/ADH3ter | X19551/X19513 | pMU3399(PTA) | 2671 bp |
| ADH1pro/PDC1ter | X19514/X18955 | pMU3401(PTA) | 2921 bp |
| FCY 3' Flank | X19950/X18869 | M2390 gDNA | 2166 bp |
| MA449.1 4PTA/2ACK | | | |
| FCY 5' Flank | X21754/X19552 | M2390 gDNA | 2049 bp |
| TEF2pro/ADH3ter | X19551/X19513 | pMU3399(PTA) | 2671 bp |
| ADH1pro/PDC1ter | X19514/X19360 | pMU3401(PTA) | 2921 bp |
| TPIpro/FBA1ter | X19361/X19903 | pMU3407(ACK) | 2180 bp |
| FCY 3' Flank | X19902/X18869 | gDNA | 2166 bp |
| MA434.6 ACK | | | |
| FCY 5' Flank | X21754/X18859 | M2390 gDNA | 2049 bp |
| TP1pro/FBA1ter | X18858/X18861 | pMU3407(ACK) | 2180 bp |
| FCY 3' Flank | X18860/X18869 | M2390 gDNA | 2166 bp |

| MA415.3 Lcasei PHK | | | |
|---|---|---|---|
| Fragment | Primers | Template | Exp Size |
| FCY 5' Flank | X21754/X19552 | M2390 gDNA | 2049 bp |
| TEF2pro/ADH3ter | X19551/X19513 | pMU3399 (PTA) | 2671 bp |
| ADH1pro/PDC1ter | X19514/X18955 | pMU3416 (PHK) | 3632 bp |
| FCY 3' Flank | X19950/X18869 | M2390 gDNA | 2166 bp |

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

Those skilled in the art will recognize, or be able to ascertain using no more than routine experimentation, many equivalents to the specific embodiments of the invention described herein. Such equivalents are intended to be encompassed by the following claims.

The invention claimed is:

1. A recombinant microorganism comprising:

a) at least one heterologous nucleic acid encoding an enzyme in an acetyl-CoA production pathway; and b) a heterologous nucleic acid encoding a bifunctional acetaldehyde-alcohol dehydrogenase.

2. The recombinant microorganism of claim 1, wherein said enzyme in the acetyl-CoA production pathway is a phosphotransacetylase with Enzyme Commission Number 2.3.1.8.

3. The recombinant microorganism of claim 2, wherein said phosphotransacetylase is derived from a genus selected from the group consisting of *Bifidobacterium, Lactobacillus, Clostridium, Leuconostoc* and *Oenococcus*.

4. The recombinant microorganism of claim 3, wherein said phosphotransacetylase corresponds to a polypeptide selected from a group consisting of SEQ ID NOs: 10, 34, 80, 82, 84, 86, and 96.

5. The recombinant microorganism of claim 1, wherein said enzyme in the acetyl-CoA production pathway is an acetate kinase with Enzyme Commission Number 2.7.2.12.

6. The recombinant microorganism of claim 5, wherein said acetate kinase is derived from a genus selected from the group consisting of *Bifidobacterium, Lactobacillus, Clostridium, Leuconostoc* and *Oenococcus*.

7. The recombinant microorganism of claim 6, wherein said acetate kinase corresponds to a polypeptide selected from a group consisting of SEQ ID NOs: 16, 76, 88, 92, and 100.

8. The recombinant microorganism of claim 1, wherein said bifunctional acetaldehyde-alcohol dehydrogenase is selected from a group of enzymes having both of the following Enzyme Commission Numbers: EC 1.2.1.10 and 1.1.1.1.

9. The recombinant microorganism of claim 8, wherein said bifunctional acetaldehyde-alcohol dehydrogenase is from *B. adolescentis* and corresponds to a polypeptide encoded by SEQ ID NO: 44.

10. The recombinant microorganism of claim 1, wherein said bifunctional acetaldehyde-alcohol dehydrogenase is an NADPH dependent bifunctional acetaldehyde-alcohol dehydrogenase selected from a group of enzymes having the following Enzyme Commission Numbers: EC 1.2.1.10 and 1.1.1.2.

11. The recombinant microorganism of claim 10, wherein said NADPH dependent bifunctional acetaldehyde-alcohol dehydrogenase is derived from a genus selected from the group consisting of *Leuconostoc* and *Oenococcus*.

12. The recombinant microorganism of claim 11, wherein said NADPH dependent bifunctional acetaldehyde-alcohol dehydrogenase corresponds to polypeptide selected from a group consisting of SEQ ID NOs: 90 and 98.

13. The recombinant microorganism of claim 1, further comprising:

c) at least one genetic modification that leads to the down-regulation of an enzyme in a glycerol-production pathway.

14. The recombinant microorganism of claim 13, wherein said enzyme in the glycerol-production pathway is a glycerol-3-phosphate dehydrogenase with Enzyme Commission Number 1.1.1.8.

15. The recombinant microorganism of claim 14, wherein said glycerol-3-phosphate dehydrogenase is selected from the group consisting of glycerol-3-phosphate dehydrogenase 1, glycerol-3-phosphate dehydrogenase 2, and combinations thereof.

16. The recombinant microorganism of claim 15, wherein said glycerol-3-phosphate dehydrogenase 1 is from *S. cerevisiae* and corresponds to a polypeptide encoded by SEQ ID NO: 28.

17. The recombinant microorganism of claim 15, wherein said glycerol-3-phosphate dehydrogenase 2 is from *S. cerevisiae* and corresponds to a polypeptide encoded by SEQ ID NO: 30.

18. The recombinant microorganism of claim 13, wherein said enzyme in the glycerol-production pathway is a glycerol-3-phosphate phosphatase with Enzyme Commission Number 3.1.3.21.

19. The recombinant microorganism of claim 1, wherein said microorganism further comprises at least one additional up-regulated enzyme.

20. The recombinant microorganism of claim 19, wherein a transaldolase with Enzyme Commission Number 2.2.1.2 is up-regulated.

21. The recombinant microorganism of claim 20, wherein said transaldolase is from *S. cerevisiae* and corresponds to a polypeptide encoded by SEQ ID NO: 36.

22. The recombinant microorganism of claim 19, wherein a transketolase with Enzyme Commission Number 2.2.1.1 is up-regulated.

23. The recombinant microorganism of claim 22, wherein said transketolase is from *S. cerevisiae* and corresponds to a polypeptide encoded by SEQ ID NO: 38.

24. The recombinant microorganism of claim 19, wherein a ribose-5-P isomerase with Enzyme Commission Number 5.3.1.6 is up-regulated.

25. The recombinant microorganism of claim 24, wherein said ribose-5-P isomerase is from *S. cerevisiae* and corresponds to a polypeptide encoded by SEQ ID NO: 40.

26. The recombinant microorganism of claim 19, wherein a ribulose-5-P 3-epimerase with Enzyme Commission Number 5.1.3.1 is up-regulated.

27. The recombinant microorganism of claim 26, wherein said ribulose-5-P 3-epimerase is from *S. cerevisiae* and corresponds to a polypeptide encoded by SEQ ID NO: 42.

28. The recombinant microorganism of claim 1, wherein at least one enzyme in a glycolysis pathway is up-regulated.

29. The recombinant microorganism of claim 28, wherein said enzyme in the glycolysis pathway is a pyruvate decarboxylase with Enzyme Commission Number 4.1.1.1.

30. The recombinant microorganism of claim 28, wherein said enzyme in the glycolysis pathway is an alcohol dehydrogenase selected from a group of enzymes having the following Enzyme Commission Numbers: 1.1.1.1 and 1.1.1.2.

31. The recombinant microorganism of claim 1, additionally comprising at least one genetic modification that leads to the down-regulation of aldehyde dehydrogenase selected from a group of enzymes having the following Enzyme Commission Numbers: 1.2.1.3, 1.2.1.4 and 1.2.1.10.

32. The recombinant microorganism of claim 1, additionally comprising at least one genetic modification that leads to the up-regulation of aldehyde dehydrogenase selected from a group of enzymes having the following Enzyme Commission Numbers: 1.2.1.3, 1.2.1.4 and 1.2.1.10.

33. The recombinant microorganism of claim 1, wherein said aldehyde dehydrogenase is acetaldehyde dehydrogenase from *S. cerevisiae* and corresponds to a polypeptide sequence selected from the group consisting of: SEQ ID NO: 18, SEQ ID NO: 20, SEQ ID NO: 22, SEQ ID NO: 24, and SEQ ID NO: 26.

34. The recombinant microorganism of claim 1, additionally comprising at least one genetic modification that leads to the down-regulation of formate dehydrogenase selected from a group of enzymes having the following Enzyme Commission Numbers: 1.2.1.43 and 1.2.1.2.

35. The recombinant microorganism of claim 34, wherein said formate dehydrogenase is from *S. cerevisiae* and corresponds to a sequence selected from the group consisting of: a polypeptide sequence corresponding to SEQ ID NO: 32 and a polynucleotide sequence corresponding to SEQ ID NO: 33.

36. The recombinant microorganism of claim 1, additionally comprising at least one genetic modification that leads to the up-regulation of a pyruvate formate lyase with Enzyme Commission Number: 2.3.1.54.

37. The recombinant microorganism of claim 36, wherein said pyruvate formate lyase corresponds to a polypeptide encoded by SEQ ID NO: 48.

38. The recombinant microorganism of claim 1, additionally comprising at least one genetic modification that leads to the up-regulation of a pyruvate formate lyase activating enzyme with Enzyme Commission Number 1.97.1.4.

39. The recombinant microorganism of claim 38, wherein said pyruvate formate lyase activating enzyme corresponds to a polypeptide encoded by SEQ ID NO: 46.

40. The recombinant microorganism of claim 1, wherein said microorganism is a yeast.

41. The recombinant microorganism of claim 40, wherein said microorganism is from the genus *Saccharomyces*.

42. The recombinant microorganism of claim 41, wherein said microorganism is *Saccharomyces cerevisiae*.

43. The recombinant microorganism of claim 1, wherein said microorganism produces ethanol at a higher yield than an otherwise identical microorganism lacking said genetic modifications.

44. The recombinant microorganism of claim 1, wherein said microorganism produces an ethanol titer from about 1% to about 10% more than an otherwise identical microorganism lacking said genetic modifications.

45. The recombinant microorganism of claim 1, wherein said microorganism produces glycerol at a lower yield than an otherwise identical microorganism lacking said genetic modifications.

46. The recombinant microorganism of claim 1, wherein said microorganism produces a glycerol titer from about 10 to about 100% less than an otherwise identical microorganism lacking said genetic modifications.

47. A composition comprising a recombinant microorganism from claim 1 and a carbon-containing feedstock.

48. The composition of claim 47, wherein said feedstock is selected from the group consisting of woody biomass, grasses, sugar-processing residues, municipal waste, agricultural wastes or any combination thereof.

49. The composition of claim 48, wherein said feedstock comprises recycled wood pulp fiber, sawdust, hardwood, softwood, rice straw, rice hulls, barley straw, corn cobs, cereal straw, wheat straw, canola straw, oat straw, oat hulls, corn fiber, stover, succulents, agave, cane bagasse, switchgrass, miscanthus, paper sludge, municipal waste or any combination thereof.

50. A co-culture comprising at least two host cells wherein a) one of the host cells comprises a recombinant microorganism from claim 1; and, b) another host cell that is genetically distinct from (a).

51. The co-culture of claim 50, wherein the genetically distinct host cell is a yeast or bacterium.

52. The co-culture of claim 50, wherein the genetically distinct host cell is any organism from the genus *Saccharomyces, Issatchenkia, Pichia, Clavispora, Candida, Hansenula, Kluyveromyces, Trichoderma, Thermoascus, Escherichia, Clostridium, Caldicellulosiruptor, Zymomonas, Thermoanaerobacter* or *Thermoanaerobacterium.*

* * * * *

SEQUENCE LISTING

<160> NUMBER OF SEQ ID NOS: 103

<210> SEQ ID NO 1
<211> LENGTH: 1671
<212> TYPE: DNA
<213> ORGANISM: Bifidobacterium adolescentis
<220> FEATURE:
<223> OTHER INFORMATION: PTA

<400> SEQUENCE: 1

```
gtgagtttta ccagcgtcac catcatcagt cccgaagcgg ctaacggccg taatgttgtc     60
gcccttggag tcaccaagac acttgccgca gccggcaaga ccggagtgtt ccgtccggcg    120
gtctgcagaa aagacacctt cacggacgtg ctgatcgaag cttccaatgc cggtttgagc    180
cgggaacagt ccgtcggcgt gtgccccaag cgcgctcgta acgataagga aggttcgcgg    240
gcggatatcg ttgcggccta cacccaagcc gtagaaacag cccgaccgga tgccatggtg    300
attgtcggca ccgacaggtc agcagtcaat gatcccgcga tgttctcttt caacgctgac    360
gtcgcggcag acctccaatc gccggtcctg ctggccgtat gcactatcga acgcacaccg    420
gaacaagtca aaagcacggt tgaggcatcc accaaggtca tcgaagacgc cgggagcaaa    480
gtcgtcggcg tgttcattac tgggtgtgac gacacgcagc cgaatccact caaagcatgc    540
ttcgtcgact acccggtgcc ggtgtggacg ctacctgccg tcgatttcaa cgacgatgac    600
gccatcagca aggcagacga agcgttcgcg acgaacgtcg acgccgtgga actgaccgtg    660
gcactcgaat cgccattcga cgccccgacc acaccctatg ctttccaata cggtctgctg    720
ggcaaggcga aggcggacaa gaagaccatc gtgctgccgg agggcaacga ggatcgcatc    780
atcaaagccg ccgattatct gctggagcgc gacatcgtcg atctgatcat cgtcggagac    840
gaaaacgcca ttctcgcccg cggccaggaa ttgggattga aatcgcttgg caaggcgaaa    900
ttccaagcca aggatgatga aacggtgctg gaacccatgg tggcgaagct gtgcgagctg    960
cgcgccaaga aaggcatgac cgaagagcag gcgcgcaaac agctggccga tgacagctat   1020
ttcggcacca tgcttgtggt gatgggcatg gcggacggtc tcgtgtccgg ttccgtcaac   1080
tccacggcca ataccgtgcg tccggccctg caggtcatca agaccaagcc aggaacgtcg   1140
ctggtctccg gagcgttcct gatgtgtttc aaggaccatg ccgccgtgtt cgccgactgt   1200
gccatcaacc ttaaccccaa tgccgagcag ctcgccgaaa tagcaatcca atccgccgaa   1260
acggccaagg cgttcggcct tgaaccgaag gtgggcatgc tgtcctattc cacgctgggc   1320
tccggaaaag gacccgacgt cgacctcgtc gaggaagcca ccaccatcgt caaagacaag   1380
gctcccgacc ttgcggtggt cggatcgatc cagttcgacg cggcatggtc tccgaccgtg   1440
gccgcgacca aagccaaggg cgatccggtg gcgggccatg tcaatgtgtt cgtattcccg   1500
gatctgtgcg cgggcaacat cgcatacaag gcggtacagc gttcctcggg agcggccgcc   1560
gtcgggccgg tgctgcaggg tctcaaccgc ccggtgaacg atctgagccg tggcgccacg   1620
gtccaggaca tcatcaacac catcgccctg accgccatcg aggcccagta a            1671
```

<210> SEQ ID NO 2
<211> LENGTH: 1230
<212> TYPE: DNA
<213> ORGANISM: Bifidobacterium adolescentis
<220> FEATURE:
<223> OTHER INFORMATION: ACK

<400> SEQUENCE: 2

```
atggcgaaaa ccgtccttgt catcaattcc ggttccagct ctatcaagta tcagctggtt     60
```

```
gatcttgaaa ccggcgaagg tatcgcttcc ggtctggtcg agaagatcgg cgagccggtt    120

gacggtcatt acaagcacga gtacaacggc gagaagcatg agctcgaaga gccgattcac    180

gaccatgagc agggtctgaa gcgcgtgctc ggcttcttcg acgagttcgg cccgaagctc    240

gccgacgcag gcatcgtggc cgtcggccat cgcgtggtgc agggtggttc catcttcccg    300

aagccggctc tggtcaacga caagaccatc ggccaggtca aggacctcgc cgtgctcgcc    360

ccgctgcaca acggtccgga ggccaagggc gctgaggtca tgcgctccct gctgccggat    420

gttccgcaga tcttcgtgtt cgattcctcc ttcttcttcc agctgccgaa ggcttccagc    480

acctacgcgc tgaacaagga agtcgcccag cagtaccata tccgccgtta cggcgcccat    540

ggcacctccc acgagttcat ctcctccgtc gtgccgtccg tcatcggcaa gccggccgaa    600

ggcctcaagc agatcgtgct gcacatcggc aacggtgctt ccgcctccgc cgaaatctcc    660

ggcaagccgg ttgagacctc catgggtctg accccgctgg aaggcctcgt gatgggtggc    720

cgtaccggcg acatcgatcc ggccgtcgtc ttccacctga ttcgcaacgc ccacatgagc    780

gtggacgaac tggacaccct gttcaacaag cgttccggca tgatgggtct gaccggcttc    840

ggcgacctgc gtgaagtgca tcgtctggtc gaagagggca acgaggacgc caagctggct    900

ctcgacatct acgtgcaccg catcgtcggc tacatcggca actacaccgc tcagatgggt    960

ggcgtcgacg tgatcacctt caccgcaggc gttggcgaga acgatgacgt cgtgcgcaag   1020

atggtctgcg acaagctcgc tccgttcggc gtcaagttgg atgaggagaa gaacgcgacc   1080

cgttccaagg aaccgcgcat catctccacc ccggattccg cagtcaccat ctgcgtcatc   1140

ccgaccaacg aggagctggc catcgcccgc aagtccgccg ccatcgcaga agaaggcaag   1200

gactcctacg gcaacgtctt ctccaagtga                                    1230
```

<210> SEQ ID NO 3
<211> LENGTH: 2421
<212> TYPE: DNA
<213> ORGANISM: Aspergillus niger
<220> FEATURE:
<223> OTHER INFORMATION: PHK

<400> SEQUENCE: 3

```
atgcctggag aggtcatcga caggccaaat cccaaggctg agccttcaca catccccgat     60

cttgtcaatc aattgcaggt caaacttcaa gagacgcgtt tggaggaaac tgattacaat    120

gcccttctga aattccgccg tgcagcggcc tacattgctg ctgcaatgat ctttctccaa    180

gacaatgtgc tgctgaagca gaatctaagg cacgaggaca tcaagcccag gcttcttggc    240

cactggggaa catgtcccgg gttgattctt gtatactctc acttgaacta catcatcaga    300

aagcagaacc tggatatgtt gtatgtcgtc gggcctggcc acggcgcgcc agctattttg    360

gcctcactgt ggcttgaggg ctctttagag aaattctacc cccactactc acgagacatg    420

gatggtctcc atgagctcat ctcgaccttc agcacaagtg ctggattacc aagccatatc    480

aatgcggaaa ctcccggtgc aatccatgaa ggtggtgaat tgggttatgc gttagctgtc    540

tcttttggtg ctgttatgga caatcccgac atgatcgtca cctgcgtggt tggtgacggg    600

gaagcagaaa ctggtcctac cgcgacgtcc tggcatgcaa tcaagtacat tgaccccgca    660

gaatcaggtg ccgtcctgcc gattctccac gttaatggct ttaagatcag cgagcgcacc    720

atttatggct gcatggacaa caaagagctg gtctccctct tcacgggtta tggataccag    780

gtgcgcattg ttgagaacct ggatgacatc gacgcagatc tccatagctc tatgatgtgg    840
```

```
gcagttgagg agatccacaa gatccaaaaa gcggcgcgtt ccggcaagcc aattatgaag    900

cctagatggc caatgattgt tttgcgcaca ccgaagggtt ggtcaggacc taaagagctc    960

cacgggtcat tcatagaggg atctttccac tcacatcagg ttcctctacc taatgcaaag   1020

aaggataaag aggagcttca ggctctgcag aaatggctgt cctcgtataa tccgcacgaa   1080

cttttcactg agacgggaga catcattgac gacatcaagt cagtgatccc tctggaagac   1140

accaagaagc ttgggcagcg agcagaagcc tacaagggct atagggcacc cgatctccca   1200

gactggcgca agtttggcgt agaaaagggc tcccagcaga gcgctatgaa aacaattgga   1260

aagttcattg accaagtgtt tacccaaaat cctcatggcg tccgtgtatt ttcgccagac   1320

gagctagaga gcaacaagct ggatgcagca ctggcgcaca cgggaaggaa ctttcagtgg   1380

gatcaattct cgaatgccaa aggcggccgc gtcatcgagg tgctcagtga gcacctgtgc   1440

cagggcttta tgcagggata cacgttgacg ggccgggtgg gcattttccc atcgtacgaa   1500

agcttcttgg gaatcatcca taccatgatg gtgcaatatg ccaaatttaa caaaatggct   1560

caagagacga cctggcataa gccggttagt agcatcaact atatcgaaac gagtacgtgg   1620

gctcgtcagg agcacaatgg attctctcac cagaacccct cctttatcgg agctgtgctc   1680

aggctgaagc ccaccgccgc gcgagtttat ctgccacctg atgctaacac atttttgacc   1740

acccttcacc actgtctcaa gtccaagaat tatgtcaacc tcatggtagg ttcaaaacag   1800

ccaactcccg tgtacttgag ccccgaggaa gcagagagcc actgccgagc cggcgcatcg   1860

atctggagat tctgtagtac cgacaatggg ctgaacccgg atgtcgtgct ggttggcatt   1920

ggagtagagg tgatgttcga ggtcatctac gcggcggcca tcctccgcaa gcgttgtcca   1980

gaactccggg tgcgtgtggt caatgtgacc gacttgatga ttctggagaa ggaaggtcta   2040

catccacatg cattgacgac cgaagctttc gacagtctgt ttggctcgga ccggccgata   2100

cacttcaact accacggata cccgggcgag ctcaaaggtc tgctctttgg gcggccccgc   2160

ctggaccgag tttcagtaga aggatacatg gaggaaggaa gcacgacgac gccgttcgat   2220

atgatgttgc tgaaccgcgt ctcacgatac cacgtggcgc aggcagccgt gatcggggcg   2280

tccagacgga atgagaaggt tcaagttcgg cagcacgaac tggtcagcga attcggccac   2340

aacatcgtgg agacacgcaa atacattctg gccaaccgca aagacccgga tgatacgtat   2400

gatatgccct cctttgaata a                                             2421
```

<210> SEQ ID NO 4
<211> LENGTH: 2448
<212> TYPE: DNA
<213> ORGANISM: Neurospora crassa
<220> FEATURE:
<223> OTHER INFORMATION: PHK

<400> SEQUENCE: 4

```
atgggcggaa cacagatcac aattcccaac ccccctcctc taccatccca cctccccgac     60

aatgtcctcg acctggcagt ccaaattgag cgcaagaacc tcccagacaa tgtccgcgag    120

tcgctgcgcg cattccagcg tgcaggatgc tacattgccg cctccatgat cttcttgcgc    180

gacaatgtcc tcctccaaga caaactccaa gtttcgcaca tcaagccccg actcctcggt    240

cattggggaa catgccccgg cctaatcctg gtctggtcgc atctcaacgt cttgatccgc    300

aaccatgacc tcaacatgat ttacgttatc ggccccggcc acggcgcccc tgccgccctc    360

gcctctctgt ggctcgaagg ctcccttgag cgcttctacc ctggcgaata cgaccgcaat    420

gctactggtt tgcgcaacct catcacccgt ttctctgtcc ccggcggttt tcctagccac    480
```

```
atcaacgctg agactccagg tgcgatccat gagggtggtg agctcggata tgccctttct    540

gtctcgttcg gcgccgtcat ggacaacccc gatttgatcg tcacttgtgt ggtaggcgat    600

ggtgaggcgg agactggccc gacagcaacc gcctggcatg ctatcaagta catcgacccc    660

aaggagtcag gtgccgtcat ccccattctg catgtcaacg gcttcaagat cagcgagcgc    720

accatttttg ggtgcatgga cgacaaggag atcgcctgct tgtttagtgg ctacggatac    780

caggtgcgca ttgtggaaga cctggagaac attgatgatg acctgcaaag ttcgctggaa    840

tgggctctag tcgagatcaa gaagatccag aaggctgcga gggaggacaa caagccgatt    900

gtgaagccga gatggccgat gattgtcctc agaacgccca agggatggac tggtcccaag    960

gaggtggagg gccaaatcat cgaaggatcc ttccactccc atcaagtccc ccttcctaag   1020

gctggtagtg atgagaagca actccaggct ctagacgagt ggctttccag ctacaggatc   1080

agcgagctcc ttgatgatga gggcaagcct actgaggcca tcactcgtgt cttgcccaag   1140

gcagaaaaga ggctcggtca actcaagatc acatatgacc catacattcc tctgaaactg   1200

attgactgga agcagtttgg cgttcaaaag ggcgtcgacg aaagctgcat gaagagtgcc   1260

ggcaagttcc tcgacaagtt gttccaagag aaccccaaaa ccctccggct attctcccct   1320

gacgagctcg agtcgaacaa gctcaacgcc atcctggatc acacacagcg cgactttcag   1380

tgggacgagt tctcgagggc acatggcggt cgcgtcatcg aggttctctc cgagcacaat   1440

tgccagggct tcatgcaagg atacactctc acgggccgca ccgccctctt cccctcctat   1500

gagtccttcc tgggtatcgt tcacaccatg atggtgcaat actccaagtt cgtcaagatc   1560

gcgcgtgaag taccctggcg tggcgacctg gcctccatca actacatcga gacttcgacc   1620

tgggcgcgtc aagaacacaa tggcttttcc catcagaacc cctccttcat tggtgctgta   1680

cttaacctga aggccgaggc cgctcgcgtt tacctcccgc ccgacgccaa ctgcttcctc   1740

agcaccgtgc atcatgtcat ggacagcaag aacaagacca acctcatcat cggctccaag   1800

cagcccacgg ccgtctacct ctctcccgcc gaagcagccg accactgtcg ccagggtgcc   1860

tcgatctggc atttcgcctc ttcctccgac cccaactcat ccgcaggaga gtcggtacaa   1920

gacccagatg tagtcctcgt cggcatcggc gtcgaagtta cttttgaggt gattaaagct   1980

gctgaactct tgcgctccat tgcgcccgcc ctcaagatcc gcgtcgtcaa tgtgacggat   2040

ctgatgattc tcatcgaaga gtccaagcac ccgcatgccc tggccaaggc caagttcatc   2100

gaaatgttca ccgccgacag accggtgttg ttcaactacc atggctaccc gacggaactg   2160

cagggtctct tgtttgggag ggaaaaggcg gagcgcatgg atgtcgaggg ttaccaagaa   2220

gagggaagca cgaccacgcc gtttgatatg atgttgagga accgggtcag tcggttcgat   2280

gtggcgagct gggcgctgaa gaggggtgcg gagaggaatg cggaggtgaa gaatgatttg   2340

gaaggtttgt tgggtgacgt ggataggaga gtgaaggagg ttcgtgagtt tattgggaat   2400

gaaggaaagg atcccgatga tatctaccaa ctgcccaagt tcgagtag                2448
```

<210> SEQ ID NO 5
<211> LENGTH: 2382
<212> TYPE: DNA
<213> ORGANISM: Lactobacillus casei
<220> FEATURE:
<223> OTHER INFORMATION: PHK

<400> SEQUENCE: 5

```
atggatacaa aagtaaagac tgttgattac tcatccaagg aatactttga caagatgacc     60
```

-continued

```
gcttattggc gggcagccaa ctatatttca gttggtcaac tttatttgaa ggacaacccg    120
ctgctggaac ggccactgaa gagcgaagac gtcaagccgc atccgatcgg ccattggggc    180
acgattgctg ggcagaactt catttatacc cacttgaacc gggtgatcaa taagtatgac    240
ttgaacatgt tttatattga aggcccgggt catggcggcc aagtgatggt ttccaattcc    300
tatctagacg gttcgtattc ggagatttat ccgcgtgtgt cgcaggataa agaaggcatg    360
aagaacctat ttacgcagtt ctcatggcca ggtggcgttg cttcacatgc gagtgcacaa    420
acgccaggtt ccatccatga aggtggcgaa ttaggttatg ctttgagtca cgcaaccggc    480
gcgattcttg ataatcctga ggtcatcgcg gcggttgtca cgggtgatgg tgaaactgaa    540
accggcccat tggctgcatc atggttcagc aatacgttca ttaacccaat cacggatggc    600
gcgattttac cgattgtgca tatgaacggg tttaagattt ccaacccaac tatcttgtca    660
cgtaagtcag atgaagatct agacaaatac ttcagtggta tgggttggaa gccattcttc    720
gttgaaggcg atgatccaga gaagctgaat ccggaaatgg ctaaagtttt ggatgaagca    780
attgaagaca ttaaggccat tcagaaacat gcacgtgaga ctggcgacac cacgatgcca    840
cactggccag tgattatttt ccggtcacca aagggctgga caggcccgaa gagttggaat    900
ggcgaaccaa tcgaaggttc cttccgtgcg caccagattc cgattcctgt cgacgctgaa    960
gacatggaac acgctgattc cttggcaggc tggctgaagt cctaccatcc agaggaactg   1020
ttcgatgaaa acggcaagtt gatccctgaa ttggctgcat tgccgccaaa gggtgagcag   1080
cggatggctg ctaacccaat tacgaacggt gggattgatc cgaagccgtt ggtattgcca   1140
gattatcgca agtatgcgct ggacaacaag gaacacggca agcagattaa gcaagacatg   1200
atcgtgtggt ctgattatct gcgtgatttg atcaagctga atccgcataa tttccggatc   1260
tttggccctg acgaaaccat gagtaaccgg ttgtatagct tgtttgaagt gaccaaccgt   1320
caatggctgg aaccaatcaa ggaaccggct gaccaatatt tggcaccggc tggccggatt   1380
attgactcgc agttgtccga acatcaggcg gaaggcttta acgaaggcta cacgttgacc   1440
ggccgtcatg gcttattcac cagttacgaa gctttcctcc gggtcgtcga ttccatgctc   1500
actcagcact tcaagtggat tcggaaggca catgaagaac catggcataa ggcttatcca   1560
agtctgaacg tggtctcaac atcgacttcc ttccagcagg atcacaatgg gtacacccat   1620
caggacccag gtattttgac acacatggct gaaaagaagg ctgaatacat tcgcgagtat   1680
ctaccagctg atgccaacag cttgctggcc atttctccga agttgttcag ctcacaaaat   1740
accgtgaacg tgctcatcac atccaagcag ccgcggccac agttctatag cattgatgaa   1800
gccactgttt tggctaattc cggcttgaag cggattgatt gggcttccaa tgatgatggc   1860
gtcgaaccag atgttgtcat tgccgctgcc ggaaccgaac caaacatgga aagtcttgct   1920
gccattaact tgctgcacga cgccttccca gatttgaaga ttcgcttcat taacgtggtt   1980
gacctgctga agctgcgcag tccggaaatc gatccgcgcg gtttgagtga tgctgaattc   2040
aacagctact tcaccaccga caaaccgatc ctcttcgctt atcatggctt tgaagggttg   2100
attcgcgaca tcttcttcac tcgcccgaat cgcaatgtgc tgattcacgg ctatcgtgaa   2160
gaaggtgaca ttaccacacc atttgacatg cgggtactca acgaacttga ccgttaccac   2220
ttggccaagg atgttattca gcatgtgcca gcctacgctg aaaaggctgc cgcgtttgtt   2280
cagaagatgg atgatacctt gcaatatcat catgacttca tccgcgcaaa cggcgatgat   2340
attccagaag ttcaggaatg gacctggaaa ccaatcaagt aa                      2382
```

<210> SEQ ID NO 6
<211> LENGTH: 2391
<212> TYPE: DNA
<213> ORGANISM: Lactobacillus plantarum
<220> FEATURE:
<223> OTHER INFORMATION: PHK2

<400> SEQUENCE: 6

```
atgagtgaag caattaaatc caaaacagtt gattactctt ctgatgaata tctaaaacgc      60

gttgatgaat attggcgtgc tgctaactac atctcagttg gtcaactcta tctactaaat     120

aacccgttac ttcgggaacc actaaaggcg accgacgtga aagttcatcc aatcggccat     180

tggggcacga ttgctggtca aactttatt  tatgcccatt taaaccgggc aatcaataag     240

tatggcttga acatgttcta cattgaaggc cctggtcatg gtggtcaagt aatggtttct     300

aactcctact tagatggcac ctatacggaa acgtatccta aaatcaccca agacaaagct     360

gggatgaaac gcttattcaa gcaattctca ttcccaggcg gggttgcttc ccatgccgat     420

cctaagacgc ctggttcgat ccatgaaggt ggcgaacttg gctactcaat cctgcatggt     480

gctggtgcag tattagataa tccaggttta attgccgcta ccgttgttgg tgatggtgaa     540

tctgaaactg ggccattggc aacttcttgg caagttaaca agttccttaa cccaattaca     600

gacgggacag tcttgccaat cttgaactta aacggcttca agatttctaa tccaacagtt     660

ctttcacgtg aatcacatga agaacttgaa gactacttta aaggtctagg ctgggatcca     720

cactttgttg aaggtacaga ccctgccaag atgcacaaaa ttatggctga agaattggat     780

aaagtcattg aagaaatcca cgcaattcgt aagaacgcca aggataacaa tgatgaatct     840

cgtcctaagt ggccaatgat tgttttccgg gcacctaagg gctggaccgg tcctaagagt     900

tgggacggcg aaccaattga aggttcattc cgggctcacc aaattccaat tcctgtcgat     960

cgcaatcaca tggaacacgc cgacaaatta gttgactggc tcaaatcata caaaccagaa    1020

gaattatttg atgaaaatgg tactttaaaa ccagaaattg ccgcaatcat ccctgaaggc    1080

caagctcgta tggctgctaa ccccgttact aacggcggta agttaactaa agacttaatt    1140

acaccaaata tcgatgatta tgctttggac aacaagagtc acggtaagga agacggttca    1200

gacatgactg aacttggtaa gtatatccgt gatttaattg agttgaacaa agacaacaag    1260

aacttccgtg gctggggtcc tgacgaaacc ttatctaaca aactaggcgc tgcttttgaa    1320

gataccaaac gtcagtggat ggaaccaatc cacgaaccta atgatgcttt gttagcacct    1380

caaggccgga ttattgactc catgttgtca gaacacatgg atgaagggat gttggaagct    1440

tacaatttaa ccggacgtta cggtttcttc gcaagttatg aatcattcct gcgcgttgtg    1500

gattcaatgt taacccaaca cttcaagtgg ttacggaatt ctcacgaaga aaccccttgg    1560

cgggctgatg taccttcact gaatgtgatt gcatcatcaa cagccttcca acaagatcac    1620

aatggttact ctcaccaaga tccaggtatc atttcacact tggctgaaaa gaagaccgaa    1680

tacgttcgtg cctatcttcc aggtgatgcc aatactttga ttgcaacctt tgataaggct    1740

atccaaagca aacaattgat taatttaatc attgccagca agcaccctcg tccacaatgg    1800

ttcacaatgg acgaagctaa gcgcttagtt cgtgatggcc ttggtgttgt tgattgggca    1860

agcactgatc atggtgaaga acccgacgtt gtcttcgcaa ctgccggctc tgaaccaacg    1920

actgaaagct tagctgccgt atcaatcttg catgcacgct tccctgaaat gaagattcgc    1980

ttcattaacg ttgttgatct tctgaagctg aagaaagacg accctcgtgg tttatcagat    2040

gctgaatttg atgctttctt cactaaggac aaaccagtta tctttgctta tcatgcatac    2100
```

gacgacttag taaagaccat cttcttcgat cgccataacc ataacttaca cgttcatggt 2160
taccgcgaag aaggcgacat tacaacgcca ttcgacatgc gtgttcgcaa cgaactcgat 2220
cgtttccact tagtcaaagc tgccttatta gcaacgccag cttatgccga aaaaggtgcc 2280
catgtcattc aagagatgaa cagcatttta gacaagcatc atgactatat ccgtgctgaa 2340
ggtaccgata ttccagaagt tgaaaactgg aaatggactg cattgaagta g 2391

<210> SEQ ID NO 7
<211> LENGTH: 2367
<212> TYPE: DNA
<213> ORGANISM: Lactobacillus plantarum
<220> FEATURE:
<223> OTHER INFORMATION: PHK1

<400> SEQUENCE: 7
atgacaacag attactcatc accagcatat ttgcaaaaag ttgataagta ctggcgtgct 60
gccaactact tatcagttgg tcaactttat ttaaaagata atccactatt acaacggcca 120
ttgaaggcca gtgacgttaa ggttcatcca attggtcact gggggacgat tgccggtcaa 180
aactttatct atgctcatct taaccgggtc atcaacaagt acggtttgaa gatgttctac 240
gttgaaggtc caggtcatgg tggtcaagtg atggtttcaa actcttacct tgacggtact 300
tacaccgata tttatccaga aattacgcag gatgttgaag ggatgcaaaa gctcttcaag 360
caattctcat tcccaggtgg ggttgcttcc catgcggcac ctgaaacacc cggttcaatc 420
cacgaaggtg gcgaacttgg ttactcaatt tcacacgggg ttggggcaat tcttgacaat 480
cctgacgaaa tcgccgcggt tgttgttggt gatggggaat ccgaaacggg tccattagca 540
acttcatggc aatcaacgaa gttcattaac ccaatcaacg acggggctgt tttaccaatc 600
ttgaacttaa atggttttaa gatttctaat ccaacgattt ttggtcggac ttctgatgct 660
aagattaagg aatacttcga aagcatgaat tgggaaccaa tcttcgttga aggtgacgat 720
cctgaaaagg ttcacccagc cttagctaag gccatggatg aagccgttga aaagatcaag 780
gcaatccaga agcatgctcg cgaaaataac gatgcaacat tgccagtatg gccaatgatc 840
gtcttccgcg cacctaaggg ctggactggt ccgaagtcat gggacggtga taagatcgaa 900
ggttcattcc gtgctcatca aattccgatt cctgttgatc aaaatgacat ggaacatgcg 960
gatgctttag ttgattggct cgaatcatat caaccaaaag aactcttcaa tgaagatggc 1020
tctttgaagg atgatattaa agaaattatt cctactgggg acagtcggat ggctgctaac 1080
ccaatcacca atggtggggt cgatccgaaa gccttgaact taccaaactt ccgtgattat 1140
gcggtcgata cgtccaaaga aggcgcgaat gttaagcaag atatgatcgt ttggtcagac 1200
tatttgcggg atgtcatcaa gaaaaatcct gataacttcc ggttgttcgg acctgatgaa 1260
accatgtcta accgtttata tggtgtcttc gaaaccacta atcgtcaatg gatggaagac 1320
attcatccag atagtgacca atatgaagca ccagctggcc gggtcttaga tgctcagtta 1380
tctgaacacc aagctgaagg ttggttagaa ggttacgtct taactggacg tcatgggtta 1440
tttgccagtt atgaagcctt cctacgcgtt gtggactcaa tgttgacgca acacttcaag 1500
tggttacgta aagccaatga acttgattgg cgtaaaaagt acccatcact taacattatc 1560
gcggcttcaa ctgtattcca acaagaccat aatggttata cccaccaaga tccaggtgca 1620
ttaactcatt tggccgaaaa gaaaccagaa tacattcgtg aatatttacc agccgatgcc 1680
aacacgttat tagctgtcgg tgacgtcatt ttccggagcc aagaaaagat caactacgtg 1740
gttacgtcaa aacacccacg tcaacaatgg ttcagcattg aagaagctaa gcaattagtt 1800

```
gacaatggtc ttggtatcat tgattgggca agtacggacc aaggtagcga accagacatt   1860

gtctttgcag ctgctgggac ggaaccaacg cttgaaacgt tggctgccat ccaattacta   1920

cacgacagtt tcccagagat gaagattcgt ttcgtgaacg tggtcgacat cttgaagtta   1980

cgtagtcctg aaaaggatcc gcggggcttg tcagatgctg agtttgacca ttactttact   2040

aaggacaaac cagtggtctt tgctttccac ggttacgaag acttagttcg tgacatcttc   2100

tttgatcgtc acaaccataa cttatacgtc cacggttacc gtgaaaatgg tgatattacc   2160

acaccattcg acgtacgggt catgaaccag atggaccgct tcgacttagc taagtcggca   2220

attgcggcgc aaccagcaat ggaaaacact ggtgcggcct tcgttcaatc catggataat   2280

atgcttgcta aacacaatgc ctatatccgg gatgccggaa ctgacttgcc agaagttaat   2340

gattggcaat ggaagggttt aaaataa                                       2367
```

<210> SEQ ID NO 8
<211> LENGTH: 2478
<212> TYPE: DNA
<213> ORGANISM: Bifidobacterium adolescentis
<220> FEATURE:
<223> OTHER INFORMATION: PHK

<400> SEQUENCE: 8

```
atgacgagtc ctgttattgg caccccttgg aagaagctga acgctccggt ttccgaggaa     60

gctatcgaag gcgtggataa gtactggcgc gcagccaact acctctccat cggccagatc    120

tatctgcgta gcaacccgct gatgaaggag cctttcaccc gcgaagacgt caagcaccgt    180

ctggtcggtc actggggcac caccccgggc ctgaacttcc tcatcggcca catcaaccgt    240

ctcattgctg atcaccagca gaacactgtg atcatcatgg gcccgggcca cggcggcccg    300

gctggtaccg ctcagtccta cctggacggc acctacaccg agtacttccc gaacatcacc    360

aaggatgagg ctggcctgca gaagttcttc cgccagttct cctacccggg tggcatcccg    420

tcccactacg ctccggagac cccgggctcc atccacgaag gcggcgagct gggttacgcc    480

ctgtcccacg cctacggcgc tgtgatgaac aacccgagcc tgttcgtccc ggccatcgtc    540

ggcgacggtg aagctgagac cggcccgctg gccaccggct ggcagtccaa caagctcatc    600

aacccgcgca ccgacggtat cgtgctgccg atcctgcacc tcaacggcta caagatcgcc    660

aacccgacca tcctgtcccg catctccgac gaagagctcc acgagttctt ccacggcatg    720

ggctatgagc cgtacgagtt cgtcgctggc ttcgacaacg aggatcacct gtcgatccac    780

cgtcgtttcg ccgagctgtt cgagaccgtc ttcgacgaga tctgcgacat caaggccgcc    840

gctcagaccg acgacatgac tcgtccgttc tacccgatga tcatcttccg taccccgaag    900

ggctggacct gcccgaagtt catcgacggc aagaagaccg agggctcctg gcgttcccac    960

caggtgccgc tggcttccgc ccgcgatacc gaggcccact tcgaggtcct caagaactgg   1020

ctcgagtcct acaagccgga agagctgttc gacgagaacg gcgccgtgaa gccggaagtc   1080

accgccttca tgccgaccgg cgaactgcgc atcggtgaga acccgaacgc caacggtggc   1140

cgcatccgcg aagagctgaa gctgccgaag ctggaagact acgaggtcaa ggaagtcgcc   1200

gagtacggcc acggctgggg ccagctcgag gccacccgtc gtctgggcgt ctacacccgc   1260

gacatcatca agaacaaccc ggactccttc cgtatcttcg gaccggatga gaccgcttcc   1320

aaccgtctgc aggccgctta cgacgtcacc aacaagcagt gggacgccgg ctacctgtcc   1380

gctcaggtcg acgagcacat ggctgtcacc ggccaggtca ccgagcagct ttccgagcac   1440
```

-continued

```
cagatggaag gcttcctcga gggctacctg ctgaccggcc gtcacggcat ctggagctcc   1500

tatgagtcct tcgtgcacgt gatcgactcc atgctgaacc agcacgccaa gtggctcgag   1560

gctaccgtcc gcgagattcc gtggcgcaag ccgatctcct ccatgaacct gctcgtctcc   1620

tcccacgtgt ggcgtcagga tcacaacggc ttctcccacc aggatccggg tgtcacctcc   1680

gtcctgctga acaagtgctt caacaacgat cacgtgatcg gcatctactt cccggtggat   1740

tccaacatgc tgctcgctgt ggctgagaag tgctacaagt ccaccaacaa gatcaacgcc   1800

atcatcgccg gcaagcagcc ggccgccacc tggctgaccc tggacgaagc tcgcgccgag   1860

ctcgagaagg gtgctgccga gtggaagtgg gcttccaacg tgaagtccaa cgatgaggct   1920

cagatcgtgc tcgccgccac cggtgatgtt ccgactcagg aaatcatggc cgctgccgac   1980

aagctggacg ccatgggcat caagttcaag gtcgtcaacg tggttgacct ggtcaagctg   2040

cagtccgcca aggagaacaa cgaggccctc tccgatgagg agttcgctga gctgttcacc   2100

gaggacaagc cggtcctgtt cgcttaccac tcctatgccc gcgatgtgcg tggtctgatc   2160

tacgatcgcc cgaaccacga caacttcaac gttcacggct acgaggagca gggctccacc   2220

accaccccgt acgacatggt tcgcgtgaac aacatcgatc gctacgagct ccaggctgaa   2280

gctctgcgca tgattgacgc tgacaagtac gccgacaaga tcaacgagct cgaggccttc   2340

cgtcaggaag ccttccagtt cgctgtcgac aacggctacg atcacccgga ttacaccgac   2400

tgggtctact ccggtgtcaa caccaacaag cagggtgcta tctccgctac cgccgcaacc   2460

gctggcgata acgagtga                                                 2478
```

```
<210> SEQ ID NO 9
<211> LENGTH: 788
<212> TYPE: PRT
<213> ORGANISM: Lactobacillus plantarum
<220> FEATURE:
<223> OTHER INFORMATION: PHK1

<400> SEQUENCE: 9

Met Thr Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Asn Pro Leu Leu Gln Arg Pro Leu Lys Ala Ser Asp Val Lys Val
        35                  40                  45

His Pro Ile Gly His Trp Gly Thr Ile Ala Gly Gln Asn Phe Ile Tyr
    50                  55                  60

Ala His Leu Asn Arg Val Ile Asn Lys Tyr Gly Leu Lys Met Phe Tyr
65                  70                  75                  80

Val Glu Gly Pro Gly His Gly Gly Gln Val Met Val Ser Asn Ser Tyr
                85                  90                  95

Leu Asp Gly Thr Tyr Thr Asp Ile Tyr Pro Glu Ile Thr Gln Asp Val
            100                 105                 110

Glu Gly Met Gln Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ser Ile Ser His Gly Val Gly Ala Ile Leu Asp Asn
145                 150                 155                 160

Pro Asp Glu Ile Ala Ala Val Val Val Gly Asp Gly Glu Ser Glu Thr
                165                 170                 175
```

```
Gly Pro Leu Ala Thr Ser Trp Gln Ser Thr Lys Phe Ile Asn Pro Ile
            180                 185                 190

Asn Asp Gly Ala Val Leu Pro Ile Leu Asn Leu Asn Gly Phe Lys Ile
        195                 200                 205

Ser Asn Pro Thr Ile Phe Gly Arg Thr Ser Asp Ala Lys Ile Lys Glu
    210                 215                 220

Tyr Phe Glu Ser Met Asn Trp Glu Pro Ile Phe Val Glu Gly Asp Asp
225                 230                 235                 240

Pro Glu Lys Val His Pro Ala Leu Ala Lys Ala Met Asp Glu Ala Val
                245                 250                 255

Glu Lys Ile Lys Ala Ile Gln Lys His Ala Arg Glu Asn Asn Asp Ala
            260                 265                 270

Thr Leu Pro Val Trp Pro Met Ile Val Phe Arg Ala Pro Lys Gly Trp
        275                 280                 285

Thr Gly Pro Lys Ser Trp Asp Gly Asp Lys Ile Glu Gly Ser Phe Arg
    290                 295                 300

Ala His Gln Ile Pro Ile Pro Val Asp Gln Asn Asp Met Glu His Ala
305                 310                 315                 320

Asp Ala Leu Val Asp Trp Leu Glu Ser Tyr Gln Pro Lys Glu Leu Phe
                325                 330                 335

Asn Glu Asp Gly Ser Leu Lys Asp Asp Ile Lys Glu Ile Ile Pro Thr
            340                 345                 350

Gly Asp Ser Arg Met Ala Ala Asn Pro Ile Thr Asn Gly Gly Val Asp
        355                 360                 365

Pro Lys Ala Leu Asn Leu Pro Asn Phe Arg Asp Tyr Ala Val Asp Thr
    370                 375                 380

Ser Lys Glu Gly Ala Asn Val Lys Gln Asp Met Ile Val Trp Ser Asp
385                 390                 395                 400

Tyr Leu Arg Asp Val Ile Lys Lys Asn Pro Asp Asn Phe Arg Leu Phe
                405                 410                 415

Gly Pro Asp Glu Thr Met Ser Asn Arg Leu Tyr Gly Val Phe Glu Thr
            420                 425                 430

Thr Asn Arg Gln Trp Met Glu Asp Ile His Pro Asp Ser Asp Gln Tyr
        435                 440                 445

Glu Ala Pro Ala Gly Arg Val Leu Asp Ala Gln Leu Ser Glu His Gln
    450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr
                485                 490                 495

Gln His Phe Lys Trp Leu Arg Lys Ala Asn Glu Leu Asp Trp Arg Lys
            500                 505                 510

Lys Tyr Pro Ser Leu Asn Ile Ile Ala Ala Ser Thr Val Phe Gln Gln
        515                 520                 525

Asp His Asn Gly Tyr Thr His Gln Asp Pro Gly Ala Leu Thr His Leu
    530                 535                 540

Ala Glu Lys Lys Pro Glu Tyr Ile Arg Glu Tyr Leu Pro Ala Asp Ala
545                 550                 555                 560

Asn Thr Leu Leu Ala Val Gly Asp Val Ile Phe Arg Ser Gln Glu Lys
                565                 570                 575

Ile Asn Tyr Val Val Thr Ser Lys His Pro Arg Gln Gln Trp Phe Ser
            580                 585                 590

Ile Glu Glu Ala Lys Gln Leu Val Asp Asn Gly Leu Gly Ile Ile Asp
```

```
        595                 600                 605

Trp Ala Ser Thr Asp Gln Gly Ser Glu Pro Asp Ile Val Phe Ala Ala
    610                 615                 620

Ala Gly Thr Glu Pro Thr Leu Glu Thr Leu Ala Ala Ile Gln Leu Leu
625                 630                 635                 640

His Asp Ser Phe Pro Glu Met Lys Ile Arg Phe Val Asn Val Val Asp
                645                 650                 655

Ile Leu Lys Leu Arg Ser Pro Glu Lys Asp Pro Arg Gly Leu Ser Asp
            660                 665                 670

Ala Glu Phe Asp His Tyr Phe Thr Lys Asp Lys Pro Val Val Phe Ala
        675                 680                 685

Phe His Gly Tyr Glu Asp Leu Val Arg Asp Ile Phe Phe Asp Arg His
    690                 695                 700

Asn His Asn Leu Tyr Val His Gly Tyr Arg Glu Asn Gly Asp Ile Thr
705                 710                 715                 720

Thr Pro Phe Asp Val Arg Val Met Asn Gln Met Asp Arg Phe Asp Leu
                725                 730                 735

Ala Lys Ser Ala Ile Ala Ala Gln Pro Ala Met Glu Asn Thr Gly Ala
            740                 745                 750

Ala Phe Val Gln Ser Met Asp Asn Met Leu Ala Lys His Asn Ala Tyr
        755                 760                 765

Ile Arg Asp Ala Gly Thr Asp Leu Pro Glu Val Asn Asp Trp Gln Trp
    770                 775                 780

Lys Gly Leu Lys
785


<210> SEQ ID NO 10
<211> LENGTH: 556
<212> TYPE: PRT
<213> ORGANISM: Bifidobacterium adolescentis
<220> FEATURE:
<223> OTHER INFORMATION: PTA

<400> SEQUENCE: 10

Met Ser Phe Thr Ser Val Thr Ile Ile Ser Pro Glu Ala Ala Asn Gly
1               5                   10                  15

Arg Asn Val Val Ala Leu Gly Val Thr Lys Thr Leu Ala Ala Ala Gly
            20                  25                  30

Lys Thr Gly Val Phe Arg Pro Ala Val Cys Arg Lys Asp Thr Phe Thr
        35                  40                  45

Asp Val Leu Ile Glu Ala Ser Asn Ala Gly Leu Ser Arg Glu Gln Ser
    50                  55                  60

Val Gly Val Cys Pro Lys Arg Ala Arg Asn Asp Lys Glu Gly Ser Arg
65                  70                  75                  80

Ala Asp Ile Val Ala Ala Tyr Thr Gln Ala Val Glu Thr Ala Arg Pro
                85                  90                  95

Asp Ala Met Val Ile Val Gly Thr Asp Arg Ser Ala Val Asn Asp Pro
            100                 105                 110

Ala Met Phe Ser Phe Asn Ala Asp Val Ala Ala Asp Leu Gln Ser Pro
        115                 120                 125

Val Leu Leu Ala Val Cys Thr Ile Glu Arg Thr Pro Glu Gln Val Lys
    130                 135                 140

Ser Thr Val Glu Ala Ser Thr Lys Val Ile Glu Asp Ala Gly Ser Lys
145                 150                 155                 160

Val Val Gly Val Phe Ile Thr Gly Cys Asp Asp Thr Gln Pro Asn Pro
```

```
                165                 170                 175

Leu Lys Ala Cys Phe Val Asp Tyr Pro Val Pro Val Trp Thr Leu Pro
            180                 185                 190

Ala Val Asp Phe Asn Asp Asp Asp Ala Ile Ser Lys Ala Asp Glu Ala
        195                 200                 205

Phe Ala Thr Asn Val Asp Ala Val Glu Leu Thr Val Ala Leu Glu Ser
    210                 215                 220

Pro Phe Asp Ala Pro Thr Thr Pro Tyr Ala Phe Gln Tyr Gly Leu Leu
225                 230                 235                 240

Gly Lys Ala Lys Ala Asp Lys Lys Thr Ile Val Leu Pro Glu Gly Asn
                245                 250                 255

Glu Asp Arg Ile Ile Lys Ala Ala Asp Tyr Leu Leu Glu Arg Asp Ile
            260                 265                 270

Val Asp Leu Ile Ile Val Gly Asp Glu Asn Ala Ile Leu Ala Arg Gly
        275                 280                 285

Gln Glu Leu Gly Leu Lys Ser Leu Gly Lys Ala Lys Phe Gln Ala Lys
    290                 295                 300

Asp Asp Glu Thr Val Leu Glu Pro Met Val Ala Lys Leu Cys Glu Leu
305                 310                 315                 320

Arg Ala Lys Lys Gly Met Thr Glu Glu Gln Ala Arg Lys Gln Leu Ala
                325                 330                 335

Asp Asp Ser Tyr Phe Gly Thr Met Leu Val Val Met Gly Met Ala Asp
            340                 345                 350

Gly Leu Val Ser Gly Ser Val Asn Ser Thr Ala Asn Thr Val Arg Pro
        355                 360                 365

Ala Leu Gln Val Ile Lys Thr Lys Pro Gly Thr Ser Leu Val Ser Gly
    370                 375                 380

Ala Phe Leu Met Cys Phe Lys Asp His Ala Ala Val Phe Ala Asp Cys
385                 390                 395                 400

Ala Ile Asn Leu Asn Pro Asn Ala Glu Gln Leu Ala Glu Ile Ala Ile
                405                 410                 415

Gln Ser Ala Glu Thr Ala Lys Ala Phe Gly Leu Glu Pro Lys Val Gly
            420                 425                 430

Met Leu Ser Tyr Ser Thr Leu Gly Ser Gly Lys Gly Pro Asp Val Asp
        435                 440                 445

Leu Val Glu Glu Ala Thr Thr Ile Val Lys Asp Lys Ala Pro Asp Leu
    450                 455                 460

Ala Val Val Gly Ser Ile Gln Phe Asp Ala Ala Trp Ser Pro Thr Val
465                 470                 475                 480

Ala Ala Thr Lys Ala Lys Gly Asp Pro Val Ala Gly His Val Asn Val
                485                 490                 495

Phe Val Phe Pro Asp Leu Cys Ala Gly Asn Ile Ala Tyr Lys Ala Val
            500                 505                 510

Gln Arg Ser Ser Gly Ala Ala Ala Val Gly Pro Val Leu Gln Gly Leu
        515                 520                 525

Asn Arg Pro Val Asn Asp Leu Ser Arg Gly Ala Thr Val Gln Asp Ile
    530                 535                 540

Ile Asn Thr Ile Ala Leu Thr Ala Ile Glu Ala Gln
545                 550                 555
```

<210> SEQ ID NO 11
<211> LENGTH: 793
<212> TYPE: PRT
<213> ORGANISM: Lactobacillus casei

<220> FEATURE:
<223> OTHER INFORMATION: PHK

<400> SEQUENCE: 11

```
Met Asp Thr Lys Val Lys Thr Val Asp Tyr Ser Ser Lys Glu Tyr Phe
1               5                   10                  15

Asp Lys Met Thr Ala Tyr Trp Arg Ala Ala Asn Tyr Ile Ser Val Gly
            20                  25                  30

Gln Leu Tyr Leu Lys Asp Asn Pro Leu Leu Glu Arg Pro Leu Lys Ser
        35                  40                  45

Glu Asp Val Lys Pro His Pro Ile Gly His Trp Gly Thr Ile Ala Gly
    50                  55                  60

Gln Asn Phe Ile Tyr Thr His Leu Asn Arg Val Ile Asn Lys Tyr Asp
65                  70                  75                  80

Leu Asn Met Phe Tyr Ile Glu Gly Pro Gly His Gly Gly Gln Val Met
                85                  90                  95

Val Ser Asn Ser Tyr Leu Asp Gly Ser Tyr Ser Glu Ile Tyr Pro Arg
            100                 105                 110

Val Ser Gln Asp Lys Glu Gly Met Lys Asn Leu Phe Thr Gln Phe Ser
        115                 120                 125

Trp Pro Gly Gly Val Ala Ser His Ala Ser Ala Gln Thr Pro Gly Ser
    130                 135                 140

Ile His Glu Gly Gly Glu Leu Gly Tyr Ala Leu Ser His Ala Thr Gly
145                 150                 155                 160

Ala Ile Leu Asp Asn Pro Glu Val Ile Ala Ala Val Val Thr Gly Asp
                165                 170                 175

Gly Glu Thr Glu Thr Gly Pro Leu Ala Ala Ser Trp Phe Ser Asn Thr
            180                 185                 190

Phe Ile Asn Pro Ile Thr Asp Gly Ala Ile Leu Pro Ile Val His Met
        195                 200                 205

Asn Gly Phe Lys Ile Ser Asn Pro Thr Ile Leu Ser Arg Lys Ser Asp
    210                 215                 220

Glu Asp Leu Asp Lys Tyr Phe Ser Gly Met Gly Trp Lys Pro Phe Phe
225                 230                 235                 240

Val Glu Gly Asp Asp Pro Glu Lys Leu Asn Pro Glu Met Ala Lys Val
                245                 250                 255

Leu Asp Glu Ala Ile Glu Asp Ile Lys Ala Ile Gln Lys His Ala Arg
            260                 265                 270

Glu Thr Gly Asp Thr Thr Met Pro His Trp Pro Val Ile Ile Phe Arg
        275                 280                 285

Ser Pro Lys Gly Trp Thr Gly Pro Lys Ser Trp Asn Gly Glu Pro Ile
    290                 295                 300

Glu Gly Ser Phe Arg Ala His Gln Ile Pro Ile Pro Val Asp Ala Glu
305                 310                 315                 320

Asp Met Glu His Ala Asp Ser Leu Ala Gly Trp Leu Lys Ser Tyr His
                325                 330                 335

Pro Glu Glu Leu Phe Asp Glu Asn Gly Lys Leu Ile Pro Glu Leu Ala
            340                 345                 350

Ala Leu Pro Pro Lys Gly Glu Gln Arg Met Ala Ala Asn Pro Ile Thr
        355                 360                 365

Asn Gly Gly Ile Asp Pro Lys Pro Leu Val Leu Pro Asp Tyr Arg Lys
    370                 375                 380

Tyr Ala Leu Asp Asn Lys Glu His Gly Lys Gln Ile Lys Gln Asp Met
385                 390                 395                 400
```

```
Ile Val Trp Ser Asp Tyr Leu Arg Asp Leu Ile Lys Leu Asn Pro His
                405                 410                 415

Asn Phe Arg Ile Phe Gly Pro Asp Glu Thr Met Ser Asn Arg Leu Tyr
            420                 425                 430

Ser Leu Phe Glu Val Thr Asn Arg Gln Trp Leu Glu Pro Ile Lys Glu
        435                 440                 445

Pro Ala Asp Gln Tyr Leu Ala Pro Ala Gly Arg Ile Ile Asp Ser Gln
    450                 455                 460

Leu Ser Glu His Gln Ala Glu Gly Phe Asn Glu Gly Tyr Thr Leu Thr
465                 470                 475                 480

Gly Arg His Gly Leu Phe Thr Ser Tyr Glu Ala Phe Leu Arg Val Val
                485                 490                 495

Asp Ser Met Leu Thr Gln His Phe Lys Trp Ile Arg Lys Ala His Glu
            500                 505                 510

Glu Pro Trp His Lys Ala Tyr Pro Ser Leu Asn Val Val Ser Thr Ser
        515                 520                 525

Thr Ser Phe Gln Gln Asp His Asn Gly Tyr Thr His Gln Asp Pro Gly
    530                 535                 540

Ile Leu Thr His Met Ala Glu Lys Lys Ala Glu Tyr Ile Arg Glu Tyr
545                 550                 555                 560

Leu Pro Ala Asp Ala Asn Ser Leu Leu Ala Ile Ser Pro Lys Leu Phe
                565                 570                 575

Ser Ser Gln Asn Thr Val Asn Val Leu Ile Thr Ser Lys Gln Pro Arg
            580                 585                 590

Pro Gln Phe Tyr Ser Ile Asp Glu Ala Thr Val Leu Ala Asn Ser Gly
        595                 600                 605

Leu Lys Arg Ile Asp Trp Ala Ser Asn Asp Asp Gly Val Glu Pro Asp
    610                 615                 620

Val Val Ile Ala Ala Ala Gly Thr Glu Pro Asn Met Glu Ser Leu Ala
625                 630                 635                 640

Ala Ile Asn Leu Leu His Asp Ala Phe Pro Asp Leu Lys Ile Arg Phe
                645                 650                 655

Ile Asn Val Val Asp Leu Leu Lys Leu Arg Ser Pro Glu Ile Asp Pro
            660                 665                 670

Arg Gly Leu Ser Asp Ala Glu Phe Asn Ser Tyr Phe Thr Thr Asp Lys
        675                 680                 685

Pro Ile Leu Phe Ala Tyr His Gly Phe Glu Gly Leu Ile Arg Asp Ile
    690                 695                 700

Phe Phe Thr Arg Pro Asn Arg Asn Val Leu Ile His Gly Tyr Arg Glu
705                 710                 715                 720

Glu Gly Asp Ile Thr Thr Pro Phe Asp Met Arg Val Leu Asn Glu Leu
                725                 730                 735

Asp Arg Tyr His Leu Ala Lys Asp Val Ile Gln His Val Pro Ala Tyr
            740                 745                 750

Ala Glu Lys Ala Ala Ala Phe Val Gln Lys Met Asp Asp Thr Leu Gln
        755                 760                 765

Tyr His His Asp Phe Ile Arg Ala Asn Gly Asp Asp Ile Pro Glu Val
    770                 775                 780

Gln Glu Trp Thr Trp Lys Pro Ile Lys
785                 790
```

<210> SEQ ID NO 12
<211> LENGTH: 825

```
<212> TYPE: PRT
<213> ORGANISM: Bifidobacterium adolescentis
<220> FEATURE:
<223> OTHER INFORMATION: PHK

<400> SEQUENCE: 12

Met Thr Ser Pro Val Ile Gly Thr Pro Trp Lys Lys Leu Asn Ala Pro
1               5                   10                  15

Val Ser Glu Glu Ala Ile Glu Gly Val Asp Lys Tyr Trp Arg Ala Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Ile Met Gly Pro Gly
                85                  90                  95

His Gly Gly Pro Ala Gly Thr Ala Gln Ser Tyr Leu Asp Gly Thr Tyr
            100                 105                 110

Thr Glu Tyr Phe Pro Asn Ile Thr Lys Asp Glu Ala Gly Leu Gln Lys
        115                 120                 125

Phe Phe Arg Gln Phe Ser Tyr Pro Gly Gly Ile Pro Ser His Tyr Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Ile Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asn Glu Asp His
                245                 250                 255

Leu Ser Ile His Arg Arg Phe Ala Glu Leu Phe Glu Thr Val Phe Asp
            260                 265                 270

Glu Ile Cys Asp Ile Lys Ala Ala Ala Gln Thr Asp Asp Met Thr Arg
        275                 280                 285

Pro Phe Tyr Pro Met Ile Ile Phe Arg Thr Pro Lys Gly Trp Thr Cys
    290                 295                 300

Pro Lys Phe Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Glu
            340                 345                 350

Asn Gly Ala Val Lys Pro Glu Val Thr Ala Phe Met Pro Thr Gly Glu
        355                 360                 365

Leu Arg Ile Gly Glu Asn Pro Asn Ala Asn Gly Gly Arg Ile Arg Glu
    370                 375                 380
```

-continued

```
Glu Leu Lys Leu Pro Lys Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Ile Lys Asn Asn Pro Asp Ser Phe Arg Ile
            420                 425                 430

Phe Gly Pro Asp Glu Thr Ala Ser Asn Arg Leu Gln Ala Ala Tyr Asp
        435                 440                 445

Val Thr Asn Lys Gln Trp Asp Ala Gly Tyr Leu Ser Ala Gln Val Asp
    450                 455                 460

Glu His Met Ala Val Thr Gly Gln Val Thr Glu Gln Leu Ser Glu His
465                 470                 475                 480

Gln Met Glu Gly Phe Leu Glu Gly Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Met Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Cys Phe Asn Asn Asp His Val Ile Gly Ile Tyr
                565                 570                 575

Phe Pro Val Asp Ser Asn Met Leu Leu Ala Val Ala Glu Lys Cys Tyr
            580                 585                 590

Lys Ser Thr Asn Lys Ile Asn Ala Ile Ile Ala Gly Lys Gln Pro Ala
        595                 600                 605

Ala Thr Trp Leu Thr Leu Asp Glu Ala Arg Ala Glu Leu Glu Lys Gly
    610                 615                 620

Ala Ala Glu Trp Lys Trp Ala Ser Asn Val Lys Ser Asn Asp Glu Ala
625                 630                 635                 640

Gln Ile Val Leu Ala Ala Thr Gly Asp Val Pro Thr Gln Glu Ile Met
                645                 650                 655

Ala Ala Ala Asp Lys Leu Asp Ala Met Gly Ile Lys Phe Lys Val Val
            660                 665                 670

Asn Val Val Asp Leu Val Lys Leu Gln Ser Ala Lys Glu Asn Asn Glu
        675                 680                 685

Ala Leu Ser Asp Glu Glu Phe Ala Glu Leu Phe Thr Glu Asp Lys Pro
    690                 695                 700

Val Leu Phe Ala Tyr His Ser Tyr Ala Arg Asp Val Arg Gly Leu Ile
705                 710                 715                 720

Tyr Asp Arg Pro Asn His Asp Asn Phe Asn Val His Gly Tyr Glu Glu
                725                 730                 735

Gln Gly Ser Thr Thr Thr Pro Tyr Asp Met Val Arg Val Asn Asn Ile
            740                 745                 750

Asp Arg Tyr Glu Leu Gln Ala Glu Ala Leu Arg Met Ile Asp Ala Asp
        755                 760                 765

Lys Tyr Ala Asp Lys Ile Asn Glu Leu Glu Ala Phe Arg Gln Glu Ala
    770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asn Lys Gln Gly Ala Ile Ser Ala
```

805 810 815

Thr Ala Ala Thr Ala Gly Asp Asn Glu
820 825

<210> SEQ ID NO 13
<211> LENGTH: 806
<212> TYPE: PRT
<213> ORGANISM: Aspergillus niger
<220> FEATURE:
<223> OTHER INFORMATION: PHK

<400> SEQUENCE: 13

Met Pro Gly Glu Val Ile Asp Arg Pro Asn Pro Lys Ala Glu Pro Ser
1 5 10 15

His Ile Pro Asp Leu Val Asn Gln Leu Gln Val Lys Leu Gln Glu Thr
20 25 30

Arg Leu Glu Glu Thr Asp Tyr Asn Ala Leu Leu Lys Phe Arg Arg Ala
35 40 45

Ala Ala Tyr Ile Ala Ala Ala Met Ile Phe Leu Gln Asp Asn Val Leu
50 55 60

Leu Lys Gln Asn Leu Arg His Glu Asp Ile Lys Pro Arg Leu Leu Gly
65 70 75 80

His Trp Gly Thr Cys Pro Gly Leu Ile Leu Val Tyr Ser His Leu Asn
85 90 95

Tyr Ile Ile Arg Lys Gln Asn Leu Asp Met Leu Tyr Val Val Gly Pro
100 105 110

Gly His Gly Ala Pro Ala Ile Leu Ala Ser Leu Trp Leu Glu Gly Ser
115 120 125

Leu Glu Lys Phe Tyr Pro His Tyr Ser Arg Asp Met Asp Gly Leu His
130 135 140

Glu Leu Ile Ser Thr Phe Ser Thr Ser Ala Gly Leu Pro Ser His Ile
145 150 155 160

Asn Ala Glu Thr Pro Gly Ala Ile His Glu Gly Gly Glu Leu Gly Tyr
165 170 175

Ala Leu Ala Val Ser Phe Gly Ala Val Met Asp Asn Pro Asp Met Ile
180 185 190

Val Thr Cys Val Val Gly Asp Gly Glu Ala Glu Thr Gly Pro Thr Ala
195 200 205

Thr Ser Trp His Ala Ile Lys Tyr Ile Asp Pro Ala Glu Ser Gly Ala
210 215 220

Val Leu Pro Ile Leu His Val Asn Gly Phe Lys Ile Ser Glu Arg Thr
225 230 235 240

Ile Tyr Gly Cys Met Asp Asn Lys Glu Leu Val Ser Leu Phe Thr Gly
245 250 255

Tyr Gly Tyr Gln Val Arg Ile Val Glu Asn Leu Asp Asp Ile Asp Ala
260 265 270

Asp Leu His Ser Ser Met Met Trp Ala Val Glu Glu Ile His Lys Ile
275 280 285

Gln Lys Ala Ala Arg Ser Gly Lys Pro Ile Met Lys Pro Arg Trp Pro
290 295 300

Met Ile Val Leu Arg Thr Pro Lys Gly Trp Ser Gly Pro Lys Glu Leu
305 310 315 320

His Gly Ser Phe Ile Glu Gly Ser Phe His Ser His Gln Val Pro Leu
325 330 335

Pro Asn Ala Lys Lys Asp Lys Glu Glu Leu Gln Ala Leu Gln Lys Trp

```
            340                 345                 350

Leu Ser Ser Tyr Asn Pro His Glu Leu Phe Thr Glu Thr Gly Asp Ile
        355                 360                 365

Ile Asp Asp Ile Lys Ser Val Ile Pro Leu Glu Asp Thr Lys Lys Leu
    370                 375                 380

Gly Gln Arg Ala Glu Ala Tyr Lys Gly Tyr Arg Ala Pro Asp Leu Pro
385                 390                 395                 400

Asp Trp Arg Lys Phe Gly Val Glu Lys Gly Ser Gln Gln Ser Ala Met
                405                 410                 415

Lys Thr Ile Gly Lys Phe Ile Asp Gln Val Phe Thr Gln Asn Pro His
            420                 425                 430

Gly Val Arg Val Phe Ser Pro Asp Glu Leu Glu Ser Asn Lys Leu Asp
        435                 440                 445

Ala Ala Leu Ala His Thr Gly Arg Asn Phe Gln Trp Asp Gln Phe Ser
    450                 455                 460

Asn Ala Lys Gly Gly Arg Val Ile Glu Val Leu Ser Glu His Leu Cys
465                 470                 475                 480

Gln Gly Phe Met Gln Gly Tyr Thr Leu Thr Gly Arg Val Gly Ile Phe
                485                 490                 495

Pro Ser Tyr Glu Ser Phe Leu Gly Ile Ile His Thr Met Met Val Gln
            500                 505                 510

Tyr Ala Lys Phe Asn Lys Met Ala Gln Glu Thr Thr Trp His Lys Pro
        515                 520                 525

Val Ser Ser Ile Asn Tyr Ile Glu Thr Ser Thr Trp Ala Arg Gln Glu
    530                 535                 540

His Asn Gly Phe Ser His Gln Asn Pro Ser Phe Ile Gly Ala Val Leu
545                 550                 555                 560

Arg Leu Lys Pro Thr Ala Ala Arg Val Tyr Leu Pro Pro Asp Ala Asn
                565                 570                 575

Thr Phe Leu Thr Thr Leu His His Cys Leu Lys Ser Lys Asn Tyr Val
            580                 585                 590

Asn Leu Met Val Gly Ser Lys Gln Pro Thr Pro Val Tyr Leu Ser Pro
        595                 600                 605

Glu Glu Ala Glu Ser His Cys Arg Ala Gly Ala Ser Ile Trp Arg Phe
    610                 615                 620

Cys Ser Thr Asp Asn Gly Leu Asn Pro Asp Val Val Leu Val Gly Ile
625                 630                 635                 640

Gly Val Glu Val Met Phe Glu Val Ile Tyr Ala Ala Ala Ile Leu Arg
                645                 650                 655

Lys Arg Cys Pro Glu Leu Arg Val Arg Val Val Asn Val Thr Asp Leu
            660                 665                 670

Met Ile Leu Glu Lys Glu Gly Leu His Pro His Ala Leu Thr Thr Glu
        675                 680                 685

Ala Phe Asp Ser Leu Phe Gly Ser Asp Arg Pro Ile His Phe Asn Tyr
    690                 695                 700

His Gly Tyr Pro Gly Glu Leu Lys Gly Leu Leu Phe Gly Arg Pro Arg
705                 710                 715                 720

Leu Asp Arg Val Ser Val Glu Gly Tyr Met Glu Glu Gly Ser Thr Thr
                725                 730                 735

Thr Pro Phe Asp Met Met Leu Leu Asn Arg Val Ser Arg Tyr His Val
            740                 745                 750

Ala Gln Ala Ala Val Ile Gly Ala Ser Arg Arg Asn Glu Lys Val Gln
        755                 760                 765
```

```
Val Arg Gln His Glu Leu Val Ser Glu Phe Gly His Asn Ile Val Glu
    770                 775                 780

Thr Arg Lys Tyr Ile Leu Ala Asn Arg Lys Asp Pro Asp Asp Thr Tyr
785                 790                 795                 800

Asp Met Pro Ser Phe Glu
                805


<210> SEQ ID NO 14
<211> LENGTH: 815
<212> TYPE: PRT
<213> ORGANISM: Neurospora crassa
<220> FEATURE:
<223> OTHER INFORMATION: PHK

<400> SEQUENCE: 14

Met Gly Gly Thr Gln Ile Thr Ile Pro Asn Pro Pro Pro Leu Pro Ser
1               5                   10                  15

His Leu Pro Asp Asn Val Leu Asp Leu Ala Val Gln Ile Glu Arg Lys
            20                  25                  30

Asn Leu Pro Asp Asn Val Arg Glu Ser Leu Arg Ala Phe Gln Arg Ala
        35                  40                  45

Gly Cys Tyr Ile Ala Ala Ser Met Ile Phe Leu Arg Asp Asn Val Leu
    50                  55                  60

Leu Gln Asp Lys Leu Gln Val Ser His Ile Lys Pro Arg Leu Leu Gly
65                  70                  75                  80

His Trp Gly Thr Cys Pro Gly Leu Ile Leu Val Trp Ser His Leu Asn
                85                  90                  95

Val Leu Ile Arg Asn His Asp Leu Asn Met Ile Tyr Val Ile Gly Pro
            100                 105                 110

Gly His Gly Ala Pro Ala Ala Leu Ala Ser Leu Trp Leu Glu Gly Ser
        115                 120                 125

Leu Glu Arg Phe Tyr Pro Gly Glu Tyr Asp Arg Asn Ala Thr Gly Leu
    130                 135                 140

Arg Asn Leu Ile Thr Arg Phe Ser Val Pro Gly Gly Phe Pro Ser His
145                 150                 155                 160

Ile Asn Ala Glu Thr Pro Gly Ala Ile His Glu Gly Gly Glu Leu Gly
                165                 170                 175

Tyr Ala Leu Ser Val Ser Phe Gly Ala Val Met Asp Asn Pro Asp Leu
            180                 185                 190

Ile Val Thr Cys Val Val Gly Asp Gly Glu Ala Glu Thr Gly Pro Thr
        195                 200                 205

Ala Thr Ala Trp His Ala Ile Lys Tyr Ile Asp Pro Lys Glu Ser Gly
    210                 215                 220

Ala Val Ile Pro Ile Leu His Val Asn Gly Phe Lys Ile Ser Glu Arg
225                 230                 235                 240

Thr Ile Phe Gly Cys Met Asp Asp Lys Glu Ile Ala Cys Leu Phe Ser
                245                 250                 255

Gly Tyr Gly Tyr Gln Val Arg Ile Val Glu Asp Leu Glu Asn Ile Asp
            260                 265                 270

Asp Asp Leu Gln Ser Ser Leu Glu Trp Ala Leu Val Glu Ile Lys Lys
        275                 280                 285

Ile Gln Lys Ala Ala Arg Glu Asp Asn Lys Pro Ile Val Lys Pro Arg
    290                 295                 300

Trp Pro Met Ile Val Leu Arg Thr Pro Lys Gly Trp Thr Gly Pro Lys
305                 310                 315                 320
```

```
Glu Val Glu Gly Gln Ile Ile Glu Gly Ser Phe His Ser His Gln Val
                325                 330                 335

Pro Leu Pro Lys Ala Gly Ser Asp Glu Lys Gln Leu Gln Ala Leu Asp
            340                 345                 350

Glu Trp Leu Ser Ser Tyr Arg Ile Ser Glu Leu Leu Asp Asp Glu Gly
        355                 360                 365

Lys Pro Thr Glu Ala Ile Thr Arg Val Leu Pro Lys Ala Glu Lys Arg
    370                 375                 380

Leu Gly Gln Leu Lys Ile Thr Tyr Asp Pro Tyr Ile Pro Leu Lys Leu
385                 390                 395                 400

Ile Asp Trp Lys Gln Phe Gly Val Gln Lys Gly Val Asp Glu Ser Cys
                405                 410                 415

Met Lys Ser Ala Gly Lys Phe Leu Asp Lys Leu Phe Gln Glu Asn Pro
            420                 425                 430

Lys Thr Leu Arg Leu Phe Ser Pro Asp Glu Leu Glu Ser Asn Lys Leu
        435                 440                 445

Asn Ala Ile Leu Asp His Thr Gln Arg Asp Phe Gln Trp Asp Glu Phe
    450                 455                 460

Ser Arg Ala His Gly Gly Arg Val Ile Glu Val Leu Ser Glu His Asn
465                 470                 475                 480

Cys Gln Gly Phe Met Gln Gly Tyr Thr Leu Thr Gly Arg Thr Ala Leu
                485                 490                 495

Phe Pro Ser Tyr Glu Ser Phe Leu Gly Ile Val His Thr Met Met Val
            500                 505                 510

Gln Tyr Ser Lys Phe Val Lys Ile Ala Arg Glu Val Pro Trp Arg Gly
        515                 520                 525

Asp Leu Ala Ser Ile Asn Tyr Ile Glu Thr Ser Thr Trp Ala Arg Gln
    530                 535                 540

Glu His Asn Gly Phe Ser His Gln Asn Pro Ser Phe Ile Gly Ala Val
545                 550                 555                 560

Leu Asn Leu Lys Ala Glu Ala Ala Arg Val Tyr Leu Pro Pro Asp Ala
                565                 570                 575

Asn Cys Phe Leu Ser Thr Val His His Val Met Asp Ser Lys Asn Lys
            580                 585                 590

Thr Asn Leu Ile Ile Gly Ser Lys Gln Pro Thr Ala Val Tyr Leu Ser
        595                 600                 605

Pro Ala Glu Ala Ala Asp His Cys Arg Gln Gly Ala Ser Ile Trp His
    610                 615                 620

Phe Ala Ser Ser Ser Asp Pro Asn Ser Ser Ala Gly Glu Ser Val Gln
625                 630                 635                 640

Asp Pro Asp Val Val Leu Val Gly Ile Gly Val Glu Val Thr Phe Glu
                645                 650                 655

Val Ile Lys Ala Ala Glu Leu Leu Arg Ser Ile Ala Pro Ala Leu Lys
            660                 665                 670

Ile Arg Val Val Asn Val Thr Asp Leu Met Ile Leu Ile Glu Glu Ser
        675                 680                 685

Lys His Pro His Ala Leu Ala Lys Ala Lys Phe Ile Glu Met Phe Thr
    690                 695                 700

Ala Asp Arg Pro Val Leu Phe Asn Tyr His Gly Tyr Pro Thr Glu Leu
705                 710                 715                 720

Gln Gly Leu Leu Phe Gly Arg Glu Lys Ala Glu Arg Met Asp Val Glu
                725                 730                 735
```

```
Gly Tyr Gln Glu Glu Gly Ser Thr Thr Thr Pro Phe Asp Met Met Leu
            740                 745                 750

Arg Asn Arg Val Ser Arg Phe Asp Val Ala Ser Trp Ala Leu Lys Arg
        755                 760                 765

Gly Ala Glu Arg Asn Ala Glu Val Lys Asn Asp Leu Glu Gly Leu Leu
    770                 775                 780

Gly Asp Val Asp Arg Arg Val Lys Glu Val Arg Glu Phe Ile Gly Asn
785                 790                 795                 800

Glu Gly Lys Asp Pro Asp Asp Ile Tyr Gln Leu Pro Lys Phe Glu
                805                 810                 815


<210> SEQ ID NO 15
<211> LENGTH: 796
<212> TYPE: PRT
<213> ORGANISM: Lactobacillus plantarum PHK2

<400> SEQUENCE: 15

Met Ser Glu Ala Ile Lys Ser Lys Thr Val Asp Tyr Ser Ser Asp Glu
1               5                   10                  15

Tyr Leu Lys Arg Val Asp Glu Tyr Trp Arg Ala Ala Asn Tyr Ile Ser
            20                  25                  30

Val Gly Gln Leu Tyr Leu Leu Asn Asn Pro Leu Leu Arg Glu Pro Leu
        35                  40                  45

Lys Ala Thr Asp Val Lys Val His Pro Ile Gly His Trp Gly Thr Ile
    50                  55                  60

Ala Gly Gln Asn Phe Ile Tyr Ala His Leu Asn Arg Ala Ile Asn Lys
65                  70                  75                  80

Tyr Gly Leu Asn Met Phe Tyr Ile Glu Gly Pro Gly His Gly Gly Gln
                85                  90                  95

Val Met Val Ser Asn Ser Tyr Leu Asp Gly Thr Tyr Thr Glu Thr Tyr
            100                 105                 110

Pro Lys Ile Thr Gln Asp Lys Ala Gly Met Lys Arg Leu Phe Lys Gln
        115                 120                 125

Phe Ser Phe Pro Gly Gly Val Ala Ser His Ala Asp Pro Lys Thr Pro
    130                 135                 140

Gly Ser Ile His Glu Gly Gly Glu Leu Gly Tyr Ser Ile Leu His Gly
145                 150                 155                 160

Ala Gly Ala Val Leu Asp Asn Pro Gly Leu Ile Ala Ala Thr Val Val
                165                 170                 175

Gly Asp Gly Glu Ser Glu Thr Gly Pro Leu Ala Thr Ser Trp Gln Val
            180                 185                 190

Asn Lys Phe Leu Asn Pro Ile Thr Asp Gly Thr Val Leu Pro Ile Leu
        195                 200                 205

Asn Leu Asn Gly Phe Lys Ile Ser Asn Pro Thr Val Leu Ser Arg Glu
    210                 215                 220

Ser His Glu Glu Leu Glu Asp Tyr Phe Lys Gly Leu Gly Trp Asp Pro
225                 230                 235                 240

His Phe Val Glu Gly Thr Asp Pro Ala Lys Met His Lys Ile Met Ala
                245                 250                 255

Glu Glu Leu Asp Lys Val Ile Glu Glu Ile His Ala Ile Arg Lys Asn
            260                 265                 270

Ala Lys Asp Asn Asn Asp Glu Ser Arg Pro Lys Trp Pro Met Ile Val
        275                 280                 285

Phe Arg Ala Pro Lys Gly Trp Thr Gly Pro Lys Ser Trp Asp Gly Glu
    290                 295                 300
```

```
Pro Ile Glu Gly Ser Phe Arg Ala His Gln Ile Pro Ile Pro Val Asp
305                 310                 315                 320

Arg Asn His Met Glu His Ala Asp Lys Leu Val Asp Trp Leu Lys Ser
                325                 330                 335

Tyr Lys Pro Glu Glu Leu Phe Asp Glu Asn Gly Thr Leu Lys Pro Glu
            340                 345                 350

Ile Ala Ala Ile Ile Pro Glu Gly Gln Ala Arg Met Ala Ala Asn Pro
        355                 360                 365

Val Thr Asn Gly Gly Lys Leu Thr Lys Asp Leu Ile Thr Pro Asn Ile
    370                 375                 380

Asp Asp Tyr Ala Leu Asp Asn Lys Ser His Gly Lys Glu Asp Gly Ser
385                 390                 395                 400

Asp Met Thr Glu Leu Gly Lys Tyr Ile Arg Asp Leu Ile Glu Leu Asn
                405                 410                 415

Lys Asp Asn Lys Asn Phe Arg Gly Trp Gly Pro Asp Glu Thr Leu Ser
            420                 425                 430

Asn Lys Leu Gly Ala Ala Phe Glu Asp Thr Lys Arg Gln Trp Met Glu
        435                 440                 445

Pro Ile His Glu Pro Asn Asp Ala Leu Leu Ala Pro Gln Gly Arg Ile
    450                 455                 460

Ile Asp Ser Met Leu Ser Glu His Met Asp Glu Gly Met Leu Glu Ala
465                 470                 475                 480

Tyr Asn Leu Thr Gly Arg Tyr Gly Phe Phe Ala Ser Tyr Glu Ser Phe
                485                 490                 495

Leu Arg Val Val Asp Ser Met Leu Thr Gln His Phe Lys Trp Leu Arg
            500                 505                 510

Asn Ser His Glu Glu Thr Pro Trp Arg Ala Asp Val Pro Ser Leu Asn
        515                 520                 525

Val Ile Ala Ser Ser Thr Ala Phe Gln Gln Asp His Asn Gly Tyr Ser
    530                 535                 540

His Gln Asp Pro Gly Ile Ile Ser His Leu Ala Glu Lys Lys Thr Glu
545                 550                 555                 560

Tyr Val Arg Ala Tyr Leu Pro Gly Asp Ala Asn Thr Leu Ile Ala Thr
                565                 570                 575

Phe Asp Lys Ala Ile Gln Ser Lys Gln Leu Ile Asn Leu Ile Ile Ala
            580                 585                 590

Ser Lys His Pro Arg Pro Gln Trp Phe Thr Met Asp Glu Ala Lys Arg
        595                 600                 605

Leu Val Arg Asp Gly Leu Gly Val Val Asp Trp Ala Ser Thr Asp His
    610                 615                 620

Gly Glu Glu Pro Asp Val Val Phe Ala Thr Ala Gly Ser Glu Pro Thr
625                 630                 635                 640

Thr Glu Ser Leu Ala Ala Val Ser Ile Leu His Ala Arg Phe Pro Glu
                645                 650                 655

Met Lys Ile Arg Phe Ile Asn Val Val Asp Leu Leu Lys Leu Lys Lys
            660                 665                 670

Asp Asp Pro Arg Gly Leu Ser Asp Ala Glu Phe Asp Ala Phe Phe Thr
        675                 680                 685

Lys Asp Lys Pro Val Ile Phe Ala Tyr His Ala Tyr Asp Asp Leu Val
    690                 695                 700

Lys Thr Ile Phe Phe Asp Arg His Asn His Asn Leu His Val His Gly
705                 710                 715                 720
```

```
Tyr Arg Glu Glu Gly Asp Ile Thr Thr Pro Phe Asp Met Arg Val Arg
                725                 730                 735

Asn Glu Leu Asp Arg Phe His Leu Val Lys Ala Ala Leu Leu Ala Thr
            740                 745                 750

Pro Ala Tyr Ala Glu Lys Gly Ala His Val Ile Gln Glu Met Asn Ser
        755                 760                 765

Ile Leu Asp Lys His His Asp Tyr Ile Arg Ala Glu Gly Thr Asp Ile
    770                 775                 780

Pro Glu Val Glu Asn Trp Lys Trp Thr Ala Leu Lys
785                 790                 795


<210> SEQ ID NO 16
<211> LENGTH: 409
<212> TYPE: PRT
<213> ORGANISM: Bifidobacterium adolescentis
<220> FEATURE:
<223> OTHER INFORMATION: ACK

<400> SEQUENCE: 16

Met Ala Lys Thr Val Leu Val Ile Asn Ser Gly Ser Ser Ser Ile Lys
1               5                   10                  15

Tyr Gln Leu Val Asp Leu Glu Thr Gly Glu Gly Ile Ala Ser Gly Leu
            20                  25                  30

Val Glu Lys Ile Gly Glu Pro Val Asp Gly His Tyr Lys His Glu Tyr
        35                  40                  45

Asn Gly Glu Lys His Glu Leu Glu Glu Pro Ile His Asp His Glu Gln
    50                  55                  60

Gly Leu Lys Arg Val Leu Gly Phe Phe Asp Glu Phe Gly Pro Lys Leu
65                  70                  75                  80

Ala Asp Ala Gly Ile Val Ala Val Gly His Arg Val Val Gln Gly Gly
                85                  90                  95

Ser Ile Phe Pro Lys Pro Ala Leu Val Asn Asp Lys Thr Ile Gly Gln
            100                 105                 110

Val Lys Asp Leu Ala Val Leu Ala Pro Leu His Asn Gly Pro Glu Ala
        115                 120                 125

Lys Gly Ala Glu Val Met Arg Ser Leu Leu Pro Asp Val Pro Gln Ile
    130                 135                 140

Phe Val Phe Asp Ser Ser Phe Phe Phe Gln Leu Pro Lys Ala Ser Ser
145                 150                 155                 160

Thr Tyr Ala Leu Asn Lys Glu Val Ala Gln Gln Tyr His Ile Arg Arg
                165                 170                 175

Tyr Gly Ala His Gly Thr Ser His Glu Phe Ile Ser Ser Val Val Pro
            180                 185                 190

Ser Val Ile Gly Lys Pro Ala Glu Gly Leu Lys Gln Ile Val Leu His
        195                 200                 205

Ile Gly Asn Gly Ala Ser Ala Ser Ala Glu Ile Ser Gly Lys Pro Val
    210                 215                 220

Glu Thr Ser Met Gly Leu Thr Pro Leu Glu Gly Leu Val Met Gly Gly
225                 230                 235                 240

Arg Thr Gly Asp Ile Asp Pro Ala Val Val Phe His Leu Ile Arg Asn
                245                 250                 255

Ala His Met Ser Val Asp Glu Leu Asp Thr Leu Phe Asn Lys Arg Ser
            260                 265                 270

Gly Met Met Gly Leu Thr Gly Phe Gly Asp Leu Arg Glu Val His Arg
        275                 280                 285
```

```
Leu Val Glu Glu Gly Asn Glu Asp Ala Lys Leu Ala Leu Asp Ile Tyr
    290                 295                 300

Val His Arg Ile Val Gly Tyr Ile Gly Asn Tyr Thr Ala Gln Met Gly
305                 310                 315                 320

Gly Val Asp Val Ile Thr Phe Thr Ala Gly Val Gly Glu Asn Asp Asp
                325                 330                 335

Val Val Arg Lys Met Val Cys Asp Lys Leu Ala Pro Phe Gly Val Lys
            340                 345                 350

Leu Asp Glu Glu Lys Asn Ala Thr Arg Ser Lys Glu Pro Arg Ile Ile
        355                 360                 365

Ser Thr Pro Asp Ser Ala Val Thr Ile Cys Val Ile Pro Thr Asn Glu
    370                 375                 380

Glu Leu Ala Ile Ala Arg Lys Ser Ala Ala Ile Ala Glu Glu Gly Lys
385                 390                 395                 400

Asp Ser Tyr Gly Asn Val Phe Ser Lys
                405


<210> SEQ ID NO 17
<211> LENGTH: 6671
<212> TYPE: DNA
<213> ORGANISM: Saccharomyces cerevisiae
<220> FEATURE:
<223> OTHER INFORMATION: ALD2

<400> SEQUENCE: 17

atgtggcaag agtcacagta acgacaaaag ttaaagaaga cagatgtgca tggagagttt      60

catatgcaga aggtaagatg ttggaaagcc ccaaacctgt tgctggaaaa gacggtacca     120

cgatcctagt tgaagacctt tttttcaata ttccttctag attaagggcc ttgaggtccc     180

ataatgatga atactctaaa atattagatg ttgtcgggcg atacgccatt cattccaagg     240

acattggctt ttcttgtaaa aagttcggag actctaatta ttctttatca gttaaacctt     300

catataccgt ccaggatagg attaggactg tgttcaataa atctgtggct tcgaatttaa     360

ttacttttca tatcagcaaa gtagaagatt taaacctgga aagcgttgat ggaaaggtgt     420

gtaatttgaa tttcatatcc aaaaagtcca tttcaccaat ttttttcatt aataatagac     480

tagtgacatg tgatcttcta agaagagctt tgaacagcgt ttactccaat tatctgccaa     540

agggcaacag accttttatt tatttgggaa ttgttataga tccggcggct gttgatgtta     600

acgttcaccc gacaaagaga gaggttcgtt tcctgagcca agatgagatc atagagaaaa     660

tcgccaatca attgcacgcc gaattatctg ccattgatac ttcacgtact ttcaaggctt     720

cttcaatttc aacaaacaag ccagagtcat tgataccatt taatgacacc atagaaagtg     780

ataggaatag gaagagtctc cgacaagccc aagtggtaga gaattcatat acgacagcca     840

atagtcaact aaggaaagcg aaaagacaag agaataaact agtcagaata gatgcttcac     900

aagctaaaat tacgtcattt ttatcctcaa gtcaacagtt caactttgaa ggatcgtcta     960

caaagcgaca actgagtgaa cccaaggtaa caaatgtaag ccactcccaa gaggcagaaa    1020

agctgacact aaatgaaagc gaacaaccgc gtgatgccaa tacaatcaat gataatgact    1080

tgaaggatca acctaagaag aaacaaaagt tgggggatta taaagttcca agcattgccg    1140

atgacgaaaa gaatgcactc ccgatttcaa aagacgggta tattagagta cctaaggagc    1200

gagttaatgt taatcttacg agtatcaaga aattgcgtga aaaagtagat gattcgatac    1260

atcgagaact aacagacatt tttgcaaatt tgaattacgt tggggttgta gatgaggaaa    1320

gaagattagc cgctattcag catgacttaa agcttttttt aatagattac ggatctgtgt    1380
```

```
gctatgagct attctatcag attggtttga cagacttcgc aaactttggt aagataaacc   1440

tacagagtac aaatgtgtca gatgatatag ttttgtataa tctcctatca gaatttgacg   1500

agttaaatga cgatgcttcc aaagaaaaaa taattagtaa aatatgggac atgagcagta   1560

tgctaaatga gtactattcc atagaattgg tgaatgatgg tctagataat gacttaaagt   1620

ctgtgaagct aaaatctcta ccactacttt taaaaggcta cattccatct ctggtcaagt   1680

taccattttt tatatatcgc ctgggtaaag aagttgattg ggaggatgaa caagagtgtc   1740

tagatggtat tttaagagag attgcattac tctatatacc tgatatggtt ccgaaagtcg   1800

atacatctga tgcatcgttg tcagaagacg aaaaagccca gtttataaat agaaaggaac   1860

acatatcctc attactagaa cacgttctct tcccttgtat caaacgaagg ttcctggccc   1920

ctagacacat tctcaaggat gtcgtggaaa tagccaacct tccagatcta tacaaagttt   1980

ttgagaggtg ttaactttaa aacgttttgg ctgtaatacc aaagtttttt gtttatttcc   2040

tgagtgtgat tgtgtttcat ttgaaagtgt atgccctttc ctttaacgat tcatccgcga   2100

gatttcaaag gatatgaaat atggttgcag ttaggaaagt atgtcagaaa tgttatattc   2160

ggattgaaac tcttctacaa tagttctgaa gtcacttggt tccgtattgt tttcgtcctc   2220

ttcctcaagc aacgattctt gtctaagctt attcaacggt accaaagacc cgagtccttt   2280

tatgagagaa aacatttcat catttttcaa ctcaattatc ttaatatcat tttgtagtat   2340

tttgaaaaca ggatggtaaa acgaatcacc tgaatctaga agctgtacct tgtcccataa   2400

aagttttaat ttactgagcc tttcggtcaa gtaaactagt ttatctagtt ttgaaccgaa   2460

tattgtgggc agatttgcag taagttcagt tagatctact aaaagttgtt tgacagcagc   2520

cgattccaca aaaatttggt aaaaggagat gaaagagacc acgcgcgtaa tggtttgcat   2580

caccatcgga tgtctgttga aaaactcact ttttgcatgg aagttattaa caataagact   2640

aatgattacc ttagaataat gtataacctt tagtagtgaa tctgcggtat cataataaat   2700

gagatacatc ttaaacaatt tccaggaaac agtagatatt tgaaaaagtg caataaattt   2760

ttgaaatctg ctgttatttg atctaaaatc ttcttccaac gaatctactt tgtattgaaa   2820

aatatcgagc tccctcctta tagcatccaa tgtttttaag ggaggtttag aactcttgtt   2880

caagtattga tctaaatctc tgtctaatga gatgattttc caatacaaga cctctgtgct   2940

gttttcttcc ctgtaaacat caacgttagg caaatcctgc aaatatgctg catgttgtaa   3000

tagggaggat acttctgtat gaagtgcaat tggtttgcgt ggccccgatt gaagataatc   3060

gcatccacac aggcgataga atattcttcc caaggttact ttagcgatgc tttcaacggg   3120

gtcatcatta agtaaaggtc taaagtcatc cacatgaaaa tttttaaagg tatggatgca   3180

ctgtgttagg agcgaatttg ccaacaacgg ttcatcgtag gggaaagttg tagtggctaa   3240

aatcagatat gcttgaacga gccttatatc gggatgcgcc atgaaatcac attgtttcaa   3300

ttggaataat gagcagcgtg caaaattttg gcacatgact aattgcatac catcttccca   3360

attgagcctt ttgttgctac ccaaatattc atggagagga tatactgaaa atatttctgc   3420

taacttctcg actggcatat aataaatgca catggtaaag acagaccata ttagtgcgtc   3480

ccagtatttg ccgtctacac tgtgattctt gtctgccctt ctatcccagt actgttccac   3540

cctcaaatat aattcactga tatctccaat ggaaccaaaa tacaaagcac ctaagttttc   3600

catagcaaag ttcatcaatt ggaatgattg gtctttttga agataattca tccaaaacat   3660

acattcttca gtatcagtat ccaaattagc tggtgttcta gtaagatctc tttgttttgt   3720
```

```
tttgtacagc ccaatattcg ttatccaata ttcataattt tgccagaata acaataggtc   3780
agggagatat tccttggaag atgaagccgt tattagtttt gttgatttca tacattcgga   3840
gtcctgtcct ctcttcctgc agtttccaca cggtatcata cgatcacatt tgacttttcg   3900
cctcgtacac acggaacagg gatgcttgga tttcagttga gtggtacggt taaacattat   3960
tattaggatg caaactcgtg ttcgtaactt ttgtcatcac ctgctctctg aaggttggtt   4020
ataatatttc attctcttac gcttagctta catggctgcg cgcacttcat ttaaagccgt   4080
aaaaaataaa gatttcatag aatatgaagc tttgaatctc atgtaaacat ttatataact   4140
atgtaacgaa ttatttatcc aatgaaagat ccacatggac tgattttatt tgtaaatagt   4200
tatcaacgcc ggtgtcgcct gattctctac caataccact catcttaaat ccgccaaaag   4260
gaactttagc ttcttcttga ttggtttgat tgatccaaac agttcctgct ttaatatcgc   4320
gagcaaacat gtgcgctttc ttgacatctt tggtgaagac cgcagaggcg agcccgtagc   4380
aagtatcatt agccagcttc agagcgtcat cataatttgt gaacttgcta acaaccacaa   4440
ccgggccaaa tatttcatca cgcagcaact tagatgtttc tggtacatca gtgaagatgg   4500
ttgggggaat gaagtagcct ttagctccac caataggaaa ttcagaggtc tggaacatgt   4560
ccaactttc ctccttttta ccacgttcta tgtaactttt gatgcggtca tactgtgtac    4620
ttgatataac tggaccaacg atgcatttct catcaaacgg atcaaatttt cctgcaacat   4680
cccactcctt ctttgcagtt tctttaaact tttcaacaaa cttgtcgtag atcgaacttt   4740
gaacataaac tcttgagttt gcagtgcaga tctgtcccga attaaaaaaa ataccatttg   4800
ctacccattc tatagcctta tcaaggtctg catcttcaaa tacaagagca ggagacttac   4860
caccgcattc tagtgtgata tccttaaggt tcgattggcc ggaagcttcc aatactgagc   4920
cgccaacctt agtacttccc gtaaaagata ttttgtcgat atccatgtgg gttcctaaag   4980
ctttccccac aacggaacca taaccaggaa tgacattgac aacaccaggt ggaaaacctg   5040
ctttttaat taaagtagca aaataaagta gagatagaga ggtattttca gcaggtttga    5100
tgataaccgt gttaccggcc gctaaggcac cttgcatttt tctacaagcc atagctagag   5160
gataattcca tggaacgatt tgagcaacaa cgccaaaagg aacttttaga gtatatgcaa   5220
acttgttaaa agtcaatgga atggtttcac ccatattgaa cttgtcgacc gcccccgcat   5280
agtatcttgt aagttctata atctgggcta agtcttgttt agcattggaa tggaaaggct   5340
taccagcgtc taaagtctct aatgcggcaa gtgtgtcttg ctcctcctca ataagtttta   5400
ataagtttga aagataaata ccacgttgct cagaagatgt cttcgaccaa acgttatcaa   5460
aagcagccct ggcagctttc acagctttgt ctacatcctt ttcgttagct gcttggaagg   5520
atgttatcgg ttcgccagta gctgggttca cagtttcgat ggtctttcca tctgatgatg   5580
gacaaaactc attgttgata aacaacccta gcggttgctt taaagagatt ttcaattgtg   5640
ggatttcgat atcagtatac aaggtaggca tttttctttt ggctaatttt ctaaatgtgt   5700
ataatctata tctctatgat acaagtccaa ggtataatta cctggcatga gtcaaattta   5760
ttcccatcca gatttgccat tttatacaat tagtttctga ggtatgatca gttaaatcta   5820
cgctattcgt ttgaacaatc tccctgtctc ctccctaaac ttactaattc cttaaccctt   5880
agggagttta gcaatcagct taagaagggg gctgatcaac aatccggttc aagtcttgga   5940
ttagcagtaa tgaaaatccc taaatgcact aaagggcgtg gaagaaaggt actgtagagt   6000
tctaatagtg atactttcct tgtactccag ggggggaagg aagaacagac gtcatatgca   6060
gaaaaagaaa aaaaaaagac ggaagatcta cgtaatggtg ggaatagaga aaactaacac   6120
```

```
gcaagtataa tttcttgaca caaaaataaa tctcactgag tttatagctc tattttttta   6180

ccatcttaag ggatttctag gacctagtaa caacaattgt tccgcatgct gaaataatgg   6240

tgcttacagt tttatatcga gtagtggact actactgttt gctagactgt caacatattc   6300

atccgtcgtc aggctaagct atttaggtac ttacgcactt acataatgat aactatcaca   6360

ttagttgtcc aaagagagat ttatgtgaac tgcttttgtt tgaagatagg tatcaacacc   6420

actttgcccc agttctctac caataccact cattttaaac ccgccaaaag gaacggtaac   6480

atcttcatcg ttagatgagt tgatccaaac agttcctgct ttaatatcgc gagcaaacat   6540

gtgcgctttc ttgacatctt ttgtgaagac cgcagaggcg agcccgtagc aagtatcatt   6600

agccagcttc agagcgtcat cataatttgt gaacttgcta acaaccacaa ccgggccaaa   6660

tatctcatcc t                                                        6671


<210> SEQ ID NO 18
<211> LENGTH: 506
<212> TYPE: PRT
<213> ORGANISM: Saccharomyces cerevisiae
<220> FEATURE:
<223> OTHER INFORMATION: ALD2

<400> SEQUENCE: 18

Met Pro Thr Leu Tyr Thr Asp Ile Glu Ile Pro Gln Leu Lys Ile Ser
1               5                   10                  15

Leu Lys Gln Pro Leu Gly Leu Phe Ile Asn Asn Glu Phe Cys Pro Ser
            20                  25                  30

Ser Asp Gly Lys Thr Ile Glu Thr Val Asn Pro Ala Thr Gly Glu Pro
        35                  40                  45

Ile Thr Ser Phe Gln Ala Ala Asn Glu Lys Asp Val Asp Lys Ala Val
    50                  55                  60

Lys Ala Ala Arg Ala Ala Phe Asp Asn Val Trp Ser Lys Thr Ser Ser
65                  70                  75                  80

Glu Gln Arg Gly Ile Tyr Leu Ser Asn Leu Leu Lys Leu Ile Glu Glu
                85                  90                  95

Glu Gln Asp Thr Leu Ala Ala Leu Glu Thr Leu Asp Ala Gly Lys Pro
            100                 105                 110

Phe His Ser Asn Ala Lys Gln Asp Leu Ala Gln Ile Ile Glu Leu Thr
        115                 120                 125

Arg Tyr Tyr Ala Gly Ala Val Asp Lys Phe Asn Met Gly Glu Thr Ile
    130                 135                 140

Pro Leu Thr Phe Asn Lys Phe Ala Tyr Thr Leu Lys Val Pro Phe Gly
145                 150                 155                 160

Val Val Ala Gln Ile Val Pro Trp Asn Tyr Pro Leu Ala Met Ala Cys
                165                 170                 175

Arg Lys Met Gln Gly Ala Leu Ala Ala Gly Asn Thr Val Ile Ile Lys
            180                 185                 190

Pro Ala Glu Asn Thr Ser Leu Ser Leu Leu Tyr Phe Ala Thr Leu Ile
        195                 200                 205

Lys Lys Ala Gly Phe Pro Pro Gly Val Val Asn Val Ile Pro Gly Tyr
    210                 215                 220

Gly Ser Val Val Gly Lys Ala Leu Gly Thr His Met Asp Ile Asp Lys
225                 230                 235                 240

Ile Ser Phe Thr Gly Ser Thr Lys Val Gly Gly Ser Val Leu Glu Ala
                245                 250                 255
```

```
Ser Gly Gln Ser Asn Leu Lys Asp Ile Thr Leu Glu Cys Gly Gly Lys
            260                 265                 270

Ser Pro Ala Leu Val Phe Glu Asp Ala Asp Leu Asp Lys Ala Ile Glu
        275                 280                 285

Trp Val Ala Asn Gly Ile Phe Phe Asn Ser Gly Gln Ile Cys Thr Ala
    290                 295                 300

Asn Ser Arg Val Tyr Val Gln Ser Ser Ile Tyr Asp Lys Phe Val Glu
305                 310                 315                 320

Lys Phe Lys Glu Thr Ala Lys Lys Glu Trp Asp Val Ala Gly Lys Phe
                325                 330                 335

Asp Pro Phe Asp Glu Lys Cys Ile Val Gly Pro Val Ile Ser Ser Thr
            340                 345                 350

Gln Tyr Asp Arg Ile Lys Ser Tyr Ile Glu Arg Gly Lys Lys Glu Glu
        355                 360                 365

Lys Leu Asp Met Phe Gln Thr Ser Glu Phe Pro Ile Gly Gly Ala Lys
    370                 375                 380

Gly Tyr Phe Ile Pro Pro Thr Ile Phe Thr Asp Val Pro Glu Thr Ser
385                 390                 395                 400

Lys Leu Leu Arg Asp Glu Ile Phe Gly Pro Val Val Val Val Ser Lys
                405                 410                 415

Phe Thr Asn Tyr Asp Asp Ala Leu Lys Leu Ala Asn Asp Thr Cys Tyr
            420                 425                 430

Gly Leu Ala Ser Ala Val Phe Thr Lys Asp Val Lys Lys Ala His Met
        435                 440                 445

Phe Ala Arg Asp Ile Lys Ala Gly Thr Val Trp Ile Asn Gln Thr Asn
    450                 455                 460

Gln Glu Glu Ala Lys Val Pro Phe Gly Gly Phe Lys Met Ser Gly Ile
465                 470                 475                 480

Gly Arg Glu Ser Gly Asp Thr Gly Val Asp Asn Tyr Leu Gln Ile Lys
                485                 490                 495

Ser Val His Val Asp Leu Ser Leu Asp Lys
            500                 505
```

<210> SEQ ID NO 19
<211> LENGTH: 1824
<212> TYPE: DNA
<213> ORGANISM: Saccharomyces cerevisiae
<220> FEATURE:
<223> OTHER INFORMATION: ALD3

<400> SEQUENCE: 19

```
atgtttaacc gtaccactca actgaaatcc aagcatccct gttccgtgtg tacgaggcga      60

aaagtcaaat gtgatcgtat gataccgtgt ggaaactgca ggaagagagg acaggactcc     120

gaatgtatga aatcaacaaa actaataacg gcttcatctt ccaaggaata tctccctgac     180

ctattgttat tctggcaaaa ttatgaatat tggataacga atattgggct gtacaaaaca     240

aaacaaagag atcttactag aacaccagct aatttggata ctgatactga agaatgtatg     300

ttttggatga attatcttca aaaagaccaa tcattccaat tgatgaactt tgctatggaa     360

aacttaggtg ctttgtattt tggttccatt ggagatatca gtgaattata tttgagggtg     420

gaacagtact gggatagaag ggcagacaag aatcacagtg tagacggcaa atactgggac     480

gcactaatat ggtctgtctt taccatgtgc atttattata tgccagtcga gaagttagca     540

gaaatatttt cagtatatcc tctccatgaa tatttgggta gcaacaaaag gctcaattgg     600

gaagatggta tgcaattagt catgtgccaa aattttgcac gctgctcatt attccaattg     660
```

```
aaacaatgtg atttcatggc gcatcccgat ataaggctcg ttcaagcata tctgatttta    720

gccactacaa ctttccccta cgatgaaccg ttgttggcaa attcgctcct aacacagtgc    780

atccatacct ttaaaaattt tcatgtggat gactttagac ctttacttaa tgatgacccc    840

gttgaaagca tcgctaaagt aaccttggga agaatattct atcgcctgtg tggatgcgat    900

tatcttcaat cggggccacg caaaccaatt gcacttcata cagaagtatc ctccctatta    960

caacatgcag catatttgca ggatttgcct aacgttgatg tttacaggga agaaaacagc   1020

acagaggtct tgtattggaa aatcatctca ttagacagag atttagatca atacttgaac   1080

aagagttcta aacctccctt aaaaacattg gatgctataa ggagggagct cgatattttt   1140

caatacaaag tagattcgtt ggaagaagat tttagatcaa ataacagcag atttcaaaaa   1200

tttattgcac tttttcaaat atctactgtt tcctggaaat tgtttaagat gtatctcatt   1260

tattatgata ccgcagattc actactaaag gttatacatt attctaaggt aatcattagt   1320

cttattgtta ataacttcca tgcaaaaagt gagtttttca acagacatcc gatggtgatg   1380

caaaccatta cgcgcgtggt ctctttcatc tccttttacc aaatttttgt ggaatcggct   1440

gctgtcaaac aacttttagt agatctaact gaacttactg caaatctgcc cacaatattc   1500

ggttcaaaac tagataaact agtttacttg accgaaaggc tcagtaaatt aaaactttta   1560

tgggacaagg tacagcttct agattcaggt gattcgtttt accatcctgt tttcaaaata   1620

ctacaaaatg atattaagat aattgagttg aaaaatgatg aaatgttttc tctcataaaa   1680

ggactcgggt ctttggtacc gttgaataag cttagacaag aatcgttgct tgaggaagag   1740

gacgaaaaca atacggaacc aagtgacttc agaactattg tagaagagtt tcaatccgaa   1800

tataacattt ctgacatact ttcc                                          1824
```

<210> SEQ ID NO 20
<211> LENGTH: 608
<212> TYPE: PRT
<213> ORGANISM: Saccharomyces cerevisiae
<220> FEATURE:
<223> OTHER INFORMATION: ALD3

<400> SEQUENCE: 20

```
Met Phe Asn Arg Thr Thr Gln Leu Lys Ser Lys His Pro Cys Ser Val
1               5                   10                  15

Cys Thr Arg Arg Lys Val Lys Cys Asp Arg Met Ile Pro Cys Gly Asn
            20                  25                  30

Cys Arg Lys Arg Gly Gln Asp Ser Glu Cys Met Lys Ser Thr Lys Leu
        35                  40                  45

Ile Thr Ala Ser Ser Ser Lys Glu Tyr Leu Pro Asp Leu Leu Leu Phe
    50                  55                  60

Trp Gln Asn Tyr Glu Tyr Trp Ile Thr Asn Ile Gly Leu Tyr Lys Thr
65                  70                  75                  80

Lys Gln Arg Asp Leu Thr Arg Thr Pro Ala Asn Leu Asp Thr Asp Thr
                85                  90                  95

Glu Glu Cys Met Phe Trp Met Asn Tyr Leu Gln Lys Asp Gln Ser Phe
            100                 105                 110

Gln Leu Met Asn Phe Ala Met Glu Asn Leu Gly Ala Leu Tyr Phe Gly
        115                 120                 125

Ser Ile Gly Asp Ile Ser Glu Leu Tyr Leu Arg Val Glu Gln Tyr Trp
    130                 135                 140

Asp Arg Arg Ala Asp Lys Asn His Ser Val Asp Gly Lys Tyr Trp Asp
```

```
145                 150                 155                 160

Ala Leu Ile Trp Ser Val Phe Thr Met Cys Ile Tyr Tyr Met Pro Val
                165                 170                 175

Glu Lys Leu Ala Glu Ile Phe Ser Val Tyr Pro Leu His Glu Tyr Leu
            180                 185                 190

Gly Ser Asn Lys Arg Leu Asn Trp Glu Asp Gly Met Gln Leu Val Met
        195                 200                 205

Cys Gln Asn Phe Ala Arg Cys Ser Leu Phe Gln Leu Lys Gln Cys Asp
    210                 215                 220

Phe Met Ala His Pro Asp Ile Arg Leu Val Gln Ala Tyr Leu Ile Leu
225                 230                 235                 240

Ala Thr Thr Thr Phe Pro Tyr Asp Glu Pro Leu Leu Ala Asn Ser Leu
                245                 250                 255

Leu Thr Gln Cys Ile His Thr Phe Lys Asn Phe His Val Asp Asp Phe
            260                 265                 270

Arg Pro Leu Leu Asn Asp Asp Pro Val Glu Ser Ile Ala Lys Val Thr
        275                 280                 285

Leu Gly Arg Ile Phe Tyr Arg Leu Cys Gly Cys Asp Tyr Leu Gln Ser
    290                 295                 300

Gly Pro Arg Lys Pro Ile Ala Leu His Thr Glu Val Ser Ser Leu Leu
305                 310                 315                 320

Gln His Ala Ala Tyr Leu Gln Asp Leu Pro Asn Val Asp Val Tyr Arg
                325                 330                 335

Glu Glu Asn Ser Thr Glu Val Leu Tyr Trp Lys Ile Ile Ser Leu Asp
            340                 345                 350

Arg Asp Leu Asp Gln Tyr Leu Asn Lys Ser Ser Lys Pro Pro Leu Lys
        355                 360                 365

Thr Leu Asp Ala Ile Arg Arg Glu Leu Asp Ile Phe Gln Tyr Lys Val
    370                 375                 380

Asp Ser Leu Glu Glu Asp Phe Arg Ser Asn Asn Ser Arg Phe Gln Lys
385                 390                 395                 400

Phe Ile Ala Leu Phe Gln Ile Ser Thr Val Ser Trp Lys Leu Phe Lys
                405                 410                 415

Met Tyr Leu Ile Tyr Tyr Asp Thr Ala Asp Ser Leu Leu Lys Val Ile
            420                 425                 430

His Tyr Ser Lys Val Ile Ile Ser Leu Ile Val Asn Asn Phe His Ala
        435                 440                 445

Lys Ser Glu Phe Phe Asn Arg His Pro Met Val Met Gln Thr Ile Thr
    450                 455                 460

Arg Val Val Ser Phe Ile Ser Phe Tyr Gln Ile Phe Val Glu Ser Ala
465                 470                 475                 480

Ala Val Lys Gln Leu Leu Val Asp Leu Thr Glu Leu Thr Ala Asn Leu
                485                 490                 495

Pro Thr Ile Phe Gly Ser Lys Leu Asp Lys Leu Val Tyr Leu Thr Glu
            500                 505                 510

Arg Leu Ser Lys Leu Lys Leu Leu Trp Asp Lys Val Gln Leu Leu Asp
        515                 520                 525

Ser Gly Asp Ser Phe Tyr His Pro Val Phe Lys Ile Leu Gln Asn Asp
    530                 535                 540

Ile Lys Ile Ile Glu Leu Lys Asn Asp Glu Met Phe Ser Leu Ile Lys
545                 550                 555                 560

Gly Leu Gly Ser Leu Val Pro Leu Asn Lys Leu Arg Gln Glu Ser Leu
                565                 570                 575
```

```
Leu Glu Glu Glu Asp Glu Asn Asn Thr Glu Pro Ser Asp Phe Arg Thr
            580                 585                 590

Ile Val Glu Glu Phe Gln Ser Glu Tyr Asn Ile Ser Asp Ile Leu Ser
        595                 600                 605


<210> SEQ ID NO 21
<211> LENGTH: 1557
<212> TYPE: DNA
<213> ORGANISM: Saccharomyces cerevisiae
<220> FEATURE:
<223> OTHER INFORMATION: ALD4

<400> SEQUENCE: 21

atgttcagta gatctacgct ctgcttaaag acgtctgcat cctccattgg gagacttcaa      60

ttgagatatt tctcacacct tcctatgaca gtgcctatca agctgcccaa tgggttggaa     120

tatgagcaac caacggggtt gttcatcaac aacaagtttg ttccttctaa acagaacaag     180

accttcgaag tcattaaccc ttccacggaa gaagaaatat gtcatattta tgaaggtaga     240

gaggacgatg tggaagaggc cgtgcaggcc gccgaccgtg ccttctctaa tgggtcttgg     300

aacggtatcg accctattga caggggtaag gctttgtaca ggttagccga attaattgaa     360

caggacaagg atgtcattgc ttccatcgag actttggata acggtaaagc tatctcttcc     420

tcgagaggag atgttgattt agtcatcaac tatttgaaat cttctgctgg ctttgctgat     480

aaaattgatg gtagaatgat tgatactggt agaacccatt tttcttacac taagagacag     540

cctttgggtg tttgtgggca gattattcct tggaatttcc cactgttgat gtgggcctgg     600

aagattgccc ctgctttggt caccggtaac accgtcgtgt tgaagactgc cgaatccacc     660

ccattgtccg ctttgtatgt gtctaaatac atcccacagg cgggtattcc acctggtgtg     720

atcaacattg tatccgggtt tggtaagatt gtgggtgagg ccattacaaa ccatccaaaa     780

atcaaaaagg ttgccttcac agggtccacg gctacgggta gacacattta ccagtccgca     840

gccgcaggct tgaaaaaagt gactttggag ctgggtggta aatcaccaaa cattgtcttc     900

gcggacgccg agttgaaaaa agccgtgcaa aacattatcc ttggtatcta ctacaattct     960

ggtgaggtct gttgtgcggg ttcaagggtg tatgttgaag aatctattta cgacaaattc    1020

attgaagagt tcaaagccgc ttctgaatcc atcaaggtgg gcgacccatt cgatgaatct    1080

actttccaag gtgcacaaac ctctcaaatg caactaaaca aaatcttgaa atacgttgac    1140

attggtaaga atgaaggtgc tactttgatt accggtggtg aaagattagg tagcaagggt    1200

tacttcatta agccaactgt ctttggtgac gttaaggaag acatgagaat tgtcaaagag    1260

gaaatctttg gccctgttgt cactgtaacc aaattcaaat ctgccgacga agtcattaac    1320

atggcgaacg attctgaata cggttggct gctggtattc acacctctaa tattaatacc    1380

gccttaaaag tggctgatag agttaatgcg ggtacggtct ggataaacac ttataacgat    1440

ttccaccacg cagttccttt cggtgggttc aatgcatctg gtttgggcag ggaaatgtct    1500

gttgatgctt tacaaaacta cttgcaagtt aaagcggtcc gtgccaaatt ggacgag       1557


<210> SEQ ID NO 22
<211> LENGTH: 519
<212> TYPE: PRT
<213> ORGANISM: Saccharomyces cerevisiae
<220> FEATURE:
<223> OTHER INFORMATION: ALD4

<400> SEQUENCE: 22
```

```
Met Phe Ser Arg Ser Thr Leu Cys Leu Lys Thr Ser Ala Ser Ser Ile
1               5                   10                  15

Gly Arg Leu Gln Leu Arg Tyr Phe Ser His Leu Pro Met Thr Val Pro
            20                  25                  30

Ile Lys Leu Pro Asn Gly Leu Glu Tyr Glu Gln Pro Thr Gly Leu Phe
        35                  40                  45

Ile Asn Asn Lys Phe Val Pro Ser Lys Gln Asn Lys Thr Phe Glu Val
    50                  55                  60

Ile Asn Pro Ser Thr Glu Glu Glu Ile Cys His Ile Tyr Glu Gly Arg
65                  70                  75                  80

Glu Asp Asp Val Glu Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
            100                 105                 110

Tyr Arg Leu Ala Glu Leu Ile Glu Gln Asp Lys Asp Val Ile Ala Ser
        115                 120                 125

Ile Glu Thr Leu Asp Asn Gly Lys Ala Ile Ser Ser Ser Arg Gly Asp
    130                 135                 140

Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
                165                 170                 175

Thr Lys Arg Gln Pro Leu Gly Val Cys Gly Gln Ile Ile Pro Trp Asn
            180                 185                 190

Phe Pro Leu Leu Met Trp Ala Trp Lys Ile Ala Pro Ala Leu Val Thr
        195                 200                 205

Gly Asn Thr Val Val Leu Lys Thr Ala Glu Ser Thr Pro Leu Ser Ala
    210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
                245                 250                 255

Asn His Pro Lys Ile Lys Lys Val Ala Phe Thr Gly Ser Thr Ala Thr
            260                 265                 270

Gly Arg His Ile Tyr Gln Ser Ala Ala Ala Gly Leu Lys Lys Val Thr
        275                 280                 285

Leu Glu Leu Gly Gly Lys Ser Pro Asn Ile Val Phe Ala Asp Ala Glu
    290                 295                 300

Leu Lys Lys Ala Val Gln Asn Ile Ile Leu Gly Ile Tyr Tyr Asn Ser
305                 310                 315                 320

Gly Glu Val Cys Cys Ala Gly Ser Arg Val Tyr Val Glu Glu Ser Ile
                325                 330                 335

Tyr Asp Lys Phe Ile Glu Glu Phe Lys Ala Ala Ser Glu Ser Ile Lys
            340                 345                 350

Val Gly Asp Pro Phe Asp Glu Ser Thr Phe Gln Gly Ala Gln Thr Ser
        355                 360                 365

Gln Met Gln Leu Asn Lys Ile Leu Lys Tyr Val Asp Ile Gly Lys Asn
    370                 375                 380

Glu Gly Ala Thr Leu Ile Thr Gly Gly Glu Arg Leu Gly Ser Lys Gly
385                 390                 395                 400

Tyr Phe Ile Lys Pro Thr Val Phe Gly Asp Val Lys Glu Asp Met Arg
                405                 410                 415

Ile Val Lys Glu Glu Ile Phe Gly Pro Val Val Thr Val Thr Lys Phe
```

```
            420                 425                 430

Lys Ser Ala Asp Glu Val Ile Asn Met Ala Asn Asp Ser Glu Tyr Gly
        435                 440                 445

Leu Ala Ala Gly Ile His Thr Ser Asn Ile Asn Thr Ala Leu Lys Val
    450                 455                 460

Ala Asp Arg Val Asn Ala Gly Thr Val Trp Ile Asn Thr Tyr Asn Asp
465                 470                 475                 480

Phe His His Ala Val Pro Phe Gly Gly Phe Asn Ala Ser Gly Leu Gly
                485                 490                 495

Arg Glu Met Ser Val Asp Ala Leu Gln Asn Tyr Leu Gln Val Lys Ala
            500                 505                 510

Val Arg Ala Lys Leu Asp Glu
        515


<210> SEQ ID NO 23
<211> LENGTH: 1560
<212> TYPE: DNA
<213> ORGANISM: Saccharomyces cerevisiae
<220> FEATURE:
<223> OTHER INFORMATION: ALD5

<400> SEQUENCE: 23

atgctttctc gcacaagagc tgcagctccg aattccagaa tattcactag aagcttgtta     60

cgtctttatt ctcaagcacc attacgcgtt ccaattactc ttccaaatgg tttcacctac    120

gaacagccaa cagggttatt catcaatggt gaatttgttg cctcgaagca aaagaaaacg    180

tttgacgtga tcaatccatc taacgaagaa aagataacaa ctgtatacaa ggctatggaa    240

gatgatgttg atgaagccgt tgcagcggct aaaaaagctt ttgaaacgaa gtggtctatt    300

gtagagccgg aggttcgcgc taaagcttta ttcaatctcg ctgacttggt tgagaaacac    360

caagaaacac tggctgccat tgagtcaatg gataatggta agtcattgtt ttgtgcgcgc    420

ggtgacgtcg ctttagtatc taaatacttg cgttcttgcg gtggttgggc agataaaatc    480

tacggtaacg ttattgacac aggtaaaaac cattttacct actcaattaa ggaaccatta    540

ggcgtttgcg gccaaataat cccttggaac ttccctttat tgatgtggtc atggaaaatt    600

gggcctgctc tggctacagg taacaccgtc gtattgaaac ccgctgaaac aacaccttta    660

tctgcccttt tcgcttccca gttgtgtcag gaagcaggca tacccgctgg tgtagtcaat    720

atccttccgg gttccggtag agttgttgga gaaagattga gtgcacaccc agacgtgaag    780

aagattgctt ttacaggctc tactgccacc ggccgccata ttatgaaggt cgctgccgat    840

actgtcaaga aagtcacttt ggagctggga ggtaaatcac caaatattgt gtttgctgac    900

gctgatctag ataaagccgt caagaacatt gccttcggta ttttttacaa ctctggtgaa    960

gtttgctgcg ctggttccag aatatacatt caagatacag tatacgagga ggtgttgcaa   1020

aaactaaagg attacaccga gtcactaaag gtcggtgacc catttgatga ggaagttttc   1080

caaggtgctc aaacatctga caaacagctg cataaaattt tagactatgt cgatgtagca   1140

aaatcagagg gggctcgtct tgtgactgga ggggccagac atggcagtaa aggttatttt   1200

gtcaagccaa cagtgtttgc tgatgtcaaa gaagatatga gaattgttaa ggaggaagtg   1260

tttggtccca ttgtaactgt atccaagttt tctactgttg atgaagtgat tgctatggca   1320

aatgattctc aatatgggtt agccgcaggt attcacacta acgatattaa caaggctgtt   1380

gatgtgtcca aaagagtgaa agctggtact gtttggataa atacctataa caacttccac   1440

caaaatgttc ctttcggtgg cttcggccag tcaggtattg gccgtgaaat gggtgaggct   1500
```

gctttaagta actacactca aacaaaatct gtcagaattg ccattgacaa gccaattcgt 1560

<210> SEQ ID NO 24
<211> LENGTH: 520
<212> TYPE: PRT
<213> ORGANISM: Saccharomyces cerevisiae
<220> FEATURE:
<223> OTHER INFORMATION: ALD5

<400> SEQUENCE: 24

```
Met Leu Ser Arg Thr Arg Ala Ala Ala Pro Asn Ser Arg Ile Phe Thr
1               5                   10                  15

Arg Ser Leu Leu Arg Leu Tyr Ser Gln Ala Pro Leu Arg Val Pro Ile
            20                  25                  30

Thr Leu Pro Asn Gly Phe Thr Tyr Glu Gln Pro Thr Gly Leu Phe Ile
        35                  40                  45

Asn Gly Glu Phe Val Ala Ser Lys Gln Lys Lys Thr Phe Asp Val Ile
    50                  55                  60

Asn Pro Ser Asn Glu Glu Lys Ile Thr Thr Val Tyr Lys Ala Met Glu
65                  70                  75                  80

Asp Asp Val Asp Glu Ala Val Ala Ala Ala Lys Lys Ala Phe Glu Thr
                85                  90                  95

Lys Trp Ser Ile Val Glu Pro Glu Val Arg Ala Lys Ala Leu Phe Asn
            100                 105                 110

Leu Ala Asp Leu Val Glu Lys His Gln Glu Thr Leu Ala Ala Ile Glu
        115                 120                 125

Ser Met Asp Asn Gly Lys Ser Leu Phe Cys Ala Arg Gly Asp Val Ala
    130                 135                 140

Leu Val Ser Lys Tyr Leu Arg Ser Cys Gly Gly Trp Ala Asp Lys Ile
145                 150                 155                 160

Tyr Gly Asn Val Ile Asp Thr Gly Lys Asn His Phe Thr Tyr Ser Ile
                165                 170                 175

Lys Glu Pro Leu Gly Val Cys Gly Gln Ile Ile Pro Trp Asn Phe Pro
            180                 185                 190

Leu Leu Met Trp Ser Trp Lys Ile Gly Pro Ala Leu Ala Thr Gly Asn
        195                 200                 205

Thr Val Val Leu Lys Pro Ala Glu Thr Thr Pro Leu Ser Ala Leu Phe
    210                 215                 220

Ala Ser Gln Leu Cys Gln Glu Ala Gly Ile Pro Ala Gly Val Val Asn
225                 230                 235                 240

Ile Leu Pro Gly Ser Gly Arg Val Val Gly Glu Arg Leu Ser Ala His
                245                 250                 255

Pro Asp Val Lys Lys Ile Ala Phe Thr Gly Ser Thr Ala Thr Gly Arg
            260                 265                 270

His Ile Met Lys Val Ala Ala Asp Thr Val Lys Lys Val Thr Leu Glu
        275                 280                 285

Leu Gly Gly Lys Ser Pro Asn Ile Val Phe Ala Asp Ala Asp Leu Asp
    290                 295                 300

Lys Ala Val Lys Asn Ile Ala Phe Gly Ile Phe Tyr Asn Ser Gly Glu
305                 310                 315                 320

Val Cys Cys Ala Gly Ser Arg Ile Tyr Ile Gln Asp Thr Val Tyr Glu
                325                 330                 335

Glu Val Leu Gln Lys Leu Lys Asp Tyr Thr Glu Ser Leu Lys Val Gly
            340                 345                 350
```

```
Asp Pro Phe Asp Glu Glu Val Phe Gln Gly Ala Gln Thr Ser Asp Lys
        355                 360                 365

Gln Leu His Lys Ile Leu Asp Tyr Val Asp Val Ala Lys Ser Glu Gly
    370                 375                 380

Ala Arg Leu Val Thr Gly Gly Ala Arg His Gly Ser Lys Gly Tyr Phe
385                 390                 395                 400

Val Lys Pro Thr Val Phe Ala Asp Val Lys Glu Asp Met Arg Ile Val
                405                 410                 415

Lys Glu Glu Val Phe Gly Pro Ile Val Thr Val Ser Lys Phe Ser Thr
            420                 425                 430

Val Asp Glu Val Ile Ala Met Ala Asn Asp Ser Gln Tyr Gly Leu Ala
        435                 440                 445

Ala Gly Ile His Thr Asn Asp Ile Asn Lys Ala Val Asp Val Ser Lys
    450                 455                 460

Arg Val Lys Ala Gly Thr Val Trp Ile Asn Thr Tyr Asn Asn Phe His
465                 470                 475                 480

Gln Asn Val Pro Phe Gly Gly Phe Gly Gln Ser Gly Ile Gly Arg Glu
                485                 490                 495

Met Gly Glu Ala Ala Leu Ser Asn Tyr Thr Gln Thr Lys Ser Val Arg
            500                 505                 510

Ile Ala Ile Asp Lys Pro Ile Arg
        515                 520
```

<210> SEQ ID NO 25
<211> LENGTH: 1503
<212> TYPE: DNA
<213> ORGANISM: Saccharomyces cerevisiae
<220> FEATURE:
<223> OTHER INFORMATION: ALD6

<400> SEQUENCE: 25

```
atgactaagc tacactttga cactgctgaa ccagtcaaga tcacacttcc aaatggtttg      60

acatacgagc aaccaaccgg tctattcatt aacaacaagt ttatgaaagc tcaagacggt     120

aagacctatc ccgtcgaaga tccttccact gaaaacaccg tttgtgaggt ctcttctgcc     180

accactgaag atgttgaata tgctatcgaa tgtgccgacc gtgctttcca cgacactgaa     240

tgggctaccc aagacccaag agaaagaggc cgtctactaa gtaagttggc tgacgaattg     300

gaaagccaaa ttgacttggt ttcttccatt gaagctttgg acaatggtaa aactttggcc     360

ttagcccgtg gggatgttac cattgcaatc aactgtctaa gagatgctgc tgcctatgcc     420

gacaaagtca acggtagaac aatcaacacc ggtgacggct acatgaactt caccacctta     480

gagccaatcg gtgtctgtgg tcaaattatt ccatggaact ttccaataat gatgttggct     540

tggaagatcg ccccagcatt ggccatgggt aacgtctgta tcttgaaacc cgctgctgtc     600

acacctttaa atgccctata ctttgcttct ttatgtaaga aggttggtat tccagctggt     660

gtcgtcaaca tcgttccagg tcctggtaga actgttggtg ctgctttgac caacgaccca     720

agaatcagaa agctggcttt taccggttct acagaagtcg gtaagagtgt tgctgtcgac     780

tcttctgaat ctaacttgaa gaaaatcact ttggaactag gtggtaagtc cgcccatttg     840

gtctttgacg atgctaacat taagaagact ttaccaaatc tagtaaacgg tattttcaag     900

aacgctggtc aaatttgttc ctctggttct agaatttacg ttcaagaagg tatttacgac     960

gaactattgg ctgctttcaa ggcttacttg gaaaccgaaa tcaaagttgg taatccattt    1020

gacaaggcta acttccaagg tgctatcact aaccgtcaac aattcgacac aattatgaac    1080
```

```
tacatcgata tcggtaagaa agaaggcgcc aagatcttaa ctggtggcga aaaagttggt   1140

gacaagggtt acttcatcag accaaccgtt ttctacgatg ttaatgaaga catgagaatt   1200

gttaaggaag aaatttttgg accagttgtc actgtcgcaa agttcaagac tttagaagaa   1260

ggtgtcgaaa tggctaacag ctctgaattc ggtctaggtt ctggtatcga aacagaatct   1320

ttgagcacag gtttgaaggt ggccaagatg ttgaaggccg gtaccgtctg gatcaacaca   1380

tacaacgatt ttgactccag agttccattc ggtggtgtta agcaatctgg ttacggtaga   1440

gaaatgggtg aagaagtcta ccatgcatac actgaagtaa aagctgtcag aattaagttg   1500

taa                                                                 1503
```

<210> SEQ ID NO 26
<211> LENGTH: 500
<212> TYPE: PRT
<213> ORGANISM: Saccharomyces cerevisiae
<220> FEATURE:
<223> OTHER INFORMATION: ALD6

<400> SEQUENCE: 26

```
Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285
```

```
Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500
```

<210> SEQ ID NO 27
<211> LENGTH: 1176
<212> TYPE: DNA
<213> ORGANISM: Saccharomyces cerevisiae
<220> FEATURE:
<223> OTHER INFORMATION: GDP1

<400> SEQUENCE: 27

```
atgtctgctg ctgctgatag attaaactta acttccggcc acttgaatgc tggtagaaag     60

agaagttcct cttctgtttc tttgaaggct gccgaaaagc ctttcaaggt tactgtgatt    120

ggatctggta actggggtac tactattgcc aaggtggttg ccgaaaattg taagggatac    180

ccagaagttt tcgctccaat agtacaaatg tgggtgttcg aagaagagat caatggtgaa    240

aaattgactg aaatcataaa tactagacat caaaacgtga aatacttgcc tggcatcact    300

ctacccgaca atttggttgc taatccagac ttgattgatt cagtcaagga tgtcgacatc    360

atcgttttca acattccaca tcaatttttg ccccgtatct gtagccaatt gaaaggtcat    420

gttgattcac acgtcagagc tatctcctgt ctaaagggtt ttgaagttgg tgctaaaggt    480

gtccaattgc tatcctctta catcactgag gaactaggta ttcaatgtgg tgctctatct    540

ggtgctaaca ttgccaccga agtcgctcaa gaacactggt ctgaaacaac agttgcttac    600

cacattccaa aggatttcag aggcgagggc aaggacgtcg accataaggt tctaaaggcc    660

ttgttccaca gaccttactt ccacgttagt gtcatcgaag atgttgctgg tatctccatc    720

tgtggtgctt tgaagaacgt tgttgcctta ggttgtggtt tcgtcgaagg tctaggctgg    780
```

```
ggtaacaacg cttctgctgc catccaaaga gtcggtttgg gtgagatcat cagattcggt    840

caaatgtttt tcccagaatc tagagaagaa acatactacc aagagtctgc tggtgttgct    900

gatttgatca ccacctgcgc tggtggtaga aacgtcaagg ttgctaggct aatggctact    960

tctggtaagg acgcctggga atgtgaaaag gagttgttga atggccaatc cgctcaaggt   1020

ttaattacct gcaaagaagt tcacgaatgg ttggaaacat gtggctctgt cgaagacttc   1080

ccattatttg aagccgtata ccaaatcgtt tacaacaact acccaatgaa gaacctgccg   1140

gacatgattg aagaattaga tctacatgaa gattag                             1176


<210> SEQ ID NO 28
<211> LENGTH: 391
<212> TYPE: PRT
<213> ORGANISM: Saccharomyces cerevisiae
<220> FEATURE:
<223> OTHER INFORMATION: GDP1

<400> SEQUENCE: 28

Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
```

```
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 29
<211> LENGTH: 1320
<212> TYPE: DNA
<213> ORGANISM: Saccharomyces cerevisiae
<220> FEATURE:
<223> OTHER INFORMATION: GDP2

<400> SEQUENCE: 29

atgcttgctg tcagaagatt aacaagatac acattcctta agcgaacgca tccggtgtta     60

tatactcgtc gtgcatataa aattttgcct tcaagatcta ctttcctaag aagatcatta    120

ttacaaacac aactgcactc aaagatgact gctcatacta atatcaaaca gcacaaacac    180

tgtcatgagg accatcctat cagaagatcg gactctgccg tgtcaattgt acatttgaaa    240

cgtgcgccct tcaaggttac agtgattggt tctggtaact gggggaccac catcgccaaa    300

gtcattgcgg aaaacacaga attgcattcc catatcttcg agccagaggt gagaatgtgg    360

gtttttgatg aaaagatcgg cgacgaaaat ctgacggata tcataaatac aagacaccag    420

aacgttaaat atctacccaa tattgacctg ccccataatc tagtggccga tcctgatctt    480

ttacactcca tcaagggtgc tgacatcctt gttttcaaca tccctcatca atttttacca    540

aacatagtca aacaattgca aggccacgtg gcccctcatg taagggccat ctcgtgtcta    600

aaagggttcg agttgggctc caagggtgtg caattgctat cctcctatgt tactgatgag    660

ttaggaatcc aatgtggcgc actatctggt gcaaacttgg caccggaagt ggccaaggag    720

cattggtccg aaaccaccgt ggcttaccaa ctaccaaagg attatcaagg tgatggcaag    780

gatgtagatc ataagatttt gaaattgctg ttccacagac cttacttcca cgtcaatgtc    840

atcgatgatg ttgctggtat atccattgcc ggtgccttga agaacgtcgt ggcacttgca    900

tgtggtttcg tagaaggtat gggatggggt aacaatgcct ccgcagccat tcaaaggctg    960

ggtttaggtg aaattatcaa gttcggtaga atgtttttcc cagaatccaa agtcgagacc   1020

tactatcaag aatccgctgg tgttgcagat ctgatcacca cctgctcagg cggtagaaac   1080

gtcaaggttg ccacatacat ggccaagacc ggtaagtcag ccttggaagc agaaaaggaa   1140

ttgcttaacg gtcaatccgc ccaagggata atcacatgca gagaagttca cgagtggcta   1200

caaacatgtg agttgaccca agaattccca ttattcgagg cagtctacca gatagtctac   1260

aacaacgtcc gcatggaaga cctaccggag atgattgaag agctagacat cgatgacgaa   1320


<210> SEQ ID NO 30
<211> LENGTH: 440
<212> TYPE: PRT
<213> ORGANISM: Saccharomyces cerevisiae
```

<220> FEATURE:
<223> OTHER INFORMATION: GDP2

<400> SEQUENCE: 30

```
Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

Ser Thr Phe Leu Arg Arg Ser Leu Leu Gln Thr Gln Leu His Ser Lys
        35                  40                  45

Met Thr Ala His Thr Asn Ile Lys Gln His Lys His Cys His Glu Asp
    50                  55                  60

His Pro Ile Arg Arg Ser Asp Ser Ala Val Ser Ile Val His Leu Lys
65                  70                  75                  80

Arg Ala Pro Phe Lys Val Thr Val Ile Gly Ser Gly Asn Trp Gly Thr
                85                  90                  95

Thr Ile Ala Lys Val Ile Ala Glu Asn Thr Glu Leu His Ser His Ile
            100                 105                 110

Phe Glu Pro Glu Val Arg Met Trp Val Phe Asp Glu Lys Ile Gly Asp
        115                 120                 125

Glu Asn Leu Thr Asp Ile Ile Asn Thr Arg His Gln Asn Val Lys Tyr
    130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
    210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
    290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
    370                 375                 380

Gln Ser Ala Gln Gly Ile Ile Thr Cys Arg Glu Val His Glu Trp Leu
385                 390                 395                 400
```

```
Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
            420                 425                 430

Glu Glu Leu Asp Ile Asp Asp Glu
        435                 440


<210> SEQ ID NO 31
<211> LENGTH: 1131
<212> TYPE: DNA
<213> ORGANISM: Saccharomyces cerevisiae
<220> FEATURE:
<223> OTHER INFORMATION: FDH1

<400> SEQUENCE: 31

atgtcgaagg gaaaggtttt gctggttctt tacgaaggtg gtaagcatgc tgaagagcag      60

gaaaagttat tggggtgtat tgaaaatgaa cttggtatca gaaatttcat tgaagaacag     120

ggatacgagt tggttactac cattgacaag gaccctgagc caacctcaac ggtagacagg     180

gagttgaaag acgctgaaat tgtcattact acgccctttt tccccgccta catctcgaga     240

aacaggattg cagaagctcc taacctgaag ctctgtgtaa ccgctggcgt cggttcagac     300

catgtcgatt tagaagctgc aaatgaacgg aaaatcacgg tcaccgaagt tactggttct     360

aacgtcgttt ctgtcgcaga gcacgttatg gccacaattt tggttttgat aagaaactat     420

aatggtggtc atcaacaagc aattaatggt gagtgggata ttgccggcgt ggctaaaaat     480

gagtatgatc tggaagacaa aataatttca acggtaggtg ccggtagaat tggatatagg     540

gttctggaaa gattggtcgc atttaatccg aagaagttac tgtactacga ctaccaggaa     600

ctacctgcgg aagcaatcaa tagattgaac gaggccagca agcttttcaa tggcagaggt     660

gatattgttc agagagtaga gaaattggag gatatggttg ctcagtcaga tgttgttacc     720

atcaactgtc cattgcacaa ggactcaagg ggtttattca ataaaaagct tatttcccac     780

atgaaagatg gtgcatactt ggtgaatacc gctagaggtg ctatttgtgt cgcagaagat     840

gttgccgagg cagtcaagtc tggtaaattg gctggctatg gtggtgatgt ctgggataag     900

caaccagcac caaaagacca tccctggagg actatggaca ataaggacca cgtgggaaac     960

gcaatgactg ttcatatcag tggcacatct ctggatgctc aaaagaggta cgctcaggga    1020

gtaaagaaca tcctaaatag ttacttttcc aaaaagtttg attaccgtcc acaggatatt    1080

attgtgcaga atggttctta tgccaccaga gcttatggac agaagaaata a             1131


<210> SEQ ID NO 32
<211> LENGTH: 376
<212> TYPE: PRT
<213> ORGANISM: Saccharomyces cerevisiae
<220> FEATURE:
<223> OTHER INFORMATION: FDH1

<400> SEQUENCE: 32

Met Ser Lys Gly Lys Val Leu Leu Val Leu Tyr Glu Gly Gly Lys His
1               5                   10                  15

Ala Glu Glu Gln Glu Lys Leu Leu Gly Cys Ile Glu Asn Glu Leu Gly
            20                  25                  30

Ile Arg Asn Phe Ile Glu Glu Gln Gly Tyr Glu Leu Val Thr Thr Ile
        35                  40                  45

Asp Lys Asp Pro Glu Pro Thr Ser Thr Val Asp Arg Glu Leu Lys Asp
    50                  55                  60
```

```
Ala Glu Ile Val Ile Thr Thr Pro Phe Phe Pro Ala Tyr Ile Ser Arg
65                  70                  75                  80

Asn Arg Ile Ala Glu Ala Pro Asn Leu Lys Leu Cys Val Thr Ala Gly
                85                  90                  95

Val Gly Ser Asp His Val Asp Leu Glu Ala Ala Asn Glu Arg Lys Ile
            100                 105                 110

Thr Val Thr Glu Val Thr Gly Ser Asn Val Val Ser Val Ala Glu His
        115                 120                 125

Val Met Ala Thr Ile Leu Val Leu Ile Arg Asn Tyr Asn Gly Gly His
    130                 135                 140

Gln Gln Ala Ile Asn Gly Glu Trp Asp Ile Ala Gly Val Ala Lys Asn
145                 150                 155                 160

Glu Tyr Asp Leu Glu Asp Lys Ile Ile Ser Thr Val Gly Ala Gly Arg
                165                 170                 175

Ile Gly Tyr Arg Val Leu Glu Arg Leu Val Ala Phe Asn Pro Lys Lys
            180                 185                 190

Leu Leu Tyr Tyr Asp Tyr Gln Glu Leu Pro Ala Glu Ala Ile Asn Arg
        195                 200                 205

Leu Asn Glu Ala Ser Lys Leu Phe Asn Gly Arg Gly Asp Ile Val Gln
    210                 215                 220

Arg Val Glu Lys Leu Glu Asp Met Val Ala Gln Ser Asp Val Val Thr
225                 230                 235                 240

Ile Asn Cys Pro Leu His Lys Asp Ser Arg Gly Leu Phe Asn Lys Lys
                245                 250                 255

Leu Ile Ser His Met Lys Asp Gly Ala Tyr Leu Val Asn Thr Ala Arg
            260                 265                 270

Gly Ala Ile Cys Val Ala Glu Asp Val Ala Glu Ala Val Lys Ser Gly
        275                 280                 285

Lys Leu Ala Gly Tyr Gly Gly Asp Val Trp Asp Lys Gln Pro Ala Pro
    290                 295                 300

Lys Asp His Pro Trp Arg Thr Met Asp Asn Lys Asp His Val Gly Asn
305                 310                 315                 320

Ala Met Thr Val His Ile Ser Gly Thr Ser Leu Asp Ala Gln Lys Arg
                325                 330                 335

Tyr Ala Gln Gly Val Lys Asn Ile Leu Asn Ser Tyr Phe Ser Lys Lys
            340                 345                 350

Phe Asp Tyr Arg Pro Gln Asp Ile Ile Val Gln Asn Gly Ser Tyr Ala
        355                 360                 365

Thr Arg Ala Tyr Gly Gln Lys Lys
    370                 375
```

<210> SEQ ID NO 33
<211> LENGTH: 1129
<212> TYPE: DNA
<213> ORGANISM: Saccharomyces cerevisiae
<220> FEATURE:
<223> OTHER INFORMATION: FDH2

<400> SEQUENCE: 33

```
atgtcgaagg gaaaggtttt gctggttctt tatgaaggtg gtaagcatgc tgaagagcag      60

gaaaagttat tggggtgtat tgaaaatgaa cttggtatca gaaatttcat tgaagaacag     120

ggatacgagt tggttactac cattgacaag gaccctgagc caacctcaac ggtagacagg     180

gagttgaaag acgctgaaat tgtcattact acgccctttt tccccgccta catctcgaga     240
```

```
aacaggattg cagaagctcc taacctgaag ctctgtgtaa ccgctggcgt cggttcagac    300

catgtcgatt tagaagctgc aaatgaacgg aaaatcacgg tcaccgaagt tactggttct    360

aacgtcgttt ctgtcgcaga gcacgttatg gccacaattt tggttttgat aagaaactat    420

aatggtggtc atcaataagc aattaatggt gagtgggata ttgccggcgt ggctaaaaaa    480

tgagtatgat ctggaagaca aaataatttc aacggtaggt gccggtagaa ttggatatag    540

ggttctggaa agattggtcg catttaatcc gaagaagtta ctgtactacg actaccagga    600

actacctgcg gaagcaatca atagattgaa cgaggccagc aagcttttca atggcagagg    660

tgatattgtt cagagagtag agaaattgga ggatatggtt gctcagtcag atgttgttac    720

catcaactgt ccattgcaca aggactcaag ggtttattc aataaaaagc ttatttccca    780

catgaaagat ggtgcatact tggtgaatac cgctagaggt gctatttgtg tcgcagaaga    840

tgttgccgag gcagtcaagt ctggtaaatt ggctggctat ggtggtgatg tctgggataa    900

gcaaccagca ccaaaagacc atccctggag gactatggac aataaggacc acgtgggaaa    960

cgcaatgact gttcatatca gtggcacatc tctgcatgct caaaagaggt acgctcaggg   1020

agtaaagaac atcctaaata gttacttttc caaaaagttt gattaccgtc cacaggatat   1080

tattgtgcag aatggttctt atgccaccag agcttatgga cagaagaaa              1129
```

```
<210> SEQ ID NO 34
<211> LENGTH: 329
<212> TYPE: PRT
<213> ORGANISM: Oenococcus oenii
<220> FEATURE:
<223> OTHER INFORMATION: PTA

<400> SEQUENCE: 34

Met Thr Asn Leu Phe Thr Glu Leu Ala Asp Lys Ile Lys Glu Lys Lys
1               5                   10                  15

Leu Arg Leu Val Phe Pro Glu Gly Asp Asp Ser Arg Val Gln Gly Ala
            20                  25                  30

Ala Ile Arg Leu Lys Lys Asp Gly Leu Leu Thr Pro Ile Leu Leu Gly
        35                  40                  45

Asp Gln Ala Ala Val Glu Lys Thr Ala Ala Asp Asn His Phe Asp Leu
    50                  55                  60

Ser Gly Ile Lys Leu Ile Asp Pro Leu Lys Phe Asp Glu Lys Gln Phe
65                  70                  75                  80

Asn Gln Leu Ile Asp Lys Leu Val Thr Arg Arg Lys Gly Lys Thr Asp
                85                  90                  95

Pro Gln Thr Val Ala Met Trp Leu Gln Glu Val Asn Tyr Phe Gly Thr
            100                 105                 110

Met Leu Val Tyr Thr Gly Lys Ala Asp Ala Met Val Ser Gly Ala Val
        115                 120                 125

His Pro Thr Gly Asp Thr Val Arg Pro Ala Leu Gln Ile Ile Lys Thr
    130                 135                 140

Ala Pro Gly Val Ser Arg Ile Ser Gly Ala Phe Ile Met Gln Lys Asn
145                 150                 155                 160

Asp Glu Arg Tyr Leu Phe Ala Asp Ser Ala Ile Asn Ile Glu Leu Asp
                165                 170                 175

Ala Gln Thr Met Ala Glu Ile Ala Val Gln Ser Ala His Thr Ala Lys
            180                 185                 190

Ile Phe Gly Ile Asp Pro Lys Val Ala Met Leu Ser Phe Ser Thr Lys
        195                 200                 205
```

```
Gly Ser Ala Lys His Ala Leu Val Asp Lys Val Ala Gln Ala Thr Lys
    210                 215                 220

Leu Ala Gln Glu Met Ala Pro Asp Leu Ala Asp Asn Ile Asp Gly Glu
225                 230                 235                 240

Leu Gln Phe Asp Ala Ala Phe Val Glu Ser Val Ala Lys Leu Lys Ala
                245                 250                 255

Pro Gly Ser Lys Val Ala Gly His Ala Asn Val Phe Ile Phe Pro Ser
            260                 265                 270

Leu Glu Ala Gly Asn Ile Gly Tyr Lys Ile Ala Gln Arg Leu Gly Gly
        275                 280                 285

Tyr Glu Ala Ile Gly Pro Ile Leu Gln Gly Leu Ala Ala Pro Val Ser
    290                 295                 300

Asp Leu Ser Arg Gly Ala Ser Gln Glu Asp Val Tyr Lys Val Ala Ile
305                 310                 315                 320

Ile Thr Ala Ala Gln Ala Leu Lys Asn
                325
```

<210> SEQ ID NO 35
<211> LENGTH: 1008
<212> TYPE: DNA
<213> ORGANISM: Saccharomyces cerevisiae
<220> FEATURE:
<223> OTHER INFORMATION: TAL1

<400> SEQUENCE: 35

```
atgtctgaac cagctcaaaa gaaacaaaag gttgctaaca actctctaga acaattgaaa      60

gcctccggca ctgtcgttgt tgccgacact ggtgatttcg gctctattgc caagtttcaa     120

cctcaagact ccacaactaa cccatcattg atcttggctg ctgccaagca accaacttac     180

gccaagttga tcgatgttgc cgtggaatac ggtaagaagc atggtaagac caccgaagaa     240

caagtcgaaa atgctgtgga cagattgtta gtcgaattcg gtaaggagat cttaaagatt     300

gttccaggca gagtctccac cgaagttgat gctagattgt cttttgacac tcaagctacc     360

attgaaaagg ctagacatat cattaaattg tttgaacaag aaggtgtctc caaggaaaga     420

gtccttatta aaattgcttc cacttgggaa ggtattcaag ctgccaaaga attggaagaa     480

aaggacggta tccactgtaa tttgactcta ttattctcct tcgttcaagc agttgcctgt     540

gccgaggccc aagttacttt gatttcccca tttgttggta gaattctaga ctggtacaaa     600

tccagcactg gtaaagatta caagggtgaa gccgacccag gtgttatttc cgtcaagaaa     660

atctacaact actacaagaa gtacggttac aagactattg ttatgggtgc ttctttcaga     720

agcactgacg aaatcaaaaa cttggctggt gttgactatc taacaatttc tccagcttta     780

ttggacaagt tgatgaacag tactgaacct ttcccaagag ttttggaccc tgtctccgct     840

aagaaggaag ccggcgacaa gatttcttac atcagcgacg aatctaaatt cagattcgac     900

ttgaatgaag acgctatggc cactgaaaaa ttgtccgaag gtatcagaaa attctctgcc     960

gatattgtta ctctattcga cttgattgaa aagaaagtta ccgcttaa                1008
```

<210> SEQ ID NO 36
<211> LENGTH: 335
<212> TYPE: PRT
<213> ORGANISM: Saccharomyces cerevisiae
<220> FEATURE:
<223> OTHER INFORMATION: TAL1

<400> SEQUENCE: 36

```
Met Ser Glu Pro Ala Gln Lys Lys Gln Lys Val Ala Asn Asn Ser Leu
```

```
1               5                   10                  15

Glu Gln Leu Lys Ala Ser Gly Thr Val Val Ala Asp Thr Gly Asp
            20                  25                  30

Phe Gly Ser Ile Ala Lys Phe Gln Pro Gln Asp Ser Thr Thr Asn Pro
        35                  40                  45

Ser Leu Ile Leu Ala Ala Ala Lys Gln Pro Thr Tyr Ala Lys Leu Ile
    50                  55                  60

Asp Val Ala Val Glu Tyr Gly Lys Lys His Gly Lys Thr Thr Glu Glu
65                  70                  75                  80

Gln Val Glu Asn Ala Val Asp Arg Leu Leu Val Glu Phe Gly Lys Glu
                85                  90                  95

Ile Leu Lys Ile Val Pro Gly Arg Val Ser Thr Glu Val Asp Ala Arg
            100                 105                 110

Leu Ser Phe Asp Thr Gln Ala Thr Ile Glu Lys Ala Arg His Ile Ile
        115                 120                 125

Lys Leu Phe Glu Gln Glu Gly Val Ser Lys Glu Arg Val Leu Ile Lys
    130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
                165                 170                 175

Ala Val Ala Cys Ala Glu Ala Gln Val Thr Leu Ile Ser Pro Phe Val
            180                 185                 190

Gly Arg Ile Leu Asp Trp Tyr Lys Ser Ser Thr Gly Lys Asp Tyr Lys
        195                 200                 205

Gly Glu Ala Asp Pro Gly Val Ile Ser Val Lys Lys Ile Tyr Asn Tyr
    210                 215                 220

Tyr Lys Lys Tyr Gly Tyr Lys Thr Ile Val Met Gly Ala Ser Phe Arg
225                 230                 235                 240

Ser Thr Asp Glu Ile Lys Asn Leu Ala Gly Val Asp Tyr Leu Thr Ile
                245                 250                 255

Ser Pro Ala Leu Leu Asp Lys Leu Met Asn Ser Thr Glu Pro Phe Pro
            260                 265                 270

Arg Val Leu Asp Pro Val Ser Ala Lys Lys Glu Ala Gly Asp Lys Ile
        275                 280                 285

Ser Tyr Ile Ser Asp Glu Ser Lys Phe Arg Phe Asp Leu Asn Glu Asp
    290                 295                 300

Ala Met Ala Thr Glu Lys Leu Ser Glu Gly Ile Arg Lys Phe Ser Ala
305                 310                 315                 320

Asp Ile Val Thr Leu Phe Asp Leu Ile Glu Lys Lys Val Thr Ala
                325                 330                 335
```

<210> SEQ ID NO 37
<211> LENGTH: 2040
<212> TYPE: DNA
<213> ORGANISM: Saccharomyces cerevisiae
<220> FEATURE:
<223> OTHER INFORMATION: TKL1

<400> SEQUENCE: 37

```
atgactcaat tcactgacat tgataagcta gccgtctcca ccataagaat tttggctgtg      60

gacaccgtat ccaaggccaa ctcaggtcac ccaggtgctc cattgggtat ggcaccagct     120

gcacacgttc tatggagtca aatgcgcatg aacccaacca acccagactg gatcaacaga     180

gatagatttg tcttgtctaa cggtcacgcg gtcgctttgt tgtattctat gctacatttg     240
```

```
actggttacg atctgtctat tgaagacttg aaacagttca gacagttggg ttccagaaca    300
ccaggtcatc ctgaatttga gttgccaggt gttgaagtta ctaccggtcc attaggtcaa    360
ggtatctcca acgctgttgg tatggccatg gctcaagcta acctggctgc cacttacaac    420
aagccgggct ttaccttgtc tgacaactac acctatgttt tcttgggtga cggttgtttg    480
caagaaggta tttcttcaga agcttcctcc ttggctggtc atttgaaatt gggtaacttg    540
attgccatct acgatgacaa caagatcact atcgatggtg ctaccagtat ctcattcgat    600
gaagatgttg ctaagagata cgaagcctac ggttgggaag ttttgtacgt agaaaatggt    660
aacgaagatc tagccggtat tgccaaggct attgctcaag ctaagttatc caaggacaaa    720
ccaactttga tcaaaatgac cacaaccatt ggttacggtt ccttgcatgc cggctctcac    780
tctgtgcacg gtgccccatt gaaagcagat gatgttaaac aactaaagag caaattcggt    840
ttcaacccag acaagtcctt tgttgttcca caagaagttt acgaccacta ccaaaagaca    900
attttaaagc caggtgtcga agccaacaac aagtggaaca agttgttcag cgaataccaa    960
aagaaattcc cagaattagg tgctgaattg gctagaagat tgagcggcca actacccgca   1020
aattgggaat ctaagttgcc aacttacacc gccaaggact ctgccgtggc cactagaaaa   1080
ttatcagaaa ctgttcttga ggatgtttac aatcaattgc cagagttgat tggtggttct   1140
gccgatttaa caccttctaa cttgaccaga tggaaggaag cccttgactt ccaacctcct   1200
tcttccggtt caggtaacta ctctggtaga tacattaggt acggtattag agaacacgct   1260
atgggtgcca taatgaacgg tatttcagct ttcggtgcca actacaaacc atacggtggt   1320
actttcttga acttcgtttc ttatgctgct ggtgccgtta gattgtccgc tttgtctggc   1380
cacccagtta tttgggttgc tacacatgac tctatcggtg tcggtgaaga tggtccaaca   1440
catcaaccta ttgaaacttt agcacacttc agatccctac caaacattca agtttggaga   1500
ccagctgatg gtaacgaagt ttctgccgcc tacaagaact ctttagaatc caagcatact   1560
ccaagtatca ttgctttgtc cagacaaaac ttgccacaat tggaaggtag ctctattgaa   1620
agcgcttcta agggtggtta cgtactacaa gatgttgcta acccagatat tattttagtg   1680
gctactggtt ccgaagtgtc tttgagtgtt gaagctgcta agactttggc cgcaaagaac   1740
atcaaggctc gtgttgtttc tctaccagat ttcttcactt ttgacaaaca acccctagaa   1800
tacagactat cagtcttacc agacaacgtt ccaatcatgt ctgttgaagt tttggctacc   1860
acatgttggg gcaaatacgc tcatcaatcc ttcggtattg acagatttgg tgcctccggt   1920
aaggcaccag aagtcttcaa gttcttcggt ttcaccccag aaggtgttgc tgaaagagct   1980
caaaagacca ttgcattcta taagggtgac aagctaattt ctcctttgaa aaaagctttc   2040
```

<210> SEQ ID NO 38
<211> LENGTH: 680
<212> TYPE: PRT
<213> ORGANISM: Saccharomyces cerevisiae
<220> FEATURE:
<223> OTHER INFORMATION: TKL1

<400> SEQUENCE: 38

```
Met Thr Gln Phe Thr Asp Ile Asp Lys Leu Ala Val Ser Thr Ile Arg
1               5                   10                  15

Ile Leu Ala Val Asp Thr Val Ser Lys Ala Asn Ser Gly His Pro Gly
            20                  25                  30

Ala Pro Leu Gly Met Ala Pro Ala Ala His Val Leu Trp Ser Gln Met
        35                  40                  45
```

```
Arg Met Asn Pro Thr Asn Pro Asp Trp Ile Asn Arg Asp Arg Phe Val
    50                  55                  60

Leu Ser Asn Gly His Ala Val Ala Leu Leu Tyr Ser Met Leu His Leu
65                  70                  75                  80

Thr Gly Tyr Asp Leu Ser Ile Glu Asp Leu Lys Gln Phe Arg Gln Leu
                85                  90                  95

Gly Ser Arg Thr Pro Gly His Pro Glu Phe Glu Leu Pro Gly Val Glu
            100                 105                 110

Val Thr Thr Gly Pro Leu Gly Gln Gly Ile Ser Asn Ala Val Gly Met
        115                 120                 125

Ala Met Ala Gln Ala Asn Leu Ala Ala Thr Tyr Asn Lys Pro Gly Phe
    130                 135                 140

Thr Leu Ser Asp Asn Tyr Thr Tyr Val Phe Leu Gly Asp Gly Cys Leu
145                 150                 155                 160

Gln Glu Gly Ile Ser Ser Glu Ala Ser Ser Leu Ala Gly His Leu Lys
                165                 170                 175

Leu Gly Asn Leu Ile Ala Ile Tyr Asp Asp Asn Lys Ile Thr Ile Asp
            180                 185                 190

Gly Ala Thr Ser Ile Ser Phe Asp Glu Asp Val Ala Lys Arg Tyr Glu
        195                 200                 205

Ala Tyr Gly Trp Glu Val Leu Tyr Val Glu Asn Gly Asn Glu Asp Leu
    210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Thr Ile Gly Tyr Gly Ser Leu His
                245                 250                 255

Ala Gly Ser His Ser Val His Gly Ala Pro Leu Lys Ala Asp Asp Val
            260                 265                 270

Lys Gln Leu Lys Ser Lys Phe Gly Phe Asn Pro Asp Lys Ser Phe Val
        275                 280                 285

Val Pro Gln Glu Val Tyr Asp His Tyr Gln Lys Thr Ile Leu Lys Pro
    290                 295                 300

Gly Val Glu Ala Asn Asn Lys Trp Asn Lys Leu Phe Ser Glu Tyr Gln
305                 310                 315                 320

Lys Lys Phe Pro Glu Leu Gly Ala Glu Leu Ala Arg Arg Leu Ser Gly
                325                 330                 335

Gln Leu Pro Ala Asn Trp Glu Ser Lys Leu Pro Thr Tyr Thr Ala Lys
            340                 345                 350

Asp Ser Ala Val Ala Thr Arg Lys Leu Ser Glu Thr Val Leu Glu Asp
        355                 360                 365

Val Tyr Asn Gln Leu Pro Glu Leu Ile Gly Gly Ser Ala Asp Leu Thr
    370                 375                 380

Pro Ser Asn Leu Thr Arg Trp Lys Glu Ala Leu Asp Phe Gln Pro Pro
385                 390                 395                 400

Ser Ser Gly Ser Gly Asn Tyr Ser Gly Arg Tyr Ile Arg Tyr Gly Ile
                405                 410                 415

Arg Glu His Ala Met Gly Ala Ile Met Asn Gly Ile Ser Ala Phe Gly
            420                 425                 430

Ala Asn Tyr Lys Pro Tyr Gly Gly Thr Phe Leu Asn Phe Val Ser Tyr
        435                 440                 445

Ala Ala Gly Ala Val Arg Leu Ser Ala Leu Ser Gly His Pro Val Ile
    450                 455                 460
```

```
Trp Val Ala Thr His Asp Ser Ile Gly Val Gly Glu Asp Gly Pro Thr
465                 470                 475                 480

His Gln Pro Ile Glu Thr Leu Ala His Phe Arg Ser Leu Pro Asn Ile
                485                 490                 495

Gln Val Trp Arg Pro Ala Asp Gly Asn Glu Val Ser Ala Ala Tyr Lys
            500                 505                 510

Asn Ser Leu Glu Ser Lys His Thr Pro Ser Ile Ile Ala Leu Ser Arg
        515                 520                 525

Gln Asn Leu Pro Gln Leu Glu Gly Ser Ser Ile Glu Ser Ala Ser Lys
    530                 535                 540

Gly Gly Tyr Val Leu Gln Asp Val Ala Asn Pro Asp Ile Ile Leu Val
545                 550                 555                 560

Ala Thr Gly Ser Glu Val Ser Leu Ser Val Glu Ala Ala Lys Thr Leu
                565                 570                 575

Ala Ala Lys Asn Ile Lys Ala Arg Val Val Ser Leu Pro Asp Phe Phe
            580                 585                 590

Thr Phe Asp Lys Gln Pro Leu Glu Tyr Arg Leu Ser Val Leu Pro Asp
        595                 600                 605

Asn Val Pro Ile Met Ser Val Glu Val Leu Ala Thr Thr Cys Trp Gly
    610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
                645                 650                 655

Ala Glu Arg Ala Gln Lys Thr Ile Ala Phe Tyr Lys Gly Asp Lys Leu
            660                 665                 670

Ile Ser Pro Leu Lys Lys Ala Phe
        675                 680
```

<210> SEQ ID NO 39
<211> LENGTH: 774
<212> TYPE: DNA
<213> ORGANISM: Saccharomyces cerevisiae
<220> FEATURE:
<223> OTHER INFORMATION: RKI1

<400> SEQUENCE: 39

```
atggctgccg gtgtcccaaa aattgatgcg ttagaatctt tgggcaatcc tttggaggat     60

gccaagagag ctgcagcata cagagcagtt gatgaaaatt taaaatttga tgatcacaaa    120

attattggaa ttggtagtgg tagcacagtg gtttatgttg ccgaaagaat tggacaatat    180

ttgcatgacc ctaaatttta tgaagtagcg tctaaattca tttgcattcc aacaggattc    240

caatcaagaa acttgatttt ggataacaag ttgcaattag gctccattga acagtatcct    300

cgcattgata tagcgtttga cggtgctgat gaagtggatg agaatttaca attaattaaa    360

ggtggtggtg cttgtctatt tcaagaaaaa ttggttagta ctagtgctaa aaccttcatt    420

gtcgttgctg attcaagaaa aaagtcacca aaacatttag gtaagaactg gaggcaaggt    480

gttcccattg aaattgtacc ttcctcatac gtgagggtca agaatgatct attagaacaa    540

ttgcatgctg aaaaagttga catcagacaa ggaggttctg ctaaagcagg tcctgttgta    600

actgacaata ataacttcat tatcgatgcg gatttcggtg aaatttccga tccaagaaaa    660

ttgcatagag aaatcaaact gttagtgggc gtggtggaaa caggtttatt catcgacaac    720

gcttcaaaag cctacttcgg taattctgac ggtagtgttg aagttaccga aaag          774
```

<210> SEQ ID NO 40
<211> LENGTH: 258
<212> TYPE: PRT
<213> ORGANISM: Saccharomyces cerevisiae RKI1

<400> SEQUENCE: 40

```
Met Ala Ala Gly Val Pro Lys Ile Asp Ala Leu Glu Ser Leu Gly Asn
1               5                   10                  15

Pro Leu Glu Asp Ala Lys Arg Ala Ala Ala Tyr Arg Ala Val Asp Glu
            20                  25                  30

Asn Leu Lys Phe Asp Asp His Lys Ile Ile Gly Ile Gly Ser Gly Ser
        35                  40                  45

Thr Val Val Tyr Val Ala Glu Arg Ile Gly Gln Tyr Leu His Asp Pro
    50                  55                  60

Lys Phe Tyr Glu Val Ala Ser Lys Phe Ile Cys Ile Pro Thr Gly Phe
65                  70                  75                  80

Gln Ser Arg Asn Leu Ile Leu Asp Asn Lys Leu Gln Leu Gly Ser Ile
                85                  90                  95

Glu Gln Tyr Pro Arg Ile Asp Ile Ala Phe Asp Gly Ala Asp Glu Val
            100                 105                 110

Asp Glu Asn Leu Gln Leu Ile Lys Gly Gly Gly Ala Cys Leu Phe Gln
        115                 120                 125

Glu Lys Leu Val Ser Thr Ser Ala Lys Thr Phe Ile Val Val Ala Asp
    130                 135                 140

Ser Arg Lys Lys Ser Pro Lys His Leu Gly Lys Asn Trp Arg Gln Gly
145                 150                 155                 160

Val Pro Ile Glu Ile Val Pro Ser Ser Tyr Val Arg Val Lys Asn Asp
                165                 170                 175

Leu Leu Glu Gln Leu His Ala Glu Lys Val Asp Ile Arg Gln Gly Gly
            180                 185                 190

Ser Ala Lys Ala Gly Pro Val Val Thr Asp Asn Asn Asn Phe Ile Ile
        195                 200                 205

Asp Ala Asp Phe Gly Glu Ile Ser Asp Pro Arg Lys Leu His Arg Glu
    210                 215                 220

Ile Lys Leu Leu Val Gly Val Val Glu Thr Gly Leu Phe Ile Asp Asn
225                 230                 235                 240

Ala Ser Lys Ala Tyr Phe Gly Asn Ser Asp Gly Ser Val Glu Val Thr
                245                 250                 255

Glu Lys
```

<210> SEQ ID NO 41
<211> LENGTH: 714
<212> TYPE: DNA
<213> ORGANISM: Saccharomyces cerevisiae
<220> FEATURE:
<223> OTHER INFORMATION: RPE1

<400> SEQUENCE: 41

```
atggtcaaac caattatagc tcccagtatc cttgcttctg acttcgccaa cttgggttgc      60

gaatgtcata aggtcatcaa cgccggcgca gattggttac atatcgatgt catggacggc     120

cattttgttc caaacattac tctgggccaa ccaattgtta cctccctacg tcgttctgtg     180

ccacgccctg gcgatgctag caacacagaa aagaagccca ctgcgttctt cgattgtcac     240

atgatggttg aaaatcctga aaaatgggtc gacgattttg ctaaatgtgg tgctgaccaa     300

tttacgttcc actacgaggc cacacaagac cctttgcatt tagttaagtt gattaagtct     360
```

```
aagggcatca aagctgcatg cgccatcaaa cctggtactt ctgttgacgt tttatttgaa    420

ctagctcctc atttggatat ggctcttgtt atgactgtgg aacctgggtt tggaggccaa    480

aaattcatgg aagacatgat gccaaaagtg gaaactttga gagccaagtt cccccatttg    540

aatatccaag tcgatggtgg tttgggcaag gagaccatcc cgaaagccgc caaagccggt    600

gccaacgtta ttgtcgctgg taccagtgtt ttcactgcag ctgacccgca cgatgttatc    660

tccttcatga aagaagaagt ctcgaaggaa ttgcgttcta gagatttgct agat          714


<210> SEQ ID NO 42
<211> LENGTH: 238
<212> TYPE: PRT
<213> ORGANISM: Saccharomyces cerevisiae
<220> FEATURE:
<223> OTHER INFORMATION: RPE1

<400> SEQUENCE: 42

Met Val Lys Pro Ile Ile Ala Pro Ser Ile Leu Ala Ser Asp Phe Ala
1               5                   10                  15

Asn Leu Gly Cys Glu Cys His Lys Val Ile Asn Ala Gly Ala Asp Trp
            20                  25                  30

Leu His Ile Asp Val Met Asp Gly His Phe Val Pro Asn Ile Thr Leu
        35                  40                  45

Gly Gln Pro Ile Val Thr Ser Leu Arg Arg Ser Val Pro Arg Pro Gly
    50                  55                  60

Asp Ala Ser Asn Thr Glu Lys Lys Pro Thr Ala Phe Phe Asp Cys His
65                  70                  75                  80

Met Met Val Glu Asn Pro Glu Lys Trp Val Asp Asp Phe Ala Lys Cys
                85                  90                  95

Gly Ala Asp Gln Phe Thr Phe His Tyr Glu Ala Thr Gln Asp Pro Leu
            100                 105                 110

His Leu Val Lys Leu Ile Lys Ser Lys Gly Ile Lys Ala Ala Cys Ala
        115                 120                 125

Ile Lys Pro Gly Thr Ser Val Asp Val Leu Phe Glu Leu Ala Pro His
    130                 135                 140

Leu Asp Met Ala Leu Val Met Thr Val Glu Pro Gly Phe Gly Gly Gln
145                 150                 155                 160

Lys Phe Met Glu Asp Met Met Pro Lys Val Glu Thr Leu Arg Ala Lys
                165                 170                 175

Phe Pro His Leu Asn Ile Gln Val Asp Gly Gly Leu Gly Lys Glu Thr
            180                 185                 190

Ile Pro Lys Ala Ala Lys Ala Gly Ala Asn Val Ile Val Ala Gly Thr
        195                 200                 205

Ser Val Phe Thr Ala Ala Asp Pro His Asp Val Ile Ser Phe Met Lys
    210                 215                 220

Glu Glu Val Ser Lys Glu Leu Arg Ser Arg Asp Leu Leu Asp
225                 230                 235


<210> SEQ ID NO 43
<211> LENGTH: 2733
<212> TYPE: DNA
<213> ORGANISM: Bifidobacterium adolescentis
<220> FEATURE:
<223> OTHER INFORMATION: adhE

<400> SEQUENCE: 43

atggcagacg caaagaagaa ggaagagccg accaagccga ctccggaaga gaagctcgcc     60
```

-continued

```
gcagccgagg ctgaggtcga cgctctggtc aagaagggcc tgaaggctct tgatgaattc    120
gagaagctcg atcagaagca ggttgaccac atcgtggcca aggcttccgt cgcagccctg    180
aacaagcact tggtgctcgc caagatggcc gtcgaggaga cccaccgtgg tctggtcgaa    240
gacaaggcca ccaagaacat cttcgcctgc gagcatgtca ccaactacct ggctggtcag    300
aagaccgtcg gcatcatccg cgaggacgac gtgctgggca tcgacgaaat cgccgagccg    360
gttggcgtcg tcgctggcgt gaccccggtc accaacccga cctccaccgc catcttcaag    420
tcgctgatcg cactgaagac ccgctgcccg atcatcttcg gcttccaccc gggcgcacag    480
aactgctccg tcgcggccgc caagatcgtt cgcgatgccg ctatcgcagc aggcgctcct    540
gagaactgta ttcagtggat cgagcatccg tccatcgagg ccactggcgc cctgatgaag    600
catgatggtg tcgccaccat cctcgccacc ggtggtccgg gcatggtcaa ggccgcatac    660
tcctccggca agccggccct gggcgtcggc gcgggcaatg ctccggcata cgttgacaag    720
aacgtcgacg tcgtgcgtgc agccaacgat ctgattcttt ccaagcactt cgattacggc    780
atgatctgcg ctaccgagca ggccatcatc gccgacaagg acatctacgc tccgctcgtt    840
aaggaactca agcgtcgcaa ggcctatttc gtgaacgctg acgagaaggc caagctcgag    900
cagtacatgt tcggctgcac cgcttactcc ggacagaccc cgaagctcaa ctccgtggtg    960
ccgggcaagt ccccgcagta catcgccaag gccgccggct tcgagattcc ggaagacgcc   1020
accatccttg ccgctgagtg caaggaagtc ggcgagaacg agccgctgac catggagaag   1080
cttgctccgg tccaggccgt gctgaagtcc gacaacaagg aacaggcctt cgagatgtgc   1140
gaagccatgc tgaagcatgg cgccggccac accgccgcca tccacaccaa cgaccgtgac   1200
ctggtccgcg agtacggcca gcgcatgcac gcctgccgta tcatctggaa ctccccgagc   1260
tccctcggcg gcgtgggcga catctacaac gccatcgctc cgtccctgac cctgggctgc   1320
ggctcctacg gcggcaactc cgtgtccggc aacgtccagg cagtcaacct catcaacatc   1380
aagcgcatcg ctcggaggaa caacaacatg cagtggttca agattccggc caagacctac   1440
ttcgagccga acgccatcaa gtacctgcgc gacatgtacg gcatcgaaaa ggccgtcatc   1500
gtgtgcgata aggtcatgga gcagctcggc atcgttgaca agatcatcga tcagctgcgt   1560
gcacgttcca accgcgtgac cttccgtatc atcgattatg tcgagccgga gccgagcgtg   1620
gagaccgtcg aacgtggcgc cgccatgatg cgcgaggagt tcgagccgga taccatcatc   1680
gccgtcggcg gtggttcccc gatggatgcg tccaagatta tgtggctgct gtacgagcac   1740
ccggaaatct ccttctccga tgtgcgtgag aagttcttcg atatccgtaa gcgcgcgttc   1800
aagattccgc cgctgggcaa gaaggccaag ctggtctgca ttccgacttc ttccggcacc   1860
ggttccgaag tcacgccgtt cgctgtgatt accgaccaca agaccggcta taagtacccg   1920
atcaccgatt acgcgctgac cccgtccgtc gctatcgtcg atccggtgct ggcacgtact   1980
cagccgcgca agctggcttc cgatgctggt ttcgatgctc tgacccacgc ttttgaggct   2040
tatgtgtccg tgtatgccaa cgacttcacc gatggtatgg cattgcacgc tgccaagctg   2100
gtttgggaca acctcgctga gtccgtcaat ggcgagccgg gtgaggagaa gacccgtgcc   2160
caggagaaga tgcataatgc cgccaccatg gccggcatgg ctttcggctc cgccttcctc   2220
ggcatgtgcc acggcatggc ccacaccatt ggtgcactgt gccacgttgc ccacggtcgt   2280
accaactcca tcctcctgcc gtacgtgatc cgttacaacg gttccgtccc ggaggagccg   2340
accagctggc cgaagtacaa caagtacatc gctccggaac gctaccagga gatcgccaag   2400
aaccttggcg tgaacccggg caagactccg gaagagggcg tcgagaacct ggccaaggct   2460
```

```
gttgaggatt accgtgacaa caagctcggt atgaacaaga gcttccagga gtgcggtgtg   2520

gatgaggact actattggtc catcatcgac cagatcggca tgcgcgccta cgaagaccag   2580

tgcgcaccgg cgaacccgcg tatcccgcag atcgaggata tgaaggatat cgccattgcc   2640

gcctactacg gcgtcagcca ggcggaaggc cacaagctgc gcgtccagcg tcagggcgaa   2700

gccgctacgg aggaagcttc cgagcgcgcc tga                                2733


<210> SEQ ID NO 44
<211> LENGTH: 910
<212> TYPE: PRT
<213> ORGANISM: Bifidobacterium adolescentis
<220> FEATURE:
<223> OTHER INFORMATION: adhE

<400> SEQUENCE: 44

Met Ala Asp Ala Lys Lys Lys Glu Glu Pro Thr Lys Pro Thr Pro Glu
1               5                   10                  15

Glu Lys Leu Ala Ala Ala Glu Ala Glu Val Asp Ala Leu Val Lys Lys
            20                  25                  30

Gly Leu Lys Ala Leu Asp Glu Phe Glu Lys Leu Asp Gln Lys Gln Val
        35                  40                  45

Asp His Ile Val Ala Lys Ala Ser Val Ala Ala Leu Asn Lys His Leu
    50                  55                  60

Val Leu Ala Lys Met Ala Val Glu Glu Thr His Arg Gly Leu Val Glu
65                  70                  75                  80

Asp Lys Ala Thr Lys Asn Ile Phe Ala Cys Glu His Val Thr Asn Tyr
                85                  90                  95

Leu Ala Gly Gln Lys Thr Val Gly Ile Ile Arg Glu Asp Asp Val Leu
            100                 105                 110

Gly Ile Asp Glu Ile Ala Glu Pro Val Gly Val Val Ala Gly Val Thr
        115                 120                 125

Pro Val Thr Asn Pro Thr Ser Thr Ala Ile Phe Lys Ser Leu Ile Ala
    130                 135                 140

Leu Lys Thr Arg Cys Pro Ile Ile Phe Gly Phe His Pro Gly Ala Gln
145                 150                 155                 160

Asn Cys Ser Val Ala Ala Ala Lys Ile Val Arg Asp Ala Ala Ile Ala
                165                 170                 175

Ala Gly Ala Pro Glu Asn Cys Ile Gln Trp Ile Glu His Pro Ser Ile
            180                 185                 190

Glu Ala Thr Gly Ala Leu Met Lys His Asp Gly Val Ala Thr Ile Leu
        195                 200                 205

Ala Thr Gly Gly Pro Gly Met Val Lys Ala Ala Tyr Ser Ser Gly Lys
    210                 215                 220

Pro Ala Leu Gly Val Gly Ala Gly Asn Ala Pro Ala Tyr Val Asp Lys
225                 230                 235                 240

Asn Val Asp Val Val Arg Ala Ala Asn Asp Leu Ile Leu Ser Lys His
                245                 250                 255

Phe Asp Tyr Gly Met Ile Cys Ala Thr Glu Gln Ala Ile Ile Ala Asp
            260                 265                 270

Lys Asp Ile Tyr Ala Pro Leu Val Lys Glu Leu Lys Arg Arg Lys Ala
        275                 280                 285

Tyr Phe Val Asn Ala Asp Glu Lys Ala Lys Leu Glu Gln Tyr Met Phe
    290                 295                 300

Gly Cys Thr Ala Tyr Ser Gly Gln Thr Pro Lys Leu Asn Ser Val Val
```

```
305                 310                 315                 320

Pro Gly Lys Ser Pro Gln Tyr Ile Ala Lys Ala Ala Gly Phe Glu Ile
                325                 330                 335

Pro Glu Asp Ala Thr Ile Leu Ala Ala Glu Cys Lys Glu Val Gly Glu
            340                 345                 350

Asn Glu Pro Leu Thr Met Glu Lys Leu Ala Pro Val Gln Ala Val Leu
        355                 360                 365

Lys Ser Asp Asn Lys Glu Gln Ala Phe Glu Met Cys Glu Ala Met Leu
    370                 375                 380

Lys His Gly Ala Gly His Thr Ala Ala Ile His Thr Asn Asp Arg Asp
385                 390                 395                 400

Leu Val Arg Glu Tyr Gly Gln Arg Met His Ala Cys Arg Ile Ile Trp
                405                 410                 415

Asn Ser Pro Ser Ser Leu Gly Gly Val Gly Asp Ile Tyr Asn Ala Ile
            420                 425                 430

Ala Pro Ser Leu Thr Leu Gly Cys Gly Ser Tyr Gly Gly Asn Ser Val
        435                 440                 445

Ser Gly Asn Val Gln Ala Val Asn Leu Ile Asn Ile Lys Arg Ile Ala
    450                 455                 460

Arg Arg Asn Asn Asn Met Gln Trp Phe Lys Ile Pro Ala Lys Thr Tyr
465                 470                 475                 480

Phe Glu Pro Asn Ala Ile Lys Tyr Leu Arg Asp Met Tyr Gly Ile Glu
                485                 490                 495

Lys Ala Val Ile Val Cys Asp Lys Val Met Glu Gln Leu Gly Ile Val
            500                 505                 510

Asp Lys Ile Ile Asp Gln Leu Arg Ala Arg Ser Asn Arg Val Thr Phe
        515                 520                 525

Arg Ile Ile Asp Tyr Val Glu Pro Glu Pro Ser Val Glu Thr Val Glu
    530                 535                 540

Arg Gly Ala Ala Met Met Arg Glu Glu Phe Glu Pro Asp Thr Ile Ile
545                 550                 555                 560

Ala Val Gly Gly Gly Ser Pro Met Asp Ala Ser Lys Ile Met Trp Leu
                565                 570                 575

Leu Tyr Glu His Pro Glu Ile Ser Phe Ser Asp Val Arg Glu Lys Phe
            580                 585                 590

Phe Asp Ile Arg Lys Arg Ala Phe Lys Ile Pro Pro Leu Gly Lys Lys
        595                 600                 605

Ala Lys Leu Val Cys Ile Pro Thr Ser Ser Gly Thr Gly Ser Glu Val
    610                 615                 620

Thr Pro Phe Ala Val Ile Thr Asp His Lys Thr Gly Tyr Lys Tyr Pro
625                 630                 635                 640

Ile Thr Asp Tyr Ala Leu Thr Pro Ser Val Ala Ile Val Asp Pro Val
                645                 650                 655

Leu Ala Arg Thr Gln Pro Arg Lys Leu Ala Ser Asp Ala Gly Phe Asp
            660                 665                 670

Ala Leu Thr His Ala Phe Glu Ala Tyr Val Ser Val Tyr Ala Asn Asp
        675                 680                 685

Phe Thr Asp Gly Met Ala Leu His Ala Ala Lys Leu Val Trp Asp Asn
    690                 695                 700

Leu Ala Glu Ser Val Asn Gly Glu Pro Gly Glu Glu Lys Thr Arg Ala
705                 710                 715                 720

Gln Glu Lys Met His Asn Ala Ala Thr Met Ala Gly Met Ala Phe Gly
                725                 730                 735
```

```
Ser Ala Phe Leu Gly Met Cys His Gly Met Ala His Thr Ile Gly Ala
            740                 745                 750

Leu Cys His Val Ala His Gly Arg Thr Asn Ser Ile Leu Leu Pro Tyr
        755                 760                 765

Val Ile Arg Tyr Asn Gly Ser Val Pro Glu Glu Pro Thr Ser Trp Pro
    770                 775                 780

Lys Tyr Asn Lys Tyr Ile Ala Pro Glu Arg Tyr Gln Glu Ile Ala Lys
785                 790                 795                 800

Asn Leu Gly Val Asn Pro Gly Lys Thr Pro Glu Glu Gly Val Glu Asn
                805                 810                 815

Leu Ala Lys Ala Val Glu Asp Tyr Arg Asp Asn Lys Leu Gly Met Asn
            820                 825                 830

Lys Ser Phe Gln Glu Cys Gly Val Asp Glu Asp Tyr Tyr Trp Ser Ile
        835                 840                 845

Ile Asp Gln Ile Gly Met Arg Ala Tyr Glu Asp Gln Cys Ala Pro Ala
    850                 855                 860

Asn Pro Arg Ile Pro Gln Ile Glu Asp Met Lys Asp Ile Ala Ile Ala
865                 870                 875                 880

Ala Tyr Tyr Gly Val Ser Gln Ala Glu Gly His Lys Leu Arg Val Gln
                885                 890                 895

Arg Gln Gly Glu Ala Ala Thr Glu Glu Ala Ser Glu Arg Ala
            900                 905                 910
```

<210> SEQ ID NO 45
<211> LENGTH: 879
<212> TYPE: DNA
<213> ORGANISM: Bifidobacterium adolescentis
<220> FEATURE:
<223> OTHER INFORMATION: PFLA

<400> SEQUENCE: 45

```
atgtctgaac atattttccg ttccacgacc agacacatgc tgagggattc caaggactac     60

gtcaatcaga cgctgatggg aggcctgtcc ggattcgaat cgccaatcgg cttggaccgt    120

ctcgaccgca tcaaggcgtt gaaaagcggc gatatcggtt tcgtgcactc gtgggacatc    180

aacacttccg tggatggtcc tggcaccaga atgaccgtgt tcatgagcgg atgccctctg    240

cgctgccagt actgccagaa tccggatact tggaagatgc gcgacggcaa gcccgtctac    300

tacgaagcca tggtcaagaa aatcgagcgg tatgccgatt tattcaaggc caccggcggc    360

ggcatcactt tctccggcgg cgaatccatg atgcagccgg ctttcgtgtc acgcgtgttc    420

catgccgcca agcagatggg agtgcatacc tgcctcgaca cgtccggatt cctcggggcg    480

agctacaccg atgacatggt ggatgacatc gacctgtgcc tgcttgacgt caaatccggc    540

gatgaggaga cctaccataa ggtgaccggc ggcatcctgc agccgaccat cgacttcgga    600

cagcgtctgg ccaaggcagg caagaagatc tgggtgcgtt tcgtgctcgt gccgggcctc    660

acatcctccg aagaaaacgt cgagaacgtg gcgaagatct gcgagacctt cggcgacgcg    720

ttggaacata tcgacgtatt gcccttccac cagcttggcc gtccgaagtg gcacatgctg    780

aacatcccat acccgttgga ggaccagaaa ggcccgtccg cggcaatgaa acaacgtgtg    840

gtcgagcagt tccagtcgca cggcttcacc gtgtactaa                           879
```

<210> SEQ ID NO 46
<211> LENGTH: 292
<212> TYPE: PRT
<213> ORGANISM: Bifidobacterium adolescentis

```
<220> FEATURE:
<223> OTHER INFORMATION: PFLA

<400> SEQUENCE: 46

Met Ser Glu His Ile Phe Arg Ser Thr Thr Arg His Met Leu Arg Asp
1               5                   10                  15

Ser Lys Asp Tyr Val Asn Gln Thr Leu Met Gly Gly Leu Ser Gly Phe
            20                  25                  30

Glu Ser Pro Ile Gly Leu Asp Arg Leu Asp Arg Ile Lys Ala Leu Lys
        35                  40                  45

Ser Gly Asp Ile Gly Phe Val His Ser Trp Asp Ile Asn Thr Ser Val
    50                  55                  60

Asp Gly Pro Gly Thr Arg Met Thr Val Phe Met Ser Gly Cys Pro Leu
65                  70                  75                  80

Arg Cys Gln Tyr Cys Gln Asn Pro Asp Thr Trp Lys Met Arg Asp Gly
                85                  90                  95

Lys Pro Val Tyr Tyr Glu Ala Met Val Lys Lys Ile Glu Arg Tyr Ala
            100                 105                 110

Asp Leu Phe Lys Ala Thr Gly Gly Gly Ile Thr Phe Ser Gly Gly Glu
        115                 120                 125

Ser Met Met Gln Pro Ala Phe Val Ser Arg Val Phe His Ala Ala Lys
    130                 135                 140

Gln Met Gly Val His Thr Cys Leu Asp Thr Ser Gly Phe Leu Gly Ala
145                 150                 155                 160

Ser Tyr Thr Asp Asp Met Val Asp Asp Ile Asp Leu Cys Leu Leu Asp
                165                 170                 175

Val Lys Ser Gly Asp Glu Glu Thr Tyr His Lys Val Thr Gly Gly Ile
            180                 185                 190

Leu Gln Pro Thr Ile Asp Phe Gly Gln Arg Leu Ala Lys Ala Gly Lys
        195                 200                 205

Lys Ile Trp Val Arg Phe Val Leu Val Pro Gly Leu Thr Ser Ser Glu
    210                 215                 220

Glu Asn Val Glu Asn Val Ala Lys Ile Cys Glu Thr Phe Gly Asp Ala
225                 230                 235                 240

Leu Glu His Ile Asp Val Leu Pro Phe His Gln Leu Gly Arg Pro Lys
                245                 250                 255

Trp His Met Leu Asn Ile Pro Tyr Pro Leu Glu Asp Gln Lys Gly Pro
            260                 265                 270

Ser Ala Ala Met Lys Gln Arg Val Val Glu Gln Phe Gln Ser His Gly
        275                 280                 285

Phe Thr Val Tyr
    290


<210> SEQ ID NO 47
<211> LENGTH: 2376
<212> TYPE: DNA
<213> ORGANISM: Bifidobacterium adolescentis
<220> FEATURE:
<223> OTHER INFORMATION: PFLB

<400> SEQUENCE: 47

atggcagcag ttgatgcaac ggcggtctcc caggaggaac ttgaggctaa ggcttgggaa      60

ggcttcaccg agggcaactg gcagaaggac attgatgtcc gcgacttcat ccagaagaac     120

tacacgccat atgagggcga cgagtccttc ctggctgacg ccaccgacaa gaccaagcac     180

ctgtggaagt atctggacga caactatctg tccgtggagc gcaagcagcg cgtctacgac     240
```

```
gtggacaccc acaccccggc gggcatcgac gccttcccgg ccggctacat cgattccccg    300
gaagtcgaca atgtgattgt cggtctgcag accgatgtgc cgtgcaagcg cgccatgatg    360
ccgaacggcg gctggcgtat ggtcgagcag gccatcaagg aagccggcaa ggagcccgat    420
ccggagatca agaagatctt caccaagtac cgcaagaccc acaacgacgg cgtcttcggc    480
gtctacacca agcagatcaa ggtagctcgc cacaacaaga tcctcaccgg cctgccggat    540
gcctacggcc gtggccgcat catcggcgat taccgtcgtg tggccctgta cggcgtgaac    600
gcgctgatca agttcaagca gcgcgacaag gactccatcc cgtaccgcaa cgacttcacc    660
gagccggaga tcgagcactg gatccgcttc cgtgaggagc atgacgagca gatcaaggcc    720
ctgaagcagc tgatcaacct cggcaacgag tacggcctcg acctgtcccg cccggcacag    780
accgcacagg aagccgtgca gtggacctac atgggctacc tcgcctccgt caagagccag    840
gacggcgccg ccatgtcctt cggccgtgtc tccaccttct tcgacgtcta cttcgagcgc    900
gacctgaagg ccggcaagat caccgagacc gacgcacagg agatcatcga taacctggtc    960
atgaagctgc gcatcgtgcg cttcctgcgc accaaggatt acgacgcgat cttctccggc   1020
gatccgtact gggcgacttg gtccgacgcc ggcttcggcg acgacggccg taccatggtc   1080
accaagacct cgttccgtct gctcaacacc ctgaccctcg agcacctcgg acctggcccg   1140
gagccgaaca tcaccatctt ctgggatccg aagctgccgg aagcctacaa gcgcttctgc   1200
gcccgaatct ccatcgacac ctcggccatc cagtacgagt ccgataagga aatccgctcc   1260
cactggggcg acgacgccgc catcgcatgc tgcgtctccc cgatgcgcgt gggcaagcag   1320
atgcagttct tcgccgcccg tgtgaactcc gccaaggccc tgctgtacgc catcaacggc   1380
ggacgcgacg agatgaccgg catgcaggtc atcgacaagg gcgtcatcga cccgatcaag   1440
ccggaagccg atggcacgct ggattacgag aaggtcaagg ccaactacga gaaggccctc   1500
gaatggctgt ccgagaccta tgtgatggct ctgaacatca tccattacat gcatgataag   1560
tacgcttacg agtccatcga gatggctctg cacgacaagg aagtgtaccg caccctcggc   1620
tgcggcatgt ccggcctgtc gatcgcggcc gactccctgt ccgcatgcaa gtacgccaag   1680
gtctacccga tctacaacaa ggacgccaag accacgccgg gccacgagaa cgagtacgtc   1740
gaaggcgccg atgacgatct gatcgtcggc taccgcaccg aaggcgactt cccgctgtac   1800
ggcaacgatg atgaccgtgc cgacgacatc gccaagtggg tcgtctccac cgtcatgggc   1860
caggtcaagc gtctgccggt gtaccgcgac gccgtcccga cccagtccat cctgaccatc   1920
acctccaatg tggaatacgg caaggccacc ggcgccttcc cgtccggcca caagaagggc   1980
accccgtacg ctccgggcgc caacccggag aacggcatgg actcccacgg catgctgccg   2040
tccatgttct ccgtcggcaa gatcgactac aacgacgctc ttgacggcat ctcgctgacc   2100
aacaccatca cccctgatgg tctgggccgc gacgaggaag agcgtatcgg caacctcgtt   2160
ggcatcctgg acgccggcaa cggccacggc ctgtaccacg ccaacatcaa cgtgctgcgc   2220
aaggagcagc tcgaggatgc cgtcgagcat ccggagaagt acccgcacct gaccgtgcgc   2280
gtctccggct acgcggtgaa cttcgtcaag ctcaccaagg aacagcagct cgacgtgatc   2340
tcccgtacgt tccaccaggg cgctgtcgtc gactga                             2376
```

<210> SEQ ID NO 48
<211> LENGTH: 791
<212> TYPE: PRT
<213> ORGANISM: Bifidobacterium adolescentis
<220> FEATURE:

<223> OTHER INFORMATION: PFLB

<400> SEQUENCE: 48

```
Met Ala Ala Val Asp Ala Thr Ala Val Ser Gln Glu Glu Leu Glu Ala
1               5                   10                  15

Lys Ala Trp Glu Gly Phe Thr Glu Gly Asn Trp Gln Lys Asp Ile Asp
            20                  25                  30

Val Arg Asp Phe Ile Gln Lys Asn Tyr Thr Pro Tyr Glu Gly Asp Glu
        35                  40                  45

Ser Phe Leu Ala Asp Ala Thr Asp Lys Thr Lys His Leu Trp Lys Tyr
    50                  55                  60

Leu Asp Asp Asn Tyr Leu Ser Val Glu Arg Lys Gln Arg Val Tyr Asp
65                  70                  75                  80

Val Asp Thr His Thr Pro Ala Gly Ile Asp Ala Phe Pro Ala Gly Tyr
                85                  90                  95

Ile Asp Ser Pro Glu Val Asp Asn Val Ile Val Gly Leu Gln Thr Asp
            100                 105                 110

Val Pro Cys Lys Arg Ala Met Met Pro Asn Gly Gly Trp Arg Met Val
        115                 120                 125

Glu Gln Ala Ile Lys Glu Ala Gly Lys Glu Pro Asp Pro Glu Ile Lys
    130                 135                 140

Lys Ile Phe Thr Lys Tyr Arg Lys Thr His Asn Asp Gly Val Phe Gly
145                 150                 155                 160

Val Tyr Thr Lys Gln Ile Lys Val Ala Arg His Asn Lys Ile Leu Thr
                165                 170                 175

Gly Leu Pro Asp Ala Tyr Gly Arg Gly Arg Ile Ile Gly Asp Tyr Arg
            180                 185                 190

Arg Val Ala Leu Tyr Gly Val Asn Ala Leu Ile Lys Phe Lys Gln Arg
        195                 200                 205

Asp Lys Asp Ser Ile Pro Tyr Arg Asn Asp Phe Thr Glu Pro Glu Ile
    210                 215                 220

Glu His Trp Ile Arg Phe Arg Glu Glu His Asp Glu Gln Ile Lys Ala
225                 230                 235                 240

Leu Lys Gln Leu Ile Asn Leu Gly Asn Glu Tyr Gly Leu Asp Leu Ser
                245                 250                 255

Arg Pro Ala Gln Thr Ala Gln Glu Ala Val Gln Trp Thr Tyr Met Gly
            260                 265                 270

Tyr Leu Ala Ser Val Lys Ser Gln Asp Gly Ala Ala Met Ser Phe Gly
        275                 280                 285

Arg Val Ser Thr Phe Phe Asp Val Tyr Phe Glu Arg Asp Leu Lys Ala
    290                 295                 300

Gly Lys Ile Thr Glu Thr Asp Ala Gln Glu Ile Ile Asp Asn Leu Val
305                 310                 315                 320

Met Lys Leu Arg Ile Val Arg Phe Leu Arg Thr Lys Asp Tyr Asp Ala
                325                 330                 335

Ile Phe Ser Gly Asp Pro Tyr Trp Ala Thr Trp Ser Asp Ala Gly Phe
            340                 345                 350

Gly Asp Asp Gly Arg Thr Met Val Thr Lys Thr Ser Phe Arg Leu Leu
        355                 360                 365

Asn Thr Leu Thr Leu Glu His Leu Gly Pro Gly Pro Glu Pro Asn Ile
    370                 375                 380

Thr Ile Phe Trp Asp Pro Lys Leu Pro Glu Ala Tyr Lys Arg Phe Cys
385                 390                 395                 400
```

```
Ala Arg Ile Ser Ile Asp Thr Ser Ala Ile Gln Tyr Glu Ser Asp Lys
                405                 410                 415

Glu Ile Arg Ser His Trp Gly Asp Asp Ala Ala Ile Ala Cys Cys Val
            420                 425                 430

Ser Pro Met Arg Val Gly Lys Gln Met Gln Phe Phe Ala Ala Arg Val
        435                 440                 445

Asn Ser Ala Lys Ala Leu Leu Tyr Ala Ile Asn Gly Gly Arg Asp Glu
    450                 455                 460

Met Thr Gly Met Gln Val Ile Asp Lys Gly Val Ile Asp Pro Ile Lys
465                 470                 475                 480

Pro Glu Ala Asp Gly Thr Leu Asp Tyr Glu Lys Val Lys Ala Asn Tyr
                485                 490                 495

Glu Lys Ala Leu Glu Trp Leu Ser Glu Thr Tyr Val Met Ala Leu Asn
            500                 505                 510

Ile Ile His Tyr Met His Asp Lys Tyr Ala Tyr Glu Ser Ile Glu Met
        515                 520                 525

Ala Leu His Asp Lys Glu Val Tyr Arg Thr Leu Gly Cys Gly Met Ser
    530                 535                 540

Gly Leu Ser Ile Ala Ala Asp Ser Leu Ser Ala Cys Lys Tyr Ala Lys
545                 550                 555                 560

Val Tyr Pro Ile Tyr Asn Lys Asp Ala Lys Thr Thr Pro Gly His Glu
                565                 570                 575

Asn Glu Tyr Val Glu Gly Ala Asp Asp Asp Leu Ile Val Gly Tyr Arg
            580                 585                 590

Thr Glu Gly Asp Phe Pro Leu Tyr Gly Asn Asp Asp Asp Arg Ala Asp
        595                 600                 605

Asp Ile Ala Lys Trp Val Val Ser Thr Val Met Gly Gln Val Lys Arg
    610                 615                 620

Leu Pro Val Tyr Arg Asp Ala Val Pro Thr Gln Ser Ile Leu Thr Ile
625                 630                 635                 640

Thr Ser Asn Val Glu Tyr Gly Lys Ala Thr Gly Ala Phe Pro Ser Gly
                645                 650                 655

His Lys Lys Gly Thr Pro Tyr Ala Pro Gly Ala Asn Pro Glu Asn Gly
            660                 665                 670

Met Asp Ser His Gly Met Leu Pro Ser Met Phe Ser Val Gly Lys Ile
        675                 680                 685

Asp Tyr Asn Asp Ala Leu Asp Gly Ile Ser Leu Thr Asn Thr Ile Thr
    690                 695                 700

Pro Asp Gly Leu Gly Arg Asp Glu Glu Glu Arg Ile Gly Asn Leu Val
705                 710                 715                 720

Gly Ile Leu Asp Ala Gly Asn Gly His Gly Leu Tyr His Ala Asn Ile
                725                 730                 735

Asn Val Leu Arg Lys Glu Gln Leu Glu Asp Ala Val Glu His Pro Glu
            740                 745                 750

Lys Tyr Pro His Leu Thr Val Arg Val Ser Gly Tyr Ala Val Asn Phe
        755                 760                 765

Val Lys Leu Thr Lys Glu Gln Gln Leu Asp Val Ile Ser Arg Thr Phe
    770                 775                 780

His Gln Gly Ala Val Val Asp
785                 790
```

<210> SEQ ID NO 49
<211> LENGTH: 59
<212> TYPE: DNA

<213> ORGANISM: Bifidobacterium adolescentis
<220> FEATURE:
<223> OTHER INFORMATION: Forward Primer

<400> SEQUENCE: 49
gctataccaa gcatacaatc aactatctca tatacaatga cgagtcctgt tattggcac 59

<210> SEQ ID NO 50
<211> LENGTH: 59
<212> TYPE: DNA
<213> ORGANISM: Bifidobacterium adolescentis
<220> FEATURE:
<223> OTHER INFORMATION: Reverse Primer

<400> SEQUENCE: 50
ttataaaact ttaactaata attagagatt aaatcgctca ctcgttatcg ccagcggtt 59

<210> SEQ ID NO 51
<211> LENGTH: 59
<212> TYPE: DNA
<213> ORGANISM: Lactobacillus plantarum
<220> FEATURE:
<223> OTHER INFORMATION: Forward Primer 1

<400> SEQUENCE: 51
ctataccaag catacaatca actatctcat atacaatgac aacagattac tcatcacca 59

<210> SEQ ID NO 52
<211> LENGTH: 59
<212> TYPE: DNA
<213> ORGANISM: Lactobacillus plantarum
<220> FEATURE:
<223> OTHER INFORMATION: Reverse Primer 1

<400> SEQUENCE: 52
aaactttaac taataattag agattaaatc gcttatttta aacccttcca ttgccaatc 59

<210> SEQ ID NO 53
<211> LENGTH: 59
<212> TYPE: DNA
<213> ORGANISM: Lactobacillus plantarum
<220> FEATURE:
<223> OTHER INFORMATION: Forward Primer 2

<400> SEQUENCE: 53
gctataccaa gcatacaatc aactatctca tatacaatga gtgaagcaat taaatccaa 59

<210> SEQ ID NO 54
<211> LENGTH: 59
<212> TYPE: DNA
<213> ORGANISM: Lactobacillus plantarum
<220> FEATURE:
<223> OTHER INFORMATION: Reverse Primer 2

<400> SEQUENCE: 54
aaaactttaa ctaataatta gagattaaat cgcctacttc aatgcagtcc atttccagt 59

<210> SEQ ID NO 55
<211> LENGTH: 59
<212> TYPE: DNA
<213> ORGANISM: Neurospora crassa
<220> FEATURE:
<223> OTHER INFORMATION: Forward Primer

<400> SEQUENCE: 55
tataccaagc atacaatcaa ctatctcata tacaatgggc ggaacacaga tcacaattc 59

<210> SEQ ID NO 56
<211> LENGTH: 59
<212> TYPE: DNA
<213> ORGANISM: Neurospora crassa
<220> FEATURE:
<223> OTHER INFORMATION: Reverse Primer

<400> SEQUENCE: 56
aaaactttaa ctaataatta gagattaaat cgcctactcg aacttgggca gttggtaga 59

<210> SEQ ID NO 57
<211> LENGTH: 59
<212> TYPE: DNA
<213> ORGANISM: Aspergillus niger
<220> FEATURE:
<223> OTHER INFORMATION: Forward Primer

<400> SEQUENCE: 57
ctataccaag catacaatca actatctcat atacaatgcc tggagaggtc atcgacagg 59

<210> SEQ ID NO 58
<211> LENGTH: 59
<212> TYPE: DNA
<213> ORGANISM: Aspergillus niger
<220> FEATURE:
<223> OTHER INFORMATION: Reverse Primer

<400> SEQUENCE: 58
aactttaact aataattaga gattaaatcg cttattcaaa ggagggcata tcatacgta 59

<210> SEQ ID NO 59
<211> LENGTH: 59
<212> TYPE: DNA
<213> ORGANISM: Lactobacillus casei
<220> FEATURE:
<223> OTHER INFORMATION: Forward Primer

<400> SEQUENCE: 59
tataccaagc atacaatcaa ctatctcata tacaatggat acaaaagtaa agactgttg 59

<210> SEQ ID NO 60
<211> LENGTH: 59
<212> TYPE: DNA
<213> ORGANISM: Lactobacillus casei
<220> FEATURE:
<223> OTHER INFORMATION: Reverse Primer

<400> SEQUENCE: 60
aaactttaac taataattag agattaaatc gcttacttga ttggtttcca ggtccattc 59

<210> SEQ ID NO 61
<211> LENGTH: 2406
<212> TYPE: DNA
<213> ORGANISM: Bifidobacterium bifidum
<220> FEATURE:
<223> OTHER INFORMATION: PHK

<400> SEQUENCE: 61
atggacaagt actggcgcgt tgccaactac ctttccatcg gccagatcta tctgcggagc 60
aacccgctga tgaaggaacc cttcacccgt gaagacgtga agcaccgtct ggtggggcac 120
tggggcacca cccctggcct gaacttcctc atcggccaca tcaaccgctt catcgctgac 180
cacggccaga acaccgtgtt catcatgggc ccgggccacg gtggccccgc cggtacctcc 240

```
cagtcctacc tggacggcac ctacaccgag acgtacccca acattaccaa ggatgaggct    300
ggcctgcaga agttcttccg ccagttctcc tacccgggcg gcatcccctc ccacttcgct    360
ccggaaaccc cgggctccat ccacgagggt ggcgagctgg gttacgccct gtcccacgct    420
tatggcgcga tcatggacaa cccgagcctg ttcgttccct gcatcgtcgg cgatggtgag    480
gccgagaccg gcccgctggc caccggctgg cagtccaaca agctcgtgaa cccgcgcacc    540
gacggtatcg tgctgccgat cctgcacctt aacggctaca agatcgccaa cccgaccatc    600
ctgtcgcgca tctccgacga agagctccac gagttcttcc acggcatggg ctacgagccc    660
tatgagttcg tcgccggctt cgacgatgag gaccacatgt ccatccaccg tcgcttcgcc    720
gagctgttcg agtccgtgtg ggacgagatc tgcgacatca aggccgcggc gaacacggac    780
aacatgcacc gtccgttcta cccgatgatc atcttccgca ccccgaaggg ctggacctgc    840
ccgaagtaca tcgacggcaa gaagaccgag ggctcctggc gcgcccacca ggtgccgctg    900
gcttccgccc gcgacaccga ggcccacttc gaggtcctca agaactggct ggagtcctac    960
aagccggaag agctgttcga cgccaacggt gccgtcaagg acgacgtcct ggccttcatg   1020
ccgaagggcg agctgcgcat cggcgccaac ccgaacgcca acggtggcgt gatccgcagg   1080
gatctcgtgc tgccggcgct cgaggactac gaggtcaagg aagtcaagga gttcggacac   1140
ggctggggcc agctcgaggc cacccgtcgt ctgggcgtct acacccgcga catcatcaag   1200
aacaacatgc acgacttccg catcttcgga ccggatgaga ccgcttccaa ccgtctgcag   1260
gcttcctacg aggtcaccaa caagcagtgg gacgccggct acatctccga cgaggttgac   1320
gagcacatgc acgtctccgg ccaggtcgtc gagcagctgt ccgagcacca gatggaaggc   1380
ttcctcgagg cctacctgct gaccggccgt cacggcatct ggagctccta cgagtccttt   1440
gtgcacgtga tcgactccat gctgaaccag cacgccaagt ggcttgaggc taccgtccgc   1500
gagattccgt ggcgcaagcc gattgcctcc atgaacctgc tggtctcctc gcacgtgtgg   1560
cgtcaggatc acaacggttt ctcgcaccag gacccgggtg tcacctccgt cctgctgaac   1620
aagtgcttcc acaacgatca cgtcatcggc atctacttcg cgaccgacgc gaacatgctg   1680
ctggccatcg ccgagaagtg ctacaagtcc accaacaaga tcaacgccat catcgccggc   1740
aagcagccgg ccgccacctg gctgaccctg gacgaggctc gtgccgagct cgccaagggt   1800
gccgccgctt gggattgggc ttccaccgcg aagaccaacg atgaggctca ggtcgtgctc   1860
gccgccgccg gcgacgtccc gacccaggag atcatggccg cttccgacaa gttgaaggcc   1920
ctgggcatca agttcaaggt cgtcaacgtg gctgatctgc tctccctgca gtctgccaag   1980
gagaacgacg aagcgctgac cgacgaggag ttcgccgaca tcttcaccgc cgacaagccg   2040
gtgctgttcg cgtaccactc ctacgcccac gacgtgcgtg gcctgatcta cgatcgcccg   2100
aaccacgata acttcaacgt ccacggctac gaggaggagg gctccaccac caccccgtac   2160
gacatggttc gcgtgaacga gctggatcgc tacgagctga ccgccgaagc cctgcgcatg   2220
atcgacgccg acaagtacgc cgacgagatc cagaagctgg aggacttccg tcaggaagcg   2280
ttccagttcg cggtcgacaa gggctacgac cacccggact acaccgactg ggtgtactcg   2340
ggcgtcaaga ccgacaagaa gggcgccgtc accgccaccg ccgccaccgc tggcgacaac   2400
gagtga                                                              2406
```

<210> SEQ ID NO 62
<211> LENGTH: 801
<212> TYPE: PRT
<213> ORGANISM: Bifidobacterium bifidum

```
<220> FEATURE:
<223> OTHER INFORMATION: PHK

<400> SEQUENCE: 62

Met Asp Lys Tyr Trp Arg Val Ala Asn Tyr Leu Ser Ile Gly Gln Ile
1               5                   10                  15

Tyr Leu Arg Ser Asn Pro Leu Met Lys Glu Pro Phe Thr Arg Glu Asp
            20                  25                  30

Val Lys His Arg Leu Val Gly His Trp Gly Thr Thr Pro Gly Leu Asn
        35                  40                  45

Phe Leu Ile Gly His Ile Asn Arg Phe Ile Ala Asp His Gly Gln Asn
    50                  55                  60

Thr Val Phe Ile Met Gly Pro Gly His Gly Gly Pro Ala Gly Thr Ser
65                  70                  75                  80

Gln Ser Tyr Leu Asp Gly Thr Tyr Thr Glu Thr Tyr Pro Asn Ile Thr
                85                  90                  95

Lys Asp Glu Ala Gly Leu Gln Lys Phe Phe Arg Gln Phe Ser Tyr Pro
            100                 105                 110

Gly Gly Ile Pro Ser His Phe Ala Pro Glu Thr Pro Gly Ser Ile His
        115                 120                 125

Glu Gly Gly Glu Leu Gly Tyr Ala Leu Ser His Ala Tyr Gly Ala Ile
    130                 135                 140

Met Asp Asn Pro Ser Leu Phe Val Pro Cys Ile Val Gly Asp Gly Glu
145                 150                 155                 160

Ala Glu Thr Gly Pro Leu Ala Thr Gly Trp Gln Ser Asn Lys Leu Val
                165                 170                 175

Asn Pro Arg Thr Asp Gly Ile Val Leu Pro Ile Leu His Leu Asn Gly
            180                 185                 190

Tyr Lys Ile Ala Asn Pro Thr Ile Leu Ser Arg Ile Ser Asp Glu Glu
        195                 200                 205

Leu His Glu Phe Phe His Gly Met Gly Tyr Glu Pro Tyr Glu Phe Val
    210                 215                 220

Ala Gly Phe Asp Asp Glu Asp His Met Ser Ile His Arg Arg Phe Ala
225                 230                 235                 240

Glu Leu Phe Glu Ser Val Trp Asp Glu Ile Cys Asp Ile Lys Ala Ala
                245                 250                 255

Ala Asn Thr Asp Asn Met His Arg Pro Phe Tyr Pro Met Ile Ile Phe
            260                 265                 270

Arg Thr Pro Lys Gly Trp Thr Cys Pro Lys Tyr Ile Asp Gly Lys Lys
        275                 280                 285

Thr Glu Gly Ser Trp Arg Ala His Gln Val Pro Leu Ala Ser Ala Arg
    290                 295                 300

Asp Thr Glu Ala His Phe Glu Val Leu Lys Asn Trp Leu Glu Ser Tyr
305                 310                 315                 320

Lys Pro Glu Glu Leu Phe Asp Ala Asn Gly Ala Val Lys Asp Asp Val
                325                 330                 335

Leu Ala Phe Met Pro Lys Gly Glu Leu Arg Ile Gly Ala Asn Pro Asn
            340                 345                 350

Ala Asn Gly Gly Val Ile Arg Arg Asp Leu Val Leu Pro Ala Leu Glu
        355                 360                 365

Asp Tyr Glu Val Lys Glu Val Lys Glu Phe Gly His Gly Trp Gly Gln
    370                 375                 380

Leu Glu Ala Thr Arg Arg Leu Gly Val Tyr Thr Arg Asp Ile Ile Lys
385                 390                 395                 400
```

```
Asn Asn Met His Asp Phe Arg Ile Phe Gly Pro Asp Glu Thr Ala Ser
                405                 410                 415

Asn Arg Leu Gln Ala Ser Tyr Glu Val Thr Asn Lys Gln Trp Asp Ala
            420                 425                 430

Gly Tyr Ile Ser Asp Glu Val Asp Glu His Met His Val Ser Gly Gln
        435                 440                 445

Val Val Glu Gln Leu Ser Glu His Gln Met Glu Gly Phe Leu Glu Ala
    450                 455                 460

Tyr Leu Leu Thr Gly Arg His Gly Ile Trp Ser Ser Tyr Glu Ser Phe
465                 470                 475                 480

Val His Val Ile Asp Ser Met Leu Asn Gln His Ala Lys Trp Leu Glu
                485                 490                 495

Ala Thr Val Arg Glu Ile Pro Trp Arg Lys Pro Ile Ala Ser Met Asn
            500                 505                 510

Leu Leu Val Ser Ser His Val Trp Arg Gln Asp His Asn Gly Phe Ser
        515                 520                 525

His Gln Asp Pro Gly Val Thr Ser Val Leu Leu Asn Lys Cys Phe His
    530                 535                 540

Asn Asp His Val Ile Gly Ile Tyr Phe Ala Thr Asp Ala Asn Met Leu
545                 550                 555                 560

Leu Ala Ile Ala Glu Lys Cys Tyr Lys Ser Thr Asn Lys Ile Asn Ala
                565                 570                 575

Ile Ile Ala Gly Lys Gln Pro Ala Ala Thr Trp Leu Thr Leu Asp Glu
            580                 585                 590

Ala Arg Ala Glu Leu Ala Lys Gly Ala Ala Ala Trp Asp Trp Ala Ser
        595                 600                 605

Thr Ala Lys Thr Asn Asp Glu Ala Gln Val Val Leu Ala Ala Ala Gly
    610                 615                 620

Asp Val Pro Thr Gln Glu Ile Met Ala Ala Ser Asp Lys Leu Lys Ala
625                 630                 635                 640

Leu Gly Ile Lys Phe Lys Val Val Asn Val Ala Asp Leu Leu Ser Leu
                645                 650                 655

Gln Ser Ala Lys Glu Asn Asp Glu Ala Leu Thr Asp Glu Glu Phe Ala
            660                 665                 670

Asp Ile Phe Thr Ala Asp Lys Pro Val Leu Phe Ala Tyr His Ser Tyr
        675                 680                 685

Ala His Asp Val Arg Gly Leu Ile Tyr Asp Arg Pro Asn His Asp Asn
    690                 695                 700

Phe Asn Val His Gly Tyr Glu Glu Glu Gly Ser Thr Thr Thr Pro Tyr
705                 710                 715                 720

Asp Met Val Arg Val Asn Glu Leu Asp Arg Tyr Glu Leu Thr Ala Glu
                725                 730                 735

Ala Leu Arg Met Ile Asp Ala Asp Lys Tyr Ala Asp Glu Ile Gln Lys
            740                 745                 750

Leu Glu Asp Phe Arg Gln Glu Ala Phe Gln Phe Ala Val Asp Lys Gly
        755                 760                 765

Tyr Asp His Pro Asp Tyr Thr Asp Trp Val Tyr Ser Gly Val Lys Thr
    770                 775                 780

Asp Lys Lys Gly Ala Val Thr Ala Thr Ala Ala Thr Ala Gly Asp Asn
785                 790                 795                 800

Glu
```

```
<210> SEQ ID NO 63
<211> LENGTH: 2481
<212> TYPE: DNA
<213> ORGANISM: Bifidobacterium gallicium
<220> FEATURE:
<223> OTHER INFORMATION: PHK

<400> SEQUENCE: 63

atgacaagtc ctgttattgg cacccccctgg cagaagctga accgtccggt ttcggaagag     60

gccatcgaag gcatggacaa gtattggcgc gcgtccaact acatgtccat cggccagatc    120

tacctgcgta gcaacccgct gatgaaggaa cctttcactc gcgatgacgt gaagtaccgc    180

ctcgtcggcc actggggtac caccccgggc ctgaacttcc ttctggccca catcaaccgc    240

ctgatcgctg accaccagca gaacaccgtg ttcatcatgg gtcctggcca cggcggtcct    300

gccggtactg cacagtccta tctggacggc acgtacaccg agtactaccc gaacatcacc    360

aaggatgagg aaggcctgca gaagttcttc cgtcagttct cttatccggg cggcattcct    420

tcgcacttcg ctccggagac cccgggctcg atccacgaag gtggcgagct gggctatgct    480

ctgtcccacg cttacggcgc tgtgatgaac aacccgagcc tgttcgtgcc ctgcatcgtc    540

ggcgacggcg aagctgagac tggccctctg gccaccggct ggcagtccaa caagctcgtg    600

aacccgcgca ccgatggcat cgtgctgccg atcctgcacc tcaacggcta caagatcgcc    660

aacccgacca tcctcgctcg cgtgtccgat gaagagctgc atgacttctt ccgcggcctg    720

ggctaccacc cgtacgagtt cgtcgccggc ttcgacaacg aggatcacct gtcgatccac    780

cgtcgtttcg ctgagctctt cgagaccatc ttcgacgaga tctgcgatat caaggctgcc    840

gccaacacgg atgacatgac ccgtccgttc tacccgatgc tgattttccg caccccgaag    900

ggttggacct gcccgaagtt catcgacggc aagaagaccg aaggctcttg gcgtgcacac    960

caggtgccgc tggcttccgc ccgcgatacc gaggctcact tcgaagtgct gaagaactgg   1020

atggcttcct acaagccgga agagctcttc gacgacaagg gcgccatcaa ggatgacgtc   1080

gtcgacttca tgccgaaggg cgatctgcgt atcggcgcca acccgaatgc taacggtggc   1140

gtgatccgtg aagagctcga tctgccggcc ctcgagaact atgaggtcaa ggaagtcaag   1200

gaattcggcc acggctgggg ccagcttgag gctacgcgta agctcggtga gtacacgcgt   1260

gacatcatca agaacaaccc ggattcgttc cgcatcttcg gacctgacga gaccgcttcg   1320

aaccgtctgc aggcttccta cgaagtcacc aacaagcagt gggacaacgg ctacctgtcc   1380

aaggacctcg tcgatgagca catggctgtc accggccagg tcactgagca gctctccgaa   1440

caccagtgcg aaggcttcct cgaggcctac ctgctcacgg gtcgtcacgg catctggagc   1500

tcctacgagt ccttcgtgca cgtcatcgac tccatgctca accagcacgc caagtggctc   1560

gaggctacgg tgcgtgagat tccgtggcgt aagccgatct cctcgatgaa cctgctcgtg   1620

tcctcgcacg tgtggcgtca ggatcacaac ggcttctcgc accaggatcc gggtgtcacc   1680

tccgtcctgt tgaacaagac gttcaacaac gatcacgtca tcggcctgta cttcgcaacc   1740

gacgccaacg tgctgctggc catcgctgag aagtgctaca agtcgaccaa catgatcaac   1800

gccatcgtcg ccggcaagca gcctgctgcc acctggacga cgctggacga agctcgtgag   1860

ctggttgcca agggcgctgg cgaattcgag tgggcttcga acgtcaagac caacgatgag   1920

gccgagattg tgctcgcttc cgctggcgat gttccgactc aggagctcat ggctgctgct   1980

gatcgtctga acaagctcgg cgtcaagttc aaggtcgtca acgtggtgga tctgatcaag   2040

ctgcagtccg ccaaggagaa cgatcaggct ctgtccgatg ccgagttcgc tgagctcttc   2100
```

```
accgaagaca agccggtgct gttcgcgtac cactcctatg cgcacgacgt gcgcggcctg   2160

atcttcgatc gcccgaacca cgacaacttc aacgtggtcg gctacaagga gcagggctcc   2220

accaccacgc cgtacgacat ggtgcgtgtc aacgacatcg atcgttatga gctgaccgct   2280

acggcactgc gcatgatcga cgccgacaag tacgccgacg agatcaagaa gctcgaggac   2340

ttccgcatcg aggcttacca gttcgctgtc gacaacggct acgacattcc ggattacacc   2400

gactgggtgt ggccgggcgt caagaccgac ctgccgggcg ccgtttccgc aacggctgcc   2460

accgcaggcg acaacgagtg a                                              2481


<210> SEQ ID NO 64
<211> LENGTH: 826
<212> TYPE: PRT
<213> ORGANISM: Bifidobacterium gallicium
<220> FEATURE:
<223> OTHER INFORMATION: PHK

<400> SEQUENCE: 64

Met Thr Ser Pro Val Ile Gly Thr Pro Trp Gln Lys Leu Asn Arg Pro
1               5                   10                  15

Val Ser Glu Glu Ala Ile Glu Gly Met Asp Lys Tyr Trp Arg Ala Ser
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys Tyr Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Leu Asp Gly Thr Tyr
            100                 105                 110

Thr Glu Tyr Tyr Pro Asn Ile Thr Lys Asp Glu Glu Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Cys Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Val Ser Asp Glu Glu Leu His Asp Phe Phe Arg Gly Leu
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Asn Thr Asp Asp Met Thr Arg
        275                 280                 285

Pro Phe Tyr Pro Met Leu Ile Phe Arg Thr Pro Lys Gly Trp Thr Cys
```

```
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Asn Trp Met Ala Ser Tyr Lys Pro Glu Glu Leu Phe Asp Asp
            340                 345                 350

Lys Gly Ala Ile Lys Asp Asp Val Val Asp Phe Met Pro Lys Gly Asp
        355                 360                 365

Leu Arg Ile Gly Ala Asn Pro Asn Ala Asn Gly Gly Val Ile Arg Glu
    370                 375                 380

Glu Leu Asp Leu Pro Ala Leu Glu Asn Tyr Glu Val Lys Glu Val Lys
385                 390                 395                 400

Glu Phe Gly His Gly Trp Gly Gln Leu Glu Ala Thr Arg Lys Leu Gly
                405                 410                 415

Glu Tyr Thr Arg Asp Ile Ile Lys Asn Asn Pro Asp Ser Phe Arg Ile
            420                 425                 430

Phe Gly Pro Asp Glu Thr Ala Ser Asn Arg Leu Gln Ala Ser Tyr Glu
        435                 440                 445

Val Thr Asn Lys Gln Trp Asp Asn Gly Tyr Leu Ser Lys Asp Leu Val
    450                 455                 460

Asp Glu His Met Ala Val Thr Gly Gln Val Thr Glu Gln Leu Ser Glu
465                 470                 475                 480

His Gln Cys Glu Gly Phe Leu Glu Ala Tyr Leu Leu Thr Gly Arg His
                485                 490                 495

Gly Ile Trp Ser Ser Tyr Glu Ser Phe Val His Val Ile Asp Ser Met
            500                 505                 510

Leu Asn Gln His Ala Lys Trp Leu Glu Ala Thr Val Arg Glu Ile Pro
        515                 520                 525

Trp Arg Lys Pro Ile Ser Ser Met Asn Leu Leu Val Ser Ser His Val
    530                 535                 540

Trp Arg Gln Asp His Asn Gly Phe Ser His Gln Asp Pro Gly Val Thr
545                 550                 555                 560

Ser Val Leu Leu Asn Lys Thr Phe Asn Asn Asp His Val Ile Gly Leu
                565                 570                 575

Tyr Phe Ala Thr Asp Ala Asn Val Leu Leu Ala Ile Ala Glu Lys Cys
            580                 585                 590

Tyr Lys Ser Thr Asn Met Ile Asn Ala Ile Val Ala Gly Lys Gln Pro
        595                 600                 605

Ala Ala Thr Trp Thr Thr Leu Asp Glu Ala Arg Glu Leu Val Ala Lys
    610                 615                 620

Gly Ala Gly Glu Phe Glu Trp Ala Ser Asn Val Lys Thr Asn Asp Glu
625                 630                 635                 640

Ala Glu Ile Val Leu Ala Ser Ala Gly Asp Val Pro Thr Gln Glu Leu
                645                 650                 655

Met Ala Ala Ala Asp Arg Leu Asn Lys Leu Gly Val Lys Phe Lys Val
            660                 665                 670

Val Asn Val Val Asp Leu Ile Lys Leu Gln Ser Ala Lys Glu Asn Asp
        675                 680                 685

Gln Ala Leu Ser Asp Ala Glu Phe Ala Glu Leu Phe Thr Glu Asp Lys
    690                 695                 700

Pro Val Leu Phe Ala Tyr His Ser Tyr Ala His Asp Val Arg Gly Leu
705                 710                 715                 720
```

```
Ile Phe Asp Arg Pro Asn His Asp Asn Phe Asn Val Val Gly Tyr Lys
                725                 730                 735

Glu Gln Gly Ser Thr Thr Thr Pro Tyr Asp Met Val Arg Val Asn Asp
            740                 745                 750

Ile Asp Arg Tyr Glu Leu Thr Ala Thr Ala Leu Arg Met Ile Asp Ala
        755                 760                 765

Asp Lys Tyr Ala Asp Glu Ile Lys Lys Leu Glu Asp Phe Arg Ile Glu
    770                 775                 780

Ala Tyr Gln Phe Ala Val Asp Asn Gly Tyr Asp Ile Pro Asp Tyr Thr
785                 790                 795                 800

Asp Trp Val Trp Pro Gly Val Lys Thr Asp Leu Pro Gly Ala Val Ser
                805                 810                 815

Ala Thr Ala Ala Thr Ala Gly Asp Asn Glu
            820                 825


<210> SEQ ID NO 65
<211> LENGTH: 2478
<212> TYPE: DNA
<213> ORGANISM: Bifidobacterium animalis
<220> FEATURE:
<223> OTHER INFORMATION: PHK

<400> SEQUENCE: 65

atgactaatc ctgttattgg taccccatgg cagaagctgg accgtccggt ttccgaagag      60

gccatcgaag gcatggacaa gtactggcgc gtcgccaact acatgtccat cggccagatc     120

tacctgcgta gcaacccgct gatgaaggag cccttcaccc gcgatgacgt gaagcaccgt     180

ctggtcggcc actggggcac caccccgggc ctgaacttcc ttctcgccca tatcaaccgc     240

ctgatcgccg atcaccagca gaacaccgtg ttcatcatgg gtcctggcca cggcggccct     300

gcaggtaccg ctcagtccta catcgacggc acctacaccg agtactaccc gaacatcacc     360

aaggacgagg ctggcctgca gaagttcttc cgccagttct cctacccggg tggcattcct     420

tcccacttcg ctccggagac gccaggctcc atccacgaag gcggcgagct gggctacgcc     480

ctgtcgcacg cctacggcgc gatcatgaac aacccgagcc tcttcgtccc gtgcatcatc     540

ggtgacggcg aagccgagac cggccctctg gccaccggct ggcagtccaa caagctcgtc     600

aacccgcgca ccgacggcat cgtgctgccg atcctgcacc tcaacggcta caagatcgcc     660

aacccgacgc tcctcgcccg catctccgac gaggagctgc acgacttctt ccgcggtatg     720

ggttaccacc cgtacgagtt cgtcgccggc ttcgacaacg aggatcacct gtcgatccac     780

cgtcgcttcg ccgagctctt cgagaccatc ttcgacgaga tctgcgatat caaggctgcg     840

gctcagaccg acgacatgac ccgtccgttc tacccgatgc tcatcttccg caccccgaag     900

ggctggacct gcccgaagtt catcgacggc aagaagaccg aaggctcctg gcgtgcacac     960

caggtcccgc tggcttccgc ccgcgacacc gaggcccact tcgaagtcct caagggctgg    1020

atggaatcct acaagccgga ggagctcttc aacgccgacg gctccatcaa ggacgacgtc    1080

accgcattca tgcctaaggg cgaactgcgc atcggcgcca acccgaacgc caacggtggc    1140

cgcatccgcg aggatctgaa gctccctgag ctcgatcagt acgagatcac cggcgtcaag    1200

gaatacggcc atggctgggg ccaggtcgag gctccgcgct ccctcggcgc gtactgccgc    1260

gacatcatca agaacaaccc ggattcgttc cgcatcttcg gacctgatga gaccgcatcc    1320

aaccgtctga acgcgaccta cgaggtcacc aagaagcagt gggacaacgg ctatctctcg    1380

gctctcgtcg acgagaacat ggctgtcacc ggccaggttg tcgagcagct ctccgagcat    1440
```

```
cagtgcgaag gcttcctcga ggcctacctg ctcacgggcc gccacggcat gtggagcacc   1500

tatgagtcct tcgcccacgt gatcgactcg atgctcaacc agcatgcgaa gtggctcgag   1560

gcgaccgtcc gcgagatccc gtggcgcaag ccgatctcct cggtcaacct cctcgtctcc   1620

tcgcacgtgt ggcgtcagga ccacaacggc ttctcgcatc aggacccggg tgtcacctcc   1680

gtcctgatca acaagacgtt caacaacgac cacgtgacga acatctactt cgcgaccgac   1740

gccaacatgc tgctcgcgat cgccgagaag tgcttcaagt ccaccaacaa gatcaacgcg   1800

atcttctccg gcaagcagcc ggctccgacc tggattaccc tcgacgaggc tcgtgccgag   1860

ctcgaggccg gcgccgccga gtggaagtgg gcttccaacg ccaagagcaa cgacgaggtc   1920

cagattgtcc tcgccgccgc aggcgatgtc ccgacccagg agatcatggc cgcttccgat   1980

gccctgaaca aggatggcat caagttcaag gtcgtcaacg ttgttgacct cctgaagctg   2040

cagtccccgg agaacaacga cgaggccatg tcgaacgaag acttcaccga gctcttcacc   2100

gccgacaaac cggttctgtt cgcctaccac tcctatgccc aggacgttcg tggtcttatc   2160

tacgaccgcc cgaaccacga caacttcaac gttgtcggct acaaggagca gggctccacg   2220

accacgccgt tcgacatggt ccgcgtcaac gacatggatc gctacgcgct cgaagctcag   2280

gctctcgagc tgatcgacgc cgacaagtat gccgacaaga tcgacgagct caacgcgttc   2340

cgcaagaccg cgttccagtt cgccgtcgac aacggctacg acatcccgga gttcaccgac   2400

tgggtgtacc cggacgtcaa ggtcgacgag acgcagatgc tctccgcgac cgcggcgacc   2460

gctggcgaca acgagtga                                                 2478
```

<210> SEQ ID NO 66
<211> LENGTH: 825
<212> TYPE: PRT
<213> ORGANISM: Bifidobacterium animalis
<220> FEATURE:
<223> OTHER INFORMATION: PHK

<400> SEQUENCE: 66

```
Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asn Asn Pro Ser Leu Phe Val
                165                 170                 175
```

```
Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Leu
    210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
        275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Gly Trp Met Glu Ser Tyr Lys Pro Glu Glu Leu Phe Asn Ala
            340                 345                 350

Asp Gly Ser Ile Lys Asp Asp Val Thr Ala Phe Met Pro Lys Gly Glu
        355                 360                 365

Leu Arg Ile Gly Ala Asn Pro Asn Ala Asn Gly Gly Arg Ile Arg Glu
    370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Ile
            420                 425                 430

Phe Gly Pro Asp Glu Thr Ala Ser Asn Arg Leu Asn Ala Thr Tyr Glu
        435                 440                 445

Val Thr Lys Lys Gln Trp Asp Asn Gly Tyr Leu Ser Ala Leu Val Asp
    450                 455                 460

Glu Asn Met Ala Val Thr Gly Gln Val Val Glu Gln Leu Ser Glu His
465                 470                 475                 480

Gln Cys Glu Gly Phe Leu Glu Ala Tyr Leu Leu Thr Gly Arg His Gly
                485                 490                 495

Met Trp Ser Thr Tyr Glu Ser Phe Ala His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Ile Asn Lys Thr Phe Asn Asn Asp His Val Thr Asn Ile Tyr
                565                 570                 575

Phe Ala Thr Asp Ala Asn Met Leu Leu Ala Ile Ala Glu Lys Cys Phe
            580                 585                 590
```

```
Lys Ser Thr Asn Lys Ile Asn Ala Ile Phe Ser Gly Lys Gln Pro Ala
        595                 600                 605

Pro Thr Trp Ile Thr Leu Asp Glu Ala Arg Ala Glu Leu Glu Ala Gly
    610                 615                 620

Ala Ala Glu Trp Lys Trp Ala Ser Asn Ala Lys Ser Asn Asp Glu Val
625                 630                 635                 640

Gln Ile Val Leu Ala Ala Ala Gly Asp Val Pro Thr Gln Glu Ile Met
                645                 650                 655

Ala Ala Ser Asp Ala Leu Asn Lys Asp Gly Ile Lys Phe Lys Val Val
            660                 665                 670

Asn Val Val Asp Leu Leu Lys Leu Gln Ser Pro Glu Asn Asn Asp Glu
        675                 680                 685

Ala Met Ser Asn Glu Asp Phe Thr Glu Leu Phe Thr Ala Asp Lys Pro
    690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Asn Val Val Gly Tyr Lys Glu
                725                 730                 735

Gln Gly Ser Thr Thr Thr Pro Phe Asp Met Val Arg Val Asn Asp Met
            740                 745                 750

Asp Arg Tyr Ala Leu Glu Ala Gln Ala Leu Glu Leu Ile Asp Ala Asp
        755                 760                 765

Lys Tyr Ala Asp Lys Ile Asp Glu Leu Asn Ala Phe Arg Lys Thr Ala
    770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Ala Thr Ala Gly Asp Asn Glu
            820                 825
```

<210> SEQ ID NO 67
<211> LENGTH: 2367
<212> TYPE: DNA
<213> ORGANISM: Lactobacillus pentosum
<220> FEATURE:
<223> OTHER INFORMATION: PHK

<400> SEQUENCE: 67

```
atgtctacag attactcatc accagcatat ttgcaaaaag ttgataagta ctggcgtgct     60

gccaactatt tatcagttgg tcaactttat ttaaaagata atcctttatt acaacggcca    120

ttaaaggcta gtgacgttaa ggttcaccca atcggtcact ggggcacgat tgccggccaa    180

aacttcatct atgcgcatct taaccgggtc atcaacaagt acggtttgaa gatgttctac    240

gttgaaggtc caggtcatgg tggccaagtg atggtctcca actcatacct tgatgggact    300

tacacggata tttatcctga aattacgcag gatgttgaag ggatgcaaaa actcttcaag    360

caattctcat tcccaggtgg cgtggcttcc catgctgctc ctgaaacacc aggctcaatc    420

cacgaaggtg gcgaacttgg ttactcaatt tcacacggtg ttggggcaat ccttgacaac    480

cctgatgaaa tcgccgcagt cgttgttggt gatggggaat ccgaaaccgg cccattagca    540

acttcatggc aatcaacgaa gttcatcaac ccaatcaacg atggggcagt gttaccaatc    600

ttgaacctta acggctttaa gatttctaac ccaacgattt ttggtcggac ttctgatgaa    660

aagatcaagc aatacttcga aagcatgaac tgggaaccaa tctttgttga aggtgacgat    720
```

```
cctgaaaagg ttcacccagc tttagctaag gccatggatg aagccgtcga aaagatcaaa     780

gccattcaaa agaacgctcg tgaaaacgat gacgctactt taccagtatg gccgatgatc     840

gtcttccgcg cacctaaggg ctggactggt cctaagtcat gggatggcga caagatcgaa     900

ggttcattcc gagctcacca aattccaatt cctgttgacc aaaccgacat ggaacatgcc     960

gatgcgttag ttgactggtt ggaatcatat caaccaaagg aactcttcaa tgaagatggt    1020

tctttgaagg atgatatcaa agaaattatc ccaactggcg atgcacggat ggccgctaac    1080

ccaatcacta atggtggggt tgatccaaag gccttgaact tacctaactt ccgtgattac    1140

gccgttgata cgtctaagca tggtgccaac gttaagcaag atatgatcgt ttggtcagac    1200

tacttgcgtg atgttatcaa gaagaaccca gataacttcc ggttatttgg ccctgatgaa    1260

accatgtcaa accggttata tggtgtcttt gaaaccacta accgtcaatg gatggaagat    1320

attcacccag atagtgacca atacgaagca cctgctggcc gggtcttgga tgctcaatta    1380

tctgaacacc aagctgaagg ttggttagaa ggttacgtct taactggtcg tcatggcttg    1440

tttgcaagtt acgaagcctt cttacgggtt gtcgactcaa tgttgacgca acacttcaag    1500

tggttacgta aggccaacga acttgactgg cggaagaagt acccgtcact caacattatc    1560

gcggcttcaa ctgtgttcca acaagaccat aatgggtaca cccaccaaga tccaggtgcc    1620

ttgactcatt tggctgaaaa gaagcctgaa tatatccgcg aatatttacc agccgacgcc    1680

aactccttgt tagctgttgg ggacgtcatc ttccgtagcc aagaaaagat caactacgtg    1740

gttacgtcga agcacccacg tcaacaatgg ttcagcattg aagaagctaa gcaattagtt    1800

gacaacggtc ttggtatcat tgactgggca agcacggacc aaggtagcga accagatatc    1860

gtgtttgctg ctgccggaac ggaaccaacg cttgaaacgt tggctgcaat ccaattgctc    1920

catgatagct tcccagacat gaagattcgt ttcgtgaacg tggtcgacat cttgaagtta    1980

cgtagccctg aaaaggaccc tcgtggcttg tcagatgctg aatttgacca ttacttcact    2040

aaggacaaac cagttgtctt cgccttccat ggttacgaag acctggttcg tgacatcttc    2100

tttgatcgtc acaaccacaa cttacacgtg catggctacc gtgaaaatgg tgacattacg    2160

acaccattcg atgtccgggt catgaaccaa atggaccgtt tcgacttagc aaaatctgca    2220

attgcggcgc aaccagcaat ggaaaacacc ggtgcagcct ttgttcaaga catggataac    2280

atgcttgcaa aacacaacgc atacatccgt gacgccggaa ccgacttgcc agaagttaac    2340

gactggcaat ggaaaggttt gaaataa                                         2367
```

```
<210> SEQ ID NO 68
<211> LENGTH: 788
<212> TYPE: PRT
<213> ORGANISM: Lactobacillus pentosum
<220> FEATURE:
<223> OTHER INFORMATION: PHK

<400> SEQUENCE: 68

Met Ser Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Asn Pro Leu Leu Gln Arg Pro Leu Lys Ala Ser Asp Val Lys Val
        35                  40                  45

His Pro Ile Gly His Trp Gly Thr Ile Ala Gly Gln Asn Phe Ile Tyr
    50                  55                  60

Ala His Leu Asn Arg Val Ile Asn Lys Tyr Gly Leu Lys Met Phe Tyr
```

```
65                  70                  75                  80

Val Glu Gly Pro Gly His Gly Gly Gln Val Met Val Ser Asn Ser Tyr
                85                  90                  95

Leu Asp Gly Thr Tyr Thr Asp Ile Tyr Pro Glu Ile Thr Gln Asp Val
            100                 105                 110

Glu Gly Met Gln Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ser Ile Ser His Gly Val Gly Ala Ile Leu Asp Asn
145                 150                 155                 160

Pro Asp Glu Ile Ala Ala Val Val Val Gly Asp Gly Glu Ser Glu Thr
                165                 170                 175

Gly Pro Leu Ala Thr Ser Trp Gln Ser Thr Lys Phe Ile Asn Pro Ile
            180                 185                 190

Asn Asp Gly Ala Val Leu Pro Ile Leu Asn Leu Asn Gly Phe Lys Ile
        195                 200                 205

Ser Asn Pro Thr Ile Phe Gly Arg Thr Ser Asp Glu Lys Ile Lys Gln
    210                 215                 220

Tyr Phe Glu Ser Met Asn Trp Glu Pro Ile Phe Val Glu Gly Asp Asp
225                 230                 235                 240

Pro Glu Lys Val His Pro Ala Leu Ala Lys Ala Met Asp Glu Ala Val
                245                 250                 255

Glu Lys Ile Lys Ala Ile Gln Lys Asn Ala Arg Glu Asn Asp Asp Ala
            260                 265                 270

Thr Leu Pro Val Trp Pro Met Ile Val Phe Arg Ala Pro Lys Gly Trp
        275                 280                 285

Thr Gly Pro Lys Ser Trp Asp Gly Asp Lys Ile Glu Gly Ser Phe Arg
    290                 295                 300

Ala His Gln Ile Pro Ile Pro Val Asp Gln Thr Asp Met Glu His Ala
305                 310                 315                 320

Asp Ala Leu Val Asp Trp Leu Glu Ser Tyr Gln Pro Lys Glu Leu Phe
                325                 330                 335

Asn Glu Asp Gly Ser Leu Lys Asp Asp Ile Lys Glu Ile Ile Pro Thr
            340                 345                 350

Gly Asp Ala Arg Met Ala Ala Asn Pro Ile Thr Asn Gly Gly Val Asp
        355                 360                 365

Pro Lys Ala Leu Asn Leu Pro Asn Phe Arg Asp Tyr Ala Val Asp Thr
    370                 375                 380

Ser Lys His Gly Ala Asn Val Lys Gln Asp Met Ile Val Trp Ser Asp
385                 390                 395                 400

Tyr Leu Arg Asp Val Ile Lys Lys Asn Pro Asp Asn Phe Arg Leu Phe
                405                 410                 415

Gly Pro Asp Glu Thr Met Ser Asn Arg Leu Tyr Gly Val Phe Glu Thr
            420                 425                 430

Thr Asn Arg Gln Trp Met Glu Asp Ile His Pro Asp Ser Asp Gln Tyr
        435                 440                 445

Glu Ala Pro Ala Gly Arg Val Leu Asp Ala Gln Leu Ser Glu His Gln
    450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr
                485                 490                 495
```

```
Gln His Phe Lys Trp Leu Arg Lys Ala Asn Glu Leu Asp Trp Arg Lys
            500                 505                 510

Lys Tyr Pro Ser Leu Asn Ile Ile Ala Ala Ser Thr Val Phe Gln Gln
        515                 520                 525

Asp His Asn Gly Tyr Thr His Gln Asp Pro Gly Ala Leu Thr His Leu
    530                 535                 540

Ala Glu Lys Lys Pro Glu Tyr Ile Arg Glu Tyr Leu Pro Ala Asp Ala
545                 550                 555                 560

Asn Ser Leu Leu Ala Val Gly Asp Val Ile Phe Arg Ser Gln Glu Lys
                565                 570                 575

Ile Asn Tyr Val Val Thr Ser Lys His Pro Arg Gln Gln Trp Phe Ser
            580                 585                 590

Ile Glu Glu Ala Lys Gln Leu Val Asp Asn Gly Leu Gly Ile Ile Asp
        595                 600                 605

Trp Ala Ser Thr Asp Gln Gly Ser Glu Pro Asp Ile Val Phe Ala Ala
    610                 615                 620

Ala Gly Thr Glu Pro Thr Leu Glu Thr Leu Ala Ala Ile Gln Leu Leu
625                 630                 635                 640

His Asp Ser Phe Pro Asp Met Lys Ile Arg Phe Val Asn Val Val Asp
                645                 650                 655

Ile Leu Lys Leu Arg Ser Pro Glu Lys Asp Pro Arg Gly Leu Ser Asp
            660                 665                 670

Ala Glu Phe Asp His Tyr Phe Thr Lys Asp Lys Pro Val Val Phe Ala
        675                 680                 685

Phe His Gly Tyr Glu Asp Leu Val Arg Asp Ile Phe Phe Asp Arg His
    690                 695                 700

Asn His Asn Leu His Val His Gly Tyr Arg Glu Asn Gly Asp Ile Thr
705                 710                 715                 720

Thr Pro Phe Asp Val Arg Val Met Asn Gln Met Asp Arg Phe Asp Leu
                725                 730                 735

Ala Lys Ser Ala Ile Ala Ala Gln Pro Ala Met Glu Asn Thr Gly Ala
            740                 745                 750

Ala Phe Val Gln Asp Met Asp Asn Met Leu Ala Lys His Asn Ala Tyr
        755                 760                 765

Ile Arg Asp Ala Gly Thr Asp Leu Pro Glu Val Asn Asp Trp Gln Trp
    770                 775                 780

Lys Gly Leu Lys
785
```

```
<210> SEQ ID NO 69
<211> LENGTH: 2313
<212> TYPE: DNA
<213> ORGANISM: Lactobacillus acidophilus
<220> FEATURE:
<223> OTHER INFORMATION: PHK

<400> SEQUENCE: 69

atgaaaaatc cgttgttaaa gaaacctta acagctgaag atgtaaaacc taagccaatc      60

ggtcactggg gtactattgc tccacaaaac tttatttatg ctcacttaaa tcgtgcgctt     120

aaaaaatatg acttggatat gttctatatt gaaggttcag gtcacggtgg ccaagtgatg     180

gtttcaaatt catatcttga tggttcatat actgaacgtt atccagaaat tacccaagat     240

gaaaagggta tggctaaatt gtttaagcgc tttagtttcc caggtggtgt agcttctcac     300

gctgctcctg aaactccagg ttctattcat gaaggtgggg aattaggata cgcactttca     360
```

```
catggggtag gtgctatttt agacaatcca gatgtaattg ctgccgttga aattggtgat    420
ggtgaagcag aaactggtcc acttgcagct agctggttca gtgacaagtt tattaatcca    480
attaaggatg gtgcagtttt accaattctt caaattaatg gtttcaagat ttctaaccca    540
actatcgttt caagaatgag cgatgaagaa ttaactgaat acttccgtgg catgggttgg    600
gatccgcact ttgtttcagt atttaagggt ggccgctttg acggtgaaaa ggatccaatg    660
caagtccacg aagaaatggc taaaaccatg gacgaagtaa ttgaagaaat taaggctatt    720
caaaagcatg ctcgtgaaaa taatgatgct actttgccac attggccatt gattatcttc    780
caatgtccaa agggctggac cggtccaaag aaggatcttg acggcaatcc aattgaaaac    840
tcatttagag cacaccaaat tccaattcct gtctcacaat acgatatgaa acatgttgat    900
atgttgactg attggcttga aagttataag ccaaacgaat tattcaacga agatggttca    960
ccaaaggaaa ttgttactga aaacactgct aagggtgatc aacgtatggc aatgaatccg   1020
atcactaatg gtggtaagga tcctaaacga ttgaacctac cagattatcg caactttgca   1080
cttaagtttg acaagccagg ttcagttgaa gcacaagaca tggttgaatg ggctaaatat   1140
ttaaacgaag ttgctaaact taacccaact actttccgtg gctttggtcc tgatgaatct   1200
aaatcaaacc gtttatttaa acttttagat gatcaaaagc gtcaatggga acctgaagtt   1260
catgaaccaa atgatgaaaa cttggcacca agtggccgcg ttatcgattc acaattatca   1320
gaacaccaag acgaaggctt ccttgaaggc tacgttttaa ctggtcgtca cggcttcttt   1380
gcaacctacg aagcatttgg tcgtgtagta gattcgatgc ttactcaaca tatgaagtgg   1440
cttagaaaag ctaaagaaca atattggcgt catgattatc catcacttaa ctttgttgct   1500
acttcaacag tattccaaca agatcacaat ggttacactc accaagatcc aggcatttta   1560
actcacttat atgaaaagaa tcgtccagat ttagttcatg aatacttgcc atcagatact   1620
aatactttac ttgctgtagg taacaaggca tttactgatc gtgaatgtat taatgtttta   1680
gtaacttcaa agcaacctcg tccacaatgg ttctcaattg aggaagcaca aaagttagtt   1740
gataaaggtt taagttacat tgattgggct tcaactgata aaggtgtaaa accagatatt   1800
gtctttgctt caacagaaac tgaaccaaca attgaaactt tggcagcaat tgatattttg   1860
catgacaagt tcccagatct taagattcgc tacattaacg taattgatgt gatgaaatta   1920
atgtcaccaa aggacaataa gaatggtatt tctgatgaag aatttgatcg cttattccca   1980
aaggacgttc ctgtaatctt tgcatggcac ggctacaaga gtatgatgga atcaatttgg   2040
tttgcacgta accgtcataa tgtacatatt cactgctacg aagaaaacgg tgatattact   2100
accccatttg atatgcgtgt tttgaaccac cttgacagat ttgatcttgc caaagatgct   2160
gttgaaagtg ttgataaatt gaagggcaag aacgctgact ttatcagtca tatggatgac   2220
ttgcttgaaa agcaccacca atacattcgt gataatggta aagatatgcc agaagttact   2280
gaatggaagt ggaagggctt gaagaatgac agt                                2313
```

<210> SEQ ID NO 70
<211> LENGTH: 799
<212> TYPE: PRT
<213> ORGANISM: Lactobacillus acidophilus
<220> FEATURE:
<223> OTHER INFORMATION: PHK

<400> SEQUENCE: 70

```
Met Thr Val Asn Tyr Asp Ser Lys Asp Tyr Leu Lys Ser Val Asp Ala
1               5                   10                  15
```

-continued

```
Tyr Trp Arg Ala Ala Asn Tyr Leu Ser Val Gly Gln Leu Phe Leu Met
            20                  25                  30

Lys Asn Pro Leu Leu Lys Lys Pro Leu Thr Ala Glu Asp Val Lys Pro
        35                  40                  45

Lys Pro Ile Gly His Trp Gly Thr Ile Ala Pro Gln Asn Phe Ile Tyr
    50                  55                  60

Ala His Leu Asn Arg Ala Leu Lys Lys Tyr Asp Leu Asp Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Thr Glu Arg Tyr Pro Glu Ile Thr Gln Asp Glu
            100                 105                 110

Lys Gly Met Ala Lys Leu Phe Lys Arg Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ala Leu Ser His Gly Val Gly Ala Ile Leu Asp Asn
145                 150                 155                 160

Pro Asp Val Ile Ala Ala Val Glu Ile Gly Asp Gly Glu Ala Glu Thr
                165                 170                 175

Gly Pro Leu Ala Ala Ser Trp Phe Ser Asp Lys Phe Ile Asn Pro Ile
            180                 185                 190

Lys Asp Gly Ala Val Leu Pro Ile Leu Gln Ile Asn Gly Phe Lys Ile
        195                 200                 205

Ser Asn Pro Thr Ile Val Ser Arg Met Ser Asp Glu Glu Leu Thr Glu
    210                 215                 220

Tyr Phe Arg Gly Met Gly Trp Asp Pro His Phe Val Ser Val Phe Lys
225                 230                 235                 240

Gly Gly Arg Phe Asp Gly Glu Lys Asp Pro Met Gln Val His Glu Glu
                245                 250                 255

Met Ala Lys Thr Met Asp Glu Val Ile Glu Glu Ile Lys Ala Ile Gln
            260                 265                 270

Lys His Ala Arg Glu Asn Asn Asp Ala Thr Leu Pro His Trp Pro Leu
        275                 280                 285

Ile Ile Phe Gln Cys Pro Lys Gly Trp Thr Gly Pro Lys Lys Asp Leu
    290                 295                 300

Asp Gly Asn Pro Ile Glu Asn Ser Phe Arg Ala His Gln Ile Pro Ile
305                 310                 315                 320

Pro Val Ser Gln Tyr Asp Met Lys His Val Asp Met Leu Thr Asp Trp
                325                 330                 335

Leu Glu Ser Tyr Lys Pro Asn Glu Leu Phe Asn Glu Asp Gly Ser Pro
            340                 345                 350

Lys Glu Ile Val Thr Glu Asn Thr Ala Lys Gly Asp Gln Arg Met Ala
        355                 360                 365

Met Asn Pro Ile Thr Asn Gly Gly Lys Asp Pro Lys Arg Leu Asn Leu
    370                 375                 380

Pro Asp Tyr Arg Asn Phe Ala Leu Lys Phe Asp Lys Pro Gly Ser Val
385                 390                 395                 400

Glu Ala Gln Asp Met Val Glu Trp Ala Lys Tyr Leu Asn Glu Val Ala
                405                 410                 415

Lys Leu Asn Pro Thr Thr Phe Arg Gly Phe Gly Pro Asp Glu Ser Lys
            420                 425                 430
```

```
Ser Asn Arg Leu Phe Lys Leu Leu Asp Asp Gln Lys Arg Gln Trp Glu
        435                 440                 445

Pro Glu Val His Glu Pro Asn Asp Glu Asn Leu Ala Pro Ser Gly Arg
    450                 455                 460

Val Ile Asp Ser Gln Leu Ser Glu His Gln Asp Glu Gly Phe Leu Glu
465                 470                 475                 480

Gly Tyr Val Leu Thr Gly Arg His Gly Phe Phe Ala Thr Tyr Glu Ala
                485                 490                 495

Phe Gly Arg Val Val Asp Ser Met Leu Thr Gln His Met Lys Trp Leu
            500                 505                 510

Arg Lys Ala Lys Glu Gln Tyr Trp Arg His Asp Tyr Pro Ser Leu Asn
        515                 520                 525

Phe Val Ala Thr Ser Thr Val Phe Gln Gln Asp His Asn Gly Tyr Thr
    530                 535                 540

His Gln Asp Pro Gly Ile Leu Thr His Leu Tyr Glu Lys Asn Arg Pro
545                 550                 555                 560

Asp Leu Val His Glu Tyr Leu Pro Ser Asp Thr Asn Thr Leu Leu Ala
                565                 570                 575

Val Gly Asn Lys Ala Phe Thr Asp Arg Glu Cys Ile Asn Val Leu Val
            580                 585                 590

Thr Ser Lys Gln Pro Arg Pro Gln Trp Phe Ser Ile Glu Glu Ala Gln
        595                 600                 605

Lys Leu Val Asp Lys Gly Leu Ser Tyr Ile Asp Trp Ala Ser Thr Asp
    610                 615                 620

Lys Gly Val Lys Pro Asp Ile Val Phe Ala Ser Thr Glu Thr Glu Pro
625                 630                 635                 640

Thr Ile Glu Thr Leu Ala Ala Ile Asp Ile Leu His Asp Lys Phe Pro
                645                 650                 655

Asp Leu Lys Ile Arg Tyr Ile Asn Val Ile Asp Val Met Lys Leu Met
            660                 665                 670

Ser Pro Lys Asp Asn Lys Asn Gly Ile Ser Asp Glu Glu Phe Asp Arg
        675                 680                 685

Leu Phe Pro Lys Asp Val Pro Val Ile Phe Ala Trp His Gly Tyr Lys
    690                 695                 700

Ser Met Met Glu Ser Ile Trp Phe Ala Arg Asn Arg His Asn Val His
705                 710                 715                 720

Ile His Cys Tyr Glu Glu Asn Gly Asp Ile Thr Thr Pro Phe Asp Met
                725                 730                 735

Arg Val Leu Asn His Leu Asp Arg Phe Asp Leu Ala Lys Asp Ala Val
            740                 745                 750

Glu Ser Val Asp Lys Leu Lys Gly Lys Asn Ala Asp Phe Ile Ser His
        755                 760                 765

Met Asp Asp Leu Leu Glu Lys His His Gln Tyr Ile Arg Asp Asn Gly
    770                 775                 780

Lys Asp Met Pro Glu Val Thr Glu Trp Lys Trp Lys Gly Leu Lys
785                 790                 795
```

<210> SEQ ID NO 71
<211> LENGTH: 2469
<212> TYPE: DNA
<213> ORGANISM: Penicillium chrysogenum
<220> FEATURE:
<223> OTHER INFORMATION: PHK

<400> SEQUENCE: 71

```
atgcctgcag aagttataag cgaaccaaat ccacaagctc tgccgtcgca tctgccagac     60
tatcttgaga aattgagcgt cagcttggaa cgtgagaaac tagatgaaaa gacctacgat    120
gccttgatca agttccgccg agcggcttgt tacattgcgg cagctatgat atttctgcaa    180
gaaaatactc ttttgaagtc agaactcaca tttcaacatg tcaagcctag actactcggt    240
cactggggaa catgcccggg cctaatcttt gtctactctc atttgaacta cctgatccgg    300
acaatgaatc tggacatgtt gtacgttgtc ggtccaggac atggcgcacc ggcaatacta    360
gccgcgctat ggttggaggg ttcgctggag aaattctatc cccactattc gcgagacgaa    420
aagggcctac acagattgat ctcgaccttt agtaccacag gtggttttcc cagccacatc    480
aattccgaga cccccggtgc aatccatgaa ggtggagaac tgggttacgc tctggcagtg    540
tcctttggcg ctgtcatgga taaccccgat ctgattgtga cttgtattgt gggggacggg    600
gaggctgaaa gcggtcccac tgctacgtcc tggcatgcga tcaagtacat tgatccaaag    660
gagtccggtg cagttttacc aattctgcat ttgaatggat tcaagatcag cgagcgcact    720
atcttcgggt gcatggacca caaagagctt ttgactctct tcagtggata cgggtaccag    780
gttcgctttg tcgaggataa caacgatatt gatgcggatt tacacacctc tatgatctgg    840
gccgtcaatg aaatccagaa gatccagaag gctgcccgtt cagggaagcc gattatgaag    900
ccaaggtggc cgatgctgat tctgcgtact tccaagggct ggactgggcc caagcagctt    960
catggcaagt ttcttgaggg ctcataccat tctcaccagg tgccattgcc caaagcaaag   1020
accgacaagg aacaactaga tctgctgcag aattggctgt ctagttataa gccagaagag   1080
ctgttcactt cgaacggtga tgtaattgat gagatcaagt ctgtgatacc cacagaagac   1140
aaaaagaagc ttggccagcg catcgaagtc tacaatagtt atacaccacc gaatctgccg   1200
gattggaagc ccttctgcgc ggataaaggc tctcaagaaa gcgctatgaa agcggctggc   1260
accttcatta atcagacatt caaggacaac ccgaacagcg tgcgactctt ctcgccggac   1320
gagttggaaa gcaacaaact cgatgcggta tttgaataca caaaccgcaa tttccaatgg   1380
gacgagttcg ccaatgcccg cggcggccgt gtaattgaag tccttagcga acatatgtgt   1440
caaggattca tgcagggcta taccttgacc gggcgcattg gtattttccc gtcctatgag   1500
agcttcctcg gcatcattca tacgatgatg gtgcagtatg ccaagttcat caagatggga   1560
ctggaaacaa cttggcactc cggcgtcagt agtgtgaact acatcgaatc gagcacctgg   1620
gcacgccaag aacacaacgg cttctctcac cagaacccat ccttcatcgg cgctgtgcta   1680
aagctgaagc ctagtgcagc tcgggtatac ttaccaccag atgcgaatac tttcctgaca   1740
accatccacc attgtttaaa atcaaagaat tacatcaacc taatggtagg ctcaaagcag   1800
ccaactccag tgtacctgac tcccaaagag gcggaaagcc actgtcgcgc aggagcatcc   1860
atttggaagt tctgcagcac ggacgatgga attaatccgg atgtcgtgct ggtcggtatt   1920
ggtgttgagg tgatgttcga agtaattgcg gcagcggcgc ttctgcgtaa gctcatccca   1980
gagcttcgtg tttgtgtcat taacgtgacg gacctgatga ttcttgataa cgagggtgcg   2040
catccgcatg ccctgtccac tgaggcattc gatggtctct ttacttccga caggcccatt   2100
cacttcaatt accacggcta tccaactgag ctgcagggtt tgctctttgg acgtccccgc   2160
cttgatcgcg tcagtgtcgc cggctatatc gaagagggta gcaccaccac gcctttcgac   2220
atgatgcttg tcaaccgtgt ctcgcgtttc catgtcgccc agcatgctat tcgtggtgct   2280
gccaaagtaa atgagaaggt cagggtgtat cagcaggagc tgaatgctca gcttgaggcg   2340
agtatggtca gcacgaggaa gtatattgtg gaaaaccggg atgaccccga cggcatttat   2400
```

gacatgccac aattccacag cttccacaaa ccggctgagt ctgagacatt ctggaatatt 2460
gcccagtag 2469

<210> SEQ ID NO 72
<211> LENGTH: 822
<212> TYPE: PRT
<213> ORGANISM: Penicillium chrysogenum
<220> FEATURE:
<223> OTHER INFORMATION: PHK

<400> SEQUENCE: 72

Met Pro Ala Glu Val Ile Ser Glu Pro Asn Pro Gln Ala Leu Pro Ser
1 5 10 15

His Leu Pro Asp Tyr Leu Glu Lys Leu Ser Val Ser Leu Glu Arg Glu
20 25 30

Lys Leu Asp Glu Lys Thr Tyr Asp Ala Leu Ile Lys Phe Arg Arg Ala
35 40 45

Ala Cys Tyr Ile Ala Ala Ala Met Ile Phe Leu Gln Glu Asn Thr Leu
50 55 60

Leu Lys Ser Glu Leu Thr Phe Gln His Val Lys Pro Arg Leu Leu Gly
65 70 75 80

His Trp Gly Thr Cys Pro Gly Leu Ile Phe Val Tyr Ser His Leu Asn
85 90 95

Tyr Leu Ile Arg Thr Met Asn Leu Asp Met Leu Tyr Val Val Gly Pro
100 105 110

Gly His Gly Ala Pro Ala Ile Leu Ala Ala Leu Trp Leu Glu Gly Ser
115 120 125

Leu Glu Lys Phe Tyr Pro His Tyr Ser Arg Asp Glu Lys Gly Leu His
130 135 140

Arg Leu Ile Ser Thr Phe Ser Thr Thr Gly Gly Phe Pro Ser His Ile
145 150 155 160

Asn Ser Glu Thr Pro Gly Ala Ile His Glu Gly Gly Glu Leu Gly Tyr
165 170 175

Ala Leu Ala Val Ser Phe Gly Ala Val Met Asp Asn Pro Asp Leu Ile
180 185 190

Val Thr Cys Ile Val Gly Asp Gly Glu Ala Glu Ser Gly Pro Thr Ala
195 200 205

Thr Ser Trp His Ala Ile Lys Tyr Ile Asp Pro Lys Glu Ser Gly Ala
210 215 220

Val Leu Pro Ile Leu His Leu Asn Gly Phe Lys Ile Ser Glu Arg Thr
225 230 235 240

Ile Phe Gly Cys Met Asp His Lys Glu Leu Leu Thr Leu Phe Ser Gly
245 250 255

Tyr Gly Tyr Gln Val Arg Phe Val Glu Asp Asn Asn Asp Ile Asp Ala
260 265 270

Asp Leu His Thr Ser Met Ile Trp Ala Val Asn Glu Ile Gln Lys Ile
275 280 285

Gln Lys Ala Ala Arg Ser Gly Lys Pro Ile Met Lys Pro Arg Trp Pro
290 295 300

Met Leu Ile Leu Arg Thr Ser Lys Gly Trp Thr Gly Pro Lys Gln Leu
305 310 315 320

His Gly Lys Phe Leu Glu Gly Ser Tyr His Ser His Gln Val Pro Leu
325 330 335

Pro Lys Ala Lys Thr Asp Lys Glu Gln Leu Asp Leu Leu Gln Asn Trp

-continued

```
            340                 345                 350

Leu Ser Ser Tyr Lys Pro Glu Glu Leu Phe Thr Ser Asn Gly Asp Val
        355                 360                 365

Ile Asp Glu Ile Lys Ser Val Ile Pro Thr Glu Asp Lys Lys Lys Leu
    370                 375                 380

Gly Gln Arg Ile Glu Val Tyr Asn Ser Tyr Thr Pro Pro Asn Leu Pro
385                 390                 395                 400

Asp Trp Lys Pro Phe Cys Ala Asp Lys Gly Ser Gln Glu Ser Ala Met
                405                 410                 415

Lys Ala Ala Gly Thr Phe Ile Asn Gln Thr Phe Lys Asp Asn Pro Asn
            420                 425                 430

Ser Val Arg Leu Phe Ser Pro Asp Glu Leu Glu Ser Asn Lys Leu Asp
        435                 440                 445

Ala Val Phe Glu Tyr Thr Asn Arg Asn Phe Gln Trp Asp Glu Phe Ala
    450                 455                 460

Asn Ala Arg Gly Gly Arg Val Ile Glu Val Leu Ser Glu His Met Cys
465                 470                 475                 480

Gln Gly Phe Met Gln Gly Tyr Thr Leu Thr Gly Arg Ile Gly Ile Phe
                485                 490                 495

Pro Ser Tyr Glu Ser Phe Leu Gly Ile Ile His Thr Met Met Val Gln
            500                 505                 510

Tyr Ala Lys Phe Ile Lys Met Gly Leu Glu Thr Thr Trp His Ser Gly
        515                 520                 525

Val Ser Ser Val Asn Tyr Ile Glu Ser Ser Thr Trp Ala Arg Gln Glu
    530                 535                 540

His Asn Gly Phe Ser His Gln Asn Pro Ser Phe Ile Gly Ala Val Leu
545                 550                 555                 560

Lys Leu Lys Pro Ser Ala Ala Arg Val Tyr Leu Pro Pro Asp Ala Asn
                565                 570                 575

Thr Phe Leu Thr Thr Ile His His Cys Leu Lys Ser Lys Asn Tyr Ile
            580                 585                 590

Asn Leu Met Val Gly Ser Lys Gln Pro Thr Pro Val Tyr Leu Thr Pro
        595                 600                 605

Lys Glu Ala Glu Ser His Cys Arg Ala Gly Ala Ser Ile Trp Lys Phe
    610                 615                 620

Cys Ser Thr Asp Asp Gly Ile Asn Pro Asp Val Val Leu Val Gly Ile
625                 630                 635                 640

Gly Val Glu Val Met Phe Glu Val Ile Ala Ala Ala Ala Leu Leu Arg
                645                 650                 655

Lys Leu Ile Pro Glu Leu Arg Val Cys Val Ile Asn Val Thr Asp Leu
            660                 665                 670

Met Ile Leu Asp Asn Glu Gly Ala His Pro His Ala Leu Ser Thr Glu
        675                 680                 685

Ala Phe Asp Gly Leu Phe Thr Ser Asp Arg Pro Ile His Phe Asn Tyr
    690                 695                 700

His Gly Tyr Pro Thr Glu Leu Gln Gly Leu Leu Phe Gly Arg Pro Arg
705                 710                 715                 720

Leu Asp Arg Val Ser Val Ala Gly Tyr Ile Glu Glu Gly Ser Thr Thr
                725                 730                 735

Thr Pro Phe Asp Met Met Leu Val Asn Arg Val Ser Arg Phe His Val
            740                 745                 750

Ala Gln His Ala Ile Arg Gly Ala Ala Lys Val Asn Glu Lys Val Arg
        755                 760                 765
```

```
Val Tyr Gln Gln Glu Leu Asn Ala Gln Leu Glu Ala Ser Met Val Ser
    770                 775                 780

Thr Arg Lys Tyr Ile Val Glu Asn Arg Asp Asp Pro Asp Gly Ile Tyr
785                 790                 795                 800

Asp Met Pro Gln Phe His Ser Phe His Lys Pro Ala Glu Ser Glu Thr
                805                 810                 815

Phe Trp Asn Ile Ala Gln
            820


<210> SEQ ID NO 73
<211> LENGTH: 2421
<212> TYPE: DNA
<213> ORGANISM: Aspergillus nidulans
<220> FEATURE:
<223> OTHER INFORMATION: PHK

<400> SEQUENCE: 73

atgcctggag aggtcatcga caggccaaat cccaaggctg agccttcaca catccccgat     60

cttgtcaatc aattgcaggt caaacttcaa gagacgcgtt tggaggaaac tgattacaat    120

gcccttctga aattccgccg tgcagcggcc tacattgctg ctgcaatgat ctttctccaa    180

gacaatgtgc tgctgaagca gaatctaagg cacgaggaca tcaagcccag gcttcttggc    240

cactggggaa catgtcccgg gttgattctt gtatactctc acttgaacta catcatcaga    300

aagcagaacc tggatatgtt gtatgtcgtc gggcctggcc acggcgcgcc agctattttg    360

gcctcactgt ggcttgaggg ctctttagag aaattctacc cccactactc acgagacatg    420

gatggtctcc atgagctcat ctcgaccttc agcacaagtg ctggattacc aagccatatc    480

aatgcggaaa ctcccggtgc aatccatgaa ggtggtgaat tgggttatgc gttagctgtc    540

tcttttggtg ctgttatgga caatcccgac atgatcgtca cctgcgtggt tggtgacggg    600

gaagcagaaa ctggtcctac cgcgacgtcc tggcatgcaa tcaagtacat tgaccccgca    660

gaatcaggtg ccgtcctgcc gattctccac gttaatggct ttaagatcag cgagcgcacc    720

atttatggct gcatggacaa caaagagctg gtctccctct tcacgggtta tggataccag    780

gtgcgcattg ttgagaacct ggatgacatc gacgcagatc tccatagctc tatgatgtgg    840

gcagttgagg agatccacaa gatccaaaaa gcggcgcgtt ccggcaagcc aattatgaag    900

cctagatggc caatgattgt tttgcgcaca ccgaagggtt ggtcaggacc taaagagctc    960

cacgggtcat tcatagaggg atctttccac tcacatcagg ttcctctacc taatgcaaag   1020

aaggataaag aggagcttca ggctctgcag aaatggctgt cctcgtataa tccgcacgaa   1080

cttttcactg agacgggaga catcattgac gacatcaagt cagtgatccc tctggaagac   1140

accaagaagc ttgggcagcg agcagaagcc tacaagggct atagggcacc cgatctccca   1200

gactggcgca agtttggcgt agaaaagggc tcccagcaga gcgctatgaa aacaattgga   1260

aagttcattg accaagtgtt tacccaaaat cctcatggcg tccgtgtatt ttcgccagac   1320

gagctagaga gcaacaagct ggatgcagca ctggcgcaca cgggaaggaa ctttcagtgg   1380

gatcaattct cgaatgccaa aggcggccgc gtcatcgagg tgctcagtga gcacctgtgc   1440

cagggcttta tgcagggata cacgttgacg ggccgggtgg gcattttccc atcgtacgaa   1500

agcttcttgg gaatcatcca taccatgatg gtgcaatatg ccaaatttaa caaaatggct   1560

caagagacga cctggcataa gccggttagt agcatcaact atatcgaaac gagtacgtgg   1620

gctcgtcagg agcacaatgg attctctcac cagaacccct cctttatcgg agctgtgctc   1680
```

```
aggctgaagc ccaccgccgc gcgagtttat ctgccacctg atgctaacac atttttgacc   1740

acccttcacc actgtctcaa gtccaagaat tatgtcaacc tcatggtagg ttcaaaacag   1800

ccaactcccg tgtacttgag ccccgaggaa gcagagagcc actgccgagc cggcgcatcg   1860

atctggagat tctgtagtac cgacaatggg ctgaacccgg atgtcgtgct ggttggcatt   1920

ggagtagagg tgatgttcga ggtcatctac gcggcggcca tcctccgcaa gcgttgtcca   1980

gaactccggg tgcgtgtggt caatgtgacc gacttgatga ttctggagaa ggaaggtcta   2040

catccacatg cattgacgac cgaagctttc gacagtctgt ttggctcgga ccggccgata   2100

cacttcaact accacggata cccgggcgag ctcaaaggtc tgctctttgg gcggccccgc   2160

ctggaccgag tttcagtaga aggatacatg gaggaaggaa gcacgacgac gccgttcgat   2220

atgatgttgc tgaaccgcgt ctcacgatac cacgtggcgc aggcagccgt gatcggggcg   2280

tccagacgga atgagaaggt tcaagttcgg cagcacgaac tggtcagcga attcggccac   2340

aacatcgtgg agacacgcaa atacattctg gccaaccgca aagacccgga tgatacgtat   2400

gatatgccct cctttgaata a                                             2421


<210> SEQ ID NO 74
<211> LENGTH: 780
<212> TYPE: PRT
<213> ORGANISM: Aspergillus nidulans
<220> FEATURE:
<223> OTHER INFORMATION: PHK

<400> SEQUENCE: 74

Met Pro Gly Glu Val Ile Glu Arg Pro Asn Pro Ala Pro Lys Pro Ser
1               5                   10                  15

His Val Pro Asp Leu Val Glu Lys Leu Ile Ile Pro Ala Gln Lys Thr
            20                  25                  30

Lys Leu Glu Lys Ser Asp Cys Asp Ala Leu His Lys Tyr Arg Arg Ala
        35                  40                  45

Ala Ala Tyr Ile Ala Ala Gly His Trp Gly Thr Cys Pro Gly Leu Ile
    50                  55                  60

Leu Val Tyr Ser His Leu Asn Tyr Leu Ile Lys Lys Gln Asn Leu Asp
65                  70                  75                  80

Met Leu Tyr Val Val Gly Pro Gly His Gly Ala Pro Gly Leu Leu Ala
                85                  90                  95

Ser Leu Trp Leu Glu Gly Ser Leu Gly Lys Phe Tyr Pro Gln Tyr Thr
            100                 105                 110

Lys Asp Lys Glu Gly Leu His Asn Leu Ile Ser Thr Phe Ser Thr Ser
        115                 120                 125

Ala Gly Leu Pro Ser His Ile Asn Ala Glu Thr Pro Gly Ala Ile His
    130                 135                 140

Glu Gly Gly Glu Leu Gly Tyr Ala Leu Ser Val Ser Phe Gly Ala Val
145                 150                 155                 160

Met Asp Asn Pro Asp Leu Ile Val Thr Cys Val Val Gly Asp Gly Glu
                165                 170                 175

Ala Glu Thr Gly Pro Thr Ala Thr Ser Trp His Ala Ile Lys Tyr Ile
            180                 185                 190

Asp Pro Ala Glu Ser Gly Ala Val Leu Pro Ile Leu His Val Asn Gly
        195                 200                 205

Phe Lys Ile Ser Glu Arg Thr Ile Phe Gly Cys Met Asp Asn Arg Glu
    210                 215                 220

Ile Val Cys Leu Phe Thr Gly Tyr Gly Tyr Gln Val Arg Ile Val Glu
```

```
225                 230                 235                 240

Asp Leu Glu Asp Ile Asp Asn Asp Leu His Ser Ala Met Ser Trp Ala
                245                 250                 255

Val Glu Glu Ile Arg Asn Ile Gln Lys Ala Ala Arg Ser Gly Lys Pro
            260                 265                 270

Ile Met Lys Pro Gln Trp Pro Met Ile Val Leu Arg Thr Pro Lys Gly
        275                 280                 285

Trp Ser Gly Pro Lys Glu Leu His Gly Gln Phe Ile Glu Gly Ser Phe
    290                 295                 300

His Ser His Gln Val Pro Leu Pro Asn Ala Lys Lys Asp Asp Glu Glu
305                 310                 315                 320

Leu Gln Ala Leu Gln Lys Trp Leu Ser Ser Tyr Lys Pro Asp Glu Leu
                325                 330                 335

Phe Thr Glu Ser Gly Asp Val Ile Asp Glu Ile Leu Ser Ile Ile Pro
            340                 345                 350

Ser Asp Asp Lys Lys Leu Gly Met Arg Pro Glu Ala Tyr Lys Thr His
        355                 360                 365

Leu Pro Pro Asp Leu Pro Asp Trp Arg Gln Phe Cys Val Lys Lys Gly
    370                 375                 380

Asp Gln Phe Ser Ala Met Lys Ala Ile Gly Ser Phe Ile Asp Gln Val
385                 390                 395                 400

Phe Val Lys Asn Pro His Thr Val Arg Leu Phe Ser Pro Asp Glu Leu
                405                 410                 415

Glu Ser Asn Lys Leu Ser Ala Ala Leu Ser His Thr Gly Arg Asn Phe
            420                 425                 430

Gln Trp Asp Glu Phe Ser Asn Ala Lys Gly Gly Arg Val Ile Glu Val
        435                 440                 445

Leu Ser Glu His Leu Cys Gln Gly Phe Met Gln Gly Tyr Thr Leu Thr
    450                 455                 460

Gly Arg Thr Gly Ile Phe Pro Ser Tyr Glu Ser Phe Leu Gly Ile Ile
465                 470                 475                 480

His Thr Met Met Val Gln Tyr Ala Lys Phe Ala Lys Met Ala Lys Glu
                485                 490                 495

Thr Ala Trp His His Asp Val Ser Ser Ile Asn Tyr Ile Glu Thr Ser
            500                 505                 510

Thr Trp Ala Arg Gln Glu His Asn Gly Phe Ser His Gln Asn Pro Ser
        515                 520                 525

Phe Ile Gly Ala Val Leu Lys Leu Lys Pro Tyr Ala Ala Arg Val Tyr
    530                 535                 540

Leu Pro Pro Asp Ala Asn Thr Phe Leu Thr Thr Leu His His Cys Leu
545                 550                 555                 560

Lys Ser Lys Asn Tyr Ile Asn Leu Met Val Gly Ser Lys Gln Pro Thr
                565                 570                 575

Pro Val Tyr Leu Ser Pro Glu Glu Ala Glu Ser His Cys Arg Ala Gly
            580                 585                 590

Ala Ser Ile Phe Lys Phe Cys Ser Thr Asp Gly Gly Leu Arg Pro Asp
        595                 600                 605

Val Val Leu Val Gly Ile Gly Val Glu Val Met Phe Glu Val Ile Lys
    610                 615                 620

Ala Ala Ala Ile Leu Arg Glu Arg Cys Pro Glu Leu Arg Val Arg Val
625                 630                 635                 640

Val Asn Val Thr Asp Leu Phe Ile Leu Glu Asn Glu Gly Ala His Pro
                645                 650                 655
```

```
His Ala Leu Lys His Glu Ala Phe Asp Asn Leu Phe Thr Glu Asp Arg
            660                 665                 670

Ser Ile His Phe Asn Tyr His Gly Tyr Val Asn Glu Leu Gln Gly Leu
        675                 680                 685

Leu Phe Gly Arg Pro Arg Leu Asp Arg Ala Thr Ile Lys Gly Tyr Lys
    690                 695                 700

Glu Glu Gly Ser Thr Thr Thr Pro Phe Asp Met Met Leu Val Asn Glu
705                 710                 715                 720

Val Ser Arg Tyr His Val Ala Lys Ala Ala Val Thr Gly Gly Ala Arg
                725                 730                 735

Phe Asn Glu Lys Val Lys Leu Arg His Gln Glu Leu Cys Ser Glu Phe
            740                 745                 750

Asp His Asn Ile Ala Glu Thr Arg Lys Tyr Ile Met Asn Asn His Gln
        755                 760                 765

Asp Pro Glu Asp Thr Tyr Asn Met Pro Ser Phe Asn
    770                 775                 780
```

```
<210> SEQ ID NO 75
<211> LENGTH: 1188
<212> TYPE: DNA
<213> ORGANISM: Clostridium phytofermentans
<220> FEATURE:
<223> OTHER INFORMATION: ACK

<400> SEQUENCE: 75

atgaaagttt tagttattaa ttgcggaagt tcttccctta aatatcagtt aatcgactct     60

gtgacagagc aagcattagc agtaggtctt tgtgaaagaa tcggtattga tggccgtctt    120

actcacaagt cagctgacgg tgagaaggta gttcttgagg atgcacttcc aaaccatgag    180

gttgctatta aaaatgtaat cgctgctctt atgaatgaaa attatggtgt gattaagtcc    240

ttagatgaaa tcaacgctgt tggacataga gtagtacatg gtggtgagaa atttgctcat    300

tccgtagtaa tcaatgatga agtcttaaat gcaattgaag agtgtaatga tcttgcacct    360

ttacacaacc cagcaaacct tattggtatc aacgcttgta aatcaattat gccaaatgta    420

ccaatggtag ctgtttttga tactgcattc catcagacaa tgccaaaaga agcttacctt    480

tatggtattc catttgagta ctatgataaa tataaggtaa gaagatatgg tttccacgga    540

acaagtcaca gctatgtttc taaaagagca accacgcttg ctggcttaga tgtaaataac    600

tcaaaagtta tcgtttgtca ccttggtaat ggcgcatcca tttccgcagt taaaaacggt    660

gagtctgtag atacaagtat gggtcttaca ccacttgaag gtttaatcat gggaacaaga    720

agtggtgatc ttgatccagc aatcattgat ttcgttgcta agaaagaaaa cttatcctta    780

gatgaagtaa tgaatatctt aaataagaaa tctggtgtat taggtatgtc cggagtatct    840

tctgacttta gagatatcga agcagcagca aacgaaggca atgagcatgc aaaagaagct    900

ttagcagttt ttgcataccg tgttgctaaa tatgtaggtt cttatatcgt agctatgaat    960

ggtgtagatg ctgttgtatt tacagcagga cttggtgaga atgataagaa catcagagca   1020

gcagtaagtt cacaccttga gttccttggt gtatctttag atgctgagaa gaattctcaa   1080

agaggtaaag aattaatcat ctctaaccca gattctaagg ttaagattat ggttatccca   1140

actaacgaag agcttgcaat ctgtagagaa gttgttgaat tagtgtag                1188

<210> SEQ ID NO 76
<211> LENGTH: 395
<212> TYPE: PRT
```

```
<213> ORGANISM: Clostridium phytofermentans
<220> FEATURE:
<223> OTHER INFORMATION: ACK

<400> SEQUENCE: 76

Met Lys Val Leu Val Ile Asn Cys Gly Ser Ser Ser Leu Lys Tyr Gln
1               5                   10                  15

Leu Ile Asp Ser Val Thr Glu Gln Ala Leu Ala Val Gly Leu Cys Glu
            20                  25                  30

Arg Ile Gly Ile Asp Gly Arg Leu Thr His Lys Ser Ala Asp Gly Glu
        35                  40                  45

Lys Val Val Leu Glu Asp Ala Leu Pro Asn His Glu Val Ala Ile Lys
    50                  55                  60

Asn Val Ile Ala Ala Leu Met Asn Glu Asn Tyr Gly Val Ile Lys Ser
65                  70                  75                  80

Leu Asp Glu Ile Asn Ala Val Gly His Arg Val Val His Gly Gly Glu
                85                  90                  95

Lys Phe Ala His Ser Val Val Ile Asn Asp Glu Val Leu Asn Ala Ile
            100                 105                 110

Glu Glu Cys Asn Asp Leu Ala Pro Leu His Asn Pro Ala Asn Leu Ile
        115                 120                 125

Gly Ile Asn Ala Cys Lys Ser Ile Met Pro Asn Val Pro Met Val Ala
    130                 135                 140

Val Phe Asp Thr Ala Phe His Gln Thr Met Pro Lys Glu Ala Tyr Leu
145                 150                 155                 160

Tyr Gly Ile Pro Phe Glu Tyr Tyr Asp Lys Tyr Lys Val Arg Arg Tyr
                165                 170                 175

Gly Phe His Gly Thr Ser His Ser Tyr Val Ser Lys Arg Ala Thr Thr
            180                 185                 190

Leu Ala Gly Leu Asp Val Asn Asn Ser Lys Val Ile Val Cys His Leu
        195                 200                 205

Gly Asn Gly Ala Ser Ile Ser Ala Val Lys Asn Gly Glu Ser Val Asp
    210                 215                 220

Thr Ser Met Gly Leu Thr Pro Leu Glu Gly Leu Ile Met Gly Thr Arg
225                 230                 235                 240

Ser Gly Asp Leu Asp Pro Ala Ile Ile Asp Phe Val Ala Lys Lys Glu
                245                 250                 255

Asn Leu Ser Leu Asp Glu Val Met Asn Ile Leu Asn Lys Lys Ser Gly
            260                 265                 270

Val Leu Gly Met Ser Gly Val Ser Ser Asp Phe Arg Asp Ile Glu Ala
        275                 280                 285

Ala Ala Asn Glu Gly Asn Glu His Ala Lys Glu Ala Leu Ala Val Phe
    290                 295                 300

Ala Tyr Arg Val Ala Lys Tyr Val Gly Ser Tyr Ile Val Ala Met Asn
305                 310                 315                 320

Gly Val Asp Ala Val Val Phe Thr Ala Gly Leu Gly Glu Asn Asp Lys
                325                 330                 335

Asn Ile Arg Ala Ala Val Ser Ser His Leu Glu Phe Leu Gly Val Ser
            340                 345                 350

Leu Asp Ala Glu Lys Asn Ser Gln Arg Gly Lys Glu Leu Ile Ile Ser
        355                 360                 365

Asn Pro Asp Ser Lys Val Lys Ile Met Val Ile Pro Thr Asn Glu Glu
    370                 375                 380

Leu Ala Ile Cys Arg Glu Val Val Glu Leu Val
```

385 390 395

<210> SEQ ID NO 77
<211> LENGTH: 2421
<212> TYPE: DNA
<213> ORGANISM: Aspergillus clavatus
<220> FEATURE:
<223> OTHER INFORMATION: PHK

<400> SEQUENCE: 77

```
atgcctgggg aagtcattga cagaccaaac ccgcaggcgc tgccttccca tattcccgat      60
gtggttgaac agttgcaggt gaagctggat ttgacgagtt tagagcaacc ggcctgcgat     120
gccttgttca aattccgtcg agctgcttca tacatcgctg cagcaatgat ctttctgcaa     180
gataatgtgc tactgaaaag aagcttgacg catgacgaca taaagcctag attgcttggt     240
cattggggaa catgtcccgg cctgatattg gtatactctc acctgaatta cctcattaca     300
aagcgcaatc tcaatatgct gtatgtcgtg ggaccaggac atggtgcacc agccatccta     360
gcctctctct ggctggaggg ctcgttggag aagttctacc cagagtattc gcgaaatgcg     420
gagggcctcg ccaatctcat ctcgactttc agtacaacag ccgggctgcc tagccatatc     480
aatgcggaaa caccaggtgc tatccacgaa ggaggggaac tgggatacgc acttgctgta     540
tcatttggtg cagttatgga caaccccaat ctgatcgttc catgcattgt gggcgatgga     600
gaagcagaaa ctggcccaac agcagcatct tggcacggca tcaaatatat cgatcctgca     660
gagtcaggcg ctgtgctgcc aatcctgcac ctgaacggat tcaagatcag cgagcgcacg     720
atctttggct gcatggacga caaggagctg acctcgcttt tcactgggta tgggtaccag     780
gtccggattg tgcaggattt gaatgacatc gacaccgatc tccatcgatc tatgacctgg     840
gctttggaag aaatccacaa gattcagcaa gcagcgcgat ccggaaagcc cattatgaag     900
ccaagatggc caatgctgat tttgcgcaca ccaaagggat ggtcaggccc aaaggaaatt     960
catggccagt tcattgaggg ctcattccat tcacatcaag tccccctgcc caacgcaaag    1020
aaggacaagg aagagctgca ggccctcgag aaatggcttt cctcgtatgg gcccagagaa    1080
cttttcactg agaatggaga tgttatagat gagattaaat ccatcatccc tacggatgat    1140
gcgatgaagc ttggtcagcg tgtggaggca tacaaggctt atctgccacc aaagctcccg    1200
gactggagga agttcgccgt ggataaaggt agccaacaga gcccgatgaa aacgaccgga    1260
aagcttatcg acgaggtctt ccaactcaac cctcacactg ttcgattgtt ttcaccggat    1320
gaattggaga gcaacaaact gagcgccgct ctggatcaca ctgggagaaa tttccagtgg    1380
gatcagttct ctagcgcgaa aggtggccgg gtcatcgaag tcctgagcga acatatgtgc    1440
cagggtttta tccagggtta cacgttgacc ggacgcacgg gtatcttccc atcgtatgag    1500
agcttcttgg gaatcgttca taccatgatg gtgcagtact ccaaattcat caaaatggct    1560
caagagacca catggcaccg tagcatagcc agcatcaatt atattgagac aagcacgtgg    1620
acacggcagg agcataatgg attttcacac cagaatccat ctttcatcgg ggcagtactc    1680
aaattgaagc ccacggctgc tcgggtttat ctgccgccgg atgctaacac tttcttaatc    1740
actctccatc actgcttgaa gtcgacgaac tacatcaatc tcatggttag ttcgaagcag    1800
cccactccgg tgtatttgac cccagaagag gcagagagcc actgcagagc aggtgcatct    1860
gtctggaaat tctgcagcac cgacgatggt ctggacccag acgtagtatt ggttggaatc    1920
ggcgtcgagg tgatgtttga agtcattgct gctgccgcca ttctgcgcaa acgttgcccc    1980
gagcttcgcg tacgggtggt taacgtcacc gatttgatga tcttggagaa cgaaggcgca    2040
```

```
cacccgcatg cgctcaccac cgacgcgttt gatagcctgt ttacatctga cagacccatc   2100

catttcaact accacggata tccgactgag ttgcagggct tgctgttcgg acggccacgt   2160

ctggagcgcg ctaccatcgg cggatacatg gaggagggaa gcaccacgac accatttgat   2220

atgatgcttg tcaaccgcgt ttcacgcttc catgtagcac aagcggccat ttgtggggcg   2280

tcaaagagaa atgaaagagt tcagatccga caacaggagc tgtacacgga gttggaccac   2340

aatatggtag agaccaagaa gtacatcctc aaaaaccgaa aggatcccga tgatatgtac   2400

gatatgccga aattcgaata a                                              2421
```

```
<210> SEQ ID NO 78
<211> LENGTH: 806
<212> TYPE: PRT
<213> ORGANISM: Aspergillus clavatus
<220> FEATURE:
<223> OTHER INFORMATION: PHK

<400> SEQUENCE: 78

Met Pro Gly Glu Val Ile Asp Arg Pro Asn Pro Gln Ala Leu Pro Ser
1               5                   10                  15

His Ile Pro Asp Val Val Glu Gln Leu Gln Val Lys Leu Asp Leu Thr
            20                  25                  30

Ser Leu Glu Gln Pro Ala Cys Asp Ala Leu Phe Lys Phe Arg Arg Ala
        35                  40                  45

Ala Ser Tyr Ile Ala Ala Ala Met Ile Phe Leu Gln Asp Asn Val Leu
    50                  55                  60

Leu Lys Arg Ser Leu Thr His Asp Asp Ile Lys Pro Arg Leu Leu Gly
65                  70                  75                  80

His Trp Gly Thr Cys Pro Gly Leu Ile Leu Val Tyr Ser His Leu Asn
                85                  90                  95

Tyr Leu Ile Thr Lys Arg Asn Leu Asn Met Leu Tyr Val Val Gly Pro
            100                 105                 110

Gly His Gly Ala Pro Ala Ile Leu Ala Ser Leu Trp Leu Glu Gly Ser
        115                 120                 125

Leu Glu Lys Phe Tyr Pro Glu Tyr Ser Arg Asn Ala Glu Gly Leu Ala
    130                 135                 140

Asn Leu Ile Ser Thr Phe Ser Thr Thr Ala Gly Leu Pro Ser His Ile
145                 150                 155                 160

Asn Ala Glu Thr Pro Gly Ala Ile His Glu Gly Gly Glu Leu Gly Tyr
                165                 170                 175

Ala Leu Ala Val Ser Phe Gly Ala Val Met Asp Asn Pro Asn Leu Ile
            180                 185                 190

Val Pro Cys Ile Val Gly Asp Gly Glu Ala Glu Thr Gly Pro Thr Ala
        195                 200                 205

Ala Ser Trp His Gly Ile Lys Tyr Ile Asp Pro Ala Glu Ser Gly Ala
    210                 215                 220

Val Leu Pro Ile Leu His Leu Asn Gly Phe Lys Ile Ser Glu Arg Thr
225                 230                 235                 240

Ile Phe Gly Cys Met Asp Asp Lys Glu Leu Thr Ser Leu Phe Thr Gly
                245                 250                 255

Tyr Gly Tyr Gln Val Arg Ile Val Gln Asp Leu Asn Asp Ile Asp Thr
            260                 265                 270

Asp Leu His Arg Ser Met Thr Trp Ala Leu Glu Glu Ile His Lys Ile
        275                 280                 285
```

```
Gln Gln Ala Ala Arg Ser Gly Lys Pro Ile Met Lys Pro Arg Trp Pro
    290                 295                 300

Met Leu Ile Leu Arg Thr Pro Lys Gly Trp Ser Gly Pro Lys Glu Ile
305                 310                 315                 320

His Gly Gln Phe Ile Glu Gly Ser Phe His Ser His Gln Val Pro Leu
                325                 330                 335

Pro Asn Ala Lys Lys Asp Lys Glu Glu Leu Gln Ala Leu Glu Lys Trp
            340                 345                 350

Leu Ser Ser Tyr Gly Pro Arg Glu Leu Phe Thr Glu Asn Gly Asp Val
        355                 360                 365

Ile Asp Glu Ile Lys Ser Ile Ile Pro Thr Asp Asp Ala Met Lys Leu
    370                 375                 380

Gly Gln Arg Val Glu Ala Tyr Lys Ala Tyr Leu Pro Pro Lys Leu Pro
385                 390                 395                 400

Asp Trp Arg Lys Phe Ala Val Asp Lys Gly Ser Gln Gln Ser Pro Met
                405                 410                 415

Lys Thr Thr Gly Lys Leu Ile Asp Glu Val Phe Gln Leu Asn Pro His
            420                 425                 430

Thr Val Arg Leu Phe Ser Pro Asp Glu Leu Glu Ser Asn Lys Leu Ser
        435                 440                 445

Ala Ala Leu Asp His Thr Gly Arg Asn Phe Gln Trp Asp Gln Phe Ser
    450                 455                 460

Ser Ala Lys Gly Gly Arg Val Ile Glu Val Leu Ser Glu His Met Cys
465                 470                 475                 480

Gln Gly Phe Ile Gln Gly Tyr Thr Leu Thr Gly Arg Thr Gly Ile Phe
                485                 490                 495

Pro Ser Tyr Glu Ser Phe Leu Gly Ile Val His Thr Met Met Val Gln
            500                 505                 510

Tyr Ser Lys Phe Ile Lys Met Ala Gln Glu Thr Thr Trp His Arg Ser
        515                 520                 525

Ile Ala Ser Ile Asn Tyr Ile Glu Thr Ser Thr Trp Thr Arg Gln Glu
    530                 535                 540

His Asn Gly Phe Ser His Gln Asn Pro Ser Phe Ile Gly Ala Val Leu
545                 550                 555                 560

Lys Leu Lys Pro Thr Ala Ala Arg Val Tyr Leu Pro Pro Asp Ala Asn
                565                 570                 575

Thr Phe Leu Ile Thr Leu His His Cys Leu Lys Ser Thr Asn Tyr Ile
            580                 585                 590

Asn Leu Met Val Ser Ser Lys Gln Pro Thr Pro Val Tyr Leu Thr Pro
        595                 600                 605

Glu Glu Ala Glu Ser His Cys Arg Ala Gly Ala Ser Val Trp Lys Phe
    610                 615                 620

Cys Ser Thr Asp Asp Gly Leu Asp Pro Asp Val Val Leu Val Gly Ile
625                 630                 635                 640

Gly Val Glu Val Met Phe Glu Val Ile Ala Ala Ala Ala Ile Leu Arg
                645                 650                 655

Lys Arg Cys Pro Glu Leu Arg Val Arg Val Val Asn Val Thr Asp Leu
            660                 665                 670

Met Ile Leu Glu Asn Glu Gly Ala His Pro His Ala Leu Thr Thr Asp
        675                 680                 685

Ala Phe Asp Ser Leu Phe Thr Ser Asp Arg Pro Ile His Phe Asn Tyr
    690                 695                 700

His Gly Tyr Pro Thr Glu Leu Gln Gly Leu Leu Phe Gly Arg Pro Arg
```

705 710 715 720

Leu Glu Arg Ala Thr Ile Gly Gly Tyr Met Glu Glu Gly Ser Thr Thr
725 730 735

Thr Pro Phe Asp Met Met Leu Val Asn Arg Val Ser Arg Phe His Val
740 745 750

Ala Gln Ala Ala Ile Cys Gly Ala Ser Lys Arg Asn Glu Arg Val Gln
755 760 765

Ile Arg Gln Gln Glu Leu Tyr Thr Glu Leu Asp His Asn Met Val Glu
770 775 780

Thr Lys Lys Tyr Ile Leu Lys Asn Arg Lys Asp Pro Asp Asp Met Tyr
785 790 795 800

Asp Met Pro Lys Phe Glu
805

<210> SEQ ID NO 79
<211> LENGTH: 996
<212> TYPE: DNA
<213> ORGANISM: Clostridium cellulolyticum
<220> FEATURE:
<223> OTHER INFORMATION: PTA

<400> SEQUENCE: 79
atgaactttt tagagcagat tgtaagcaga gcaaaaaaag atatcaaaac aatagtactt 60
cctgaaagta acgatatcag aactttgaag gctgctgcaa tgattcagga gcaaggcatt 120
gccaatgtcg tacttgtggg caacaatgat gatattaaaa aactgggcgg tgacctggat 180
atatcaaagg caaaaattgt tgatcctaca aactttgaaa gatttgacga gtatgtaaat 240
accctgtacg aacttagaaa ggcaaaggga atgacacagg aagaggcaaa aaaaatattg 300
tctgaaaatc ctttgtattt cggaattatg atggtaaaaa tgggtgaggc tgacggaatg 360
gttgcaggag caattaattc aactgcaaat acacttaggc cggctcttca aatattaaag 420
acagctcccg gagcaaaact tgtatctgca ttcttcgtaa tggttgtacc tgactgtgaa 480
tacggagaaa atggagtgtt catttatgga gacagcggac tagtcgaaaa tccaaatgca 540
gaagagcttt cagaaatagc gatagcatct tcaaaatcct tcaaaaacct tgtacaggct 600
gaacctgttg ttgcaatgct ctcatattca acatacggca gtgcaaaaag tgtattgaca 660
gaaaaggtta tagaggccac aaagcttgca aaggaaaaag ctccagatct tcagttagat 720
ggagaattgc aggcagatgc agctattgtt ccttctgtag gagcatcaaa agcacccgga 780
agcagtgttg caggaaaggc caatgtatta atattccctg acttgaactg tggtaatata 840
tcctacaagc taacacagag acttgcaaag gcagaagcct acggccctat tattcaggga 900
attgcaaaac ctgttaatga cctttcaaga ggctgtagtg ccgaggatat agtaggtgtt 960
gttgcaataa cttgtgtaca agcacaaaat atataa 996

<210> SEQ ID NO 80
<211> LENGTH: 331
<212> TYPE: PRT
<213> ORGANISM: Clostridium cellulolyticum
<220> FEATURE:
<223> OTHER INFORMATION: PTA

<400> SEQUENCE: 80

Met Asn Phe Leu Glu Gln Ile Val Ser Arg Ala Lys Lys Asp Ile Lys
1 5 10 15

Thr Ile Val Leu Pro Glu Ser Asn Asp Ile Arg Thr Leu Lys Ala Ala
20 25 30

```
Ala Met Ile Gln Glu Gln Gly Ile Ala Asn Val Val Leu Val Gly Asn
        35                  40                  45

Asn Asp Asp Ile Lys Lys Leu Gly Gly Asp Leu Asp Ile Ser Lys Ala
    50                  55                  60

Lys Ile Val Asp Pro Thr Asn Phe Glu Arg Phe Asp Glu Tyr Val Asn
65                  70                  75                  80

Thr Leu Tyr Glu Leu Arg Lys Ala Lys Gly Met Thr Gln Glu Glu Ala
                85                  90                  95

Lys Lys Ile Leu Ser Glu Asn Pro Leu Tyr Phe Gly Ile Met Met Val
            100                 105                 110

Lys Met Gly Glu Ala Asp Gly Met Val Ala Gly Ala Ile Asn Ser Thr
        115                 120                 125

Ala Asn Thr Leu Arg Pro Ala Leu Gln Ile Leu Lys Thr Ala Pro Gly
    130                 135                 140

Ala Lys Leu Val Ser Ala Phe Phe Val Met Val Val Pro Asp Cys Glu
145                 150                 155                 160

Tyr Gly Glu Asn Gly Val Phe Ile Tyr Gly Asp Ser Gly Leu Val Glu
                165                 170                 175

Asn Pro Asn Ala Glu Glu Leu Ser Glu Ile Ala Ile Ala Ser Ser Lys
            180                 185                 190

Ser Phe Lys Asn Leu Val Gln Ala Glu Pro Val Val Ala Met Leu Ser
        195                 200                 205

Tyr Ser Thr Tyr Gly Ser Ala Lys Ser Val Leu Thr Glu Lys Val Ile
    210                 215                 220

Glu Ala Thr Lys Leu Ala Lys Glu Lys Ala Pro Asp Leu Gln Leu Asp
225                 230                 235                 240

Gly Glu Leu Gln Ala Asp Ala Ala Ile Val Pro Ser Val Gly Ala Ser
                245                 250                 255

Lys Ala Pro Gly Ser Ser Val Ala Gly Lys Ala Asn Val Leu Ile Phe
            260                 265                 270

Pro Asp Leu Asn Cys Gly Asn Ile Ser Tyr Lys Leu Thr Gln Arg Leu
        275                 280                 285

Ala Lys Ala Glu Ala Tyr Gly Pro Ile Ile Gln Gly Ile Ala Lys Pro
    290                 295                 300

Val Asn Asp Leu Ser Arg Gly Cys Ser Ala Glu Asp Ile Val Gly Val
305                 310                 315                 320

Val Ala Ile Thr Cys Val Gln Ala Gln Asn Ile
                325                 330
```

<210> SEQ ID NO 81
<211> LENGTH: 996
<212> TYPE: DNA
<213> ORGANISM: Clostridium phytofermentans
<220> FEATURE:
<223> OTHER INFORMATION: PTA

<400> SEQUENCE: 81

```
atgggattta ttgatgacat caaggcaaga gctaaacaaa gtattaagac tattgtttta      60

cctgagagta tggacagaag aacaattgag gcagctgcta agactttaga agagggcaat     120

gctaacgtaa ttattatcgg tagtgaggaa gaagttaaga agaattcaga aggtcttgac     180

atttcgggag ctacaatcgt tgaccctaag acatcggaca agcttccagc ttacattaac     240

aagcttgtag aacttagaca ggcaaaaggc atgacccctg aaaaagcaaa agagctttta     300

acaacagact acattacata cggtgtaatg atggttaaga tgggcgatgc agatggttta     360
```

```
gtatctggtg cttgtcactc tacagcagat accttaagac catgtcttca gattttaaaa    420

actgctccaa atactaagtt agtttctgct ttcttcgtaa tggtagtacc taattgtgat    480

atgggcgcaa atggaacttt ccttttctct gatgctggtt taaatcagaa tccaaatgct    540

gaagagttag cagcaatcgc tggttccaca gcgaagagtt ttgaacaatt agttggctct    600

gaacctatcg tagctatgct ttctcattca acaaagggaa gcgcaaagca tgcagatgtt    660

gataaggttg tagaagcaac taagattgca aatgaattat acccagaata taagatcgac    720

ggcgagttcc agttagatgc agcaatcgtt cctagtgtag gtgcttcaaa agctcctggt    780

agtgatattg ctggaaaagc taacgtatta atcttcccag accttgatgc tggtaacatt    840

ggatataagt taacacagcg tcttgcaaag gcagaagctt atggaccatt aactcagggt    900

attgcagctc cagtaaatga tttatcaaga ggttgttctt ctgatgatat cgttggtgtt    960

gttgcaatca ctgctgttca ggcacagagt aaataa                              996
```

```
<210> SEQ ID NO 82
<211> LENGTH: 331
<212> TYPE: PRT
<213> ORGANISM: Clostridium phytofermentans
<220> FEATURE:
<223> OTHER INFORMATION: PTA

<400> SEQUENCE: 82

Met Gly Phe Ile Asp Asp Ile Lys Ala Arg Ala Lys Gln Ser Ile Lys
1               5                   10                  15

Thr Ile Val Leu Pro Glu Ser Met Asp Arg Arg Thr Ile Glu Ala Ala
            20                  25                  30

Ala Lys Thr Leu Glu Glu Gly Asn Ala Asn Val Ile Ile Ile Gly Ser
        35                  40                  45

Glu Glu Glu Val Lys Lys Asn Ser Glu Gly Leu Asp Ile Ser Gly Ala
    50                  55                  60

Thr Ile Val Asp Pro Lys Thr Ser Asp Lys Leu Pro Ala Tyr Ile Asn
65                  70                  75                  80

Lys Leu Val Glu Leu Arg Gln Ala Lys Gly Met Thr Pro Glu Lys Ala
                85                  90                  95

Lys Glu Leu Leu Thr Thr Asp Tyr Ile Thr Tyr Gly Val Met Met Val
            100                 105                 110

Lys Met Gly Asp Ala Asp Gly Leu Val Ser Gly Ala Cys His Ser Thr
        115                 120                 125

Ala Asp Thr Leu Arg Pro Cys Leu Gln Ile Leu Lys Thr Ala Pro Asn
    130                 135                 140

Thr Lys Leu Val Ser Ala Phe Phe Val Met Val Val Pro Asn Cys Asp
145                 150                 155                 160

Met Gly Ala Asn Gly Thr Phe Leu Phe Ser Asp Ala Gly Leu Asn Gln
                165                 170                 175

Asn Pro Asn Ala Glu Glu Leu Ala Ala Ile Ala Gly Ser Thr Ala Lys
            180                 185                 190

Ser Phe Glu Gln Leu Val Gly Ser Glu Pro Ile Val Ala Met Leu Ser
        195                 200                 205

His Ser Thr Lys Gly Ser Ala Lys His Ala Asp Val Asp Lys Val Val
    210                 215                 220

Glu Ala Thr Lys Ile Ala Asn Glu Leu Tyr Pro Glu Tyr Lys Ile Asp
225                 230                 235                 240

Gly Glu Phe Gln Leu Asp Ala Ala Ile Val Pro Ser Val Gly Ala Ser
```

```
                245                 250                 255

Lys Ala Pro Gly Ser Asp Ile Ala Gly Lys Ala Asn Val Leu Ile Phe
            260                 265                 270

Pro Asp Leu Asp Ala Gly Asn Ile Gly Tyr Lys Leu Thr Gln Arg Leu
        275                 280                 285

Ala Lys Ala Glu Ala Tyr Gly Pro Leu Thr Gln Gly Ile Ala Ala Pro
    290                 295                 300

Val Asn Asp Leu Ser Arg Gly Cys Ser Ser Asp Asp Ile Val Gly Val
305                 310                 315                 320

Val Ala Ile Thr Ala Val Gln Ala Gln Ser Lys
                325                 330
```

<210> SEQ ID NO 83
<211> LENGTH: 1815
<212> TYPE: DNA
<213> ORGANISM: Bifidobacterium bifidum
<220> FEATURE:
<223> OTHER INFORMATION: PTA

<400> SEQUENCE: 83

```
atgacgcacg cgcccggtcg aaccgccccg gccgcgttta ccgccatgtc aacgcccggc      60

agcgaacgat cgggtactac aatgtcagta agtgtgaaac aaggcggtca cacgagcagt     120

accatccccg acgaggagac aaacgtgaca acaacgaaca tctacatcgc aagtcctgaa     180

ggcgcaaacg gacgcaacgt cgtggcatac ggcgtgctca aggcgctgac caccaaattc     240

aagaccgccg tgttccgccc cgcggtctcc aatcacgacc acttcacccc catcctgctg     300

aacgcctcca acgccggcct cggcgtcgcg ctatccaccg gaccggacat tcaccaggtg     360

cgcaaggaca aggaaggctc ccgcggcgac atcgtcgcgg cgttcaacga cgcgatgaac     420

gtgtcccgcg cggacgcggc gctcatcgtc ggcaccgaca agtcgcacgt caacgacccg     480

accgcctacg agttcaacgc gaacatcgcc gccgacctgc aggccggcgt cttcctcgcc     540

gtgtgcacca tcgatcgttg gcctgacgag ctcaaggaca ccgtccgtct ctccatcgaa     600

ggcatggagg ccgccggcaa caaggtgctg ggcatcttcg tgacgggctg cgatccgcgc     660

cactccgtct cggtcaagga cacgctcgcg gacttcgggc tgccggtgtg gacgatcccc     720

cagatcccgt tcaccgatgc gtcacaggcc gatgcggcgc tcgccgcctt ccaggcgaac     780

gtgccgaccg aagaggtcct gcaggccatc aacgtcgaga tcgacttccc gatcacctcg     840

tacgccttcc agtacagcct gctcggccgt gccaaggcga acaagaaaac gatcgtgctg     900

cccgaaggcg aagaggaccg catcatcaag gcggccgact acctgctgga gcgcgagatc     960

gcgaacctca tcatcgtggg cgacaagggc gcgatcctcg cccggggcgc ggaactcggt    1020

ctgacccatc tgggcaaggc gcgtttccag gccatggacg acgagaacat cctcaagccc    1080

atggtcgcca agctgtgcga gctgcgcgcc aagaagggca tgaccgaaga gcaggcccgc    1140

aagcagctga ccgacgcgag ctatttcggc acgatgctcg tcgtgctcgg ttacgccgac    1200

ggtctggtgt ccggcgcggt caactccacc gcaaacaccg tgcgtccggc gctgcaggtc    1260

atcaagacca agcccgggca gaggctcgtc tccggcgcct tcctgatgtg cttcaaggac    1320

cacgtgaccg tgttctccga ctgcgccatc aacctcaacc cggacgccga acagctcgcg    1380

gagatcgcgc tgcagtccgc cgtgaccgcc aaggcgttcg gcatcgagcc caaggtcggc    1440

atgctctcct actccaccct cggctccggc aaggggccgg acgtggacat cgtcgaagag    1500

gccacgcgaa tcgtcaagga gaaggctccg gacctgcccg tcgtcggctc catccagttc    1560
```

```
gacgccgcat ggtcgcccga cgtggcagcc accaaggcca agggcaacga cgtggccgga   1620

cacgtcaacg tgttcgtgtt ccccgacctg tgctccggca acatcggcta caaggccgtg   1680

cagcgttcct ccggggcgct cgccatcggc cccgtgctgc agggcctcaa caagcccgtc   1740

aacgacctct cacgcggtgc gacggtgcag gacatcatca acaccatcgc actgaccgcc   1800

atcgaggccc agtga                                                    1815
```

<210> SEQ ID NO 84
<211> LENGTH: 604
<212> TYPE: PRT
<213> ORGANISM: Bifidobacterium bifidum
<220> FEATURE:
<223> OTHER INFORMATION: PTA

<400> SEQUENCE: 84

```
Met Thr His Ala Pro Gly Arg Thr Ala Pro Ala Ala Phe Thr Ala Met
1               5                   10                  15

Ser Thr Pro Gly Ser Glu Arg Ser Gly Thr Thr Met Ser Val Ser Val
            20                  25                  30

Lys Gln Gly Gly His Thr Ser Ser Thr Ile Pro Asp Glu Glu Thr Asn
        35                  40                  45

Val Thr Thr Thr Asn Ile Tyr Ile Ala Ser Pro Glu Gly Ala Asn Gly
    50                  55                  60

Arg Asn Val Val Ala Tyr Gly Val Leu Lys Ala Leu Thr Thr Lys Phe
65                  70                  75                  80

Lys Thr Ala Val Phe Arg Pro Ala Val Ser Asn His Asp His Phe Thr
                85                  90                  95

Pro Ile Leu Leu Asn Ala Ser Asn Ala Gly Leu Gly Val Ala Leu Ser
            100                 105                 110

Thr Gly Pro Asp Ile His Gln Val Arg Lys Asp Lys Glu Gly Ser Arg
        115                 120                 125

Gly Asp Ile Val Ala Ala Phe Asn Asp Ala Met Asn Val Ser Arg Ala
    130                 135                 140

Asp Ala Ala Leu Ile Val Gly Thr Asp Lys Ser His Val Asn Asp Pro
145                 150                 155                 160

Thr Ala Tyr Glu Phe Asn Ala Asn Ile Ala Ala Asp Leu Gln Ala Gly
                165                 170                 175

Val Phe Leu Ala Val Cys Thr Ile Asp Arg Trp Pro Asp Glu Leu Lys
            180                 185                 190

Asp Thr Val Arg Leu Ser Ile Glu Gly Met Glu Ala Ala Gly Asn Lys
        195                 200                 205

Val Leu Gly Ile Phe Val Thr Gly Cys Asp Pro Arg His Ser Val Ser
    210                 215                 220

Val Lys Asp Thr Leu Ala Asp Phe Gly Leu Pro Val Trp Thr Ile Pro
225                 230                 235                 240

Gln Ile Pro Phe Thr Asp Ala Ser Gln Ala Asp Ala Ala Leu Ala Ala
                245                 250                 255

Phe Gln Ala Asn Val Pro Thr Glu Glu Val Leu Gln Ala Ile Asn Val
            260                 265                 270

Glu Ile Asp Phe Pro Ile Thr Ser Tyr Ala Phe Gln Tyr Ser Leu Leu
        275                 280                 285

Gly Arg Ala Lys Ala Asn Lys Lys Thr Ile Val Leu Pro Glu Gly Glu
    290                 295                 300

Glu Asp Arg Ile Ile Lys Ala Ala Asp Tyr Leu Leu Glu Arg Glu Ile
305                 310                 315                 320
```

```
Ala Asn Leu Ile Ile Val Gly Asp Lys Gly Ala Ile Leu Ala Arg Gly
                325                 330                 335

Ala Glu Leu Gly Leu Thr His Leu Gly Lys Ala Arg Phe Gln Ala Met
            340                 345                 350

Asp Asp Glu Asn Ile Leu Lys Pro Met Val Ala Lys Leu Cys Glu Leu
        355                 360                 365

Arg Ala Lys Lys Gly Met Thr Glu Glu Gln Ala Arg Lys Gln Leu Thr
    370                 375                 380

Asp Ala Ser Tyr Phe Gly Thr Met Leu Val Val Leu Gly Tyr Ala Asp
385                 390                 395                 400

Gly Leu Val Ser Gly Ala Val Asn Ser Thr Ala Asn Thr Val Arg Pro
                405                 410                 415

Ala Leu Gln Val Ile Lys Thr Lys Pro Gly Gln Arg Leu Val Ser Gly
            420                 425                 430

Ala Phe Leu Met Cys Phe Lys Asp His Val Thr Val Phe Ser Asp Cys
        435                 440                 445

Ala Ile Asn Leu Asn Pro Asp Ala Glu Gln Leu Ala Glu Ile Ala Leu
    450                 455                 460

Gln Ser Ala Val Thr Ala Lys Ala Phe Gly Ile Glu Pro Lys Val Gly
465                 470                 475                 480

Met Leu Ser Tyr Ser Thr Leu Gly Ser Gly Lys Gly Pro Asp Val Asp
                485                 490                 495

Ile Val Glu Glu Ala Thr Arg Ile Val Lys Glu Lys Ala Pro Asp Leu
            500                 505                 510

Pro Val Val Gly Ser Ile Gln Phe Asp Ala Ala Trp Ser Pro Asp Val
        515                 520                 525

Ala Ala Thr Lys Ala Lys Gly Asn Asp Val Ala Gly His Val Asn Val
    530                 535                 540

Phe Val Phe Pro Asp Leu Cys Ser Gly Asn Ile Gly Tyr Lys Ala Val
545                 550                 555                 560

Gln Arg Ser Ser Gly Ala Leu Ala Ile Gly Pro Val Leu Gln Gly Leu
                565                 570                 575

Asn Lys Pro Val Asn Asp Leu Ser Arg Gly Ala Thr Val Gln Asp Ile
            580                 585                 590

Ile Asn Thr Ile Ala Leu Thr Ala Ile Glu Ala Gln
        595                 600
```

<210> SEQ ID NO 85
<211> LENGTH: 1683
<212> TYPE: DNA
<213> ORGANISM: Bifidobacterium animalis
<220> FEATURE:
<223> OTHER INFORMATION: PTA

<400> SEQUENCE: 85

```
atgagcctca aaaacgtgag catcatcagt cccgaacctg gagacggccg gaacgtggtg     60

gcattgggtg tggtggatat gctcgcccac accgcgaaga ccagcatatt ccggccggcg    120

gtgcaggcag gcgaaaagct caccgatgcc ctcctctcgg tggcgagcgc gccgcagacc    180

cgcgaacagg ccgttggcgt cacactgcgt gacgcacgtc tcgacaaaga caacgcccgc    240

cagcagatcg tctccaaatt catcgacacg aatgccgaga tcaatccgca gatccgagtg    300

atcgtcggat cagaccgcac caatgtgggc gatcccgaac ggttcacctt caatgcggac    360

gtctccgccg acctgcagtc tccggtgctg ctctcagtga gctcgatggg gcgcacggcg    420
```

```
gaagagattc gcgagacgat agacgcatgc cgcgaggtgg tcatcaacgc aggcacccaa    480
gtgattggcg tgttcatcac cgactgcacg aattcggcgc tgcccaccct caccgacgaa    540
ttcgtgagct acgacctgcc gacctggccg cttcccctcg tggaactcgg ttccgatgac    600
acgaatgtca aggccgcact cgaggccttc gacgagcatg tcgacaagga atcactcctc    660
aacgtgcttg acacaccttt cgtaccgccg accacaccat tcgcgttcca gtacgatctg    720
ctcgcacgtg cgaagaaaga caagaagacg attgtgctgc cagaaggaga ggatgaccgc    780
atcatcaccg ccgcgaacta cctgctgcag tcgaatgtgg tcgatctcgt catcatcggc    840
gaccgcgacg agattcttgc ccggggtgaa aaactcggcc tcaaggcgct tgaccaggcg    900
aagttcgttt ccatcgacga caggcatctg ctcgacacca tggtgcccaa actgtgtgaa    960
ttgcgcgcca agaagggcat gaccccccgac gtggctttga aaacgctcag agacacgaac   1020
tacttcggca ccatgctcat cgtgctcggc atggccgatg gtctggtctc aggtgccatc   1080
agctccaccg ccaacaccgt gcgccccgcg ctccagctca tcaagacgaa acccggtgtc   1140
tcctccgtat cgggtgcctt cctcatgtgt ctcaaggacc acgtgtcggt atttgctgat   1200
tgcgccatca acctcgatcc caatccgcag cagctggccg acatcgccat ccagtcagcc   1260
gagaccgcca aggcattctc catcgatcct aaaatcggtt tgctctccta ttccaccttg   1320
ggttccggta agggaccgga tgtcgatctg gtggtcgagg ccacttcgat cgcccagaac   1380
aaacgaccgg acctacccat cgtcgggccc atccagttcg acgccgcctg gtcgaagacg   1440
gttgccaagg tcaaggcctt cggcaacccg atcgccggca atgtcaccgt gttcgtgttc   1500
ccggacctcg atgcggggaa catctgctac aaggcagtgc agcgcacctc cggcgccgtg   1560
gcgatcggac cggtgcttca ggggctcaac cggcctgtca acgacctgag ccgaggcgcc   1620
ttggtgcagg acatcatcaa taccatcgcc ttgaccgcca ttgaagcgca aagcaacgaa   1680
tag                                                                  1683
```

<210> SEQ ID NO 86
<211> LENGTH: 560
<212> TYPE: PRT
<213> ORGANISM: Bifidobacterium animalis
<220> FEATURE:
<223> OTHER INFORMATION: PTA

<400> SEQUENCE: 86

```
Met Ser Leu Lys Asn Val Ser Ile Ile Ser Pro Glu Pro Gly Asp Gly
1               5                   10                  15

Arg Asn Val Val Ala Leu Gly Val Val Asp Met Leu Ala His Thr Ala
            20                  25                  30

Lys Thr Ser Ile Phe Arg Pro Ala Val Gln Ala Gly Glu Lys Leu Thr
        35                  40                  45

Asp Ala Leu Leu Ser Val Ala Ser Ala Pro Gln Thr Arg Glu Gln Ala
    50                  55                  60

Val Gly Val Thr Leu Arg Asp Ala Arg Leu Asp Lys Asp Asn Ala Arg
65                  70                  75                  80

Gln Gln Ile Val Ser Lys Phe Ile Asp Thr Asn Ala Glu Ile Asn Pro
                85                  90                  95

Gln Ile Arg Val Ile Val Gly Ser Asp Arg Thr Asn Val Gly Asp Pro
            100                 105                 110

Glu Arg Phe Thr Phe Asn Ala Asp Val Ser Ala Asp Leu Gln Ser Pro
        115                 120                 125

Val Leu Leu Ser Val Ser Ser Met Gly Arg Thr Ala Glu Glu Ile Arg
```

```
    130                 135                 140

Glu Thr Ile Asp Ala Cys Arg Glu Val Val Ile Asn Ala Gly Thr Gln
145                 150                 155                 160

Val Ile Gly Val Phe Ile Thr Asp Cys Thr Asn Ser Ala Leu Pro Thr
                165                 170                 175

Leu Thr Asp Glu Phe Val Ser Tyr Asp Leu Pro Thr Trp Pro Leu Pro
            180                 185                 190

Leu Val Glu Leu Gly Ser Asp Asp Thr Asn Val Lys Ala Ala Leu Glu
        195                 200                 205

Ala Phe Asp Glu His Val Asp Lys Glu Ser Leu Leu Asn Val Leu Asp
    210                 215                 220

Thr Pro Phe Val Pro Pro Thr Thr Pro Phe Ala Phe Gln Tyr Asp Leu
225                 230                 235                 240

Leu Ala Arg Ala Lys Lys Asp Lys Lys Thr Ile Val Leu Pro Glu Gly
                245                 250                 255

Glu Asp Asp Arg Ile Ile Thr Ala Ala Asn Tyr Leu Leu Gln Ser Asn
            260                 265                 270

Val Val Asp Leu Val Ile Ile Gly Asp Arg Asp Glu Ile Leu Ala Arg
        275                 280                 285

Gly Glu Lys Leu Gly Leu Lys Ala Leu Asp Gln Ala Lys Phe Val Ser
    290                 295                 300

Ile Asp Asp Arg His Leu Leu Asp Thr Met Val Pro Lys Leu Cys Glu
305                 310                 315                 320

Leu Arg Ala Lys Lys Gly Met Thr Pro Asp Val Ala Leu Lys Thr Leu
                325                 330                 335

Arg Asp Thr Asn Tyr Phe Gly Thr Met Leu Ile Val Leu Gly Met Ala
            340                 345                 350

Asp Gly Leu Val Ser Gly Ala Ile Ser Ser Thr Ala Asn Thr Val Arg
        355                 360                 365

Pro Ala Leu Gln Leu Ile Lys Thr Lys Pro Gly Val Ser Ser Val Ser
    370                 375                 380

Gly Ala Phe Leu Met Cys Leu Lys Asp His Val Ser Val Phe Ala Asp
385                 390                 395                 400

Cys Ala Ile Asn Leu Asp Pro Asn Pro Gln Gln Leu Ala Asp Ile Ala
                405                 410                 415

Ile Gln Ser Ala Glu Thr Ala Lys Ala Phe Ser Ile Asp Pro Lys Ile
            420                 425                 430

Gly Leu Leu Ser Tyr Ser Thr Leu Gly Ser Gly Lys Gly Pro Asp Val
        435                 440                 445

Asp Leu Val Val Glu Ala Thr Ser Ile Ala Gln Asn Lys Arg Pro Asp
    450                 455                 460

Leu Pro Ile Val Gly Pro Ile Gln Phe Asp Ala Ala Trp Ser Lys Thr
465                 470                 475                 480

Val Ala Lys Val Lys Ala Phe Gly Asn Pro Ile Ala Gly Asn Val Thr
                485                 490                 495

Val Phe Val Phe Pro Asp Leu Asp Ala Gly Asn Ile Cys Tyr Lys Ala
            500                 505                 510

Val Gln Arg Thr Ser Gly Ala Val Ala Ile Gly Pro Val Leu Gln Gly
        515                 520                 525

Leu Asn Arg Pro Val Asn Asp Leu Ser Arg Gly Ala Leu Val Gln Asp
    530                 535                 540

Ile Ile Asn Thr Ile Ala Leu Thr Ala Ile Glu Ala Gln Ser Asn Glu
545                 550                 555                 560
```

<210> SEQ ID NO 87
<211> LENGTH: 1097
<212> TYPE: DNA
<213> ORGANISM: Clostridium cellulolyticum
<220> FEATURE:
<223> OTHER INFORMATION: ACK

<400> SEQUENCE: 87

```
atgaaggttt tagttataaa tgcggggagt tcttcattaa aatatcaatt aatagatatg      60

aaaaatgaaa cagttcttgc aaagggttta tgcgacagaa tagggattga caattccttt     120

ataaagcaat caaggggttc agaagaggct gttattttga ataaagagct aaagaatcac     180

aaagatgcaa tagaggctgt tatttctgca ctgactgacg ataatatggg cgttataaaa     240

aacatgtccg aaatatcagc agtgggacac agaatagtac acggcggtga aaaattcaac     300

agttctgtag ttatagatga aaacgttatg aatgcagtaa gagagtgtat agacgttgca     360

ccgcttcata atccgccgaa tattataggt atagaggctt gccagcagat tatgcccaat     420

atacctatgg tagctgtatt tgataccact ttccacagct ccatgcctga ttatgcatac     480

ctttacgcat tgccatatga actttatgaa aagtacggta taagaaaata tggtttccac     540

ggaacatcac acaaatatgt tgcagaaaga gcttctgcaa tgcttgataa gtctttgaac     600

gaattaaaga taattacatg ccatcttggg aacggttcaa gtatttgtgc tgttaacaag     660

ggtaaatcaa ttgatacttc catgggcttt acacctttgc agggacttgc aatgggtaca     720

agaagcggta caatagaccc tgaagttgtt acattcctta tggaaaagga aaatctggat     780

gttaagggtg taagcaaact cttaaataaa aagtcaggtg ttttaggtat atcaggtgta     840

agcagcgatt tcagagattt acatgctgcc gctgatgcag gaaacagcag agctgagctg     900

gcaatagaaa ttttctgcta tggtgttaag aagtttatcg gagaatatat tgcagttatg     960

aatggtgttg atgctatagt atttacagcc ggtgttggtg agaataattc agtagtaaga    1020

aatatgatta tcagcgatat ggacttcctc ggcatcaaaa tagatgtaga aaagaataag    1080

ctcacggggg caggaag                                                  1097
```

<210> SEQ ID NO 88
<211> LENGTH: 365
<212> TYPE: PRT
<213> ORGANISM: Clostridium cellulolyticum
<220> FEATURE:
<223> OTHER INFORMATION: ACK

<400> SEQUENCE: 88

```
Met Lys Val Leu Val Ile Asn Ala Gly Ser Ser Ser Leu Lys Tyr Gln
1               5                   10                  15

Leu Ile Asp Met Lys Asn Glu Thr Val Leu Ala Lys Gly Leu Cys Asp
            20                  25                  30

Arg Ile Gly Ile Asp Asn Ser Phe Ile Lys Gln Ser Arg Gly Ser Glu
        35                  40                  45

Glu Ala Val Ile Leu Asn Lys Glu Leu Lys Asn His Lys Asp Ala Ile
    50                  55                  60

Glu Ala Val Ile Ser Ala Leu Thr Asp Asp Asn Met Gly Val Ile Lys
65                  70                  75                  80

Asn Met Ser Glu Ile Ser Ala Val Gly His Arg Ile Val His Gly Gly
                85                  90                  95

Glu Lys Phe Asn Ser Ser Val Val Ile Asp Glu Asn Val Met Asn Ala
            100                 105                 110
```

```
Val Arg Glu Cys Ile Asp Val Ala Pro Leu His Asn Pro Pro Asn Ile
        115                 120                 125

Ile Gly Ile Glu Ala Cys Gln Gln Ile Met Pro Asn Ile Pro Met Val
    130                 135                 140

Ala Val Phe Asp Thr Thr Phe His Ser Ser Met Pro Asp Tyr Ala Tyr
145                 150                 155                 160

Leu Tyr Ala Leu Pro Tyr Glu Leu Tyr Glu Lys Tyr Gly Ile Arg Lys
                165                 170                 175

Tyr Gly Phe His Gly Thr Ser His Lys Tyr Val Ala Glu Arg Ala Ser
            180                 185                 190

Ala Met Leu Asp Lys Ser Leu Asn Glu Leu Lys Ile Ile Thr Cys His
        195                 200                 205

Leu Gly Asn Gly Ser Ser Ile Cys Ala Val Asn Lys Gly Lys Ser Ile
    210                 215                 220

Asp Thr Ser Met Gly Phe Thr Pro Leu Gln Gly Leu Ala Met Gly Thr
225                 230                 235                 240

Arg Ser Gly Thr Ile Asp Pro Glu Val Val Thr Phe Leu Met Glu Lys
                245                 250                 255

Glu Asn Leu Asp Val Lys Gly Val Ser Lys Leu Leu Asn Lys Lys Ser
            260                 265                 270

Gly Val Leu Gly Ile Ser Gly Val Ser Ser Asp Phe Arg Asp Leu His
        275                 280                 285

Ala Ala Ala Asp Ala Gly Asn Ser Arg Ala Glu Leu Ala Ile Glu Ile
    290                 295                 300

Phe Cys Tyr Gly Val Lys Lys Phe Ile Gly Glu Tyr Ile Ala Val Met
305                 310                 315                 320

Asn Gly Val Asp Ala Ile Val Phe Thr Ala Gly Val Gly Glu Asn Asn
                325                 330                 335

Ser Val Val Arg Asn Met Ile Ile Ser Asp Met Asp Phe Leu Gly Ile
            340                 345                 350

Lys Ile Asp Val Glu Lys Asn Lys Leu Thr Gly Ala Gly
        355                 360                 365
```

<210> SEQ ID NO 89
<211> LENGTH: 2703
<212> TYPE: DNA
<213> ORGANISM: Leuconostoc mesenteroides
<220> FEATURE:
<223> OTHER INFORMATION: adhE

<400> SEQUENCE: 89

```
atggcagaag caattgcaaa gaaacccgca aaaagggttt tgacccctga agaaaaagcg      60

gaattacaaa cacaagctga gaagatgact gaggtattga ttgaaaaatc acaaaaggca     120

ttgtctgaat tttcaacatt ttcgcaagaa caagttgata aaattgttgc agctatggcc     180

ttggcaggtt ctgagaattc acttctgtta gcccatgctg ctcacgacga gactggacgt     240

ggggttgtgg aagataagga tacgaaaaat cgtttcgcct cagaatcagt ttataacgct     300

attaagtttg ataagactgt gggtgttatt agtgaagaca agattcaagg taaggtagaa     360

ttagcagccc cacttggtat tttggctgga atcgtcccaa cgacaaatcc aacgtcgaca     420

actattttca aatcaatgtt gacagcaaag acacgtaaca caattatctt tgctttccat     480

ccccaggctc aaaaagcatc ggttcttgct gcaaaaattg tttatgatgc tgctgttaaa     540

gcaggcgcac cggaaaactt tatccaatgg attgaaaagc cttcacttta tgcaacaagt     600
```

```
gcgctgatac aaaatcctca cattgcttca attctagcta ctggtgggcc atcaatggtt    660
aatgcagctt tgaagtcagg aaatccatcc atgggtgtcg gtgctggaaa cggtgcagtt    720
tatattgatg caactgttga cacagatcgt gccgtgtccg atttgttgtt atcaaagcgt    780
ttcgataatg gcatgatttg tgccacagaa aactcagccg ttattcaagc accaatctat    840
gacgaaattt taactaagtt acaagaacaa ggtgcatacc ttgttcctaa gaaagactac    900
aaaaaaattg ctgattatgt atttaagcct aacgcagagg gatttggtat tgctggtcct    960
gttgctggta tgtcaggacg ttggattgct gagcaagcag gcgtaaagat tcctgatggt   1020
aaagatgtac ttttgttcga attagatcag aagaacatag gtgaagcgtt atcttctgaa   1080
aagttatcgc cattactttc aatttataaa gttgagaagc gtgaagaagc tattgagact   1140
gttcaatcct tgttaaacta tcaaggcgcg ggcacaacgc cagcaattca aattggttca   1200
caagatgatc cattcattaa agagtatgct gacgctattg gtgcatcacg tattttggtt   1260
aaccaacctg actcaatcgg tggtgttgga gatatttaca cagatgctat gcgtccatcg   1320
ttgacacttg gtaccggatc atgggggaag aattcattgt ctcataactt atcaacatac   1380
gacttactta atattaagac cgtggctcgc cgccgtaatc gtcctcaatg ggttcgttta   1440
cctaaggaag tttactacga agccaatgcc attacttact tacaagactt gcctactata   1500
aaccgtgcat ttattgtcgc tgatcctggt atggttcagt tcggatttgt tggcagagta   1560
ctaggtcaac ttgagttacg tcaagaacag gttgaaacaa atatctatgg ttcagttaag   1620
cctgacccaa ctttgtcaca agctgttgaa attgctcgcc aaatggcaga cttcaaacca   1680
gatacagtta ttttacttgg cggtggttcg gcacttgacg ctggtaaaat tggtcggttc   1740
ttgtacgaat actcgacacg ccatgaagga attttagaag atgacgaggc gattaaagat   1800
ctattcttag aactacaaca aaagtttatg gatattcgta agcgaatcgt taagttttac   1860
cacgcacgtt tgacacaaat ggttgcgatt ccaacaactt caggtactgg atcagaagtc   1920
acaccatttg ccgttattac agatgatgaa acacatgtaa agtatccact agccgattat   1980
gaattgacac cggaagttgc tattgttgat ccagaatttg ttatgaccgt accacaacac   2040
acggtatctt ggtcaggatt agatgctttg tcacatgctt tggaatcgta tgtctcagtg   2100
atggcttctg aattcacacg tccttgggca ttacaagcta ttaagttgat tttgataac    2160
ttaacaaatt catacaatta tgatcctaaa cacccaacta aggaaggtca gaatgcacgc   2220
acaaagatgc actatgcgtc aacattggct ggtatgtcat ttgcgaatgc cttcttggga   2280
cttaaccact cactagcaca caaaactggt ggagaattcg gactacctca cggtatggca   2340
atcgctattg caatgccaca tgtgattaag tttaatgcgg taacaggaaa tgtaaagcgc   2400
acaccatacc cacgttacga aacctataca gcacaaaaag attatgctga tattgcacgt   2460
tacttaggtt tgaaaggtga aacagatgct gaattggtcg atgtattgat tgcagaaatc   2520
aagaagttgg ctgcatcagt gggtgtcaat caaacactat ctggcaacgg tgtttcaaag   2580
catgactttg atacaaagtt agaaaagatg attgacttag tttacaatga ccaatgcacg   2640
ccgggaaacc ctcgccaacc aagcttggca gaaattcgtc aattgttgaa agatcagttt   2700
taa                                                                 2703
```

<210> SEQ ID NO 90
<211> LENGTH: 900
<212> TYPE: PRT
<213> ORGANISM: Leuconostoc mesenteroides
<220> FEATURE:
<223> OTHER INFORMATION: adhE

<400> SEQUENCE: 90

```
Met Ala Glu Ala Ile Ala Lys Lys Pro Ala Lys Arg Val Leu Thr Pro
1               5                   10                  15

Glu Glu Lys Ala Glu Leu Gln Thr Gln Ala Glu Lys Met Thr Glu Val
            20                  25                  30

Leu Ile Glu Lys Ser Gln Lys Ala Leu Ser Glu Phe Ser Thr Phe Ser
        35                  40                  45

Gln Glu Gln Val Asp Lys Ile Val Ala Ala Met Ala Leu Ala Gly Ser
    50                  55                  60

Glu Asn Ser Leu Leu Leu Ala His Ala Ala His Asp Glu Thr Gly Arg
65                  70                  75                  80

Gly Val Val Glu Asp Lys Asp Thr Lys Asn Arg Phe Ala Ser Glu Ser
                85                  90                  95

Val Tyr Asn Ala Ile Lys Phe Asp Lys Thr Val Gly Val Ile Ser Glu
            100                 105                 110

Asp Lys Ile Gln Gly Lys Val Glu Leu Ala Ala Pro Leu Gly Ile Leu
        115                 120                 125

Ala Gly Ile Val Pro Thr Thr Asn Pro Thr Ser Thr Thr Ile Phe Lys
    130                 135                 140

Ser Met Leu Thr Ala Lys Thr Arg Asn Thr Ile Ile Phe Ala Phe His
145                 150                 155                 160

Pro Gln Ala Gln Lys Ala Ser Val Leu Ala Ala Lys Ile Val Tyr Asp
                165                 170                 175

Ala Ala Val Lys Ala Gly Ala Pro Glu Asn Phe Ile Gln Trp Ile Glu
            180                 185                 190

Lys Pro Ser Leu Tyr Ala Thr Ser Ala Leu Ile Gln Asn Pro His Ile
        195                 200                 205

Ala Ser Ile Leu Ala Thr Gly Gly Pro Ser Met Val Asn Ala Ala Leu
    210                 215                 220

Lys Ser Gly Asn Pro Ser Met Gly Val Gly Ala Gly Asn Gly Ala Val
225                 230                 235                 240

Tyr Ile Asp Ala Thr Val Asp Thr Asp Arg Ala Val Ser Asp Leu Leu
                245                 250                 255

Leu Ser Lys Arg Phe Asp Asn Gly Met Ile Cys Ala Thr Glu Asn Ser
            260                 265                 270

Ala Val Ile Gln Ala Pro Ile Tyr Asp Glu Ile Leu Thr Lys Leu Gln
        275                 280                 285

Glu Gln Gly Ala Tyr Leu Val Pro Lys Lys Asp Tyr Lys Lys Ile Ala
    290                 295                 300

Asp Tyr Val Phe Lys Pro Asn Ala Glu Gly Phe Gly Ile Ala Gly Pro
305                 310                 315                 320

Val Ala Gly Met Ser Gly Arg Trp Ile Ala Glu Gln Ala Gly Val Lys
                325                 330                 335

Ile Pro Asp Gly Lys Asp Val Leu Leu Phe Glu Leu Asp Gln Lys Asn
            340                 345                 350

Ile Gly Glu Ala Leu Ser Ser Glu Lys Leu Ser Pro Leu Leu Ser Ile
        355                 360                 365

Tyr Lys Val Glu Lys Arg Glu Glu Ala Ile Glu Thr Val Gln Ser Leu
    370                 375                 380

Leu Asn Tyr Gln Gly Ala Gly His Asn Ala Ala Ile Gln Ile Gly Ser
385                 390                 395                 400

Gln Asp Asp Pro Phe Ile Lys Glu Tyr Ala Asp Ala Ile Gly Ala Ser
```

```
                405                 410                 415

Arg Ile Leu Val Asn Gln Pro Asp Ser Ile Gly Gly Val Gly Asp Ile
            420                 425                 430

Tyr Thr Asp Ala Met Arg Pro Ser Leu Thr Leu Gly Thr Gly Ser Trp
        435                 440                 445

Gly Lys Asn Ser Leu Ser His Asn Leu Ser Thr Tyr Asp Leu Leu Asn
    450                 455                 460

Ile Lys Thr Val Ala Arg Arg Arg Asn Arg Pro Gln Trp Val Arg Leu
465                 470                 475                 480

Pro Lys Glu Val Tyr Tyr Glu Ala Asn Ala Ile Thr Tyr Leu Gln Asp
                485                 490                 495

Leu Pro Thr Ile Asn Arg Ala Phe Ile Val Ala Asp Pro Gly Met Val
            500                 505                 510

Gln Phe Gly Phe Val Gly Arg Val Leu Gly Gln Leu Glu Leu Arg Gln
        515                 520                 525

Glu Gln Val Glu Thr Asn Ile Tyr Gly Ser Val Lys Pro Asp Pro Thr
    530                 535                 540

Leu Ser Gln Ala Val Glu Ile Ala Arg Gln Met Ala Asp Phe Lys Pro
545                 550                 555                 560

Asp Thr Val Ile Leu Leu Gly Gly Gly Ser Ala Leu Asp Ala Gly Lys
                565                 570                 575

Ile Gly Arg Phe Leu Tyr Glu Tyr Ser Thr Arg His Glu Gly Ile Leu
            580                 585                 590

Glu Asp Asp Glu Ala Ile Lys Asp Leu Phe Leu Glu Leu Gln Gln Lys
        595                 600                 605

Phe Met Asp Ile Arg Lys Arg Ile Val Lys Phe Tyr His Ala Arg Leu
    610                 615                 620

Thr Gln Met Val Ala Ile Pro Thr Thr Ser Gly Thr Gly Ser Glu Val
625                 630                 635                 640

Thr Pro Phe Ala Val Ile Thr Asp Asp Glu Thr His Val Lys Tyr Pro
                645                 650                 655

Leu Ala Asp Tyr Glu Leu Thr Pro Glu Val Ala Ile Val Asp Pro Glu
            660                 665                 670

Phe Val Met Thr Val Pro Gln His Thr Val Ser Trp Ser Gly Leu Asp
        675                 680                 685

Ala Leu Ser His Ala Leu Glu Ser Tyr Val Ser Val Met Ala Ser Glu
    690                 695                 700

Phe Thr Arg Pro Trp Ala Leu Gln Ala Ile Lys Leu Ile Phe Asp Asn
705                 710                 715                 720

Leu Thr Asn Ser Tyr Asn Tyr Asp Pro Lys His Pro Thr Lys Glu Gly
                725                 730                 735

Gln Asn Ala Arg Thr Lys Met His Tyr Ala Ser Thr Leu Ala Gly Met
            740                 745                 750

Ser Phe Ala Asn Ala Phe Leu Gly Leu Asn His Ser Leu Ala His Lys
        755                 760                 765

Thr Gly Gly Glu Phe Gly Leu Pro His Gly Met Ala Ile Ala Ile Ala
    770                 775                 780

Met Pro His Val Ile Lys Phe Asn Ala Val Thr Gly Asn Val Lys Arg
785                 790                 795                 800

Thr Pro Tyr Pro Arg Tyr Glu Thr Tyr Thr Ala Gln Lys Asp Tyr Ala
                805                 810                 815

Asp Ile Ala Arg Tyr Leu Gly Leu Lys Gly Glu Thr Asp Ala Glu Leu
            820                 825                 830
```

```
Val Asp Val Leu Ile Ala Glu Ile Lys Lys Leu Ala Ala Ser Val Gly
        835                 840                 845

Val Asn Gln Thr Leu Ser Gly Asn Gly Val Ser Lys His Asp Phe Asp
    850                 855                 860

Thr Lys Leu Glu Lys Met Ile Asp Leu Val Tyr Asn Asp Gln Cys Thr
865                 870                 875                 880

Pro Gly Asn Pro Arg Gln Pro Ser Leu Ala Glu Ile Arg Gln Leu Leu
                885                 890                 895

Lys Asp Gln Phe
            900


<210> SEQ ID NO 91
<211> LENGTH: 1260
<212> TYPE: DNA
<213> ORGANISM: Leuconostoc mesenteroides
<220> FEATURE:
<223> OTHER INFORMATION: ACK

<400> SEQUENCE: 91

atggctaaaa caatggctgt taacgcaggt agttcatcac taaagtttca attattagag     60

atgcctgcag aacaagtaat tgcacaaggt gttatcgaac gcattggtat ggacgatgca    120

atagtaacga ttaaatacgg tgcagaaatc aatgcagagc gcttggttgg ccattcagaa    180

gatgacgaac atattacttt gtccaaagac ggcaaaggta agaagtacga aaacgttact    240

gcaattaaaa accaccaaca ggccattaac ttcatgttgc aaaagttaac agatctgggt    300

attattaagg actttaatga aattactggt gtcggacatc gtgttgttgc tggtggtgaa    360

tggtttaatc attccgtggt ggtaacagat gaggtgctgg ctaaaattga tcgtcttgca    420

gattatgcac cacttcataa cccagccaat gctatgggaa ttcgtgcttt ccaaaagctc    480

ctccctgatg cattgtcagt ggcggttttt gatacttctt tccatcaaac aatgcctgat    540

gaaaactttc tttatgcctt gccatatgaa tactacacgc gttatggcgc ccgcaagtat    600

ggtgctcatg gtacatcgca ccgatatgtt gcatcgcgtg cagccgagtt gctcggtaaa    660

gatttaaaaa gcttgaaatt aatcacgctg catttaggtg caggtgcctc aattacggct    720

attaaggatg gtaagtcatt agatacttct atgggatttt ctcccttagc tggtgttgct    780

atggcaacgc gttcagggga tgtcgatgct tcgcttgttt attatattca agaacgcgaa    840

ggactatcta acgaagagat gttaaatata ttgaacaaaa agtccggttt gcttggtatt    900

tcgacaattt caagtgatat gcgtgacttg ttagatgtcc aagacactaa tgagcatgct    960

gacatggcga ttagaatatt tattaatcgt gttgttaaat atgtgggaca gtatgttgcg   1020

gaaatgggag acgttgatgc tatcgtattt acagcaggaa ttggtgaaaa ctcagtccca   1080

gttcgtaaaa tgattattga taaattaaac tactttggtg tgaaattaga tgaagaaaaa   1140

aataatgttc gcggcaaaga agttgaaata tctacgaatg actccaaggt aaaagccttg   1200

ttgatcccaa ccaatgaaga actaatgatt gctagagatg ttgaatcttt gaaagcatag   1260


<210> SEQ ID NO 92
<211> LENGTH: 419
<212> TYPE: PRT
<213> ORGANISM: Leuconostoc mesenteroides
<220> FEATURE:
<223> OTHER INFORMATION: ACK

<400> SEQUENCE: 92

Met Ala Lys Thr Met Ala Val Asn Ala Gly Ser Ser Ser Leu Lys Phe
```

-continued

```
1               5                   10                  15

Gln Leu Leu Glu Met Pro Ala Glu Gln Val Ile Ala Gln Gly Val Ile
            20                  25                  30

Glu Arg Ile Gly Met Asp Asp Ala Ile Val Thr Ile Lys Tyr Gly Ala
        35                  40                  45

Glu Ile Asn Ala Glu Arg Leu Val Gly His Ser Glu Asp Asp Glu His
    50                  55                  60

Ile Thr Leu Ser Lys Asp Gly Lys Gly Lys Lys Tyr Glu Asn Val Thr
65                  70                  75                  80

Ala Ile Lys Asn His Gln Gln Ala Ile Asn Phe Met Leu Gln Lys Leu
                85                  90                  95

Thr Asp Leu Gly Ile Ile Lys Asp Phe Asn Glu Ile Thr Gly Val Gly
            100                 105                 110

His Arg Val Val Ala Gly Gly Glu Trp Phe Asn His Ser Val Val Val
        115                 120                 125

Thr Asp Glu Val Leu Ala Lys Ile Asp Arg Leu Ala Asp Tyr Ala Pro
    130                 135                 140

Leu His Asn Pro Ala Asn Ala Met Gly Ile Arg Ala Phe Gln Lys Leu
145                 150                 155                 160

Leu Pro Asp Ala Leu Ser Val Ala Val Phe Asp Thr Ser Phe His Gln
                165                 170                 175

Thr Met Pro Asp Glu Asn Phe Leu Tyr Ala Leu Pro Tyr Glu Tyr Tyr
            180                 185                 190

Thr Arg Tyr Gly Ala Arg Lys Tyr Gly Ala His Gly Thr Ser His Arg
        195                 200                 205

Tyr Val Ala Ser Arg Ala Ala Glu Leu Leu Gly Lys Asp Leu Lys Ser
    210                 215                 220

Leu Lys Leu Ile Thr Leu His Leu Gly Ala Gly Ala Ser Ile Thr Ala
225                 230                 235                 240

Ile Lys Asp Gly Lys Ser Leu Asp Thr Ser Met Gly Phe Ser Pro Leu
                245                 250                 255

Ala Gly Val Ala Met Ala Thr Arg Ser Gly Asp Val Asp Ala Ser Leu
            260                 265                 270

Val Tyr Tyr Ile Gln Glu Arg Glu Gly Leu Ser Asn Glu Glu Met Leu
        275                 280                 285

Asn Ile Leu Asn Lys Lys Ser Gly Leu Leu Gly Ile Ser Thr Ile Ser
    290                 295                 300

Ser Asp Met Arg Asp Leu Leu Asp Val Gln Asp Thr Asn Glu His Ala
305                 310                 315                 320

Asp Met Ala Ile Arg Ile Phe Ile Asn Arg Val Val Lys Tyr Val Gly
                325                 330                 335

Gln Tyr Val Ala Glu Met Gly Asp Val Asp Ala Ile Val Phe Thr Ala
            340                 345                 350

Gly Ile Gly Glu Asn Ser Val Pro Val Arg Lys Met Ile Ile Asp Lys
        355                 360                 365

Leu Asn Tyr Phe Gly Val Lys Leu Asp Glu Glu Lys Asn Asn Val Arg
    370                 375                 380

Gly Lys Glu Val Glu Ile Ser Thr Asn Asp Ser Lys Val Lys Ala Leu
385                 390                 395                 400

Leu Ile Pro Thr Asn Glu Glu Leu Met Ile Ala Arg Asp Val Glu Ser
                405                 410                 415

Leu Lys Ala
```

<210> SEQ ID NO 93
<211> LENGTH: 2367
<212> TYPE: DNA
<213> ORGANISM: Leuconostoc mesenteroides
<220> FEATURE:
<223> OTHER INFORMATION: PHK

<400> SEQUENCE: 93

```
atgaatatcg attcaacaga ttacctgaac aatttagatg cctactggcg agctaccaat     60
tatttgtcag ttggacaact ctatttgtta gataacccat tgcttaagga aaagttaacg    120
gcagaacaag ttaaaattca cccaatcggg cactggggca cgattcctag tcaaaacttt    180
atttatgccc atttaaatcg tgctattaat aaatttaatt tgaatatgtt ttacattgag    240
gggcctggcc atggcggaca agtaatgatt tcaaatgctt atcttgatgg tagttatacc    300
gaagcatttc cagaaatcac acaggatgaa gcgggtatgc agaaaatgtt taagcgtttc    360
tctttccccg gtggcgttgc ttcacatgct gatcctaaag tacctggatc gattcatgaa    420
ggtggtgctt taggctattc tatcttgcac ggtgctggtg ctgtattgga taatccagac    480
ctcattgctg cggttgttgt tggcgatggt gaagcagaaa cagcacccct agccacttca    540
tggcatgtta ataaattttt gaatcctaaa aatgatggta ctgtattacc aattttgaat    600
ttaaatggct tcaagattgc gaatcccaca gttctctctc gagaatctga tgaaacacta    660
accgattatt tccacagtct gggatggcac ccttactttg taagttcttt tgacaaaccg    720
attatgcaag ttcatgaaga aatggcaaaa accatggaca cagtatttac tgagattaaa    780
gacattagag aaaaagccgt tcagcagaca aatgaagaga ttacacgacc actttggcca    840
atgattgttt tacgttcacc taaaggctgg acagggccaa aacttggga tgacaaacca    900
attgaaaatt catttcgtgc acaccaaatt ccaattcctg ctgaccaaaa tcatcctgaa    960
tatataccac aacttgttga ttggttacaa tcttacaaac cagatgaatt atttgatgaa   1020
aacggtcagt taacacaatc tatccaagaa gtattaccga aaaaagagct acgtatggcc   1080
aataattcgg tcaccaatgc tggtattatc aaacctttga ttttacctga cattgacaat   1140
tacttggtag aaaataatca gccagacaat aacttagctc aagatgctat tttgttaggt   1200
gactatttgc gtgatatcat caaacttaat cctactaact tccgtggctt tggcccagat   1260
gaaacagctt ctaatcgttt ccaagacatt tttgaaacaa ctaatcgcca atggctatta   1320
ccaatcaaag aacctaatga tcaattcatg gcacctgaag gccgtattat tgattctatg   1380
ttatcagagc attatgatga ggggatgctt gaagcttata cgctaaccgg tcgtcatgga   1440
ttctttgcca gttatgaggt ctttattcgt gaagttgatg acatgattgt gcaacatttt   1500
aagtggttga atcattctca tgacgtttca tggcgtaagg acgtaccggc attaaatatt   1560
attgctgatt caaccgtttt ccaacaagac cataatggtt actcacacca agatcctggt   1620
gtaacaacaa tgttgtatga aaagcaacca gacttcattc gcgagttctt cccagcggat   1680
gctaatagct tggtcgcaac atttgaacat gctgcgcaag caacgcaaca gattaattat   1740
attgtggcca gcaaacatcc ccgcttacag tggttctcac ctactgaggc caaacagctt   1800
gttacgcagg gattacgtgt cattgattgg gcaagtactg acaaaggtga aaaacctgat   1860
attattatta cttcagctgg ttctgaacca acgacagaaa gtttagcagc aatacaaatt   1920
ttgcacgaac acataccatc attaaaaata cgttacatca atgtattgga tctatttaaa   1980
ctacgggccg atgccagcta tggcttaagt gatgatgaat ttgatgctta cttcactact   2040
gacacaccag tattatttgc attccatggc tatgaaccaa tgattgaatc tattttcttc   2100
```

```
aaacgacaca atcaccactt agcagttcat ggttaccgag aagttggtga cattacaaca   2160

ccatttgata tgcgtgttct taacaaaatt gatcgattta atttagttaa agctgctatt   2220

aatctcttgc cagaaaatat tcgcaccaag caagcagccc tcgtgcaaga aatgaccgat   2280

aagctcgacc tacacgttgc gtatactagg tcaaagggaa cggacttgcc cgaagtagaa   2340

gattggcgct ggcgaccact taagtga                                       2367


<210> SEQ ID NO 94
<211> LENGTH: 788
<212> TYPE: PRT
<213> ORGANISM: Leuconostoc mesenteroides
<220> FEATURE:
<223> OTHER INFORMATION: PHK

<400> SEQUENCE: 94

Met Asn Ile Asp Ser Thr Asp Tyr Leu Asn Asn Leu Asp Ala Tyr Trp
1               5                   10                  15

Arg Ala Thr Asn Tyr Leu Ser Val Gly Gln Leu Tyr Leu Leu Asp Asn
            20                  25                  30

Pro Leu Leu Lys Glu Lys Leu Thr Ala Glu Gln Val Lys Ile His Pro
        35                  40                  45

Ile Gly His Trp Gly Thr Ile Pro Ser Gln Asn Phe Ile Tyr Ala His
    50                  55                  60

Leu Asn Arg Ala Ile Asn Lys Phe Asn Leu Asn Met Phe Tyr Ile Glu
65                  70                  75                  80

Gly Pro Gly His Gly Gly Gln Val Met Ile Ser Asn Ala Tyr Leu Asp
                85                  90                  95

Gly Ser Tyr Thr Glu Ala Phe Pro Glu Ile Thr Gln Asp Glu Ala Gly
            100                 105                 110

Met Gln Lys Met Phe Lys Arg Phe Ser Phe Pro Gly Gly Val Ala Ser
        115                 120                 125

His Ala Asp Pro Lys Val Pro Gly Ser Ile His Glu Gly Gly Ala Leu
    130                 135                 140

Gly Tyr Ser Ile Leu His Gly Ala Gly Ala Val Leu Asp Asn Pro Asp
145                 150                 155                 160

Leu Ile Ala Ala Val Val Val Gly Asp Gly Glu Ala Glu Thr Ala Pro
                165                 170                 175

Leu Ala Thr Ser Trp His Val Asn Lys Phe Leu Asn Pro Lys Asn Asp
            180                 185                 190

Gly Thr Val Leu Pro Ile Leu Asn Leu Asn Gly Phe Lys Ile Ala Asn
        195                 200                 205

Pro Thr Val Leu Ser Arg Glu Ser Asp Glu Thr Leu Thr Asp Tyr Phe
    210                 215                 220

His Ser Leu Gly Trp His Pro Tyr Phe Val Ser Ser Phe Asp Lys Pro
225                 230                 235                 240

Ile Met Gln Val His Glu Glu Met Ala Lys Thr Met Asp Thr Val Phe
                245                 250                 255

Thr Glu Ile Lys Asp Ile Arg Glu Lys Ala Val Gln Gln Thr Asn Glu
            260                 265                 270

Glu Ile Thr Arg Pro Leu Trp Pro Met Ile Val Leu Arg Ser Pro Lys
        275                 280                 285

Gly Trp Thr Gly Pro Lys Thr Trp Asp Asp Lys Pro Ile Glu Asn Ser
    290                 295                 300

Phe Arg Ala His Gln Ile Pro Ile Pro Ala Asp Gln Asn His Pro Glu
```

```
305                 310                 315                 320

Tyr Ile Pro Gln Leu Val Asp Trp Leu Gln Ser Tyr Lys Pro Asp Glu
                325                 330                 335

Leu Phe Asp Glu Asn Gly Gln Leu Thr Gln Ser Ile Gln Glu Val Leu
            340                 345                 350

Pro Lys Lys Glu Leu Arg Met Ala Asn Asn Ser Val Thr Asn Ala Gly
        355                 360                 365

Ile Ile Lys Pro Leu Ile Leu Pro Asp Ile Asp Asn Tyr Leu Val Glu
    370                 375                 380

Asn Asn Gln Pro Asp Asn Asn Leu Ala Gln Asp Ala Ile Leu Leu Gly
385                 390                 395                 400

Asp Tyr Leu Arg Asp Ile Ile Lys Leu Asn Pro Thr Asn Phe Arg Gly
                405                 410                 415

Phe Gly Pro Asp Glu Thr Ala Ser Asn Arg Phe Gln Asp Ile Phe Glu
            420                 425                 430

Thr Thr Asn Arg Gln Trp Leu Leu Pro Ile Lys Glu Pro Asn Asp Gln
        435                 440                 445

Phe Met Ala Pro Glu Gly Arg Ile Ile Asp Ser Met Leu Ser Glu His
    450                 455                 460

Tyr Asp Glu Gly Met Leu Glu Ala Tyr Thr Leu Thr Gly Arg His Gly
465                 470                 475                 480

Phe Phe Ala Ser Tyr Glu Val Phe Ile Arg Glu Val Asp Asp Met Ile
                485                 490                 495

Val Gln His Phe Lys Trp Leu Asn His Ser His Asp Val Ser Trp Arg
            500                 505                 510

Lys Asp Val Pro Ala Leu Asn Ile Ile Ala Asp Ser Thr Val Phe Gln
        515                 520                 525

Gln Asp His Asn Gly Tyr Ser His Gln Asp Pro Gly Val Thr Thr Met
    530                 535                 540

Leu Tyr Glu Lys Gln Pro Asp Phe Ile Arg Glu Phe Phe Pro Ala Asp
545                 550                 555                 560

Ala Asn Ser Leu Val Ala Thr Phe Glu His Ala Ala Gln Ala Thr Gln
                565                 570                 575

Gln Ile Asn Tyr Ile Val Ala Ser Lys His Pro Arg Leu Gln Trp Phe
            580                 585                 590

Ser Pro Thr Glu Ala Lys Gln Leu Val Thr Gln Gly Leu Arg Val Ile
        595                 600                 605

Asp Trp Ala Ser Thr Asp Lys Gly Glu Lys Pro Asp Ile Ile Ile Thr
    610                 615                 620

Ser Ala Gly Ser Glu Pro Thr Thr Glu Ser Leu Ala Ala Ile Gln Ile
625                 630                 635                 640

Leu His Glu His Ile Pro Ser Leu Lys Ile Arg Tyr Ile Asn Val Leu
                645                 650                 655

Asp Leu Phe Lys Leu Arg Ala Asp Ala Ser Tyr Gly Leu Ser Asp Asp
            660                 665                 670

Glu Phe Asp Ala Tyr Phe Thr Thr Asp Thr Pro Val Leu Phe Ala Phe
        675                 680                 685

His Gly Tyr Glu Pro Met Ile Glu Ser Ile Phe Phe Lys Arg His Asn
    690                 695                 700

His His Leu Ala Val His Gly Tyr Arg Glu Val Gly Asp Ile Thr Thr
705                 710                 715                 720

Pro Phe Asp Met Arg Val Leu Asn Lys Ile Asp Arg Phe Asn Leu Val
                725                 730                 735
```

```
Lys Ala Ala Ile Asn Leu Leu Pro Glu Asn Ile Arg Thr Lys Gln Ala
            740                 745                 750

Ala Leu Val Gln Glu Met Thr Asp Lys Leu Asp Leu His Val Ala Tyr
        755                 760                 765

Thr Arg Ser Lys Gly Thr Asp Leu Pro Glu Val Glu Asp Trp Arg Trp
    770                 775                 780

Arg Pro Leu Lys
785
```

```
<210> SEQ ID NO 95
<211> LENGTH: 981
<212> TYPE: DNA
<213> ORGANISM: Leuconostoc mesenteroides
<220> FEATURE:
<223> OTHER INFORMATION: PTA

<400> SEQUENCE: 95

atggaacttt ttgagcaatt aaaaaataaa attaccggtc aaaataagac aattgtattt     60

ccggaaggtg aagatccccg tatccagggc gcagctatca gattagcagc tgataatttg    120

atcgagccaa tattgttggg ggatgcacag gaaatttcaa aaactgccca agcccataac    180

tttgatttat cgaacataga gacgattgat cctgcttcat atgatgagaa tgaattggca    240

aaattaaatg cgacacttgt cgaaaggcgc aaagggaaaa cagacgctga gacagctgcc    300

aaatggctac aaaatgttaa ctattttggg acaatgctgg tttatactgg caaagctgac    360

ggtatggtgt caggcgcagt acatccaact ggtgatacag ttcgtcctgc gttgcagatc    420

attaaaacgg cgcctggctc atcacgtatt tctggtgcat tcattatgca aaaaggcgaa    480

gagcgttatg tatttgcgga cgctgccatt aacattgaca ttgattcgga cacgatggct    540

gaaattgcaa tacaatcagc ccacacagct caagtgtttg atattgaacc aaaagttgcg    600

atgctttcat tttcaactaa gggctccgcg aaatcaccct tggtcgataa ggtggcaact    660

gccactgcat tggctaagaa gttagcacct gaactggcgg actcaattga tggagagtta    720

cagtttgatg ctgcgtttgt tgaatctgtt gctgccgcaa aggcgcctga ttcaaaagtc    780

gcaggtaaag cgaacacatt tattttccca agtctagaag caggtaatat tggctataaa    840

attgcacaac gcttgggtgg gtttgaagcg attggaccta ttttacaagg cttagcaaaa    900

cctgtttctg atttatcgcg aggagccaat gaagaggatg tttataaagt agctattatt    960

actgctgcgc aagcattata a                                              981
```

```
<210> SEQ ID NO 96
<211> LENGTH: 326
<212> TYPE: PRT
<213> ORGANISM: Leuconostoc mesenteroides
<220> FEATURE:
<223> OTHER INFORMATION: PTA

<400> SEQUENCE: 96

Met Glu Leu Phe Glu Gln Leu Lys Asn Lys Ile Thr Gly Gln Asn Lys
1               5                   10                  15

Thr Ile Val Phe Pro Glu Gly Glu Asp Pro Arg Ile Gln Gly Ala Ala
            20                  25                  30

Ile Arg Leu Ala Ala Asp Asn Leu Ile Glu Pro Ile Leu Leu Gly Asp
        35                  40                  45

Ala Gln Glu Ile Ser Lys Thr Ala Gln Ala His Asn Phe Asp Leu Ser
    50                  55                  60
```

```
Asn Ile Glu Thr Ile Asp Pro Ala Ser Tyr Asp Glu Asn Glu Leu Ala
65                  70                  75                  80

Lys Leu Asn Ala Thr Leu Val Glu Arg Arg Lys Gly Lys Thr Asp Ala
                85                  90                  95

Glu Thr Ala Ala Lys Trp Leu Gln Asn Val Asn Tyr Phe Gly Thr Met
            100                 105                 110

Leu Val Tyr Thr Gly Lys Ala Asp Gly Met Val Ser Gly Ala Val His
        115                 120                 125

Pro Thr Gly Asp Thr Val Arg Pro Ala Leu Gln Ile Ile Lys Thr Ala
    130                 135                 140

Pro Gly Ser Ser Arg Ile Ser Gly Ala Phe Ile Met Gln Lys Gly Glu
145                 150                 155                 160

Glu Arg Tyr Val Phe Ala Asp Ala Ala Ile Asn Ile Asp Ile Asp Ser
                165                 170                 175

Asp Thr Met Ala Glu Ile Ala Ile Gln Ser Ala His Thr Ala Gln Val
            180                 185                 190

Phe Asp Ile Glu Pro Lys Val Ala Met Leu Ser Phe Ser Thr Lys Gly
        195                 200                 205

Ser Ala Lys Ser Pro Leu Val Asp Lys Val Ala Thr Ala Thr Ala Leu
    210                 215                 220

Ala Lys Lys Leu Ala Pro Glu Leu Ala Asp Ser Ile Asp Gly Glu Leu
225                 230                 235                 240

Gln Phe Asp Ala Ala Phe Val Glu Ser Val Ala Ala Ala Lys Ala Pro
                245                 250                 255

Asp Ser Lys Val Ala Gly Lys Ala Asn Thr Phe Ile Phe Pro Ser Leu
            260                 265                 270

Glu Ala Gly Asn Ile Gly Tyr Lys Ile Ala Gln Arg Leu Gly Gly Phe
        275                 280                 285

Glu Ala Ile Gly Pro Ile Leu Gln Gly Leu Ala Lys Pro Val Ser Asp
    290                 295                 300

Leu Ser Arg Gly Ala Asn Glu Glu Asp Val Tyr Lys Val Ala Ile Ile
305                 310                 315                 320

Thr Ala Ala Gln Ala Leu
                325
```

<210> SEQ ID NO 97
<211> LENGTH: 2697
<212> TYPE: DNA
<213> ORGANISM: Oenococcus oenii
<220> FEATURE:
<223> OTHER INFORMATION: adhE

<400> SEQUENCE: 97

```
atggcagttg aaacgaagaa gattactaaa aagatactga cttccgacga acttaaagac      60

aaaaaggaga cagcaaaaaa atacattgga gaattagtcg ataaatcaag acaggcatta     120

ttagaattct ctcaatatag tcaatcacaa gttgacaaaa ttgttgccgc aatggcttta     180

gccggttccg aacattcttt ggaattagca cactttgctc gaaatgaaac tggaagagga     240

gttgttgaag acaaagatac gaaaaatcgt tttgcctcgg aatctgtata taacacgatt     300

aaaaatgaca aaacagttgg cgtaattgat gaagacccaa tcactggcaa agttcagtta     360

gctgcaccac ttgggatttt agccggaatt gttccaacga caaatccaac gtctaccacg     420

atttttaaat cattgttaac cgctaagaca cgtaatacga tcatttttgc ttttcacccg     480

caagcacaaa aatcgtctgt agcggctgcg aaaattgttt accaggcggc tagaaaagct     540
```

```
ggagcaccga aagatttcat tcagtggatc gaaacgcctt ccttggaaaa tacgactgct    600

ttgatgcaaa atcctgaaat agcttcaatt ttggctactg gaggcccttc tatggttcat    660

gccgcattaa catcgggaaa cccttcaatg ggtgttgggg caggaaatgg agctgttttc    720

attgaccata cggctcgtgt tcgtcgagcg gcagaagact tgttgctatc aaaacgtttt    780

gataatggaa tgatttgcgc tacagagaat tccgcagtta tcgaagcttc ggtttatgac    840

gaatttatga aattaatgca ggaaaagggt acttatctcg ttccgaagga tgattacaaa    900

aagatcgctg attttgtttt cagcgataaa catgcagtta atggtccggt tgccgggatg    960

agtggccgtt ggattgctga acatgccggt gttactttgc cgaagggcaa agatgttttg   1020

ttgtttgagt tggatcaaga cgacattggc gaaaaacttt cctcggaaaa acttagcccc   1080

ttgctttcgg tctataaagc tgctgatcgt aaagaagcga taaaagttgt tcaaagactt   1140

ttgaactatc aaggagctgg tcataatgcg gcaatccaga ttggcgctca agacgatccc   1200

tttgttaaag aatatgccga tgcagtttct gcatctagaa ttttggttaa ccagcccgat   1260

tcaataggtg gagtcggcga tatttataca gatgcattgc gtccaagtat gacgcttggt   1320

actggttcat gggggaagaa ttcattgtca cataatttat caacttacga tttgttgaat   1380

gtcaaaacgg ttgcccgcag acgtaatcgt cctcaatggg ttcgtcttcc aaaagatatc   1440

tactatgaga aaaatgccat tacctatctg caggaattac cgaacgtcaa tcgggctttc   1500

gttattaccg atcattcgtt ggtcaaatat ggattcgtcg atcggattct tgagcaattc   1560

gaattgcgtc ccgaccaggt taaaacaagt atttacagtt ctgttcaacc ggatccttat   1620

ttgagtcagg ctgttgaaat tgcaaaacaa atgcaggagt tcgaaccgga tacagtaatt   1680

gctcttggag gaggttcctc tttggatgtt gccaagattt cccgttttct ttatgaatat   1740

tctcaagaac cggaccacat tggttttttg gaaaacattg acgatattaa agaattgttt   1800

aaaggattgc agcaaaagtt tatggatatt cggaaacgga ttgttaaatt cgaacatcag   1860

aatttgactc aactggttgc tattccaaca acttcgggta ccggttcgga agtaacaccg   1920

ttttcggtta tcaccgatga tgaaactcac gttaaatacc ctttggccga ttatgaatta   1980

actccgcaag ttgcaatcgt tgatcctgaa ttggttatga ctgtaccaaa acggaccctg   2040

gcttggtctg gactggacgc cttatctcac tcgcttgaat cctacgtgtc ggttatgagt   2100

tctgaattta cacggccgtg ggctttacag gcaatcaaac tgatttttga aaacatcgtt   2160

gattcctata attacgatcc aaagcaccca actaatcggg gcgccgaggc acgtgaaaaa   2220

atgcattatg ctgcaacttt ggccggcatg tctttcggaa acgccttctt gggtataaac   2280

cattcactgg cccataaaac cggtggagag ttcggtcttc ctcatggttt ggcaatcagc   2340

atcgcgatgc cacatgtaat tcgatttaat gcggttaccg gaaacgtcaa acggactcct   2400

tttcctcgtt atgaggttta tacagcccaa aaagattatg ccgatattgc gcgccatatt   2460

ggcctcagcg gtaagaacga tgccgaattg gttgaaaaac ttatcgccaa aatcaaggaa   2520

ttaaccgatg ccttggatgt caatattact ttgagcggca atggagtcga taaaaagagc   2580

tttgaacatt ctttggatca actggttgat cttgtttacg atgaccagtg cacgccagga   2640

aatccgcgac aaccgaattt agctgaaatt aggcagttat tgatcgacca attttaa      2697
```

<210> SEQ ID NO 98
<211> LENGTH: 898
<212> TYPE: PRT
<213> ORGANISM: Oenococcus oenii
<220> FEATURE:
<223> OTHER INFORMATION: adhE

<400> SEQUENCE: 98

```
Met Ala Val Glu Thr Lys Lys Ile Thr Lys Lys Ile Leu Thr Ser Asp
1               5                   10                  15

Glu Leu Lys Asp Lys Lys Glu Thr Ala Lys Lys Tyr Ile Gly Glu Leu
            20                  25                  30

Val Asp Lys Ser Arg Gln Ala Leu Leu Glu Phe Ser Gln Tyr Ser Gln
        35                  40                  45

Ser Gln Val Asp Lys Ile Val Ala Ala Met Ala Leu Ala Gly Ser Glu
    50                  55                  60

His Ser Leu Glu Leu Ala His Phe Ala Arg Asn Glu Thr Gly Arg Gly
65                  70                  75                  80

Val Val Glu Asp Lys Asp Thr Lys Asn Arg Phe Ala Ser Glu Ser Val
                85                  90                  95

Tyr Asn Thr Ile Lys Asn Asp Lys Thr Val Gly Val Ile Asp Glu Asp
            100                 105                 110

Pro Ile Thr Gly Lys Val Gln Leu Ala Ala Pro Leu Gly Ile Leu Ala
        115                 120                 125

Gly Ile Val Pro Thr Thr Asn Pro Thr Ser Thr Thr Ile Phe Lys Ser
    130                 135                 140

Leu Leu Thr Ala Lys Thr Arg Asn Thr Ile Ile Phe Ala Phe His Pro
145                 150                 155                 160

Gln Ala Gln Lys Ser Ser Val Ala Ala Ala Lys Ile Val Tyr Gln Ala
                165                 170                 175

Ala Arg Lys Ala Gly Ala Pro Lys Asp Phe Ile Gln Trp Ile Glu Thr
            180                 185                 190

Pro Ser Leu Glu Asn Thr Thr Ala Leu Met Gln Asn Pro Glu Ile Ala
        195                 200                 205

Ser Ile Leu Ala Thr Gly Gly Pro Ser Met Val His Ala Ala Leu Thr
    210                 215                 220

Ser Gly Asn Pro Ser Met Gly Val Gly Ala Gly Asn Gly Ala Val Phe
225                 230                 235                 240

Ile Asp His Thr Ala Arg Val Arg Arg Ala Ala Glu Asp Leu Leu Leu
                245                 250                 255

Ser Lys Arg Phe Asp Asn Gly Met Ile Cys Ala Thr Glu Asn Ser Ala
            260                 265                 270

Val Ile Glu Ala Ser Val Tyr Asp Glu Phe Met Lys Leu Met Gln Glu
        275                 280                 285

Lys Gly Thr Tyr Leu Val Pro Lys Asp Asp Tyr Lys Lys Ile Ala Asp
    290                 295                 300

Phe Val Phe Ser Asp Lys His Ala Val Asn Gly Pro Val Ala Gly Met
305                 310                 315                 320

Ser Gly Arg Trp Ile Ala Glu His Ala Gly Val Thr Leu Pro Lys Gly
                325                 330                 335

Lys Asp Val Leu Leu Phe Glu Leu Asp Gln Asp Asp Ile Gly Glu Lys
            340                 345                 350

Leu Ser Ser Glu Lys Leu Ser Pro Leu Leu Ser Val Tyr Lys Ala Ala
        355                 360                 365

Asp Arg Lys Glu Ala Ile Lys Val Val Gln Arg Leu Leu Asn Tyr Gln
    370                 375                 380

Gly Ala Gly His Asn Ala Ala Ile Gln Ile Gly Ala Gln Asp Asp Pro
385                 390                 395                 400

Phe Val Lys Glu Tyr Ala Asp Ala Val Ser Ala Ser Arg Ile Leu Val
```

```
                405                 410                 415

Asn Gln Pro Asp Ser Ile Gly Gly Val Gly Asp Ile Tyr Thr Asp Ala
            420                 425                 430

Leu Arg Pro Ser Met Thr Leu Gly Thr Gly Ser Trp Gly Lys Asn Ser
        435                 440                 445

Leu Ser His Asn Leu Ser Thr Tyr Asp Leu Leu Asn Val Lys Thr Val
    450                 455                 460

Ala Arg Arg Arg Asn Arg Pro Gln Trp Val Arg Leu Pro Lys Asp Ile
465                 470                 475                 480

Tyr Tyr Glu Lys Asn Ala Ile Thr Tyr Leu Gln Glu Leu Pro Asn Val
                485                 490                 495

Asn Arg Ala Phe Val Ile Thr Asp His Ser Leu Val Lys Tyr Gly Phe
            500                 505                 510

Val Asp Arg Ile Leu Glu Gln Phe Glu Leu Arg Pro Asp Gln Val Lys
        515                 520                 525

Thr Ser Ile Tyr Ser Ser Val Gln Pro Asp Pro Tyr Leu Ser Gln Ala
    530                 535                 540

Val Glu Ile Ala Lys Gln Met Gln Glu Phe Glu Pro Asp Thr Val Ile
545                 550                 555                 560

Ala Leu Gly Gly Gly Ser Ser Leu Asp Val Ala Lys Ile Ser Arg Phe
                565                 570                 575

Leu Tyr Glu Tyr Ser Gln Glu Pro Asp His Ile Gly Phe Leu Glu Asn
            580                 585                 590

Ile Asp Asp Ile Lys Glu Leu Phe Lys Gly Leu Gln Gln Lys Phe Met
        595                 600                 605

Asp Ile Arg Lys Arg Ile Val Lys Phe Glu His Gln Asn Leu Thr Gln
    610                 615                 620

Leu Val Ala Ile Pro Thr Thr Ser Gly Thr Gly Ser Glu Val Thr Pro
625                 630                 635                 640

Phe Ser Val Ile Thr Asp Asp Glu Thr His Val Lys Tyr Pro Leu Ala
                645                 650                 655

Asp Tyr Glu Leu Thr Pro Gln Val Ala Ile Val Asp Pro Glu Leu Val
            660                 665                 670

Met Thr Val Pro Lys Arg Thr Leu Ala Trp Ser Gly Leu Asp Ala Leu
        675                 680                 685

Ser His Ser Leu Glu Ser Tyr Val Ser Val Met Ser Ser Glu Phe Thr
    690                 695                 700

Arg Pro Trp Ala Leu Gln Ala Ile Lys Leu Ile Phe Glu Asn Ile Val
705                 710                 715                 720

Asp Ser Tyr Asn Tyr Asp Pro Lys His Pro Thr Asn Arg Gly Ala Glu
                725                 730                 735

Ala Arg Glu Lys Met His Tyr Ala Ala Thr Leu Ala Gly Met Ser Phe
            740                 745                 750

Gly Asn Ala Phe Leu Gly Ile Asn His Ser Leu Ala His Lys Thr Gly
        755                 760                 765

Gly Glu Phe Gly Leu Pro His Gly Leu Ala Ile Ser Ile Ala Met Pro
    770                 775                 780

His Val Ile Arg Phe Asn Ala Val Thr Gly Asn Val Lys Arg Thr Pro
785                 790                 795                 800

Phe Pro Arg Tyr Glu Val Tyr Thr Ala Gln Lys Asp Tyr Ala Asp Ile
                805                 810                 815

Ala Arg His Ile Gly Leu Ser Gly Lys Asn Asp Ala Glu Leu Val Glu
            820                 825                 830
```

Lys Leu Ile Ala Lys Ile Lys Glu Leu Thr Asp Ala Leu Asp Val Asn
835 840 845

Ile Thr Leu Ser Gly Asn Gly Val Asp Lys Lys Ser Phe Glu His Ser
850 855 860

Leu Asp Gln Leu Val Asp Leu Val Tyr Asp Asp Gln Cys Thr Pro Gly
865 870 875 880

Asn Pro Arg Gln Pro Asn Leu Ala Glu Ile Arg Gln Leu Leu Ile Asp
885 890 895

Gln Phe

<210> SEQ ID NO 99
<211> LENGTH: 1194
<212> TYPE: DNA
<213> ORGANISM: Oenococcus oenii
<220> FEATURE:
<223> OTHER INFORMATION: ACK

<400> SEQUENCE: 99
atgacaaaaa ttttatcggt aaatgccggc tcgtcttcat tgaagttcaa attgcttaat 60
atgcccgaag agagtgttat cgccgaagga ctgattgaaa gaatcggtgg cagcctggat 120
caagacgata atgtcacgat taaattcaat ggcgaaaaac ataagagccg tcaggctttt 180
aaaaatcacg aggatgctat caacttgatg ctttctcaat ttaaaaagtt tggaatcgtt 240
gataatttta atgagatcaa aggaattggc caccgtgttg ttgccggggg tgaatggttc 300
aataaatctg tattaattaa cgatgaagtg ctgaataaaa ttgaacgttt ggctgcttac 360
gctccactcc ataatcctgc gaacgctatg ggcatcaggg ctttttccaa aataatcccc 420
gatgcaaccg aagttgccgt atttgataca gctttccatc aaacgatgcc gaaagagaat 480
tacttgtatg cggttcctta tgagtactat acgaaatacg gtgttcgtag gtatggagct 540
cacggaactt cccataaata cgtttccgaa caggctgcta aattaattgg gaaacccccta 600 gaagaactta aactgattac tttgcattta ggagccggag cgtctgtaac ggccattaag 660
aatggtcgat catttgatac ctcgatggga ttttcgcctt tggccggatt ggttatggcg 720
actcgttcag ggatgttgga cgtctcattg attgattacg ttaaagcaaa agaagatatt 780
tccgatcagg aaatgctaaa tgttcttaac caaaaatccg gattactggg tgtgtcaaca 840
atttcaagtg atatgcgtga tttgttggat gtttatgata ctaacgatca tgctaaattg 900
gctattgata tgtttgtcgg tcgtgtagtt gattatatcg gtcaatatta ttttgaatta 960
aagggagctg atgcgcttgt tttcacggcc ggaattggag agaattcggt tccaatcagg 1020
aaaatgatta tcgatcgtct ggctttcttg ggcattaaac tcgatgaaga tgcaaatgat 1080
aagcatggag tcgaaacaaa gattacaact gatgattcca aaatggctgc atatgtaatt 1140
ccaaccaatg aggaactcga aattgctcgt gatgtacaaa atttgatgaa gtaa 1194

<210> SEQ ID NO 100
<211> LENGTH: 397
<212> TYPE: PRT
<213> ORGANISM: Oenococcus oenii
<220> FEATURE:
<223> OTHER INFORMATION: ACK

<400> SEQUENCE: 100

Met Thr Lys Ile Leu Ser Val Asn Ala Gly Ser Ser Ser Leu Lys Phe
1 5 10 15

Lys Leu Leu Asn Met Pro Glu Glu Ser Val Ile Ala Glu Gly Leu Ile

```
            20                  25                  30

Glu Arg Ile Gly Gly Ser Leu Asp Gln Asp Asp Asn Val Thr Ile Lys
        35                  40                  45

Phe Asn Gly Glu Lys His Lys Ser Arg Gln Ala Phe Lys Asn His Glu
    50                  55                  60

Asp Ala Ile Asn Leu Met Leu Ser Gln Phe Lys Lys Phe Gly Ile Val
65                  70                  75                  80

Asp Asn Phe Asn Glu Ile Lys Gly Ile Gly His Arg Val Val Ala Gly
                85                  90                  95

Gly Glu Trp Phe Asn Lys Ser Val Leu Ile Asn Asp Glu Val Leu Asn
            100                 105                 110

Lys Ile Glu Arg Leu Ala Ala Tyr Ala Pro Leu His Asn Pro Ala Asn
        115                 120                 125

Ala Met Gly Ile Arg Ala Phe Ser Lys Ile Ile Pro Asp Ala Thr Glu
    130                 135                 140

Val Ala Val Phe Asp Thr Ala Phe His Gln Thr Met Pro Lys Glu Asn
145                 150                 155                 160

Tyr Leu Tyr Ala Val Pro Tyr Glu Tyr Tyr Thr Lys Tyr Gly Val Arg
                165                 170                 175

Arg Tyr Gly Ala His Gly Thr Ser His Lys Tyr Val Ser Glu Gln Ala
            180                 185                 190

Ala Lys Leu Ile Gly Lys Pro Leu Glu Glu Leu Lys Leu Ile Thr Leu
        195                 200                 205

His Leu Gly Ala Gly Ala Ser Val Thr Ala Ile Lys Asn Gly Arg Ser
    210                 215                 220

Phe Asp Thr Ser Met Gly Phe Ser Pro Leu Ala Gly Leu Val Met Ala
225                 230                 235                 240

Thr Arg Ser Gly Asp Val Asp Val Ser Leu Ile Asp Tyr Val Lys Ala
                245                 250                 255

Lys Glu Asp Ile Ser Asp Gln Glu Met Leu Asn Val Leu Asn Gln Lys
            260                 265                 270

Ser Gly Leu Leu Gly Val Ser Thr Ile Ser Ser Asp Met Arg Asp Leu
        275                 280                 285

Leu Asp Val Tyr Asp Thr Asn Asp His Ala Lys Leu Ala Ile Asp Met
    290                 295                 300

Phe Val Gly Arg Val Val Asp Tyr Ile Gly Gln Tyr Tyr Phe Glu Leu
305                 310                 315                 320

Lys Gly Ala Asp Ala Leu Val Phe Thr Ala Gly Ile Gly Glu Asn Ser
                325                 330                 335

Val Pro Ile Arg Lys Met Ile Ile Asp Arg Leu Ala Phe Leu Gly Ile
            340                 345                 350

Lys Leu Asp Glu Asp Ala Asn Asp Lys His Gly Val Glu Thr Lys Ile
        355                 360                 365

Thr Thr Asp Asp Ser Lys Met Ala Ala Tyr Val Ile Pro Thr Asn Glu
    370                 375                 380

Glu Leu Glu Ile Ala Arg Asp Val Gln Asn Leu Met Lys
385                 390                 395
```

<210> SEQ ID NO 101
<211> LENGTH: 2385
<212> TYPE: DNA
<213> ORGANISM: Oenococcus oenii
<220> FEATURE:
<223> OTHER INFORMATION: PHK

<400> SEQUENCE: 101

```
atgactatta attatgattc aaaggattat ttgaaatatg ttgatgccta ttggcgggct     60
gccaattatc tttcagtcgg tcaacttttc ttgagaaaca atccgttact taaagacgaa    120
cttcagtcca aagacgttaa gatcaagccg atcggtcatt ggggaacggt tgcgccgcag    180
aattttattt atgctcattt aaatcgagca attttaaaat acgatttaaa tatgttttat    240
attgaaggct ctggccatgg tggccaggtg atggtttcca attcatattt ggatgggtct    300
tataccgaaa cttatccaaa agtaactcag gatattcaag gaatgcaacg tttattcaag    360
caattctctt ttcctggcgg aattgcttca catgctgctc cggaaactcc tggatcgatt    420
cacgaaggag gagagctggg ttattcgatt tcgcatggag ttggtgctat tttggacaat    480
cccgatgtga ttgctgctgt tgaaatcggg gatggtgaat cagaaacggg gcctttggcc    540
gcatcgtggt tttccgacaa attcattaat ccgattcatg atggtgctgt gttgccgatt    600
gttcagatta atggatttaa aatttccaat ccaacaattc tttctcgcat gagcgatcgt    660
gatttgacca attattatca tggaatgggt tgggagcctt tgttcgttga aacggatggt    720
tcagataatt ttaaagtgca tgccgagatg gccgatgctg ttgataaggc cattgaaaaa    780
attaaagcta ttcaaaaaaa cgcccgtaat aataatgatg attcattgcc aatctggccg    840
atgattgtat tacgtgctcc taaaggttgg acaggtccaa aaaaagattt ggatggtaat    900
ccgattgaaa attcatttcg ggcacatcag gtgccgattc cagtcgatgc aaatcatttg    960
gaacataaag atatgctgat tgattggatg aagtcctaca aaccggaaga attgttcaat   1020
gaggatggca gcttaaaaga aattgttaag gtaaatcagc caaaaggcca acggcgaatg   1080
gcaatgaacc caatcacgaa tggtggaata aagccaagga cattgaatat gcctgatatg   1140
gaacgatttg cttttccgaa aaatagcttg aaaaacaata aaaaaccagg gatggacctt   1200
caggttgttt caacatttat tgccgaaata ataaagaaaa atcctatcaa tttccgtcag   1260
ttcggtcccg atgaaacaat gtccaatcgt ctctgggacg agtttaaagt cactaatcgt   1320
cagtggatgc aagcagtcca tgaaccaaat gatcaatata tggctcattc tggtcgtatt   1380
ctagatgctc aattgtctga acatcaggcc gagggatgga tggaaggata cgttttgacc   1440
ggccgacacg ctttctttgc gtcctacgaa gcctttacgc gtgtaattga ttcgatgctg   1500
actcaatatt ataagtggtt gcgaaaagcg gtcgagcaag attggcgtca cgattatcct   1560
tcgttaaatg tcattaatgc ttcacatgct tttcaacagg accataatgg ttatactcat   1620
caagatcccg gtatgcttac tcatatggct gaaaaaggtc atgagtttgt caatgaattc   1680
ttgccagccg atgctaattc ccttttggca gttatgaata agtctctgca ggttagaaac   1740
aaaattaaca ttattgtcgc ttccaaacac ccacgaactc aatggtttac gatcgacgaa   1800
gccaaggaat tggttgacaa cggtttggga attattccat gggcttccaa cgatgacgga   1860
gtggaaccgg acgttgtttt tgcagccggt ggaacggaag cgactatgga aagtttggct   1920
gctatttcgc tcttgcatga aagcttccct gaattgaagt tccgctttat taatgtaatc   1980
gatttgttga aactgcgcaa aaaaggggat aacgatgatt atcgcggtct aagcgatttg   2040
gaattcgacc attactttac gcgtgaaaaa ccagtagtct ttccttccaa cggctttgaa   2100
agtttggcac gcgacttgtt ctatgaccgc cacaatcata atgttatttt tcatggatat   2160
cgtgaaaacg gagacattac aactccgttc gatatgcgtg tcctgaatca tcttgatcgt   2220
ttccaccttg ccaaagacgc aatcaacgca actaagtacg ctgatgtggc tggccaattt   2280
gaccaacgaa tggatgatat gttggccaaa cataccgctt atatttgcga tcagggaaca   2340
```

```
gacctgcctg aagtaacctc ttggcagtgg caggatatta aataa                2385


<210> SEQ ID NO 102
<211> LENGTH: 794
<212> TYPE: PRT
<213> ORGANISM: Oenococcus oenii
<220> FEATURE:
<223> OTHER INFORMATION: PHK

<400> SEQUENCE: 102

Met Thr Ile Asn Tyr Asp Ser Lys Asp Tyr Leu Lys Tyr Val Asp Ala
1               5                   10                  15

Tyr Trp Arg Ala Ala Asn Tyr Leu Ser Val Gly Gln Leu Phe Leu Arg
            20                  25                  30

Asn Asn Pro Leu Leu Lys Asp Glu Leu Gln Ser Lys Asp Val Lys Ile
        35                  40                  45

Lys Pro Ile Gly His Trp Gly Thr Val Ala Pro Gln Asn Phe Ile Tyr
    50                  55                  60

Ala His Leu Asn Arg Ala Ile Leu Lys Tyr Asp Leu Asn Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Thr Glu Thr Tyr Pro Lys Val Thr Gln Asp Ile
            100                 105                 110

Gln Gly Met Gln Arg Leu Phe Lys Gln Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ser Ile Ser His Gly Val Gly Ala Ile Leu Asp Asn
145                 150                 155                 160

Pro Asp Val Ile Ala Ala Val Glu Ile Gly Asp Gly Glu Ser Glu Thr
                165                 170                 175

Gly Pro Leu Ala Ala Ser Trp Phe Ser Asp Lys Phe Ile Asn Pro Ile
            180                 185                 190

His Asp Gly Ala Val Leu Pro Ile Val Gln Ile Asn Gly Phe Lys Ile
        195                 200                 205

Ser Asn Pro Thr Ile Leu Ser Arg Met Ser Asp Arg Asp Leu Thr Asn
    210                 215                 220

Tyr Tyr His Gly Met Gly Trp Glu Pro Leu Phe Val Glu Thr Asp Gly
225                 230                 235                 240

Ser Asp Asn Phe Lys Val His Ala Glu Met Ala Asp Ala Val Asp Lys
                245                 250                 255

Ala Ile Glu Lys Ile Lys Ala Ile Gln Lys Asn Ala Arg Asn Asn Asn
            260                 265                 270

Asp Asp Ser Leu Pro Ile Trp Pro Met Ile Val Leu Arg Ala Pro Lys
        275                 280                 285

Gly Trp Thr Gly Pro Lys Lys Asp Leu Asp Gly Asn Pro Ile Glu Asn
    290                 295                 300

Ser Phe Arg Ala His Gln Val Pro Ile Pro Val Asp Ala Asn His Leu
305                 310                 315                 320

Glu His Lys Asp Met Leu Ile Asp Trp Met Lys Ser Tyr Lys Pro Glu
                325                 330                 335

Glu Leu Phe Asn Glu Asp Gly Ser Leu Lys Glu Ile Val Lys Val Asn
            340                 345                 350
```

```
Gln Pro Lys Gly Gln Arg Arg Met Ala Met Asn Pro Ile Thr Asn Gly
        355                 360                 365

Gly Ile Lys Pro Arg Thr Leu Asn Met Pro Asp Met Glu Arg Phe Ala
    370                 375                 380

Phe Pro Lys Asn Ser Leu Lys Asn Asn Lys Lys Pro Gly Met Asp Leu
385                 390                 395                 400

Gln Val Val Ser Thr Phe Ile Ala Glu Ile Ile Lys Lys Asn Pro Ile
                405                 410                 415

Asn Phe Arg Gln Phe Gly Pro Asp Glu Thr Met Ser Asn Arg Leu Trp
            420                 425                 430

Asp Glu Phe Lys Val Thr Asn Arg Gln Trp Met Gln Ala Val His Glu
        435                 440                 445

Pro Asn Asp Gln Tyr Met Ala His Ser Gly Arg Ile Leu Asp Ala Gln
    450                 455                 460

Leu Ser Glu His Gln Ala Glu Gly Trp Met Glu Gly Tyr Val Leu Thr
465                 470                 475                 480

Gly Arg His Ala Phe Phe Ala Ser Tyr Glu Ala Phe Thr Arg Val Ile
                485                 490                 495

Asp Ser Met Leu Thr Gln Tyr Tyr Lys Trp Leu Arg Lys Ala Val Glu
            500                 505                 510

Gln Asp Trp Arg His Asp Tyr Pro Ser Leu Asn Val Ile Asn Ala Ser
        515                 520                 525

His Ala Phe Gln Gln Asp His Asn Gly Tyr Thr His Gln Asp Pro Gly
    530                 535                 540

Met Leu Thr His Met Ala Glu Lys Gly His Glu Phe Val Asn Glu Phe
545                 550                 555                 560

Leu Pro Ala Asp Ala Asn Ser Leu Leu Ala Val Met Asn Lys Ser Leu
                565                 570                 575

Gln Val Arg Asn Lys Ile Asn Ile Ile Val Ala Ser Lys His Pro Arg
            580                 585                 590

Thr Gln Trp Phe Thr Ile Asp Glu Ala Lys Glu Leu Val Asp Asn Gly
        595                 600                 605

Leu Gly Ile Ile Pro Trp Ala Ser Asn Asp Asp Gly Val Glu Pro Asp
    610                 615                 620

Val Val Phe Ala Ala Gly Gly Thr Glu Ala Thr Met Glu Ser Leu Ala
625                 630                 635                 640

Ala Ile Ser Leu Leu His Glu Ser Phe Pro Glu Leu Lys Phe Arg Phe
                645                 650                 655

Ile Asn Val Ile Asp Leu Leu Lys Leu Arg Lys Lys Gly Asp Asn Asp
            660                 665                 670

Asp Tyr Arg Gly Leu Ser Asp Leu Glu Phe Asp His Tyr Phe Thr Arg
        675                 680                 685

Glu Lys Pro Val Val Phe Ser Phe His Gly Phe Glu Ser Leu Ala Arg
    690                 695                 700

Asp Leu Phe Tyr Asp Arg His Asn His Asn Val Ile Phe His Gly Tyr
705                 710                 715                 720

Arg Glu Asn Gly Asp Ile Thr Thr Pro Phe Asp Met Arg Val Leu Asn
                725                 730                 735

His Leu Asp Arg Phe His Leu Ala Lys Asp Ala Ile Asn Ala Thr Lys
            740                 745                 750

Tyr Ala Asp Val Ala Gly Gln Phe Asp Gln Arg Met Asp Asp Met Leu
        755                 760                 765

Ala Lys His Thr Ala Tyr Ile Cys Asp Gln Gly Thr Asp Leu Pro Glu
```

-continued

```
    770                 775                 780

Val Thr Ser Trp Gln Trp Gln Asp Ile Lys
785                 790
```

```
<210> SEQ ID NO 103
<211> LENGTH: 990
<212> TYPE: DNA
<213> ORGANISM: Oenococcus oenii
<220> FEATURE:
<223> OTHER INFORMATION: PTA

<400> SEQUENCE: 103

atgacaaatt tatttactga gttggctgat aaaattaagg aaaaaaaact gagactcgtt      60

tttccggaag gcgatgattc aagagtccag ggggcggcca tccgtttaaa aaaagatggt     120

ttactaacgc cgatattatt gggagatcag gcagcggtcg aaaagacagc tgcagataat     180

catttcgacc tgagtggcat caagcttatc gatccgctta aattcgatga gaagcagttc     240

aatcaattga tcgataaact ggttacccga cgaaaaggga aaactgaccc gcaaacggta     300

gctatgtggc tgcaggaagt aaattatttc ggtaccatgc ttgtttatac cggcaaggcc     360

gacgcaatgg tttccggtgc tgttcatcca accggcgata cggttcgtcc cgctttgcag     420

attatcaaga cagctcctgg tgtcagtcgt atttccggtg cttttattat gcaaaaaaat     480

gatgaacgct atctgtttgc cgattcggca attaatatcg aacttgatgc acaaaccatg     540

gctgagattg ccgttcaatc agcccatacg gctaaaatat ttggaatcga tccaaaagtt     600

gccatgctga gtttttcaac caaaggatcg gcaaaaacatg cattggtcga taaagttgct     660

caggcaacta agctggcgca ggagatggca ccggatttag ctgataatat tgatggtgaa     720

ttacaattcg atgcagcttt tgtcgaatcg gttgccaaat taaaagctcc gggatcaaaa     780

gtggccggtc atgcgaacgt tttcattttt ccaagtttgg aagccggaaa tattggttat     840

aaaattgccc aacgcttggg tggatacgaa gcaattggtc ctattttgca aggattggca     900

gcacctgttt ccgatctgtc gcgtggagca agtcaagaag acgtatataa agttgcaatt     960

attactgctg ctcaggcttt aaaaaattag                                     990
```